US009631197B2

(12) United States Patent
Los et al.

(10) Patent No.: US 9,631,197 B2
(45) Date of Patent: Apr. 25, 2017

(54) RASAMSONIA TRANSFORMANTS

(71) Applicant: DSM IP ASSETS B.V., Heerlen (NL)

(72) Inventors: Alrik Pieter Los, Echt (NL); Yvonne Johannes Odilia Arendsen, Echt (NL); Adrianus Wilhelmus Hermanus Vollebregt, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/382,768

(22) PCT Filed: Mar. 12, 2013

(86) PCT No.: PCT/EP2013/055051
§ 371 (c)(1),
(2) Date: Sep. 4, 2014

(87) PCT Pub. No.: WO2013/135732
PCT Pub. Date: Sep. 19, 2013

(65) Prior Publication Data

US 2015/0020235 A1 Jan. 15, 2015

(30) Foreign Application Priority Data

Mar. 12, 2012 (EP) .................................... 12159103

(51) Int. Cl.
*C12N 15/80* (2006.01)
*C12N 15/90* (2006.01)
*C12N 9/42* (2006.01)
*C12N 9/58* (2006.01)

(52) U.S. Cl.
CPC ........... *C12N 15/80* (2013.01); *C12N 9/2437* (2013.01); *C12N 9/58* (2013.01); *C12N 15/905* (2013.01); *C12N 2800/30* (2013.01); *C12Y 302/01004* (2013.01); *C12Y 304/23* (2013.01)

(58) Field of Classification Search
None
See application file for complete search history.

(56) References Cited

U.S. PATENT DOCUMENTS

| | | | | |
|---|---|---|---|---|
| 2003/0199037 | A1 | 10/2003 | Harris et al. | |
| 2003/0233675 | A1 | 12/2003 | Cao et al. | |
| 2008/0085535 | A1* | 4/2008 | Breuner et al. | 435/69.1 |

FOREIGN PATENT DOCUMENTS

| | | | |
|---|---|---|---|
| CN | 1617927 | A | 5/2005 |
| JP | 2005176602 | A | 7/2005 |
| WO | 2012123429 | A1 | 9/2012 |

OTHER PUBLICATIONS

Houbraken et al., Antonie can Leeuwenhoek, published online 2011, vol. 101, pp. 403-421.*

Sauer, Molecular and Cellular Biology, 1987, vol. 7, pp. 2087-2096.*

Waters et al., Journal of Agricultural and Food Chemistry, 2010, vol. 58, pp. 7415-7422.*

Fairhead et al., Yeast, 1996, vol. 12, pp. 1439-1457.*

International Search Report received in corresponding PCT/EP2013/055051, mailed Jul. 4, 2013.

Houbraken et al., na new genus comprising thermotolerant and thermophilicandspecies, Antonie Van Leeuwenhoek. Kluwer Academic Publishers. DO, vol. 101, No. 2, Oct. 2, 2011 (Oct. 2, 2011), pp. 403-421, XP035003862.

Heinzelman et al: "Efficient screening of fungal cellobiohydrolase class I enzymes for thermostabilizing sequence blocks by SCHEMA structure-guided recombination", protein Engineering, Design & Selection, Sep. 16, 2010 (Sep. 16, 2010), pp. 871-880, XP055045668.

Database, UniProt, Mar. 3, 2009 (Mar. 3, 2009), "SubName: Full=DNA repair protein Rad50;" XP002699061, retrieved from EBI accession No. UN I PROT:B8LXJ 1, Database accession No. B8LXJ1.

Database UniProt [Online], Mar. 3, 2009 (Mar. 3, 2009), "SubName: Full=DSB repair complex subunit Ku70, putative;", XP002699062, retrieved from EBI accession No. UNIPROT:B8MR17, Database accession No. B8MR17.

Database UniProt [Online], May 31, 2011 (May 31, 2011), "SubName: Full=Meiotic recombination protein dmc1;", XP002699063, retrieved from EBI accession No. UNIPROT:F2THH5, Database accession No. F2THH5.

Jain et al, "Development of a transformation system for the thermophilic fungus *Talaromyces* sp. CL240 based on the use of phleomycin resistamce as a dominant selectable marker." Mol Gen Genet (1992) 234: 489-493.

Murray et al., "Isolation of the glucose oxidase gene from Talaromyces flavus and characterisation of its role in the biocontrol of Verticillium dahliaa" Curr Genet (1997) 32: 367-375.

Kolb et al., "Insertion of a foreign gene into the β-casein locus by Cre-mediated site-specofoc recombination." Gene 227 (1999) 21-31.

Barascu et al., "Homologous Recombination in Mammals." 23 Topics in Current Genetics (2013) 91-120.

Capecchi, "Gene targeting in mice: functional analysis of the mammalian genome for the twenty-first century." 6 Nature Reviews (2005) 507-512.

Hartmann et al., Validation of a Self-Excising Marker in the Human Pathogen Aspergillus fumigatus by Employing the β-Rec/six Site-Specific Recombination System.: 76(18) Applied and Environmental Microbiology (2010) 6313-6317.

(Continued)

*Primary Examiner* — Mindy G Brown
(74) *Attorney, Agent, or Firm* — McBee Moore Woodward & Vanik IP, LLC

(57) ABSTRACT

The invention relates to a method for carrying out recombination at a target locus in a *Rasamsonia* cell. The invention also relates to *Rasamsonia* cells, for example *Rasamsonia* cells produced by such a process. The invention further relates to processes in which such *Rasamsonia* cells are used and to the resulting enzyme compositions. The invention further relates to nucleic acid and amino acid sequences.

12 Claims, 12 Drawing Sheets

(56) References Cited

OTHER PUBLICATIONS

Cheng et al., "Controlling gene expression in yeast by inducible site-specific recombination." Nucleic Acids Research e108 (2000) 1-6.

International Search Report dated Jun. 14, 2013, issued in PCT/EP2013/055048.

International Search Report dated Apr. 26, 2013, issued in PCT/EP2013/055047.

Cherepanov et al., "Gene disruption in *Escherichia coli*: TcR and KmR cassettes with the option of Flp-caralyzed excision of the antibiotic-resistance determinant." Gene (1995) 158(1) 9-14. XP004206666.

You et al., "Gene-specific disruption in the filamentous fungus Cercospora nicotiane using a split-marker approach." Arch Microbiol (2009) 191(7) 615-622. XP019701743.

Uemura et al., "Chromosomal Manipulation by Site-Specific Recombinases and Fluorescent Protein-Based Vectors." PLOS ONE (2010) 5(3) E9846. XP055033795.

Metzer et al., "Conditional site-specific recombination in mammalian cells using a ligand-dependent chimeric Cre recombinase." Proc. Natl. Acad. Sci. USA (1995) 92(15) 6991-6995, XP000615550.

Fu et al., "Split marker transformation increases homologous integration frequency in Cryptococcus neoformans." Fungal Genetics and Biology (2006) 43(3) 200-212. XP024918894.

Bode et al., "The Transgeneticist's Toolbox: Novel Methods for the Targeted Modification of Eukaryotic Genomes." Biol. Chem. 381 (2000) 801-813. XP002282829.

Kolb et al., "Selection-Marker-Free Modification of the Murine [beta]-Casein Gene Using a 1 ox2722 Site." Analytical Biochemistry (2001) 290(2) 260-271. XP055033798.

* cited by examiner

17% marker loss

79% marker loss

CBS393.64 deltaReKu80-2

RASAMSONIA TRANSFORMANTS

CROSS REFERENCE TO RELATED APPLICATIONS

This application is a §371 National Stage Application of PCT/EP2013/055051, filed Mar. 12, 2013, which claims priority to EP 12159103.6, filed Mar. 12, 2012.

BACKGROUND

Field of the Invention

The invention relates to a method for carrying out recombination at a target locus in a *Rasamsonia* cell. The invention also relates to *Rasamsonia* cells, for example *Rasamsonia* cells produced by such a process. The invention further relates to processes in which such *Rasamsonia* cells are used and to the resulting enzyme compositions. The invention further relates to nucleic acid and amino acid sequences.

Description of Related Art

Carbohydrates constitute the most abundant organic compounds on earth. However, much of this carbohydrate is sequestered in complex polymers including starch (the principle storage carbohydrate in seeds and grain), and a collection of carbohydrates and lignin known as lignocellulose. The main carbohydrate components of lignocellulose are cellulose, hemicellulose, and pectins. These complex polymers are often referred to collectively as lignocellulose.

Bioconversion of renewable lignocellulosic biomass to a fermentable sugar that is subsequently fermented to produce alcohol (e.g., ethanol) as an alternative to liquid fuels has attracted an intensive attention of researchers since 1970s, when the oil crisis broke out because of decreasing the output of petroleum by OPEC. Ethanol has been widely used as a 10% blend to gasoline in the USA or as a neat fuel for vehicles in Brazil in the last two decades. More recently, the use of E85, an 85% ethanol blend has been implemented especially for clean city applications. The importance of fuel bioethanol will increase in parallel with increases in prices for oil and the gradual depletion of its sources. Additionally, fermentable sugars are being used to produce plastics, polymers and other biobased products and this industry is expected to grow substantially therefore increasing the demand for abundant low cost fermentable sugars which can be used as a feed stock in lieu of petroleum based feedstocks.

The sequestration of such large amounts of carbohydrates in plant biomass provides a plentiful source of potential energy in the form of sugars, both five carbon and six carbon sugars that could be utilized for numerous industrial and agricultural processes. However, the enormous energy potential of these carbohydrates is currently under-utilized because the sugars are locked in complex polymers, and hence are not readily accessible for fermentation. Methods that generate sugars from plant biomass would provide plentiful, economically-competitive feedstocks for fermentation into chemicals, plastics, such as for instance succinic acid and (bio) fuels, including ethanol, methanol, butanol synthetic liquid fuels and biogas.

Regardless of the type of cellulosic feedstock, the cost and hydrolytic efficiency of enzymes are major factors that restrict the commercialization of the biomass bioconversion processes. The production costs of microbially produced enzymes are tightly connected with a productivity of the enzyme-producing strain and the final activity yield in the fermentation broth.

In spite of the continued research of the last few decades to understand enzymatic lignocellulosic biomass degradation and cellulase production, it remains desirable to discover or to engineer new highly active cellulases and hemicellulases. It would also be highly desirable to construct highly efficient enzyme compositions capable of performing rapid and efficient biodegradation of lignocellulosic materials.

Such enzyme compositions may be used to produce sugars for fermentation into chemicals, plastics, such as for instance succinic acid and (bio) fuels, including ethanol, methanol, butanol, synthetic liquid fuels and biogas, for ensiling, and also as enzyme in other industrial processes, for example in the food or feed, textile, pulp or paper or detergent industries and other industries.

One genus of microorganisms that is known to produce suitable enzymes for enzymatic lignocellulosic biomass degradation is the genus *Rasamsonia*. *Rasamsonia* is a filamentous fungus and is sometimes referred to as *Talaromyces*.

Jain, S. et al, Mol Gen Genet (1992), 234, 489-493 discloses a transformation system for the fungus *Talaromyces* sp CL240. No expression of polypeptides is disclosed.

Murray, F. R. et al, Curr Genet (1997), 32, 367-375 discloses over-expression of the glucose oxidase gene from *Talaromyces flavus* in *Talaromyces macrosporus*. The effect fungal isolates on growth inhibition of *V. dahliae* was studied.

WO200170998 discloses *Talaromyces emersonii* beta-glucanases. On page 16, it is described that the polynucleotide of beta-glucanase may be heterologously expressed in a host, e.g. a yeast cell.

WO200224926 discloses *Talaromyces emersonii* xylanase. On page 24, $5^{th}$ paragraph, it is described that production of the polypeptide may be achieved by recombinant expression of the xylanase DNA sequence in a suitable homologous or heterologous host cell. In paragraph 7, it is said that the host cell may over-express the polypeptide, and techniques for engineering over-expression are well known from WO99/32617. WO99/32617 relates to expression cloning, but does not disclose cloning in *Talaromyces* host.

WO2007091231 discloses strains of *Talaromyces emersonii* which are thermostable and encode thermostable enzymes, and also discloses enzyme compositions produced by the *Talaromyces emersonii* strains. No recombinant production of homologous or heterologous polypeptides is disclosed. In table 1 shows inducing carbon sources were added in an amount of 0.2 to 6%. Solka floc and glucose (2%) were included for comparative purposes. On page 78, line 28 it is said that "glucose does not completely repress exoglucosidase production by the *T. emersonii* strains (table 31A). Table 31A shows that IM1393751 produces beta-glucosidase activity of 31.90 IU with glucose as carbon source, but no other cellulase activities, e.g. glucanases or xylanases. Due to lack of such enzyme activities, the strain IM1393751 is not suitable for the production of cellulases for the conversion of lignocellulose on glucose as carbon source.

WO2011054899 discloses *Talaromyces* transformants and a process for production of polypeptides using the *Talaromyces* transformants. Transformants in which polynucleotides of interest are introduced, are selected using a selection marker such as the phleomycin resistance marker, which is introduced at the same time as the polynucleotide of interest. Such stable hosts will therefore contain a selection marker.

Additional genetic tools are required so that *Rasamsonia* may be used more effectively for the production of enzymes or other industrially relevant products.

SUMMARY

The invention concerns a method for carrying out recombination at a target locus of a *Rasamsonia* cell, or target loci, for example within a target genome. The recombination method of the invention results in alteration of the target locus, for example the insertion of nucleic acid sequence at the target locus. The method may be carried out such that insertion of new sequence at the target locus is accompanied by removal of existing sequence from the target locus. That is to say, the method may be used to substitute a sequence at the target locus with an alternative sequence. The method may conveniently be carried out in vivo in a host cell.

Typically, when carried out in vivo, the method of the invention is not carried out on a human or animal cell. That is to say, the method of the invention is not typically carried out in the form of a method of treatment. The method of the invention may be carried out in an ex vivo or in vitro format. The terms ex vivo or in vitro should be understood to encompass methods carried out on microorganisms (both on whole living cells or on non-cellular material), but to exclude methods carried out on humans or animals.

The method is typically carried out such that at least part of the sequence inserted at the target locus is subsequently removed. If the method is carried out such that substitution of a sequence occurs at the target locus, followed by removal of the inserted sequence, the result may be deletion of sequence from the target locus.

Accordingly, the method of the invention may be carried out to achieve alteration of, the sequence of, the target locus. Such alteration may be, for example addition of new sequence, replacement of existing sequence and/or deletion/removal of existing sequence.

Thus, the method may be used to generate marker-free deletion strains of *Rasamsonia*. That is to say, a target sequence may be replaced by a marker sequence and the marker sequence then removed.

The invention is carried out in vivo in a *Rasamsonia* cell. The *Rasamsonia* cell may, preferably, be one which produces a compound of interest, such as an enzyme, in particular one or more cellulases.

The *Rasamsonia* cell may be capable of producing the compound of interest prior to application of the method of the invention. In this case, the method of the invention may be used to modify the target locus so that production of the compound of interest by the host cell is altered, for example production may be increased. Alternatively, the host cell may be one which produces the compound of interest as a result of application of the method of the invention.

In particular, the method may be used to generate *Rasamsonia* cells in which the ratio of non-homologous recombination (NHR) to homologous recombination (HR) is reduced such that the resulting cell has an increased efficiency for targeted integration of a polynucleotide at a target locus. Also, the method may be used to delete the protease pepA-encoding gene such that the resulting cells show increased production of heterologous genes.

The *Rasamsonia* cells resulting from use of the method of the invention may thus be marker-free, show a greater degree of HR and show reduced activity of or be deficient in the protease pepA. Such cells form part of the invention.

According to the invention, there is thus provided a method for carrying out recombination at a target locus in a *Rasamsonia* cell, which method comprises:

providing two or more nucleic acids which, when taken together, comprise: (a) sequences capable of homologous recombination with sequences flanking the target locus; (b) two or more site-specific recombination sites; (c) a sequence encoding a recombinase which recognizes the site-specific recombination sites; and (d) a sequence encoding a marker, wherein the two or more nucleic acids are capable of homologous recombination with each other so as to give rise to a single nucleic acid, and wherein at least two of the two or more nucleic acids each comprise a sequence encoding a non-functional portion of the marker; and recombining in a *Rasamsonia* cell the said two or more nucleic acids with each other and with the sequences flanking the target locus so that a contiguous nucleic acid sequence encoding a functional marker and the sequence encoding the recombinase are inserted at the target locus, said marker-encoding and/or recombinase-encoding sequence being flanked by at least two site-specific recombination sites and the said site-specific recombination sites being flanked by the sequences capable of homologous recombination with sequences flanking the target locus, thereby to carry out recombination at a target locus in a *Rasamsonia* cell.

Thus, the at least two of the two or more nucleic acids each comprising a sequence encoding a non-functional portion of a marker gene, each comprise a partial sequence, which after recombination encodes a functional marker (and wherein the parts by itself do not encode for a functional marker. The invention also provides:

- a *Rasamsonia* cell produced by a process of the invention;
- a *Rasamsonia* cell which is marker free;
- a *Rasamsonia* cell which is a variant of a parent *Rasamsonia*, wherein the ratio of NHR/HR is decreased in the mutant as compared to said ratio in said parent cell measured under the same conditions;
- a *Rasamsonia* cell which has a ratio of NHR/HR of less than about 50, preferably less than about 10, even more preferably less than about 1, and most preferably less than about 0.001.
- a *Rasamsonia* cell which has a modification in its genome such that it has a deficiency in the production of at least one aspartic protease pepA;
- a process for the production of a polypeptide composition of one or more enzymes comprising the steps of:
  - (a) producing the polypeptide composition by culturing a *Rasamsonia* cell of the invention in a suitable culture medium whereby the cell is capable of producing a desired polypeptide such as an enzyme, optionally which is encoded by a recombinant nucleic acid; and
  - (b) optionally recovering the polypeptide composition;
- a process for the production of a polypeptide composition comprising one or more cellulase, hemicellulase and/or pectinase comprising the steps of:
  - (a) producing polypeptide composition by culturing a *Rasamsonia* cell according to the invention in a suitable culture medium whereby the cell is capable of producing the one or more cellulase, hemicellulase and/or pectinase, optionally which is encoded by a recombinant nucleic acid; and (b) optionally recovering the polypeptide composition;

a nucleic acid sequence derivable from a *Rasamsonia* cell, preferably a *Rasamsonia emersonii* cell, encoding a polypeptide involved in non-homologous end-joining, wherein the nucleic acid sequence is:

a. a nucleic acid sequence as set out in SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50 or SEQ ID NO: 53; or b. a nucleic acid sequence encoding a polypeptide having at least 60% sequence identity with an amino acid sequence as set out in SEQ ID NO SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51 or SEQ ID NO: 54;

a nucleic acid sequence derivable from a *Rasamsonia* cell, preferably a *Rasamsonia emersonii* cell, encoding a pepA aspartic protease, wherein the nucleic acid sequence is:

a. a nucleic acid sequence as set out in SEQ ID NO: 58, or b. a nucleic acid sequence encoding a polypeptide having at least 60% sequence identity with an amino acid sequence as set out in SEQ ID NO SEQ ID NO: 59;

a recombinant nucleic acid construct comprising a nucleic acid sequence of the invention; and a polypeptide encoded by the DNA sequence of the invention.

BRIEF DESCRIPTION OF THE DRAWINGS

FIG. 10 shows the phenotypic and PCR analysis of marker-free *R. emersonii* transformants. Transformant A-A4, containing multiple *R. emersonii* CbhI copies and the pDEL_Pdx-A2 plasmid carrying loxP flanked ble expression cassette, was transformed with milliQ water (control) or the pEBA513 construct for transient expression of cre-recombinase.

BRIEF DESCRIPTION OF THE SEQUENCE LISTING

Figure 1:
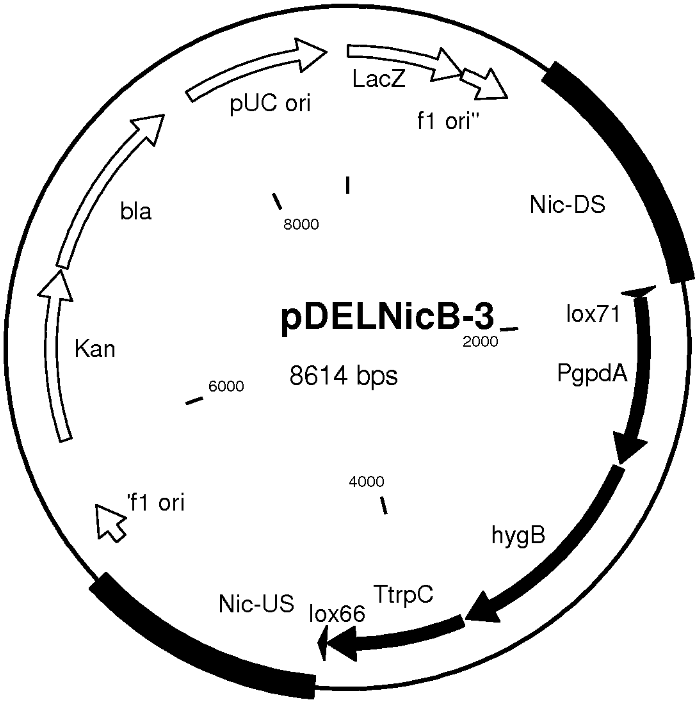
FIG. 1 sets out a schematic diagram of plasmid pDELNicB-3, which is the basis for a replacement cassette to inactivate the nicB gene in *A. niger*. The replacement cassette comprises the nicB flanking regions, the hygB marker cassette, mutant loxP sites and *E. coli* DNA. More details for pDELNicB-3 can be found in the Examples section (vide infra).

SEQ ID No: 1 sets out the mutant lox P site, lox66.

SEQ ID No: 2 sets out the mutant lox P site, lox71.

SEQ ID NO: 3 sets out the double-mutant lox72 site.

SEQ ID NO: 4 sets out a first non-functional hygB marker fragment (PgpdA-HygB sequence missing the last 27 bases of the coding sequence at the 3' end of hygB).

SEQ ID NO: 5 sets out a second non-functional hygB fragment (HygB-TtrpC sequence missing the first 44 bases of the coding sequence at the 5' end of hygB).

SEQ ID NO: 6 sets out the cre recombinase cassette containing the *A. nidulans* xylanase A promoter, a cre recombinase and xylanase A terminator, to allow xylose-inducible expression of the cre recombinase.

SEQ ID NO: 7 sets out the DNA sequence of the Ble-forward PCR primer;

SEQ ID NO: 8 sets out the DNA sequence of the Ble-reverse PCR primer;

SEQ ID NO: 9 sets out the DNA sequence of the EBA205-forward PCR primer;

SEQ ID NO: 10 sets out the DNA sequence of the EBA205-reverse PCR primer;

SEQ ID NO: 11 sets out the DNA sequence of the pGBTOPEBA4-forward PCR primer;

SEQ ID NO: 12 sets out the DNA sequence of the pGBTOPEBA4-reverse PCR primer;

SEQ ID NO: 13 sets out the DNA sequence of the pGBTOPEBA8-forward PCR;

SEQ ID NO: 14 sets out the DNA sequence of the pGBTOPEBA8-reverse PCR;

SEQ ID NO: 15 sets out the DNA sequence of the Pdx-forward PCR primer;

SEQ ID NO: 16 sets out the DNA sequence of the Pdx-reverse PCR primer;

SEQ ID NO: 17 sets out the DNA sequence of the Hyg-forward PCR primer;

SEQ ID NO: 18 sets out the DNA sequence of the Hyg-reverse PCR primer;

SEQ ID NO: 19 sets out the nucleic acid sequence of the ReKu70 genomic region including flanking sequence.

SEQ ID NO: 20 sets out the nucleic acid sequence of the ReKu70 cDNA.

SEQ ID NO: 21 sets out the amino acid sequence of the ReKu70 polypeptide.

SEQ ID NO: 22 sets out the nucleic acid sequence of the ReKu80 genomic region including flanking sequence.

SEQ ID NO: 23 sets out the nucleic acid sequence of the ReKu80 cDNA.

SEQ ID NO: 24 sets out the amino acid sequence of the ReKu80 polypeptide.

SEQ ID NO: 25 sets out the nucleic acid sequence of the ReRad50 genomic region including flanking sequence.

SEQ ID NO: 26 sets out the nucleic acid sequence of the ReRad50 cDNA.

SEQ ID NO: 27 sets out the amino acid sequence of the ReRad50 polypeptide.

SEQ ID NO: 28 sets out the nucleic acid sequence of the ReRad51 genomic region including flanking sequence.

SEQ ID NO: 29 sets out the nucleic acid sequence of the ReRad51 cDNA.

SEQ ID NO: 30 sets out the amino acid sequence of the ReRad51 polypeptide.

SEQ ID NO: 31 sets out the nucleic acid sequence of the ReRad52 genomic region including flanking sequence.

SEQ ID NO: 32 sets out the nucleic acid sequence of the ReRad52cDNA.

SEQ ID NO: 33 sets out the amino acid sequence of the ReRad52 polypeptide.

SEQ ID NO: 34 sets out the nucleic acid sequence of the ReRad54a genomic region including flanking sequence.

SEQ ID NO: 35 sets out the nucleic acid sequence of the ReRad54a cDNA.

SEQ ID NO: 36 sets out the amino acid sequence of the ReRad54a polypeptide.

SEQ ID NO: 37 sets out the nucleic acid sequence of the ReRad54b genomic region including flanking sequence.

SEQ ID NO: 38 sets out the nucleic acid sequence of the ReRad54b cDNA.

SEQ ID NO: 39 sets out the amino acid sequence of the ReRad54b polypeptide.

SEQ ID NO: 40 sets out the nucleic acid sequence of the ReRad55 genomic region including flanking sequence.

SEQ ID NO: 41 sets out the nucleic acid sequence of the ReRad55 cDNA.

SEQ ID NO: 42 sets out the amino acid sequence of the ReRad55 polypeptide.

SEQ ID NO: 43 sets out the nucleic acid sequence of the ReRad57 genomic region including flanking sequence.

SEQ ID NO: 44 sets out the nucleic acid sequence of the ReRad57 cDNA.

SEQ ID NO: 45 sets out the amino acid sequence of the ReRad57polypeptide.

SEQ ID NO: 46 sets out the nucleic acid sequence of the ReCDC2 genomic region including flanking sequence.

SEQ ID NO: 47 sets out the nucleic acid sequence of the ReCDC2 cDNA.

SEQ ID NO: 48 sets out the amino acid sequence of the ReCDC2 polypeptide.

SEQ ID NO: 49 sets out the nucleic acid sequence of the ReLIG4 genomic region including flanking sequence.

SEQ ID NO: 50 sets out the nucleic acid sequence of the ReLIG4 cDNA.

SEQ ID NO: 51 sets out the amino acid sequence of the ReLIG4 polypeptide.

SEQ ID NO: 52 sets out the nucleic acid sequence of the ReMRE11 genomic region including flanking sequence.

SEQ ID NO: 53 sets out the nucleic acid sequence of the ReMRE11 cDNA.

SEQ ID NO: 54 sets out the amino acid sequence of the ReMRE11 polypeptide.

SEQ ID NO 55: sets out the DNA sequence of the Ku80-forward PCR primer;

SEQ ID NO 56: sets out the DNA sequence of the Ku80-reverse PCR primer.

SEQ ID NO: 57 sets out the nucleic acid sequence the *Rasamsonia emersonii* pepA genomic region+flanks.

SEQ ID NO: 58 sets out sets out the nucleic acid sequence of the *Rasamsonia emersonii* pepA cDNA.

SEQ ID NO: 59 sets out sets out the amino acid sequence of the *Rasamsonia emersonii* pepA polypeptide.

SEQ ID NO: 60 sets out a first non-functional ble marker fragment (PgpdA-ble sequence missing the last 104 bases of the coding sequence at the 3' end of ble).

SEQ ID NO: 61 sets out a second non-functional ble fragment (b/e-TtrpC sequence missing the first 12 bases of the coding sequence at the 5' end of ble).

DETAILED DESCRIPTION OF A PREFERRED EMBODIMENT

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The method according to the invention is one for carrying out recombination at a target locus. Recombination refers to a process in which a molecule of nucleic acid is broken and then joined to a different one. The recombination process of the invention typically involves the artificial and deliberate recombination of disparate nucleic acid molecules, which may be from the same or different organism, so as to create recombinant nucleic acids.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

The method of the invention relies on a combination of homologous recombination and site-specific recombination.

"Homologous recombination" refers to a reaction between nucleotide sequences having corresponding sites containing a similar nucleotide sequence (i.e., homologous sequences) through which the molecules can interact (recombine) to form a new, recombinant nucleic acid sequence. The sites of similar nucleotide sequence are each referred to herein as a "homologous sequence". Generally, the frequency of homologous recombination increases as the length of the homology sequence increases. Thus, while homologous recombination can occur between two nucleic acid sequences that are less than identical, the recombination frequency (or efficiency) declines as the divergence between the two sequences increases. Recombination may be accomplished using one homology sequence on each of two molecules to be combined, thereby generating a "single-crossover" recombination product. Alternatively, two homology sequences may be placed on each of two molecules to be recombined. Recombination between two homology sequences on the donor with two homology sequences on the target generates a "double-crossover" recombination product.

If the homology sequences on the donor molecule flank a sequence that is to be manipulated (e.g., a sequence of interest), the double-crossover recombination with the target molecule will result in a recombination product wherein the sequence of interest replaces a DNA sequence that was originally between the homology sequences on the target molecule.

"Site-specific recombination", also known as conservative site-specific recombination, is a type of recombination in which nucleic acid strand exchange takes place between segments possessing only a limited degree of sequence homology. Site-specific recombinase enzymes perform rearrangements of nucleic acid segments by recognizing and binding to short DNA sequences (sites), at which they cleave the DNA backbone, exchange the two DNA helices involved and rejoin the DNA strands. In some site-specific recombination systems having just a recombinase enzyme together with the recombination sites is enough to perform all these reactions, in some other systems a number of accessory proteins and accessory sites may also needed.

The method may be use to carry out recombination at a target locus resulting in modification of that target locus. Accordingly, the invention may be used to add, delete or otherwise change a target locus. The target locus may be a coding or a non-coding sequence. The method of the invention may be used so that such coding or non-coding sequence may be disrupted and/or partially or fully deleted and/or replaced. Thus, the method of the invention may be used to replace sequence at target locus, for example with a marker-encoding sequence.

The invention is carried out in vivo in *Rasamsonia* cell. The *Rasamsonia* cell may, preferably, be one which produces a compound of interest. The cell may be capable of producing the compound of interest prior to application of the method of the invention. In this case, the method of the invention may be used to modify the target locus so that production of the compound of interest by the cell is altered, for example production may be increased. Alternatively, the *Rasamsonia* cell may be one which produces the compound of interest as a result of application of the method of the invention.

Accordingly, the invention may be used, for example, in the optimization of the productivity of a cell and/or the processes in which they are used. Alternatively, the invention may be used, for example, to introduce novel nucleic acids such that the host cell is rendered capable of producing a new compound of interest. The invention may be used sequentially, such that a plurality of novel nucleic acid sequences is introduced into the host cell, resulting in the introduction of an entirely new pathway or metabolic pathway.

A target locus may be any nucleic sequence which is to be modified. Typically, the target locus may be a sequence within a genome (the complete genetic material of an organism), for example a locus on a chromosome. Such a chromosome could be a linear or a circular chromosome. However, the target locus could be extrachromosomal for example a locus on a plasmid, a minichromosome or artificial chromosome. The target locus may be located on a plasmid, a phage, or any other nucleic acid sequence which is able to replicate or be replicated in vitro or in a *Rasamsonia* cell.

The method of the invention comprises:

providing two or more nucleic acids which, when taken together, comprise: (a) sequences capable of homologous recombination with sequences flanking the target locus; (b) two or more site-specific recombination sites; (c) a sequence encoding a recombinase which recognizes the site-specific recombination sites; and (d) a sequence encoding a marker, wherein the two or more nucleic acids are capable of homologous recombination with each other so as to give rise to a single nucleic acid, and wherein at least two of the two or more nucleic acids each comprise a sequence encoding a non-functional portion of the marker; and recombining in a *Rasamsonia* cell the said two or more nucleic acids with each other and with the sequences flanking the target locus so that a contiguous nucleic acid sequence encoding a functional marker and the sequence encoding the recombinase are inserted at the target locus, said marker-encoding and/or recombinase-encoding sequence being flanked by at least two site-specific recombination sites and the said site-specific recombination sites being flanked by the sequences capable of homologous recombination with sequences flanking the target locus.

In the invention, at least two of the two or more nucleic acids each comprise a sequence encoding a non-functional portion of a marker. That is to say, the marker-encoding sequence is split across at least two of the two or more nucleic acids. Accordingly, the method may be referred to as a split-marker approach.

Out-recombination of the nucleic acid sequence between the site-specific recombination sites, for example of the marker, may be carried out in vivo.

In the method of the invention, recombination of the nucleic acids with each other and with the target locus is carried out in vivo.

In the method of the invention, two or more nucleic acids are provided. Taken together, the two or more nucleic acids provide: (a) sequences capable of homologous recombination with sequences flanking the target locus; (b) two or more site-specific recombination sites; (c) a sequence encoding a recombinase which recognizes the site-specific recombination sites; and (d) a sequence encoding a marker It is not intended that each of the two or more nucleic acids comprises the sequences set out in (a), (b), (c) and (d). Rather, the sequences set out in (a), (b), (c) and (d) must be comprised by the two or more nucleic acids when those nucleic acids are taken together as a group. Thus, one nucleic acid may comprise one or more of the sequences set out in (a), (b), (c) (d) and a second nucleic acid may comprise the other sequences set out in (a), (b), (c) and (d). Typically, each of the two or more nucleic acids will comprise at least one of the sequences set out in (a), (b), (c) and (d). However, additional nucleic acids may be provided which do not comprise at least one of the sequences set out in (a), (b), (c) or (d).

Figure 6:
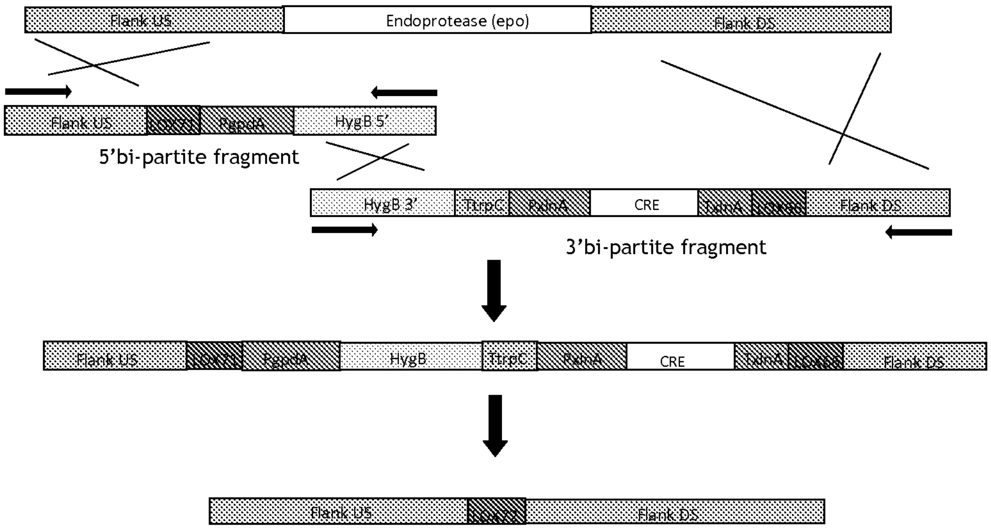
FIG. 6 sets out sets out a schematic representation for fragment generation and use of these fragments in transformation and recombination in *A. niger* as also shown in FIG. 5. The respective bipartite fragments in this specific example differ since they comprise a Cre recombinase cassette in addition. The last panel shows resulting layout of the genomic locus after a Cre induced recombination event.

One format for the method is set out in FIG. 6 in which two nucleic acids are used, but the skilled person will readily be able to conceive of further formats. The number of nucleic acids used in the method may be two, three, four, five, six or more.

Typically, the marker-encoding sequence will be split over two nucleic acid sequences (each of these two nucleic acid sequences encoding a non-functional portion of the marker, but when recombined the two will encode a functional marker). However, the marker-encoding sequence could be split of three, four or more nucleic acid sequences.

When the marker-encoding sequence is split over two nucleic acid sequences, each of those two sequences may typically also comprise a site-specific recombination site. This approach is shown is FIG. 6. Alternatively, the site-specific recombination sites may be provided on additional nucleic acid sequences capable of recombining with the nuclei acid sequences comprising the marker-encoding sequence. In the method of the invention, the two or more nucleic acids are capable of homologous recombination with each other so as to give rise to a single nucleic acid. The nucleic acids are incorporated as a single contiguous sequence at a target locus due to the presence of the sequences capable of homologous recombination with sequences flanking the target locus. In addition, at least two of the two or more nucleic acids each comprise a sequence encoding a non-functional portion of the marker.

Accordingly, in the method of the invention, the two or more nucleic acids are recombined with each other and with sequences flanking the target locus. In this way, a contiguous nucleic acid sequence encoding a functional marker may be inserted at the target locus together with a recombinase-encoding sequence and at least two site-specific recombination sites. This functional marker-encoding sequence is typically inserted at the target locus such that it is flanked by at least two site-specific recombination sites. When the recombinase is expressed, the sequence situated between the site-specific recombination sites may be out-recombined. If the marker-encoding and/or recombinase-encoding sequence is located between the site-specific recombination sites, it/they will be out-recombined. However, if the marker-encoding and/or recombinase-encoding sequence sequence lies outside the site-specific recombination sites, it will be retained at the target locus.

When recombination has taken place, the site-specific recombination sites, marker and recombinase sequence will be flanked by the sequences capable of homologous recombination with sequences flanking the target locus.

It also be possible to carry out the method of the invention by adding the recombinase separately, using for example a plasmid (comprising a sequence encoding the recombinase), or by use of direct addition of a recombinase protein.

The method of the invention may be carried out so that more than one, for example two, three, four, five or more target loci are targeted simultaneously. In such a method, the two or more nucleic acids, when taken together, comprise sequences capable of homologous recombination with sequences flanking two or more target loci. In this way, recombination of the said two or more nucleic acids with each other and with the sequences flanking the target loci results in the insertion of at least two site-specific recombination sites at each target loci. The two or more nucleic acids provided are such that a nucleic acid sequence encoding a functional recombinase is inserted in at least one target locus, optionally located between at least two site-specific recombination sites. It is not necessary for other target loci to comprise a function recombinase-encoding sequence, but each target loci will comprise at least two site-specific recombination sites (which may be targeted by the recombinase). At least two nucleic acids are provided, each comprising sequence encoding a non-functional marker. Thus, one or more functional marker-encoding sequences may be inserted at one or more of the target loci. The method of the invention may though be carried out such that a sequence encoding a functional marker is inserted at all or some of the target loci.

Again, at each target locus, the said site-specific recombination sites and any marker-encoding and recombinase-encoding sequence will be flanked by the sequences capable of homologous recombination with sequences flanking the target locus.

In the method of the invention, the two or more nucleic acids are capable of homologous recombination with each other so as to give rise to a single nucleic acid. The nucleic acids are incorporated as a single contiguous sequence at a target locus due to the presence of the sequences capable of homologous recombination with sequences flanking the target locus.

In more detail, the two or more nucleic acids provided in the invention, when taken together, comprise sequences capable of homologous recombination two or more homologous recombination sites directed against the target locus. Where the method targets a single target locus typically, the two or more nucleic acids will provide two such sequences. These sequences are provided such that a contiguous nucleic acid sequence comprising the at least two or more nucleic acids (when recombined with each other) is inserted at the target locus via recombination with substantially homologous sequences which flank the target sequence.

It will be obvious to the skilled person that, in order to achieve homologous recombination via a double cross-over event, these flanking sequences need to be present at both sides/ends of the contiguous sequence resulting from recombination of the two or more nucleic acids and need to be substantially homologous to sequences at both sides of the target loci. Thus, the sequences capable of homologous recombination are typically provided such that they are located at the "5'" and "3'" ends of the nucleic acid sequence resulting from recombination of the two or more nucleic acids.

Moreover, the at least two nucleic acids provided according to the invention are capable of undergoing recombination with each other. Thus, the ends of the nucleic acids are conveniently designed such that this may take place and that the nucleic acids will be assembled in the desired orientation and order. Accordingly the sequence of the ends of a provided nucleic acid will be substantially homologous to the sequences of the ends of the nucleic acids with which it is intended to be recombined.

With the term "substantially homologous" as used in this invention is meant that a first nucleic acid sequence has a degree of identity with a second nucleic acid sequence with which it is to be recombined of at least about 70%, at least about 80%, preferably at least about 90%, at least 95%, at least 98%, at least 99%, most preferably 100% over a region of not more than about 3 kb, preferably not more than about 2 kb, more preferably not more than about 1 kb, even more preferably not more than about 0.5 kb, even more preferably not more than about 0.2 kb, even more preferably not more than about 0.1 kb, such not more than about 0.05 kb, for example not more than about 0.03 kb. In filamentous fungi, the optimal size may be from about 500 bp to about 2.5 kb. The degree of required identity may thereby depend on the length of the substantially homologous sequence. The shorter the homologous sequence, the higher the percentage homology may be.

In the invention, the two or more nucleic acids, taken together, comprise two or more site-specific recombination sites. These site-specific recombination sites are recognised by a recombinase which is encoded by the two or more nucleic acids, taken together.

The site-specific recombination sites and recombinase are selected such that the recombinase may target the site-specific recombination sites leading to out-recombination of sequence locate between the recombination sites.

The terms "recombinase" or "site-specific recombinase" or the like refers to enzymes or recombinases that recognize and bind to a short nucleic acid site or "site-specific recombinase site", i.e., a recombinase recognition site, and catalyze the recombination of nucleic acid in relation to these sites. These enzymes include recombinases, transposases and integrases.

The "site-specific recombinase site" or the like refers to short nucleic acid sites or sequences, i.e., recombinase recognition sites, which are recognized by a sequence- or site-specific recombinase and which become the crossover regions during a site-specific recombination event. Examples of sequence-specific recombinase target sites include, but are not limited to, lox sites, att sites, dif sites and frt sites.

The term "lox site" as used herein refers to a nucleotide sequence at which the product of the cre gene of bacteriophage P1, the Cre recombinase, can catalyze a site-specific recombination event. A variety of lox sites are known in the art, including the naturally occurring loxP, loxB, loxL and loxR, as well as a number of mutant, or variant, lox sites, such as lox66, lox71, loxP511, loxP514, loxΔ86, loxΔ117, loxC2, loxP2, loxP3 and lox P23.

The term "frt site" as used herein refers to a nucleotide sequence at which the product of the FLP gene of the yeast 2 micron plasmid, FLP recombinase, can catalyze site-specific recombination.

The site-specific recombination sites may be such that out-recombination following recombinase expression gives rise to a single mutant site-specific recombination site at the target locus which is not recognized by the recombinase. In particular, the lox sites may be lox66 and lox 71 (Albert, H., Dale, E. C., Lee, E., & Ow, D. W. (1995). Site-specific integration of DNA into wild-type and mutant lox sites placed in the plant genome. *Plant Journal,* 7(4), 649-659).

In a specific embodiment, the lox66 and lox71 site-specific recombination sites may be such that out-recombination following recombinase expression gives rise to a lox72 mutant site-specific recombination site at the target locus which is not recognized by the recombinase.

In addition to the recombinase, site-specific recombination site and sequences capable of homologous recombination with sequences flanking the target locus, the method of the invention is carried out, wherein the two or more nucleic acids, taken together, comprise a marker-encoding sequence such that recombination of the two or more nucleic acids results in the said marker gene-encoding sequence being inserted at the target locus or loci. Such a marker-encoding sequence may be located between the at least two of the sequences capable of homologous recombination with sequences flanking the target locus or loci.

Critically, the two or more nucleic acids are provided so that at least two of the nucleic acids each comprise a sequence encoding a non-functional part of the marker-encoding sequence. When the two or more nucleic acids are recombined, this gives rise to a contiguous sequence encoding a functional marker. Accordingly, the method of the invention is referred to as a "split-marker" approach.

Non-functional in the context of this invention refers a sequence which does not encode a product capable of acting as a functional selection marker. Accordingly the method is especially applicable if a limited set of markers is available.

Typically, the method may be carried out so that a marker-encoding sequence is located between two or more site-specific recombination sites. In this way, the marker gene may be out-recombined on expression of the recombinase. Accordingly the method can be used for dominant markers and counter selectable markers.

In this way, the method may be carried out in a repeated fashion with more than one cycle of homologous recombination with sequences flanking the target locus followed by out-recombination following recombinase expression using the same marker. This approach may be further combined with the use of mutant site-specific recombination sites which cannot be targeted by the recombinase once the marker has out-recombined.

One advantage of the invention is that it allows multiple recombination events to be carried out simultaneously, sequentially or separately.

Accordingly the method may be carried out in a repeated fashion with more than one cycle of recombination using the same marker. Accordingly the method is especially applicable if a limited set of markers is available. This approach may be further combined with the use of mutant site-specific recombination sites which cannot be targeted by the recombinase once the marker has out-recombined. This allows multiple sites to be targeted and the amount of sites targeted is not limited by the availability of different markers since the marker is eliminated via activation of the recombinase.

In a method of the invention, the two or more nucleic acids, taken together, may comprise two or more different marker-encoding sequences such that recombination of the two or more nucleic acids results in two or more different marker gene-encoding sequence being inserted at a target locus or loci. This method may be carried out where sequences capable of homologous recombination with sequences flanking two or more target loci are provided. It is further possible, that one marker may be used to target at least two target loci and a different marker used to target a one or more further target loci.

In a method of the invention, one of the marker-encoding sequences will be split. In another preferred embodiment of the invention, two or more or even all of the marker-encoding sequences will typically be split. That is to say, for each marker the two or more nucleic acids are provided so that at least two of the nucleic acids each comprise a sequence encoding a non-functional part of the marker-encoding sequence. When the two or more nucleic acids are recombined, this gives rise to a contiguous sequence encoding a functional marker. A method of the invention may include at least one split marker. Typically, all marker-encoding sequences used are provided in a split format.

The method may be carried out such that a one or more identical or non-identical markers, each marker being flanked by lox sites are recombined into a cell. The method of the invention may then be used to provide a further recombination event and at the same time remove all of such markers.

In the method of the invention, the target locus comprises a coding sequence which is disrupted and/or partially or fully deleted. Typically, the method adds new sequence at the target locus; this new sequence will typically replace, delete and/or modify a sequence at the target locus.

As set out above, the replacement sequence may for instance confer a selectable phenotype when the recombination is carried out in vivo in a host cell. In that case, the replacement sequence comprises a selection marker. Preferentially, such a method is carried out so that the marker may be out-recombined on expression of the recombinase.

The replacement sequence may also be a modified version of the target sequence, for instance to provide for altered regulation of a sequence of interest or expression of a modified gene product with altered properties as compared to the original gene product.

The replacement sequence may also constitute additional copies of a sequence of interest being present in the genome of the host cell, to obtain amplification of that sequence of interest.

The replacement sequence may be a sequence homologous or heterologous to the host cell. It may be obtainable from any suitable source or may be prepared by custom synthesis.

The target sequence may be any sequence of interest. For instance, the target sequence may be a sequence of which the function is to be investigated by inactivating or modifying the sequence. The target sequence may also be a sequence of which inactivation, modification or over expression is desirable to confer on the host cell with a desired phenotype. Typically, the method of the invention will result in some nucleic acid sequence being removed at the target locus. However, the method of the invention may be used to insert sequence at the target locus without any sequence being lost from the target locus.

In the context of this disclosure, the terms "nucleic acid", "nucleic acid sequence", "polynucleotide", "polynucleotide sequence", "nucleic acid fragment", "isolated nucleic acid fragment" may be used interchangeably herein.

These terms encompass nucleotide sequences and the like. A nucleic acid may be a polymer of DNA or RNA that may be single- or double-stranded, that optionally contains synthetic, non-natural or altered nucleotide bases.

A nucleic acid in the form of a polymer of DNA may be comprised of one or more segments of cDNA, genomic DNA, synthetic DNA, or mixtures thereof.

The term "isolated nucleic acid" and the like refers to a nucleic acid that is substantially free from other nucleic acid sequences, such as and not limited to other chromosomal and extrachromosomal DNA and/or RNA. Isolated nucleic acids may be purified from a host cell in which they naturally occur.

Conventional nucleic acid purification methods known to skilled artisans may be used to obtain isolated nucleic acids. The term also embraces recombinant nucleic acids and chemically synthesized nucleic acids. Typically, each of the two or more nucleic acids suitable for use in the invention may be generated by any amplification process known in the art (e.g., PCR, RT-PCR and the like). The terms "amplify", "amplification", "amplification reaction", or "amplifying" as used herein refer to any in vitro process for multiplying the copies of a target sequence of nucleic acid. Amplification sometimes refers to an "exponential" increase in target nucleic acid. However, "amplifying" as used herein can also refer to linear increases in the numbers of a select target sequence of nucleic acid, but is typically different than a one-time, single primer extension step.

The two or more nucleic acids are typically introduced into a host cell so that the recombination events may take place. The two or more nucleic acids can be introduced into a host cell using various techniques which are well-known to those skilled in the art. Non-limiting examples of methods used to introduce heterologous nucleic acids into various organisms include; transformation, transfection, transduction, electroporation, ultrasound-mediated transformation, particle bombardment and the like. In some instances the addition of carrier molecules can increase the uptake of DNA in cells typically though to be difficult to transform by conventional methods. Conventional methods of transformation are readily available to the skilled person.

The procedures used to generate the two or more nucleic acids and to then introduce them into a host cell are well known to one skilled in the art (see, e.g. Sambrook & Russell, *Molecular Cloning: A Laboratory Manual,* 3rd Ed., CSHL Press, Cold Spring Harbor, N.Y., 2001; and Ausubel et al., *Current Protocols in Molecular Biology*, Wiley Inter-Science, N.Y., 1995).

Furthermore, standard molecular biology techniques such as DNA isolation, gel electrophoresis, enzymatic restriction modifications of nucleic acids, Southern analyses, transformation of cells, etc., are known to the skilled person and are for example described by Sambrook et al. (1989) "Molecular Cloning: a laboratory manual", Cold Spring Harbor Laboratories, Cold Spring Harbor, N.Y. and Innis et al. (1990) "PCR protocols, a guide to methods and applications" Academic Press, San Diego.

A nucleic acid suitable for use in the method of the invention may be amplified using cDNA, mRNA or alternatively, genomic DNA, as a template and appropriate oligonucleotide primers according to standard PCR amplification techniques. The nucleic acid so amplified can be cloned into an appropriate vector if desirable and/or characterized by nucleic acid sequence analysis.

The method of the invention may be carried out such that the two or more nucleic acids are recombined as a single nucleic acid which is then recombined with the target locus.

The method of the invention may be carried out where recombination of the said two or more nucleic acids with each other and with the target locus takes place simultaneously.

In a method of the invention two of the at least two nucleic acids may each comprise a part of the marker-encoding sequence such that together they comprise the entire marker-encoding sequence.

The method of the invention may be carried out so that the recombinase directed against the site-specific recombination sites is expressed such that the sequence located between the two site-specific recombination sites is out-recombined.

The expression of the marker and recombinase will typically be under the t of a control sequences including a promoter which enable expression of the recombinase within the host cell. That is to say, the marker- and recombinase-encoding sequences will typically be in operable linkage with a promoter sequence.

The term "operable linkage" or "operably linked" or the like are defined herein as a configuration in which a control sequence is appropriately placed at a position relative to the coding sequence of the DNA sequence such that the control sequence directs the production of an mRNA or a polypeptide.

The term "control sequences" is defined herein to include all components, which are necessary or advantageous for the production of mRNA or a polypeptide, either in vitro or in a host cell. Each control sequence may be native or foreign to the nucleic acid sequence encoding the polypeptide. Such control sequences include, but are not limited to, a leader, Shine-Delgarno sequence, optimal translation initiation sequences (as described in Kozak, 1991, J. Biol. Chem. 266:19867-19870), a polyadenylation sequence, a pro-peptide sequence, a pre-pro-peptide sequence, a promoter, a signal sequence, and a transcription terminator. At a minimum, the control sequences include a promoter, and a transcriptional stop signal as well as translational start and stop signals. Control sequences may be optimized to their specific purpose. Preferred optimized control sequences used in the present invention are those described in WO2006/077258.

The term "promoter" is defined herein as a DNA sequence that binds RNA polymerase and directs the polymerase to the correct downstream transcriptional start site of a nucleic acid sequence encoding a biological compound to initiate transcription. RNA polymerase effectively catalyzes the assembly of messenger RNA complementary to the appropriate DNA strand of a coding region. The term "promoter" will also be understood to include the 5'-non-coding region (between promoter and translation start) for translation after transcription into mRNA, cis-acting transcription control elements such as enhancers, and other nucleotide sequences capable of interacting with transcription factors.

Accordingly, a marker may be split by providing a promoter on a first nucleic acid and the coding sequence on a second nucleic acid such that the promoter and coding sequence are brought into operable linkage on recombination, i.e. recombination will give rise to a functional marker-encoding sequence.

The promoter may be any appropriate promoter sequence suitable for a eukaryotic or prokaryotic host cell, which shows transcriptional activity, including mutant, truncated, and hybrid promoters, and may be obtained from polynucleotides encoding extra-cellular or intracellular polypeptides either homologous (native) or heterologous (foreign) to the cell. The promoter may be a constitutive or inducible promoter. Expression of the recombinase by an inducible promoter will allow out-recombination of the sequence located between the site-specific recombination sites to be controlled, for example including the recombinase encoding sequence.

The promoter may be a constitutive or inducible promoter.

Examples of inducible promoters that can be used are a starch-, cellulose-, hemicellulose (such as xylan- and/or xylose-inducible), copper-, oleic acid-inducible promoters. The promoter may be selected from the group, which includes but is not limited to promoters obtained from the polynucleotides encoding *A. oryzae* TAKA amylase, *Rhizomucor miehei* aspartic proteinase, *A. niger* neutral alpha-amylase, *A. niger* acid stable alpha-amylase, *A. niger* or *A. awamori* glucoamylase (glaA), *A. niger* or *A. awamori* endoxylanase (xlnA) or beta-xylosidase (xlnD), *T. reesei* cellobiohydrolase I (CBHI), *R. miehei* lipase, *A. oryzae* alkaline protease, *A. oryzae* triose phosphate isomerase, *A. nidulans* acetamidase, *Fusarium venenatum* amyloglucosidase (WO 00/56900), *Fusarium venenatum* Dania (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the polynucleotides encoding *A. niger* neutral alpha-amylase and *A. oryzae* triose phosphate isomerase), and mutant, truncated, and hybrid promoters thereof. Other examples of promoters are the promoters described in WO2006/092396 and WO2005/100573, which are herein incorporated by reference. An even other example of the use of promoters is described in WO2008/098933. Other examples of inducible (heterologous) promoters are the alcohol inducible promoter alcA, the tet system using the tetracycline-responsive promoter, the estrogen-responsive promoter (Pachlinger et al. (2005), Appl & Environmental Microbiol 672-678).

The control sequences may also include suitable transcription terminator (terminator) sequence, a sequence recognized by a filamentous fungal cell to terminate transcription. The terminator sequence is operably linked to the 3'-terminus of the nucleic acid sequence encoding the polypeptide. Any terminator, which is functional in the cell, may be used in the present invention.

The control sequence may also be a suitable leader sequence (leaders), a non-translated region of an mRNA which is important for translation by the filamentous fungal cell. The leader sequence is operably linked to the 5'-terminus of the nucleic acid sequence encoding the polypeptide. Any leader sequence, which is functional in the cell, may be used in the present invention.

Depending on the host, suitable leaders may be obtained from the polynucleotides encoding *A. oryzae* TAKA amylase and *A. nidulans* triose phosphate isomerase and *A. niger* GlaA and phytase.

Other control sequences may be isolated from the *Penicillium* IPNS gene, or pcbC gene, the beta tubulin gene. All the control sequences cited in WO 01/21779 are herewith incorporated by reference.

The control sequence may also be a polyadenylation sequence, a sequence which is operably linked to the 3'-terminus of the nucleic acid sequence and which, when transcribed, is recognized by the filamentous fungal cell as a signal to add polyadenosine residues to transcribed mRNA. Any polyadenylation sequence, which is functional in the cell, may be used in the present invention.

As set out herein, in a method of the invention, the two or more nucleic acids, taken together, may comprise a sequence encoding a marker so that recombination of the two or more nucleic acids results in the said marker-encoding sequence being located between the homologous recombination sites.

Recombination of the two or more nucleic acids may result in the said marker-encoding sequence being located between the site-specific recombination sites such that the marker may be out-recombined on expression of the recombinase.

Any suitable marker may be used and such markers are well-known to determine whether a nucleic acid is included in a cell. Typically, a marker, such as a selectable marker, permits easy selection of transformed cells. A selectable marker is a gene the product of which provides for biocide or viral resistance, resistance to heavy metals, prototrophy to auxotrophs, and the like.

Examples of marker genes include, but are not limited to, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotic resistance markers (e.g., β-lactamase), β-galactosidase, fluorescent or other coloured markers, such as green fluorescent protein (GFP), yellow fluorescent protein (YFP), red fluorescent protein (RFP) and cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments as described in 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise nonfunctional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; (13) nucleic acid segments that encode conditional replication functions, e.g., replication in certain hosts or host cell strains or under certain environmental conditions (e.g., temperature, nutritional conditions, and the like); and/or nucleic acid segments that encode an essential gene.

A selectable marker for use in a *Rasamsonia* cell may be selected from the group including, but not limited to, amdS (acetamidase), argB (ornithine carbamoyltransferase), bar (phosphinothricinacetyltransferase), bleA (phleomycin binding), hygB (hygromycinphosphotransferase), niaD (nitrate reductase), pyrG (orotidine-5'-phosphate decarboxylase), sC (sulfate adenyltransferase), NAT or NTC (Nourseothricin) and trpC (anthranilate synthase), as well as equivalents from other species.

In the method of the invention, the in vivo recombination is carried out in a *Rasamsonia* cell. Accordingly, a cell for use in the invention belongs to the genus *Rasamsonia* also known as *Talaromyces*, more preferably the host cell belongs to the species *Talaromyces emersonii* also known as *Rasamsonia emersonii*. When the host cell according to the invention is a *Talaromyces emersonii* also known as *Rasamsonia emersonii* host cell, the host cell preferably is TEC-142S a single isolate of TEC-142 (CBS 124.902) or a derivative thereof.

The scope of the disclosure herein covers *Rasamsonia* and *Talaromyces* cells, for example thermophilic or thermotolerant *Talaromyces* strains such as *Talaromyces baciffisporus, Talaromyces leycettanus* and *Talaromyces thermophilus.*

Typically, a *Rasamsonia* cell used in the method according to the invention may be one suitable for the production of a compound of interest. Specific uses include, but are not limited to, food, (animal) feed, pharmaceutical, agricultural such as crop-protection, and/or personal care applications.

The method of the invention may be used to confer on a *Rasamsonia* cell the ability to produce a compound of interest and/or to modify the way in which an existing compound of interest is produced, for example to increase the production of such a compound of interest.

The invention relates to a *Rasamsonia* cell produced by a process as described herein. Such a cell will typically comprise at least one site-specific recombinase recognition site, for example a loxP site. Preferably, such a cell of the invention will comprise a mutant loxP site (for example a lox72 site) that cannot be recognized by a recombinase. In that way, the cell of the invention may be used to multiple sequential rounds of recombination at a target locus. Accordingly, a *Rasamsonia* cell produced by the method of the invention may comprise more than one mutant loxP site, for example two, three, four, five or more such sites.

The invention relates to a *Rasamsonia* cell which is a marker-free *Rasamsonia* cell. Typically, such a *Rasamsonia* cell is marker-free and comprises one or more recombinant genes, for example encoding one or more cellulases. The invention relates to a *Rasamsonia* cell produced by a process of the invention. Typically, such a cell will be a marker-free cell and will typically be a *Rasamsonia* cell which is a variant of a parent *Rasamsonia*, wherein the ratio of NHR/HR is decreased in the mutant as compared to said ratio in said parent cell measured under the same conditions. That is to say, the *Rasamsonia* cell of the invention may be a mutant cell.

Eukaryotic cells have at least two separate pathways (one via homologous recombination (HR) and one via non-homologous recombination (NHR)) through which nucleic acids (in particular DNA) can be integrated into the host genome. The yeast *Saccharomyces cerevisiae* is an organism with a preference for homologous recombination (HR). The ratio of non-homologous to homologous recombination (NHR/HR) of this organism may vary from about 0.07 to 0.007.

WO 02/052026 discloses mutants of *S. cerevisiae* having an improved targeting efficiency of DNA sequences into its genome. Such mutant strains are deficient in a gene involved in NHR (KU70).

Contrary to *S. cerevisiae*, most higher eukaryotes such as filamentous fungal cells up to mammalian cells have a preference for NHR. Among filamentous fungi, the NHR/HR ratio ranges between 1 and more than 100. In such organisms, targeted integration frequency is rather low.

Thus, to improve the efficiency of polynucleotide assembly at the target locus, the invention relates to a *Rasamsonia* cell in which the efficiency of homologous recombination (HR) is enhanced. The method of the invention may be used to generate such a cell.

Accordingly, the invention provides a *Rasamsonia* cell, for example one produced according to the recombination method of the invention, may be a mutant of a parent *Rasamsonia*, wherein the ratio of non-homologous recombination/homologous recombination is decreased in the mutant as compared to said ratio in said parent cell measured under the same conditions.

Accordingly, preferably in the method according to the invention, a *Rasamsonia* cell is provided which is, optionally inducibly, increased in its efficiency of homologous recombination (HR).

Since the NHR and HR pathways are interlinked, the efficiency of HR can be increased by modulation of either one or both pathways. Increase of expression of HR components will increase the efficiency of HR and decrease the ratio of NHR/HR. Decrease of expression of NHR components will also decrease the ratio of NHR/HR The increase in efficiency of HR in the host cell of the vector-host system according to the invention is preferably depicted as a decrease in ratio of NHR/HR and is preferably calculated relative to a parent host cell wherein the HR and/or NHR pathways are not modulated. The efficiency of both HR and NHR can be measured by various methods available to the person skilled in the art. A preferred method comprises determining the efficiency of targeted integration and ectopic integration of a single vector construct in both parent and modulated host cell. The ratio of NHR/HR can then be calculated for both cell types. Subsequently, the decrease in NHR/HR ration can be calculated. In WO2005/095624, this preferred method is described. The skilled person could though use other methods to determine the NHR/HR ratio.

A *Rasamsonia* cell having a decreased NHR/HR ratio as compared to a parent cell may be obtained by modifying the parent eukaryotic cell by increasing the efficiency of the HR pathway and/or by decreasing the efficiency of the NHR pathway. Preferably, the NHR/HR ratio thereby is decreased at least twice, preferably at least 4 times, more preferably at least 10 times. Preferably, the NHR/HR ratio is decreased in the host cell of the vector-host system according to the invention as compared to a parent host cell by at least 5%, more preferably at least 10%, even more preferably at least 20%, even more preferably at least 30%, even more preferably at least 40%, even more preferably at least 50%, even more preferably at least 60%, even more preferably at least 70%, even more preferably at least 80%, even more preferably at least 90% and most preferably by at least 100%.

In a *Rasamsonia* cell of the invention, the ratio of NHR/HR may be decreased by increasing the expression level of an HR component. HR components are herein defined as all genes and elements being involved in the control of the targeted integration of polynucleotides into the genome of a host, said polynucleotides having a certain homology with a certain pre-determined site of the genome of a host wherein the integration is targeted.

In a *Rasamsonia* cell of the invention, the ratio of NHR/HR may be decreased by decreasing the expression level of an NHR component. NHR components are herein defined as all genes and elements being involved in the control of the integration of polynucleotides into the genome of a host, irrespective of the degree of homology of said polynucleotides with the genome sequence of the host. NHR components are well-known to the person skilled in the art.

Preferred NHR components are a component selected from the group consisting of the homolog or ortholog in *Rasamsonia* of the yeast genes involved in the NHR pathway: KU70, KU80, RAD50, MRE11, XRS2, LIG4, LIF1, NEJ1 and SIR4 (van den Bosch et al., 2002, Biol. Chem. 383: 873-892 and Allen et al., 2003, Mol. Cancer Res. 1:913-920). Most preferred are one of KU70, KU80, and LIG4 and both KU70 and KU80. The decrease in expression level of the NHR component can be achieved using the methods as described herein for carrying out recombination at a target locus, i.e. a component of NHR may be disrupted or deleted entirely.

In a *Rasamsonia* cell of the invention, which is a mutant of a parent *Rasamsonia*, the ratio of NHR/HR may be decreased in the mutant as compared to said ratio in said parent cell measured under the same conditions.

A suitable *Rasamsonia* cell of the invention may be deficient in a gene encoding a component involved in NHR, and/or may have a decreased level of a component involved in NHR.

Such a *Rasamsonia* cell may have reduced activity of or may be deficient in a product of a *Rasamsonia* gene corresponding to any one of the yeast genes Ku70, Ku80, Rad50, Rad51, Rad52, Rad54, Rad55, Rad57, CDC2, LIG4 or MRE11.

Herein is reported the identification of genes from *Rasamsonia emersonii* that correspond to the Ku70, Ku80, Rad50, Rad51, Rad52, Rad54, Rad55, Rad57, CDC2, LIG4 or MRE11A genes from *S. cerevisiae*. Thus, a *Rasamsonia* cell of the invention may be one which has a modification in its genome in a sequence encoding polypeptide having at least 30% sequence identity with a polypeptide as set out in any one of SEQ ID NO SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51 or SEQ ID NO: 54.

The modification results in a decreased amount and/or activity of the product in the *Rasamsonia* cell (relative to a parent *Rasamsonia* cell which does not carry the modification). The modification may be deletion of the entire sequence.

Preferably, the modification in the genome of the *Rasamsonia* cell of the invention is a modification in the genome in a sequence encoding a polypeptide having at least 35% identity, more preferably at least 40% identity, more preferably at least 45% identity, more preferably at least 50% identity, even more preferably at least 55% identity, even more preferably at least 60% identity, even more preferably at least 65% identity, even more preferably at least 70% identity, even more preferably at least 75% identity, even more preferably at least 80% identity, even more preferably at least 85% identity, even more preferably at least 90% identity, for example at least 91% identity, for example at least 92% identity, for example at least 93% identity, for example at least 94% identity, for example at least 95% identity, for example at least 96% identity, for example at least 97% identity, for example at least 98% identity, for example at least 99% identity, for example 100% identity with a sequence as set out in any one of SEQ ID NO SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51 or SEQ ID NO: 54.

The invention also provides a polypeptide having at least 30% sequence identity with a polypeptide as set out in any one of SEQ ID NO SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51 or SEQ ID NO: 54.

Such a polypeptide may be have at least 35% identity, more preferably at least 40% identity, more preferably at least 45% identity, more preferably at least 50% identity, even more preferably at least 55% identity, even more preferably at least 60% identity, even more preferably at least 65% identity, even more preferably at least 70% identity, even more preferably at least 75% identity, even more preferably at least 80% identity, even more preferably at least 85% identity, even more preferably at least 90% identity, for example at least 91% identity, for example at least 92% identity, for example at least 93% identity, for example at least 94% identity, for example at least 95% identity, for example at least 96% identity, for example at least 97% identity, for example at least 98% identity, for example at least 99% identity, for example 100% identity with a sequence as set out in any one of SEQ ID NO SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51 or SEQ ID NO: 54.

A *Rasamsonia* cell of the invention may have a ratio of NHR/HR of less than about 50, preferably less than about 10, preferably less than about 9, preferably less than about 1, even more preferably less than about 1, and most preferably less than about 0.001.

Since it is possible that decreasing the expression of components involved in NHR may result in adverse phenotypic effects, it is preferred that in the *Rasamsonia* cell according to the invention, the increase in efficiency in homologous recombination is inducible. This can be achieved by methods known to the person skilled in the art, for example by either using an inducible process for an NHR component (e.g. by placing the NHR component behind an inducible promoter) or by using a transient disruption of the NHR component, or by placing the gene encoding the NHR component back into the genome.

The invention further provides a *Rasamsonia* cell, for example one produced according to the method of the invention, comprising one or more modifications in its genome in a polynucleotide encoding the major extracellular aspartic protease PepA such that the cell has a reduced amount/activity of or is deficient in the major aspartic protease PepA. Thus, the invention provides a *Rasamsonia* cell which has been modified in its genome such that this modification results in reduced activity of or deficiency in a product of the protease pepA-encoding gene gene.

Such a *Rasamsonia* cell may comprise a modification in a sequence encoding a protease pepA having at least 30% sequence identity with a polypeptide having the sequence set out in SEQ ID NO 59.

Preferably, the modification in the genome of the *Rasamsonia* cell of the invention is a modification in the genome on at least one position of at least one nucleic acid sequence encoding a protease pepA having at least 35% identity, more preferably at least 40% identity, more preferably at least 45% identity, more preferably at least 50% identity, even more preferably at least 55% identity, even more preferably at least 60% identity, even more preferably at least 65% identity, even more preferably at least 70% identity, even more preferably at least 75% identity, even more preferably at least 80% identity, even more preferably at least 85% identity, even more preferably at least 90% identity, for example at least 91% identity, for example at least 92% identity, for example at least 93% identity, for example at least 94% identity, for example at least 95% identity, for example at least 96% identity, for example at least 97% identity, for example at least 98% identity, for example at least 99% identity, for example 100% identity with the polypeptide of SEQ ID NO: 59.

A *Rasamsonia* cell, for example one produced according to the method of the invention, comprising one or more modifications in its genome in a polynucleotide encoding a major extracellular aspartic protease PepA such that the cell has a reduced amount/activity of or is deficient in a major aspartic protease PepA typically means that such a cell is genetically engineered or a classical mutated cell having a gene which is inactivated by a non-reversible inactivation. Such inactivation includes inactivation in the protein-coding region. Deficiency of a *Rasamsonia* cell in the production of a major extracellular aspartic protease PepA protein is herein defined as a phenotypic feature wherein the cell, due to modification in the genome: a) produces less of a major extracellular aspartic protease PepA protein and/or b) has a reduced expression level of the mRNA transcribed from a gene encoding a major extracellular aspartic protease PepA protein and/or c) produces a major extracellular aspartic protease PepA protein having a decreased protein activity or decreased specific protein activity and/or d) produces less of a product produced by a major extracellular aspartic protease PepA protein and combinations of one or more of these possibilities as compared to the parent microbial host cell that has not been modified in its genome according to the invention, when analyzed under substantially identical conditions.

Therefore inactivation of a microbial host cell may be measured by determining the amount and/or (specific) activity of a major extracellular aspartic protease PepA protein produced by the microbial host cell modified in its genome and/or it may be measured by determining the amount of mRNA transcribed from a gene encoding a major extracellular aspartic protease PepA protein and/or it may be measured by determining the amount of a product produced by a major extracellular aspartic protease PepA containing protein in a microbial host cell modified in its genome as defined above and/or it may be measured by gene or genome sequencing if compared to the parent host cell which has not been modified in its genome. Inactivation in the production of a major extracellular aspartic protease PepA protein can be measured using any assay available to the skilled person, such as transcriptional profiling, Southern blotting, Northern blotting, RT-PCR, Q-PCR, MALDI-TOF analysis, LC-MS, LC/MS-MS and Western blotting. The modification in the DNA sequence can also be determined by comparing the DNA sequence of the modified cell to the sequence of the non-modified cell. Sequencing of DNA and genome sequencing can be done using standard methods known to the person skilled in the art, for example using Sanger sequencing technology and/or next generation sequencing technologies such as Illumina GA2, Roche 454, and the like, as reviewed in Elaine R. Mardis (2008), Next-Generation DNA Sequencing Methods, Annual Review of Genomics and Human Genetics 9: 387-402. The modification in the RNA sequence can also be determined by comparing the RNA sequence of the modified cell to the sequence of the non-modified cell. Sequencing of RNA can be done using standard methods known to the person skilled in the art, for example using next generation sequencing technologies such as Illumina GA2, Roche 454, and the like, as reviewed in Pareek et al., 2011 Sequencing technologies and genome sequencing, J Appl Genetics 52:413-435.

The invention provides a nucleic acid sequence derivable from a *Rasamsonia* cell, preferably a *Rasamsonia emersonii* cell, encoding a polypeptide involved in non-homologous end-joining, wherein the nucleic acid sequence is:

a. a nucleic acid sequence as set out in SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50 or SEQ ID NO: 53; or
b. a nucleic acid sequence encoding a polypeptide having at least 60% sequence identity with an amino acid sequence as set out in SEQ ID NO SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51 or SEQ ID NO: 54.

The invention also provides a nucleic acid sequence derivable from a *Rasamsonia* cell, preferably a *Rasamsonia emersonii* cell, encoding an aspartic protease PepA, wherein the nucleic acid sequence is:

a. a nucleic acid sequence as set out in SEQ ID NO: 58, or b. a nucleic acid sequence encoding a polypeptide having at least 60% sequence identity with an amino acid sequence as set out in SEQ ID NO SEQ ID NO: 59.

In a preferred embodiment, a polynucleotide of the invention encodes a polypeptide which is involved in non-homologous end-joining or which is an aspartic protease PepA, having at least about 62%, at least about 65%, at least about 68%, at least about 70%, at least about 75%, at least about 80%, at least about 85%, at least about 90%, more preferably at least about 95%, more preferably at least about 97%, more preferably at least about 98%, more preferably at least about 99% identity, and most preferably at least about 100%.sequence identity with one of the sequences of SEQ ID NO SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54 or SEQ ID NO: 59. A polypeptides encoded by such as polynucleotide is part of the invention.

Also provided by the invention is a recombinant nucleic acid construct comprising a nucleic acid sequence of the invention. A polypeptide encoded by the nucleic acid of the invention is further provided.

A *Rasamsonia* cell of the invention may be capable of producing a desired compound, such as an enzyme, which optionally may be encoded by a recombinant nucleic acid introduced into the cell.

Typically, such a *Rasamsonia* cell may harbour one or more genes capable of expressing an enzyme capable of hydrolyzing (hemi)cellulose, such as expressing a cellulase, hemicellulase and/or pectinase. The one or more nucleic acid sequence capable of expressing a cellulase, hemicellulase and/or pectinase may include cellobiohydrolase, endoglucanase, GH61-enzymes and/or beta-glucosidase gene. A suitable cellobiohydrolyse is cellobiohydrolase I and/or cellobiohydrolase II. Thus, a cell of the invention may be one which is suitable for use in feedstock hydrolysis, such as lignocellulose degradation and/or for use in the preparation of a biofuel, for example ethanol.

Typically then, in the invention, the *Rasamsonia* cell will be one which produces a compound of interest. The host cell may be capable of producing the compound of interest prior to application of the method of the invention. In this case, the method of the invention may be used to modify the target locus so that production of the compound of interest by the host cell is altered, for example production may be increased. Alternatively, the host cell may be one which produces the compound of interest as a result of application of the method of the invention.

Accordingly, the host cell preferably comprises a recombinant polynucleotide construct comprising a polynucleotide encoding a compound involved in the synthesis of a compound of interest. The polynucleotide may also directly encode a compound of interest. The recombinant polynucleotide construct encoding a compound of interest or a polypeptide involved in the synthesis of a biological compound of interest may be located on an extra-chromosomal vector or at a locus in the genome of the host cell.

The compound of interest may a primary metabolite, secondary metabolite, a biopolymer such as a peptide or polypeptide or it may include biomass comprising the host cell itself. The compound may be encoded by a single polynucleotide or a series of polynucleotides composing a biosynthetic or metabolic pathway or may be the direct product of a single polynucleotide or may be products of a series of polynucleotides. The biological compound may be native to the host cell or heterologous. The biological compound may be modified according WO2010/102982.

The term “heterologous biological compound” is defined herein as a biological compound which is not native to the cell; or a native biological compound in which structural modifications have been made to alter the native biological compound.

The term “metabolite” encompasses both primary and secondary metabolites; the metabolite may be any metabolite. Preferred metabolites are citric acid, gluconic acid and succinic acid, antibiotics, bioactive drugs, biofuels and building blocks of biomaterials.

The metabolite may be encoded by one or more genes, such as in a biosynthetic or metabolic pathway. Primary metabolites are products of primary or general metabolism of a cell, which are concerned with energy metabolism, growth, and structure. Secondary metabolites are products of secondary metabolism (see, for example, R. B. Herbert, The Biosynthesis of Secondary Metabolites, Chapman and Hall, New York, 1981).

The primary metabolite may be, but is not limited to, an amino acid, carboxylic acid, fatty acid, nucleoside, nucleotide, sugar, triglyceride, or vitamin.

The term “biopolymer” is defined herein as a chain (or polymer) of identical, similar, or dissimilar subunits (monomers). The biopolymer may be any biopolymer. The biopolymer may for example be, but is not limited to, a nucleic acid, polyamine, polyol, polypeptide (or polyamide), or polysaccharide.

The biopolymer may be a polypeptide. The polypeptide may be any polypeptide having a biological activity of interest. The term “polypeptide” is not meant herein to refer to a specific length of the encoded product and, therefore, encompasses peptides, oligopeptides, and proteins. Polypeptides further include naturally occurring allelic and engineered variations of the above-mentioned polypeptides and hybrid polypeptides. The polypeptides may be a modified polypeptide according WO2010/102982.

The polynucleotide of interest according to the invention may encode an enzyme involved in the synthesis of a primary or secondary metabolite, such as organic acids, carotenoids, antibiotics, anti-cancer drug, pigments isoprenoids, alcohols, fatty acids and vitamins. Such metabolite may be considered as a biological compound according to the present invention.

The compound of interest may be an organic compound selected from glucaric acid, gluconic acid, glutaric acid, adipic acid, succinic acid, tartaric acid, oxalic acid, acetic acid, lactic acid, formic acid, malic acid, maleic acid, malonic acid, citric acid, fumaric acid, itaconic acid, levulinic acid, xylonic acid, aconitic acid, ascorbic acid, kojic acid, coumeric acid, an amino acid, a poly unsaturated fatty acid, ethanol, 1,3-propane-diol, ethylene, glycerol, xylitol, carotene, astaxanthin, lycopene and lutein.

Alternatively, the compound of interest may be a β-lactam antibiotic such as Penicillin G or Penicillin V and fermentative derivatives thereof, a cephalosporin, cyclosporin or lovastatin. The secondary metabolite may be an antibiotic, antifeedant, attractant, bacteriocide, fungicide, hormone, insecticide, or rodenticide. Preferred antibiotics are cephalosporins and beta-lactams.

The biopolymer may be a polysaccharide. The polysaccharide may be any polysaccharide, including, but not limited to, a mucopolysaccharide (e.g., heparin and hyaluronic acid) and nitrogen-containing polysaccharide (eg., chitin). In a more preferred option, the polysaccharide is hyaluronic acid.

The compound of interest may be a peptide selected from an oligopeptide, a polypeptide, a (pharmaceutical or industrial) protein and an enzyme. In such processes the peptide is preferably secreted from the host cell, more preferably secreted into the culture medium such that the peptide may easily be recovered by separation of the host cellular biomass and culture medium comprising the peptide, e.g. by centrifugation or (ultra)filtration.

The polypeptide may be any polypeptide having a biological activity of interest. The term "polypeptide" is not meant herein to refer to a specific length of the encoded product and, therefore, encompasses peptides, oligopeptides, and proteins. Polypeptides further include naturally occurring allelic and engineered variations of the above-mentioned polypeptides and hybrid polypeptides. The polypeptides may be a modified polypeptide according WO2010/102982. The polypeptide may be native or may be heterologous to the host cell. The polypeptide may be a collagen or gelatin, or a variant or hybrid thereof. The polypeptide may be an antibody or parts thereof, an antigen, a clotting factor, an enzyme, a hormone or a hormone variant, a receptor or parts thereof, a regulatory protein, a structural protein, a reporter, or a transport protein, protein involved in secretion process, protein involved in folding process, chaperone, peptide amino acid transporter, glycosylation factor, transcription factor, synthetic peptide or oligopeptide, intracellular protein. The intracellular protein may be an enzyme such as, a protease, ceramidases, epoxide hydrolase, aminopeptidase, acylases, aldolase, hydroxylase, aminopeptidase, lipase, non-ribosomal synthetase or polyketide synthetase. The polypeptide may be an enzyme secreted extracellularly Examples of proteins or (poly)peptides with industrial applications that may be produced in the methods of the invention include enzymes such as e.g. lipases (e.g. used in the detergent industry), proteases (used inter alia in the detergent industry, in brewing and the like, such as carboxypeptidases, endo-proteases, metallo-proteases, serine-proteases), carbohydrases and cell wall degrading enzymes (such as, amylases, glucosidases, cellulases (such as endoglucanases, β-glucanases, cellobiohydrolases, GH61 enzymes or β-glucosidases), GH61-enzymes, hemicellulases or pectinolytic enzymes, beta-1,3/4- and beta-1,6-glucanases, rhamnoga-lacturonases, mannanases, xylanases, pullulanases, galactanases, esterases and the like, used in fruit processing, wine making and the like or in feed), phytases, phospholipases, asparaginases, glycosidases (such as amylases, beta.-glucosidases, arabinofuranosidases, rhamnosidases, apiosidases and the like), dairy enzymes and products (e.g. chymosin, casein), oxidoreductases such as oxidases, transferases, or isomerases or polypeptides (e.g. poly-lysine and the like, cyanophycin and its derivatives).

Mammalian, and preferably human, polypeptides with therapeutic, cosmetic or diagnostic applications include, but are not limited to, collagen and gelatin, insulin, serum albumin (HSA), lactoferrin and immunoglobulins, including fragments thereof. The polypeptide may be an antibody or a part thereof, an antigen, a clotting factor, an enzyme, a hormone or a hormone variant, a receptor or parts thereof, a regulatory protein, a structural protein, a reporter, or a transport protein, protein involved in secretion process, protein involved in folding process, chaperone, peptide amino acid transporter, glycosylation factor, transcription factor, synthetic peptide or oligopeptide, intracellular protein. The intracellular protein may be an enzyme such as, a protease, ceramidases, epoxide hydrolase, aminopeptidase, acylases, aldolase, hydroxylase, aminopeptidase, lipase.

According to the present invention, a polypeptide can also be a fused or hybrid polypeptide to which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide.

Techniques for producing fusion polypeptides are known in the art, and include, ligating the coding sequences encoding the polypeptides so that they are in frame and expression of the fused polypeptide is under control of the same promoter (s) and terminator. The hybrid polypeptides may comprise a combination of partial or complete polypeptide sequences obtained from at least two different polypeptides wherein one or more may be heterologous to the host cell.

The compound of interest may also be the product of a selectable marker. A selectable marker is a product of a polynucleotide of interest which product provides for biocide or viral resistance, resistance to heavy metals, prototrophy to auxotrophs, and the like. Selectable markers include, but are not limited to, amdS (acetamidase), argB (ornithinecarbamoyltransferase), bar (phosphinothricinacetyltransferase), hygB (hygromycin phosphotransferase), niaD (nitratereductase), pyrG (orotidine-5'-phosphate decarboxylase), sC (sulfate adenyltransferase), trpC (anthranilate synthase), ble (phleomycin resistance protein), as well as equivalents thereof.

When the compound of interest is a biopolymer as defined earlier herein, the host cell may already be capable to produce the biopolymer. The host cell may also be provided with a recombinant homologous or heterologous polynucleotide construct that encodes a polypeptide involved in the production of the biological compound of interest. The person skilled in the art knows how to modify a microbial host cell such that it is capable of production of the compound involved in the production of the biological compound of interest.

The term "recombinant polynucleotide" herein refers to a nucleic acid molecule, either single- or double-stranded, which has been introduced into a *Rasamsonia* cell, for example a nucleic acid which is present in the cell in a form or at a locus in which it would not normally be present (in relation to a corresponding cell not comprising the recombinant polynucleotide).

The term "recombinant polynucleotide construct" is herein referred to as a nucleic acid molecule, either single- or double-stranded, which is isolated from a naturally occurring gene or which has been modified to contain segments of nucleic acid which are combined and juxtaposed in a manner which would not otherwise exist in nature. The term recombinant polynucleotide construct is synonymous with the term "expression cassette" when the nucleic acid construct contains all the control sequences required for expression of a coding sequence, wherein said control sequences are operably linked to said coding sequence. Suitable control sequences are described herein.

A *Rasamsonia* cell of the invention may comprise one or more recombinant polynucleotides or recombinant polynucleotide constructs in order that a compound of interest may be produced.

In order to facilitate expression, the polynucleotide encoding the polypeptide involved in the production of the compound of interest may be a synthetic polynucleotide. The synthetic polynucleotides may be optimized in codon use, preferably according to the methods described in WO2006/077258 or WO2008/000632. WO2008/000632 addresses codon-pair optimization. Codon-pair optimization is a method wherein the nucleotide sequences encoding a polypeptide have been modified with respect to their codon-usage, in particular the codon-pairs that are used, to obtain improved expression of the nucleotide sequence encoding the polypeptide and/or improved production of the encoded polypeptide. Codon pairs are defined as a set of two subsequent triplets (codons) in a coding sequence (CDS).

Furthermore, standard molecular cloning techniques such as DNA isolation, gel electrophoresis, enzymatic restriction modifications of nucleic acids, Southern analyses, transformation of cells, etc., are known to the skilled person and are for example described by Sambrook et al. (1989) “Molecular Cloning: a laboratory manual”, Cold Spring Harbor Laboratories, Cold Spring Harbor, N.Y. and Innis et al. (1990) “PCR protocols, a guide to methods and applications” Academic Press, San Diego.

A nucleic acid may be amplified using cDNA, mRNA or alternatively, genomic DNA, as a template and appropriate oligonucleotide primers according to standard PCR amplification techniques. The nucleic acid so amplified can be cloned into an appropriate vehicle and characterized by DNA sequence analysis.

The *Rasamsonia* cells (transformants) according to the invention may be cultured using procedures known in the art. For each combination of a promoter and a host cell, culture conditions are available which are conducive to the expression the DNA sequence encoding the polypeptide. After reaching the desired cell density or titer of the polypeptide the culture is stopped and the polypeptide is recovered using known procedures.

The fermentation medium can comprise a culture medium containing a carbon source (e. g. glucose, maltose, molasses, starch, cellulose, xylan, pectin, lignocellolytic biomass hydrolysate, etc.), a nitrogen source (e. g. ammonium sulphate, ammonium nitrate, ammonium chloride, etc.), an organic nitrogen source (e. g. yeast extract, malt extract, peptone, etc.) and inorganic nutrient sources (e. g. phosphate, magnesium, potassium, zinc, iron, etc.). Optionally, an inducer (e. g. cellulose, pectin, xylan, maltose, maltodextrin or xylogalacturonan) may be included.

The selection of the appropriate medium may be based on the choice of expression host and/or based on the regulatory requirements of the expression construct. Such media are known to those skilled in the art. The medium may, if desired, contain additional components favouring the transformed expression hosts over other potentially contaminating microorganisms.

The fermentation can be performed over a period of from about 0.5 to about 30 days. It may be a batch, fed-batch, or continuous process, suitably at a temperature in the range of, for example, from about 20 to about 90° C., preferably 20-55° C. more preferably 40-50° C. and/or at a pH, for example, from about 2 to about 8, preferably from about 3 to about 5. The appropriate conditions are usually selected based on the choice of the expression host and the polypeptide to be expressed.

After fermentation, if necessary, the cells can be removed from the fermentation broth by means of centrifugation or filtration. After fermentation has stopped or after removal of the cells, the polypeptide of the invention may then be recovered and, if desired, purified and isolated by conventional means.

For the purpose of this invention, it is defined here that in order to determine the percent identity of two amino acid sequences or of two nucleic acid sequences, the complete sequences are aligned for optimal comparison purposes. In order to optimize the alignment between the two sequences gaps may be introduced in any of the two sequences that are compared. Such alignment is carried out over the full length of the sequences being compared. The identity is the percentage of identical matches between the two sequences over the reported aligned region.

A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, emboss.bioinformatics.nl/). For protein sequences, EBLOSUM62 is used for the substitution matrix. For nucleotide sequences, EDNAFULL is used. Other matrices can be specified. For purpose of the invention, the parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

The protein sequences mentioned herein can further be used as a “query sequence” to perform a search against sequence databases, for example to identify other family members or related sequences. Such searches can be performed using the BLAST programs. Software for performing BLAST analyses is publicly available through the National Center for Biotechnology Information (www.ncbi.nlm.nih.gov). BLASTP is used for amino acid sequences and BLASTN for nucleotide sequences. In the BLAST program, the default settings may be used:

Cost to open gap: default=5 for nucleotides/11 for proteins

Cost to extend gap: default=2 for nucleotides/1 for proteins

Penalty for nucleotide mismatch: default=−3

Reward for nucleotide match: default=1

Expect value: default=10

Wordsize: default=11 for nucleotides/28 for megablast/3 for proteins

The nucleic acid sequences as mentioned herein can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215: 403-10. BLAST nucleotide searches can be performed with the NBLAST program, score=100, word-length=12 to obtain nucleotide sequences homologous to the nucleic acid molecules of the invention.

The sequence information as provided herein should not be so narrowly construed as to require inclusion of erroneously identified bases. The specific sequences disclosed herein can be readily used to isolate the complete gene from filamentous fungi, in particular *A. niger* which in turn can easily be subjected to further sequence analyses thereby identifying sequencing errors.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a nucleic acid sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The person skilled in the art is capable of identifying such erroneously identified bases and knows how to correct for such errors.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present invention is further illustrated by the following Examples:

EXAMPLES

It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Strains

WT 1: This *Aspergillus niger* strain is used as a wild-type strain. This strain is deposited at the CBS Institute under the deposit number CBS 513.88. *A. niger* strain CBS513.88 was deposited on 10 Aug. 1988 at the Centraalbureau voor Schimmelcultures, Utrecht, The Netherlands.

GBA302: The strain *Aspergillus niger* GBA 302 (ΔglaA, ΔpepA, ΔhdfA) is used herein as recipient strain in transformations. Construction of GBA 302 is described in WO2011009700.

The *Rasamsonia emersonii* (*R. emersonii*) strains used herein are derived from ATCC16479, which is used as wild-type strain. ATCC16479 was formerly also known as *Talaromyces emersonii* and *Penicillium geosmithia emersonii*. Upon the use of the name *Rasamsonia emersonii* also *Talaromyces emersonii* is meant. Other strain designations of *R. emersonii* ATCC16479 are CBS393.64, IF031232 and IM1116815.

*Rasamsonia* (*Talaromyces*) *emersonii* strain TEC-142 is deposited at CENTRAAL BUREAU VOOR SCHIMMELCULTURES, Uppsalalaan 8, P.O. Box 85167, NL-3508 AD Utrecht, The Netherlands on 1 Jul. 2009 having the Accession Number CBS 124902. TEC-142S is a single isolate of TEC-142.

Molecular Biology Techniques

In these strains, using molecular biology techniques known to the skilled person (see: Sambrook & Russell, *Molecular Cloning: A Laboratory Manual,* 3rd Ed., CSHL Press, Cold Spring Harbor, N.Y., 2001), several genes were over expressed and others were down regulated as described below. Examples of the general design of expression vectors for gene over expression and disruption vectors for down-regulation, transformation, use of markers and selective media can be found in for example WO199846772, WO199932617, WO2001121779, WO2005095624, EP 635574B and WO2005100573.

Media and Solutions

Potato dextrose agar, PDA, (Fluka, Cat. No. 70139)

| | |
|---|---|
| Potato extract | 4 g/l |
| Dextrose | 20 g/l |
| Bacto agar | 15 g/l |
| pH | 5.4 |
| Water | Adjust to one liter |
| Sterilize | 20 min at 120° C. |

Minimal Medium Agar Plates 8.8 g glucose, 6.6 g agarose, $H_2O$ to 400 ml. Autoclave 20 minutes at 115° C. and cool to 55° C. Add Solution I, mix and pour plates.

Solution I 11 ml stock A, 11 ml stock B, 0.44 ml stock trace elements (1000×), 4.4 ml Penicillin/Streptomycin Solution, 13.2 ml $H_2O$.

Stock A 120 g $NaNO_3$, 10.4 g KC, 30.4 g $KH_2PO_4$, 22.5 ml 4M KOH, $H_2O$ to 500 ml. Autoclave 20 minutes at 120° C.

Stock B (40×)

10.4 g $MgSO_4.7H_2O$, $H_2O$ to 500 ml. Autoclave 20 minutes at 120° C.

Stock Trace Elements (1000×)

2.2 g $ZnSO_4.7H_2O$, 1.1 g $H_3BO_3$, 0.5 g $FeSO_4.7H_2O$, 0.17 g $CoCl_2.6H_2O$, 0.16 g $CuSO_4.5H_2O$, 0.5 g $MnC_2.4H_2O$, 0.15 g $Na_2MoO_4.2H_2O$, 5.0 g EDTA.

Dissolve EDTA and ZnSO4.7H2O in 75 ml of milliQ water and set the pH to 6.0 with NaOH 1 M. Whilst maintaining the pH at 6.0 dissolve the components one by one. When ready set the pH to 4.0 with HCl 1 M, and adjust the volume to 100 ml with milliQ water. Autoclave 20 minutes at 120° C.

*Rasamsonia* Agar Medium

| | |
|---|---|
| Salt fraction no. 3 | 15 g |
| Cellulose (3%) | 30 g |
| Bacto peptone | 7.5 g |
| Grain flour | 15 g |
| $KH_2PO_4$ | 5 g |
| CaCl2.2aq | 1 g |
| Bacto agar | 20 g |
| pH | 6.0 |
| Water | Adjust to one liter |
| Sterilize | 20 min at 120° C. |

Salt Fraction Composition

The "salt fraction no. 3" was fitting the disclosure of WO98/37179, Table 1. Deviations from the composition of this table were CaCl2.2aq 1.0 g/I, KC 1.8 g/L, citric acid 1aq 0.45 g/L (chelating agent).

Shake Flask Media for *Rasamsonia*

*Rasamsonia* Medium 1

| | |
|---|---|
| Glucose | 20 g/L |
| Yeast extract (Difco) | 20 g/L |
| Clerol FBA3107 (AF) | 4 drops/L |
| pH | 6.0 |
| Sterilize | 20 min at 120° C. |

*Rasamsonia* Medium 2

| | |
|---|---|
| Salt fraction no. 3 | 15 g |
| Cellulose | 20 g |
| Bacto peptone | 4 g |
| Grain flour | 7.5 g |
| $KH_2PO_4$ | 10 g |
| $CaCl_2$•2H20 | 0.5 g |
| Clerol FBA3107 (AF) | 0.4 ml |
| pH | 5 |
| Water | Adjust to one liter |
| Sterilize | 20 min at 120° C. |

Spore Batch Preparation for *Rasamsonia*

Strains were grown from stocks on *Rasamsonia* agar medium in 10 cm diameter Petri dishes for 5-7 days at 40° C. For MTP fermentations, strains were grown in 96-well plates containing *Rasamsonia* agar medium. Strain stocks were stored at −80° C. in 10% glycerol.

Chromosomal DNA Isolation

Strains were grown in YGG medium (per liter: 8 g KC, 16 g glucose.$H_2O$, 20 ml of 10% yeast extract, 10 ml of 100× pen/strep, 6.66 g YNB+amino acids, 1.5 g citric acid, and 6 g $K_2HPO_4$). for 16 hours at 42° C., 250 rpm, and chromosomal DNA was isolated using the DNeasy plant mini kit (Qiagen, Hilden, Germany).

MTP Fermentation of *Rasamsonia*

96 wells microtiter plates (MTP) with sporulated *Rasamsonia* strains were used to harvest spores for MTP fermentations. To do this, 200 μl of *Rasamsonia* medium 1 was added to each well and after resuspending the mixture, 100 μl of spore suspension was incubated in humidity shakers (Infors) for 44° C. at 550 rpm, and 80% humidity for 16 hours. Subsequently, 50 μl of pre-culture was used to inoculate 250 μl of *Rasamsonia* medium 2 in MTP plates. The 96-well plates were incubated in humidity shakers (Infors) for 44° C. at 550 rpm, and 80% humidity for 6 days. Plates were centrifuged and supernatants were harvested.

Protein Analysis

Protein samples were separated under reducing conditions on NuPAGE 4-12% Bis-Tris gel (Invitrogen, Breda, The Netherlands) and stained as indicated. Gels were stained with either InstantBlue (Expedeon, Cambridge, United Kingdom), SimplyBlue safestain (Invitrogen, Breda, The Netherlands) or Sypro Ruby (Invitrogen, Breda, The Netherlands)) according to manufacturer's instructions.

For Western blotting, proteins were transferred to nitrocellulose. The nitrocellulose filter was blocked with TBST (Tris buffered saline containing 0,1% Tween 40) containing 3% skim-milk and incubated for 16 hours with anti-FLAG M2 antibody (Sigma, Zwijndrecht, The Netherlands). Blots were washed twice with TBST for 10 minutes and stained with Horse-radish-peroxidase conjugated rabbit-anti-mouse antibody (DAKO, Glostrup, Denmark) for 1 hour. After washing the blots five times with TBST for 10 minutes, proteins were visualized using SuperSignal (Pierce, Rockford, U.S.A).

Enzyme Activity Measurements

Proline Specific Endoprotease Activity

The proteolytic activity of the proline specific endoprotease is spectrophoto-metrically measured at 410 nm in time using CBZ-Gly(cine)-Pro(line)-pNA at 37° C. in a citrate/disodium phosphate buffer at pH 5. 1U proline specific endoprotease is defined as the amount of enzyme which converts 1 μmol (micromol) CBZ-Gly(cine)-Pro(line)-pNA per min at pH 5 and 37° C. at the conditions described above.

Cellulase Assay: Wheat Straw Assay (WSU Assay).

Preparation of Pre-Treated, Washed Wheat Straw Substrate

Dilute-acid pre-treated wheat straw which was washed with water until the solution with wheat straw was pH 6.5 or higher and the mass was homogenised using an ultra-turrax, lyophilized and grinded prior to analysis. To obtain pre-treated wheat straw a dilute acid pre-treatment as described in Linde, M. et al, Biomass and Bioenergy 32 (2008), 326-332 and equipment as described in Schell, D. J., Applied Biochemistry and Biotechnology (2003), vol. 105-108, pp 69-85, may be used.

Measurement of Cellulase Activity in WSU/ml

With 1 WSU is meant 0.119 mg/ml glucose released from 2.1 w/v % washed pre-treated wheat straw by 200 μl of enzyme mix in 20 hours at 65° C. at pH 4.50.

The glucose release is not a linear function of the quantity of enzyme in the composition. In other words, twice the amount of enzyme does not automatically result in twice the amount of glucose in equal time. Therefore, it is preferred to choose the dilution of the composition to be tested for WSU activity such that a WSU does not exceed 40.

400 μl of supernatants harvested from shake flask experiments were diluted 4.5-fold. Diluted sample was used to perform two measurements in which 200 μl of diluted sample was analysed. In the first measurement, 200 μl diluted sample was transferred to a vial containing 700 μl water containing 3% (w/v) dry matter of the pretreated washed wheat straw substrate and 100 μl of 250 mM citrate buffer, the final pH was adjusted to pH 4.5. In the second measurement, the blank sample, 200 μl of diluted sample was transferred to a vial that contained 700 μl of water instead of pretreated washed wheat straw substrate, and 100 μl of 250 mM citrate buffer, the final pH was adjusted to pH 4.5. The assay samples were incubated for 20 hours at 65° C. After incubation of the assay samples, 100 μl of internal standard solution (20 g/L maleic acid, 40 g/L EDTA in D2O)

was added. The amount of glucose released, was based on the signal at 5.20 ppm, relative to Dimethyl-sila-pentane-sulfonate determined by means of 1D 1H NMR operating at a proton frequency of 500 MHz, using a pulse program with water suppression, at a temperature of 27° C. The WSU number was calculated from the data by subtracting by the amount of glucose that was detected in the blank sample from the amount of glucose that was measured in the sample incubated with wheat straw.

Example 1

Construction and Description of *Aspergillus* Deletion Vectors

Three genes, which are candidates for disruption were identified in the genome sequence of *A. niger* CBS513.88. All nucleotide sequences for *A. niger* genes and their genomic context can be derived for example from NCBI (www.ncbi.nlm.nih.gov/) of EMBL www.ebi.ac.uk/embl/). The nicB gene is encoded by ORF An11g10910, the PdxA gene by An03g04280, whereas the epo gene is encoded by An08g04490.

Gene replacement vectors were designed according to known principles and constructed according to routine cloning procedures as also described in EP635574B and WO 98/46772. In essence, these vectors comprise approximately 1-2 kb flanking regions of the respective ORF sequences, to target for homologous recombination at the predestined genomic loci. They may contain for example the *A. nidulans* bi-directional amdS selection marker, the hygromycin B marker or the phleomycin selection marker for transformation. The method applied for gene replacements in all examples herein uses linear DNA, which integrates into the genome at the homologous locus of the flanking sequences by a double cross-over, thus substituting the gene to be deleted by a marker gene (such as the amdS gene). Loss of the amdS marker for example can be selected for by plating on fluoro-acetamide media.

Based on genomic sequences, gene replacement vectors for nicB and PdxA and epo were designed as follows: In essence, the nicB deletion vector pDELNicB-3 comprises approximately a 1000 bp 5' upstream flanking region (Nic-US) and a 1000 bp 3' downstream flanking region (Nic-DS) of the nicB ORF to allow targeting for homologous recombination at the predestined genomic nicB locus. In addition, pDELNicB-3 contains the hygromycinB selection marker cassette (from pAN7-1, NCBI gi: 475166) and mutant loxP sites (lox66 and lox71, SEQ ID Nos: 1 and 2 respectively) were placed around the HygB marker as indicated (for general layout of pDELNicB-3 see FIG. 1).

Figure 2:
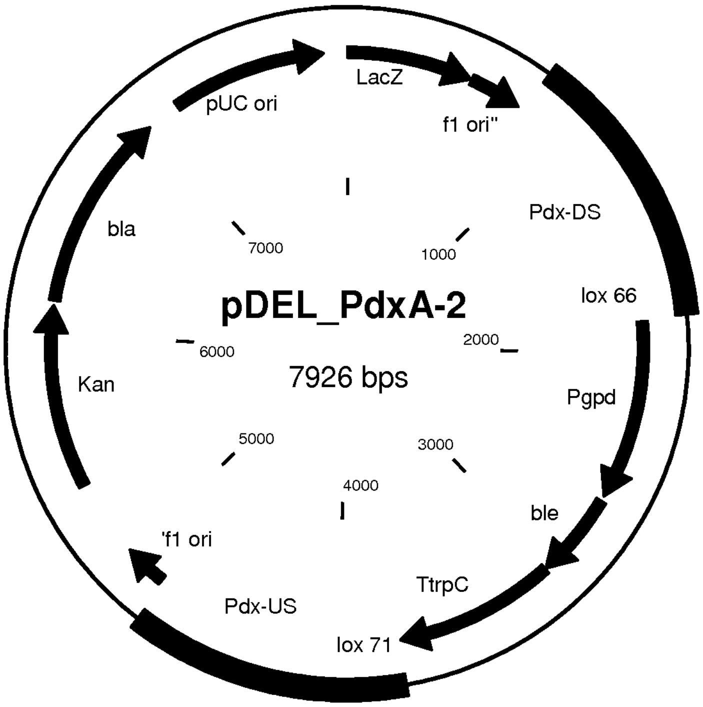
FIG. 2 sets out a schematic diagram of plasmid pDEL_PdxA-2, which is the basis for a replacement cassette to inactivate the pdxA gene in *A. niger*. The replacement cassette comprises the pdxA flanking regions, the ble marker cassette, mutant loxP sites and *E. coli* DNA. More details for pDEL_PdxA-2 can be found in the Examples section (vide infra).

The pDEL_PdxA-2 vector for pdxA deletion was constructed like-wise with 5' flanking regions (Pdx-US) and 3' flanking region (Pdx_DS) of similar length for the PdxA ORF. In contrast to pDEL_NicB-3, the pDEL_PdxA-2 vector comprises the phleomycin selection marker (phleomycin marker as in pAN8-1, NCBI gi: 475899) with mutant LoxP sites (lox66 and lox71, SEQ ID No: 1 and 2, respectively) positioned around the marker cassette. (for general layout of pDEL_PdxA-2 see FIG. 2). For reference, the double mutant lox72 site is shown in SEQ ID NO: 3.

Figure 3:
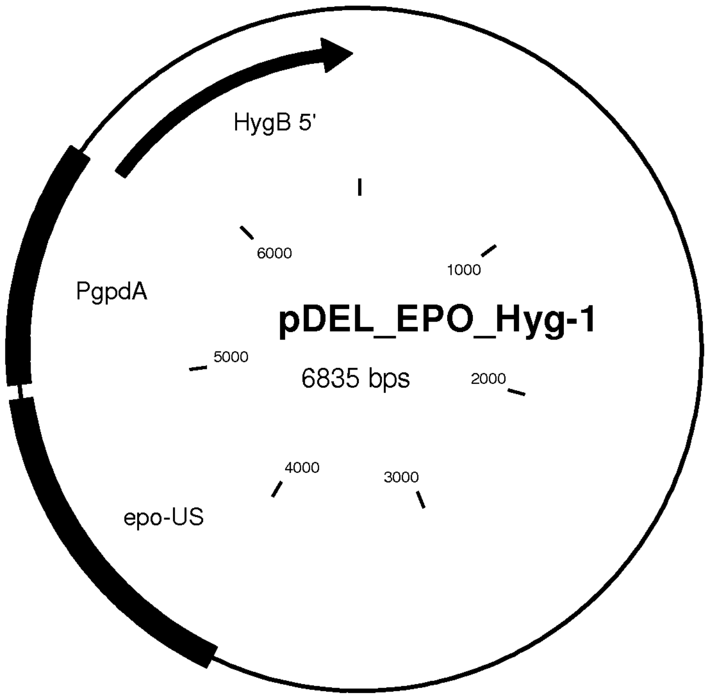
FIG. 3 sets out a schematic diagram of plasmid pDEL_EPO_Hyg-1, which comprises part of a replacement cassette to inactivate the epo gene in *A. niger*. The replacement cassette comprises an epo flanking region, part of a hygB marker cassette, a mutant loxP site and *E. coli* DNA. More details for pDEL_EPO_Hyg-1 can be found in the Examples section (vide infra).
Figure 4:
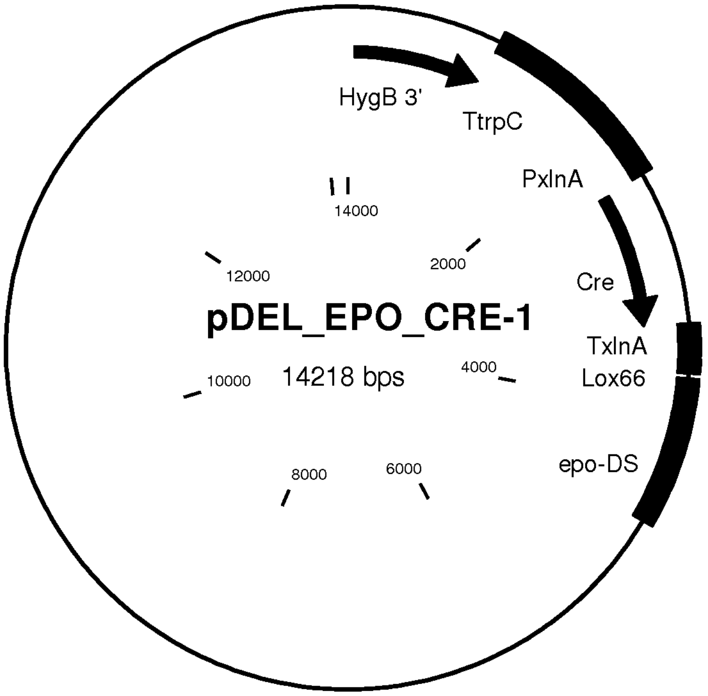
FIG. 4 sets out a schematic diagram of plasmid pDEL_EPO_CRE-1, which comprises part of a replacement cassette to inactivate the epo gene in *A. niger*. The replacement cassette comprises an epo flanking region, part of a hygB marker cassette, a mutant loxP site, a cre recombinase expression cassette and *E. coli* DNA. More details for pDEL_EPO_CRE-1 can be found in the Examples section (vide infra).

Vectors for deletion of the epo gene were designed in a slightly different way comprising the construction and use of two different vectors. The insert fragments of both vectors together can be applied in the so-called "bipartite gene-targeting" method (Nielsen et al., 2006, 43: 54-64). This method is using two non-functional DNA fragments of a selection marker which are overlapping (see also WO2008113847 for further details of the bipartite method) together with gene-targeting sequences. Upon correct homologous recombination the selection marker becomes functional by integration at a homologous target locus. As also detailed in WO 2008113847, two different deletion vectors pDEL_EPO_Hyg-1 and pDEL_EPO_CRE-1 were designed and constructed to be able to provide the two overlapping DNA molecules for bipartite gene-targeting. The first vector pDEL_EPO_Hyg-1 (General layout as in FIG. 3) comprises a first non-functional hygB marker fragment (PgpdA-HygB sequence missing the last 27 bases of the coding sequence at the 3' end of hygB, SEQ ID NO: 4) and at one side of the hygB cassette a Lox71 sequence site and the 5'-upstream gene flanking region of the epo ORF (EPO-US). The second pDEL_EPO_CRE-1 vector (General layout as in FIG. 4) comprises a non-functional hygB fragment (HygB-TtrpC sequence missing the first 44 bases of the coding sequence at the 5' end of hygB, SEQ ID NO: 5) and at one side of the hygB cassette, a cre recombinase cassette, a Lox66 sequence site and the 3'-downstream gene flanking region of the epo ORF (EPO-DS). The cre recombinase cassette contains the *A. nidulans* xylanase A promoter, a cre recombinase and xylanase A terminator, to allow xylose-inducible expression of the cre recombinase (SEQ ID NO: 6). Upon homologous recombination, the first and second non-functional fragments become functional producing a functional hygB cassette. Both epo upstream and downstream gene flanking regions target for homologous recombination of the bipartite fragments at the predestined epo genomic locus.

In the following examples we will show that the cre-lox system as used herein is a very efficient system for gene disruption and marker removal after a single transformation. In addition, when using strains deficient in NHEJ, the bipartite gene-targeting approach combined with the cre-lox system results in a highly efficient system for making marker-free strains with defined modifications.

Example 2

Figure 5:
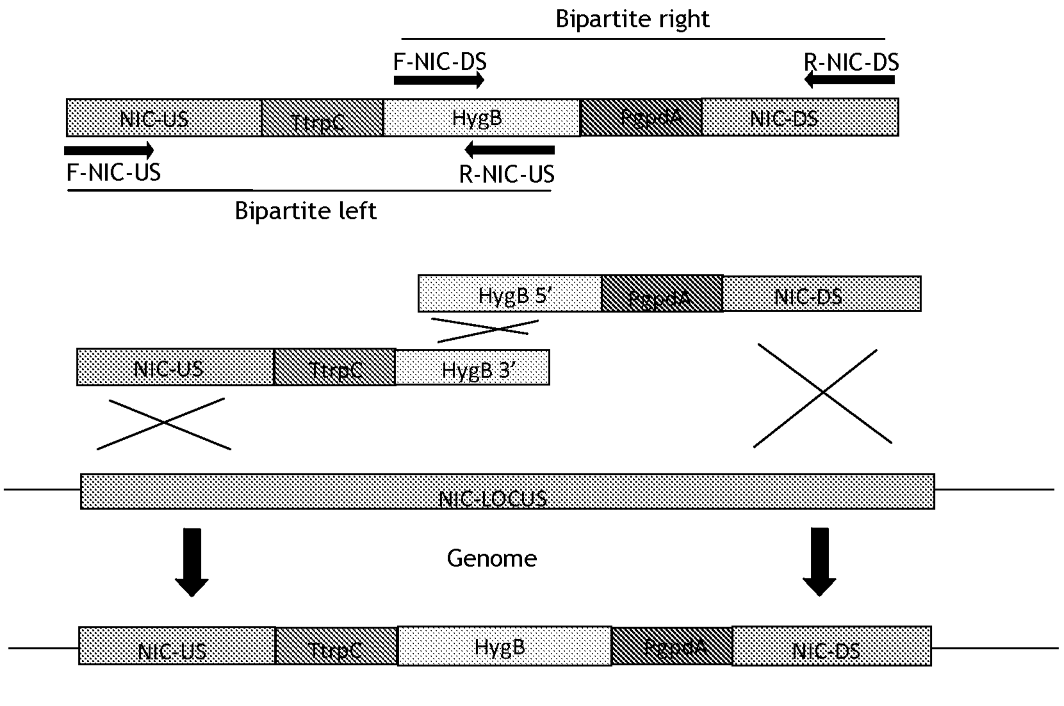
FIG. 5 sets out a schematic representation for fragment generation and use of these fragments in transformation and recombination in *A. niger*. In the top part is demonstrated the generation of the "bipartite left" and "bipartite right" fragments as amplified by PCR. In the lower panels, *A. niger* transformation through homologous recombination of the bipartite left and right fragments within the genome is shown.

Efficient Gene Deletion Using Multiple Overlapping DNA Fragments without a Functional Marker (Bipartite Gene-Targeting Approach) and a Small Overlapping Sequence In this experiment the effect of the overlap sequence size of the non-functional marker fragments on the transformation efficiency and targeting frequency through double homologous recombination was investigated. PCR fragments, encompassing the variable hygB marker length, flanked by NicB flanking regions of 1 kb (see FIG. 5), were generated using the pDELNicB-3 plasmid as template in sufficient quantities. Protoplasts of strain GBA302 (ΔglaA, ΔpepA, ΔhdfA) were transformed with 2 μg of each PCR fragment. Transformants were selected based on hygromycin B resistance, colony purified according to standard procedures as described in EP635574B and subsequently analyzed after purification. The targeting frequency was determined using diagnostic PCR using a primer within the hygB cassette and a primer within the genomic flanking region but outside the nucleotide region for targeting (see FIG. 5). The data shown in Table 1 clearly demonstrate that with good transformation efficiencies targeting frequencies of the integrative cassettes were high and efficient for the different sizes of overlapping marker sequences. Therefore, we conclude that smaller overlapping sequences than the size of roughly 1 kb mentioned in Example 1 herein and Example 4 of WO 2008113847, have no negative effect on targeting frequencies. In this manner, generation of fragments either by PCR or DNA synthesis is simplified and therefore construction of disruption mutants is more efficient.

TABLE 1

Transformation efficiency and targeting frequencies of nicB deletion cassettes using variable length of the overlapping marker sequences

| Length of overlap (bp) | Nr. of transformants | Targeting (%) |
|---|---|---|
| 960 | 236 | 100 |
| 750 | 240 | 95 |
| 640 | 88 | 85 |
| 380 | 252 | 100 |

Example 3

Simultaneous Gene Deletion Using Multiple Overlapping DNA Fragments without a Functional Marker with loxP Sites and Marker Removal after a Single Transformation Step Use of a mutant which is deficient in a gene encoding a component involved in NHEJ, such as inactivation of at least one of the hdf genes results in a significant increase of the targeting efficiency of integration vectors through (double) homologous recombination (as earlier described in WO2005095624 and WO2008113847 for example).

In addition, increase of the targeting efficiency for homologous recombination can be obtained as described in WO2008113847. This bipartite gene-targeting method comprises providing two sets of DNA molecules of which the first set comprises DNA molecules each comprising a first non-functional fragment of the replacement sequence of interest flanked at its 5'-side by a DNA sequence substantially homologous to a sequence of the chromosomal DNA flanking the target sequence and the second set comprises DNA molecules each comprising a second non-functional fragment of the DNA replacement sequence of interest overlapping with the first non-functional fragment and flanked at its 3'-side by a DNA sequence substantially homologous to a sequence of the chromosomal DNA flanking the target sequence, wherein the first and second non-functional fragments become functional upon recombination.

Gene replacement vectors pDEL_EPO_Hyg-1 and pDEL_EPO_CRE-1 (layouts as described in Example 1) both comprise approximately a 1 kb flanking region for homologous recombination at the epo ORF. In addition, they both contain a (non functional) hygB selection marker and a loxP site (lox71 or lox66). The pDEL_EPO_CRE-1 construct also contains the bacteriophage P1 Cre gene under control of the *A. nidulans* xylanase A promoter to allow inducible Cre expression upon xylose induction.

The two linear bipartite gene-targeting fragments for epo disruption were generated by PCR in sufficient quantities using the pDEL_EPO_Hyg-1 and pDEL_EPO_CRE-1 plasmids as template. The overlap of the two nucleotide fragments at the non-functional hygB gene was around 1 kb in this case. For each fragment, 2 μg of DNA was used to transform *Aspergillus niger* GBA302. Transformants were selected based on hygromycin B resistance, colony purified according to standard procedures as described in EP635574B and subsequently analyzed after purification. From Example 2, it was learned that the majority of the transformants obtained with a flanking sequence of 1 kb and an overlap of 1 kb should result in a high frequency of targeted integration at the homologous epo locus, thus substituting the target locus by the functional hygB gene as depicted in FIG. 6.

For inducing the cre-recombinase under control of the xylanase promoter, minimal medium agar plates containing 1% xylose and 1% glucose (xylanase inducing medium) were used. Transformants were transferred from PDA plates to xylanase induction medium. Subsequently, the plates were incubated for 5 days at 30° C. When Cre recombinase is induced by xylose, deletion of the DNA cassette in between the two specific loxP sites can occur by excision. Resulting colonies after growth on xylanase inducing medium were tested for their hygromycin B resistance. Spores from the transformants were transferred to PDA plates with and without hygromycin B (60 μg/ml) using toothpicks. The plates were incubated for 48 hours at 30° C.

Figure 7:
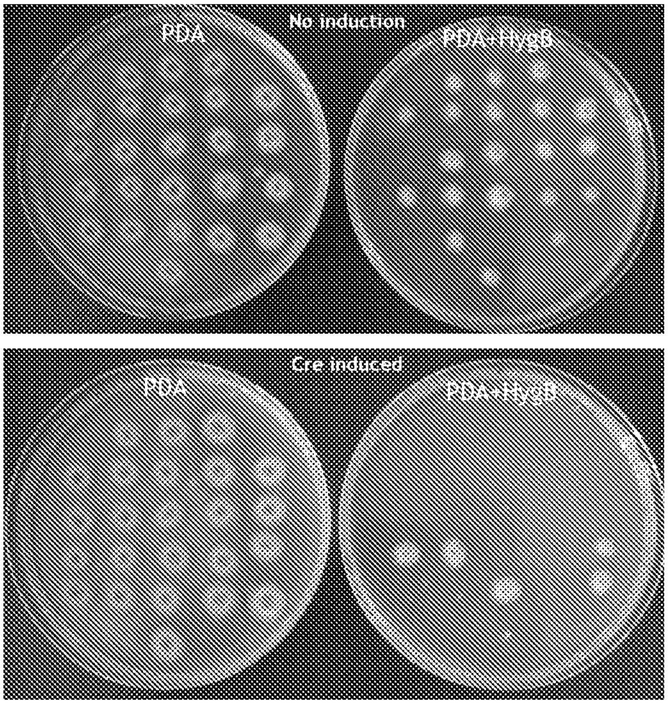
FIG. 7 sets out Cre induced loss of loxP flanked hygB selection marker. The upper plates are Cre non-induced transformants. Lower plates are Cre induced by plating on xylose as carbon source. The percentages show the percentage of marker removal in *A. niger* colonies after Cre induction.

Of 24 initial hygromycin B resistant colonies after growth on PDA starch, 4 transformants lost their hygromycin B resistance spontaneously (see also FIG. 7 for strain testing). Of 24 initial hygromycin B resistant colonies after growth on xylose, 19 transformants lost their hygromycin B resistance. Loss of hygromycin B resistance likely is coupled to loss of the hygB marker cassette through cre recombinase activity. Indeed marker removal was confirmed by PCR analysis of the epo locus.

This Example shows that in a strain deficient in NHEJ, use of bipartite gene-targeting and combination with an inducible recombination system according the invention allows for a very efficient strain construction/disruption in building marker-free strains without the need of a second transformation or counter-selection procedures in strain construction.

Example 4

Simultaneous Multiple Gene Deletions Using Multiple Overlapping DNA Fragments without Functional Markers and Multiple Marker Removal after a Single Transformation Step In this Example we describe a method to significantly shorten strain construction procedures by combining the use of multiple bipartite fragments in combination with cre-lox in a NHEJ deficient host strain to obtain multiple gene deletions. To facilitate multiple marker removal in a single transformation step, it is essential that at least one construct contains the Cre gene with the inducible xylanaseA promoter.

Two times two linear bipartite gene-targeting fragments for pdxA and epo disruption, respectively, were generated by PCR in sufficient quantities using the pDEL_Pdx-2 and pDEL_EPO_Hyg-1 & pDEL_EPO_CRE-1 plasmids as template. The overlap of the two nucleotide fragments at the non-functional phleomycin ble gene was around 350 bp and for the hygB gene it was around 1 kb. For each of the four fragments, 2 μg of DNA was used to transform *Aspergillus niger* GBA302. Double deletion transformants were selected on a medium containing both hygromycin B and phleomycin. Colony purified strains were tested for correct phenotype and diagnosed by PCR for gene replacement of PdxA and epo. Upon induction of CRE by switching to a xylose containing growth medium, both selection markers were removed. Marker removal was confirmed by PCR analysis of the NicB and PdxA loci.

This Example shows that in a strain deficient in NHEJ, use of multiple bipartite gene-targeting and combination with an inducible recombination system according the invention allows for a very efficient strain construction/disruption in building marker-free strains with two modifications without the need of a second or third transformation step or counter-selection procedures in strain construction.

Example 5

Transformation of *Rasamsonia emersonii* Resulting in Selection Marker-Free Transformants Capable of Producing a Desired Enzyme which is Encoded by a Gene Introduced in the Transformant This Example describes the construction of a marker-free *R. emersonii* transformant containing one or more additional copies of CbhI. The marker is removed by transient expression of cre-recombinase in *R. emersonii* transformants.

Figure 8:
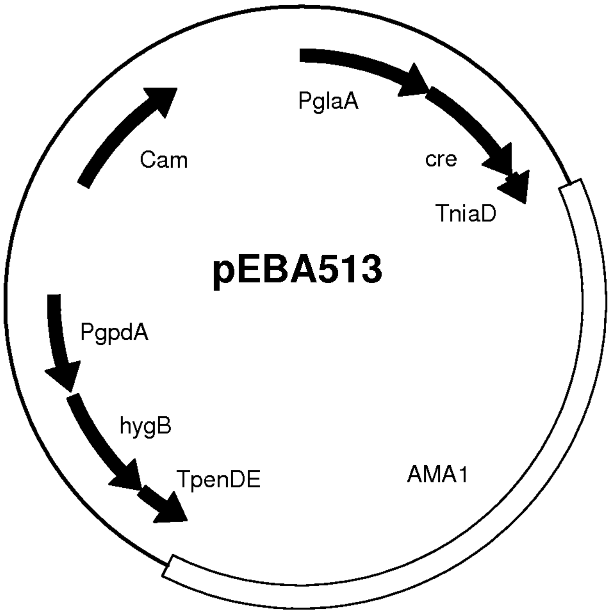
FIG. 8 depicts a map of pEBA513 for transient expression of cre recombinase in fungi. pEBA513 is a pAMPF21 derived vector containing the AMA1 region and the CAT chloramphenicol resistance gene. Depicted are the cre recombinase gene (cre) expression cassette, containing the *A. niger* glaA promoter (Pgla), cre recombinase coding region, and niaD terminator. In addition, the hygromycin resistance cassette consisting of the *A. nidulans* gpdA promoter (PgpdA), hygB coding region and the *P. chrysogenum* penDE terminator is indicated.

Cloning of Transient Expression Plasmid pEBA513 Encoding Cre Recombinase pEBA513 was constructed by DNA2.0 (Menlo Park, USA) and contains the following components: expression cassette consisting of the *A. niger* glaA promoter, ORF encoding cre-recombinase (AAY56380) and *A. nidulans* niaD terminator; expression cassette consisting of the *A. nidulans* gpdA promoter, ORF encoding hygromycin B resistance protein and *P. chrysogenum* penDE terminator (Genbank: M31454.1, nucleotides 1750-2219); pAMPF21 derived vector containing the AMA1 region and the CAT chloramphenicol resistance gene. FIG. 8 represents a map of pEBA513.

Transformation of *R. emersonii* with pDEL PdxA-2 and CbhI Expression Construct pGBTOP205

In order to obtain a *R. emersonii* strain overexpressing CbhI, *R. emersonii* was transformed to obtain a multicopy CbhI strain. Plasmid pGBTOPEBA205, described in WO2011\054899, encoding *R. emersonii* CbhI driven by the *A. niger* glucoamylase promoter was used in the transformation. *R. emersonii* transformation was performed according to the protocol described in WO2011\054899. *R. emersonii* was co-transformed with 1 μg of pDEL_pPdxA-2 (for cloning details and description see Example 1 and FIG. 2) and 9 μg of pGBTOPEBA205 and co-transformants were identified using PCR analysis. The presence of pDEL_PdxA-2 plasmid was determined using primer Ble-For (SEQ ID NO: 7) and Ble-Rev (SEQ ID NO: 8) and of pGBTOPEBA205 with primer EBA205-For (SEQ ID NO: 9 and EBA205-Rev (SEQ ID NO: 10). Primers directed against pGBTOPEBA4 (SEQ ID NO: 11 and 12) and pGBTOPEBA8 (SEQ ID NO: 13 and 14) were used as a control.

```
Ble-For (SEQ ID NO: 7):
5'-AGTTGACCAGTGCCGTTCC -3';
and

Ble-Rev (SEQ ID NO: 8):
5'-CACGAAGTGCACGCAGTTG-3'.

EBA205-For (SEQ ID NO: 9):
5'-CTTCTGCTGAGCAGCTCTGCC-3';
and
```

-continued

```
EBA205-Rev (SEQ ID NO: 10):
5'-GTTCAGACCGCAAGGAAGGTTG -3'.

EBA4-For (SEQ ID NO: 11):
5'-CGAGAACCTGGCCTACTCTCC-3'

EBA4-Rev (SEQ ID NO: 12):
5'-CAGAGTTGTAGTCGGTGTCACG-3'

EBA8-For (SEQ ID NO: 13):
5'-GAAGGGTATCAAGAAGCGTGCC-3'

EBA8-Rev (SEQ ID NO: 14):
5'-GCCGAAGTTGTGAGGGTCAATG-3'
```

PCR conditions for the reactions: 50 μl reaction mix with 5 μl of template DNA, 20 pmol of each primer, 0.2 mM of dNTPs, 1× Phusion HF buffer and 1U of Phusion DNA-Polymerase, according to Phusion High-Fidelity DNA Polymerase Manual (Finnzymes, Espoo, Finland), 30 s denaturation at 98° C., amplification in 30 cycles (10 s 98° C., 10 s 55° C., 15 s 72° C.), and a final incubation of 10 min at 72° C.

Figure 9:
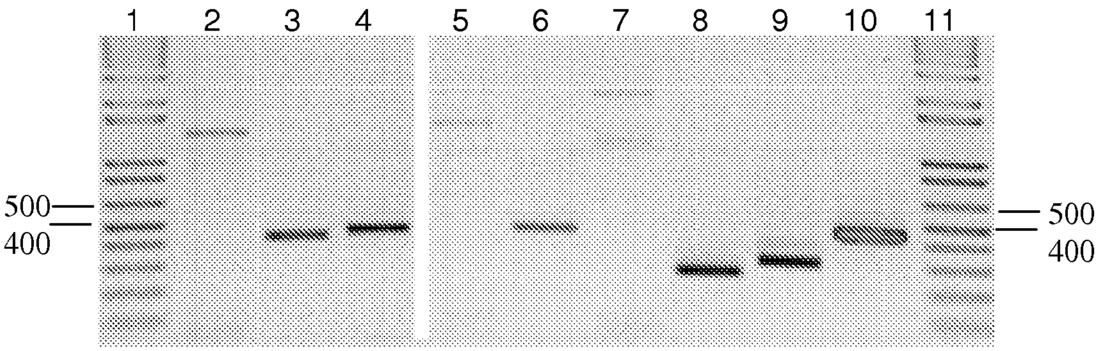
FIG. 9 shows the detection of pGBTOPEBA-205 expression plasmid in the *R. emersonii* genome by PCR. Genomic DNA was isolated and analysed by PCR from transformant A-A4 (lanes 2-4) and the empty strain (lanes 5-7). Plasmid DNA was used as control template for the PCR reactions: pGBTOPEBA-4 (lane 8), pGBTOPEBA-8 (lane 9) and pGBTOPEBA-205 (lane 10). In the PCR reactions primers were added directed against pGBTOPEBA-4 (lanes 2, 5, and 8, expected fragment: 256 bp), pGBTOPEBA-8 (lanes 3, 6, and 9, expected fragment: 306 bp), and pGBTOPEBA-205 (lanes, 4, 7, and 10, expected fragment: 452 bp). Lanes 1 and 11 contain a molecular weight marker.

Transformant A-A4 is a co-transformant that contains one or more copies of pGBTOPEBA205. In lane 4, the expected 452 bp PCR product of pGBTOPEBA-205 bp was observed in the transformant (FIG. 9, lane 4), which is detected in the control PCR in which pGBTOPEBA205 was used as a template (lane 10), but not in the empty strain (lane 7). In the EBA4 and EBA8 PCR reactions, no specific bands were observed in the transformants, but the expected PCR products of 256 bp and 306 bp, respectively, were generated when plasmid DNA was used as template (lanes 8 and 9).

In conclusion, a *R. emersonii* transformants was generated carrying multiple copies of *R. emersonii* CbhI.

Cellulase Activity Assay

Transformant A-A4 and control strains were fermented in MTP and supernatants and were analysed for cellulase activity in a WSU cellulase activity assay. A 1.25-fold increase in cellulase activity was observed in supernatants of transformant A-A4 compared to the empty strain, indicating that the obtained transformant with multiple *R. emersonii* CbhI copies is improved in cellulase activity.

Transformation of Phleomycin Resistant *R. emersonii* Transformants with AMA Plasmid pEBA513 Carrying the Cre Recombinase Gene and Selection of Phleomycin-Sensitive Transformants.

Figure 10A:
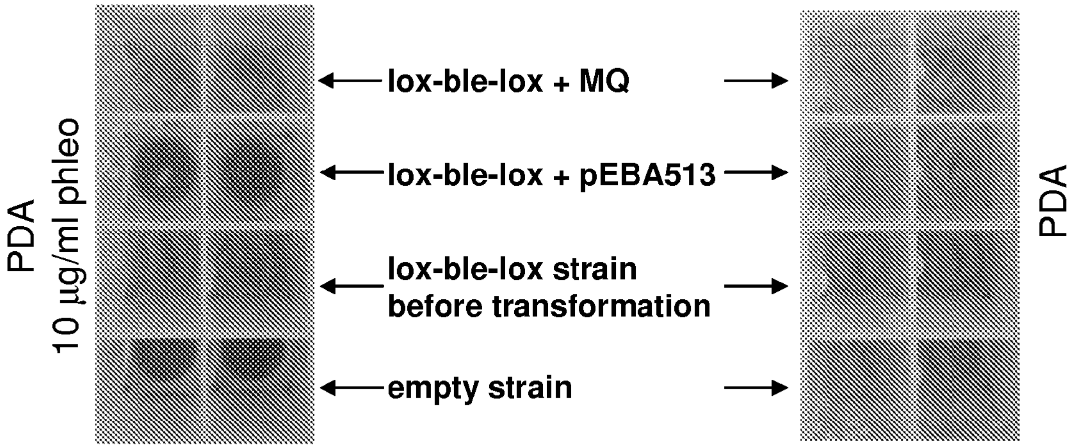
(FIG. 10A): Pictures of MTP plates of transformants and the empty strain grown on PDA medium with 10 μg/ml phleomycin (left panel) and PDA without selection (right panel). Row A shows two milliQ control transformants of A-A4 that contain the pDEL_Pdx-A2 with the loxP flanked ble expression cassette (lox-ble-lox). Growth of two pEBA513 transformed A-A4 transformants (lox-ble-lox+pEBA513) are shown in row B. The parental transformant A-A4 (lox-ble-lox, before transformation), was grown in row C. Finally, growth of the empty strain is shown in row D.

Cre recombinase was transiently expressed in *R. emersonii* transformant A-A4 to remove the loxP-flanked phleomycin resistance gene by recombination over the lox66 and lox71 site. The transformant was transformed with milliQ water (control) or with 10 μg of pEBA513 carrying a Cre recombinase and hygromycin expression cassette. pEBA513 transformed protoplasts were plated in overlay on regeneration medium containing 50 μg/ml of hygromycin B. Hygromycin-resistant transformants were grown on PDA containing 50 μg/ml of hygromycin B to allow expression of the cre recombinase. Removal of the ble marker was tested phenotypically by growing the transformants on media with and without 10 μg/ml of phleomycin. The majority (>90%) of the transformants after transformation with pEBA513 (with the cre recombinase) were phleomycin sensitive, indicating that cre recombinase works very efficiently in *R. emersonii* and that transformants lost the (ble) marker upon introduction and expression of the recombinase. In FIG. 10A, examples of different transformants and empty strains on PDA with 10 μg/ml phleomycin and PDA are shown.

A subset of transformants was also analysed by PCR. Transformants were grown in YGG medium for 16 hours at 44 degrees, 250 rpm, and chromosomal DNA was isolated using the DNeasy plant mini kit (Qiagen, Hilden, Germany). Both parental strains containing the loxP-flanked ble gene and transformants in which cre recombinase was overexpressed were analysed by PCR using pdx primers directed against the flanks just outside the loxP sites:

```
Pdx-For (SEQ ID NO: 15):
5'-TTGAGCTGTTGCTCCGGTAG -3';
and

Pdx-Rev (SEQ ID NO: 16):
5'-CTCCGTAGTCATCGTCAATGG-3'
```

In addition, the presence of pEBA513 was determined by PCR using primers directed against the HygB selection marker of the plasmid:

```
Hyg-For (SEQ ID NO: 17):
5'-GCGTCGGTTTCCACTATC-3'

Hyg-Rev (SEQ ID NO: 18):
5'-GAGGTCGCCAACATCTTC-3'
```

Figure 10B:
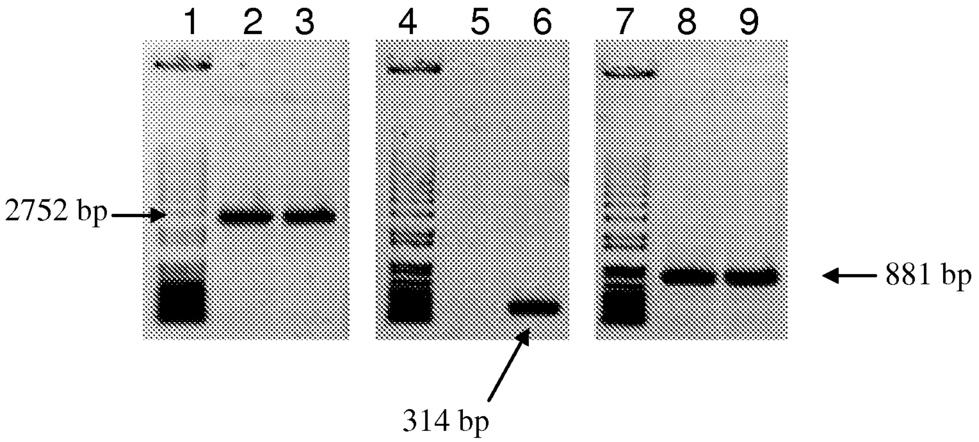
(FIG. 10B): PCR analysis of transformants before and after marker removal by cre-recombinase and of the cre-recombinase construct. Lanes 2 and 3 show PCR fragments obtained by PCR analysis of two milliQ control A-A4 transformants using primers directed against the pdx flanks of the ble expression construct. The 2752 bp PCR band is the expected amplified PCR fragment if the transformant still contains the ble selection marker. Lanes 5 and 6 show PCR analysis of two A-A4 transformants that were transformed with pEBA513 using primers directed against the hygB gene of the pEBA513 cre recombinase expression plasmid (314 bp fragment). Lanes 8 and 9 show PCR fragments of two A-A4 transformants that were transformed with pEBA513 using primers directed against the pdx flanks of the ble expression construct. The 881 bp PCR fragment is indicative for the deletion of the ble expression cassette from the *R. emersonii* transformant. Lanes 1, 4 and 7 contain a molecular weight marker.

PCR conditions for the reactions were as described above. The result of the agarose gel is presented in FIG. 10B. A specific PCR band of 2752 bp is observed in transformants containing the loxP-flanked ble expression cassette (lanes 2 and 3). In contrast, in transformants in which the ble recombinase is removed by cre recombinase a PCR fragment of 881 bp was amplified (lanes 8 and 9), indicating that the ble gene was removed by the cre recombinase. Thus, we successfully removed the loxP-flanked ble selection marker from *R. emersonii* transformants using the cre-lox system.

The presence of the pEBA513 AMA-Cre plasmid was determined by a HygB PCR. Interestingly, in one of the two transformant no HygB fragment was detectable. As the transformant were grown under conditions without hygB selection, the transformant probably already lost the episomal cre expression plasmid and linked to that the hygB marker.

Removal of the pEBA513 Plasmid to Obtain a Marker-Free Transformants.

After removing the ble selection marker, strains were identified that spontaneously lost the pEBA513 plasmid. We already observed that part of the transformants already lost the AMA plasmid while selecting for phleomycin-sensitive clones on PDA plates with and without phleomycin. In order to check spontaneous loss of the episomal AMA plasmid pEBA513 after growing the transformants without hygromycin selection, spores were transferred to plates with and without hygromycin B. After one round of growth without selection already 50-75% of the transformants were hygromycin B sensitive, which was confirmed by hygB PCRs as described above.

After marker removal, the transformant still contained multiple *R. emersonii* CbhI copies and also the cellulase activity was still 1.25-fold improved compared to the empty strain.

In conclusion, we successfully generated marker-free *R. emersonii* transformants by using two dominant markers: a loxP-flanked ble marker that was used for co-transformation with a gene of interest, and a hygromycin marker that was used to transiently transform *R. emersonii* transformants with an AMA plasmid carrying the cre recombinase gene. Transient transformation of *R. emersonii* with cre recombinase was sufficient to remove the loxP-flanked ble marker.

Example 6

Identification of *Rasamsonia emersonii* Genes Involved in Non-Homologous End-Joining and Construction of the Deletion Vectors Genomic DNA of *Rasamsonia emersonii* strain CBS393.64 was sequenced and analyzed. The genes with translated proteins annotated as homologues to known genes involved in non-homologous end-joining are listed in Table 2:

TABLE 2

Genes involved in non-homologous end-joining in *Rasamsonia emersonii* and their homologues in *A. niger*, *P. chrysogenum* and *S. cerevisiae*

| *R. emersonii* | *S. cerevisiae* | Genomic sequence | cDNA | protein |
|---|---|---|---|---|
| ReKu70 | Ku70 | SEQ ID NO: 19 | SEQ ID NO: 20 | SEQ ID NO: 21 |
| ReKu80 | Ku80 | SEQ ID NO: 22 | SEQ ID NO: 23 | SEQ ID NO: 24 |
| ReRad50 | Rad50 | SEQ ID NO: 25 | SEQ ID NO: 26 | SEQ ID NO: 27 |
| ReRad51 | Rad51 | SEQ ID NO: 28 | SEQ ID NO: 29 | SEQ ID NO: 30 |
| ReRad52 | Rad52 | SEQ ID NO: 31 | SEQ ID NO: 32 | SEQ ID NO: 33 |
| ReRad54 | Rad54 | SEQ ID NO: 34 | SEQ ID NO: 35 | SEQ ID NO: 36 |
| ReRad54 | Rad54 | SEQ ID NO: 37 | SEQ ID NO: 38 | SEQ ID NO: 39 |
| ReRad55 | Rad55 | SEQ ID NO: 40 | SEQ ID NO: 41 | SEQ ID NO: 42 |
| ReRad57 | Rad57 | SEQ ID NO: 43 | SEQ ID NO: 44 | SEQ ID NO: 45 |
| ReCDC2 | CDC2 | SEQ ID NO: 46 | SEQ ID NO: 47 | SEQ ID NO: 48 |
| ReLIG4 | LIG4 | SEQ ID NO: 49 | SEQ ID NO: 50 | SEQ ID NO: 51 |
| ReMRE11 | MRE11 | SEQ ID NO: 52 | SEQ ID NO: 53 | SEQ ID NO: 54 |

Sequences of the *R. emersonii* genes involved in non-homologous end-joining, comprising the genomic sequences of the open reading frames (ORF) (with introns) and approximately 1500 bp of the 5' and 3' flanking regions, cDNA and protein sequences.

Figure 11:
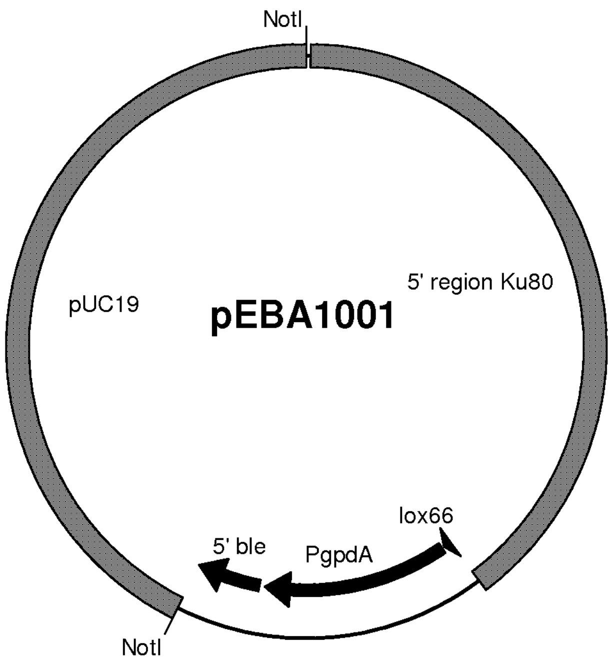
FIG. 11 depicts the pEBA1001 vector. Part of the vector fragment was used in bipartite gene-targeting method in combination with the pEBA1002 vector with the goal to delete the ReKu80 ORF in *Rasamsonia emersonii*. The vector comprises a 2500 bp 5' upstream flanking region, a lox66 site, the 5' part of the ble coding sequence driven by the *A. nidulans* gpdA promoter and the backbone of pUC19 (Invitrogen, Breda, The Netherlands). The *E. coli* DNA was removed by digestion with restriction enzyme NotI, prior to transformation of the *R. emersonii* strains.
Figure 12:
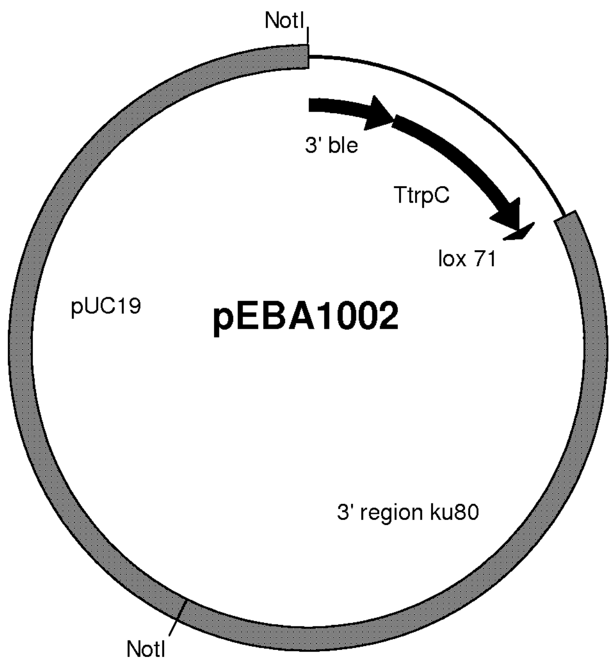
FIG. 12 depicts the pEBA1002 vector. Part of the vector fragment was used in bipartite gene-targeting method in combination with the pEBA1001 vector with the goal to delete the ReKu80 ORF in *Rasamsonia emersonii*. The vector comprises the 3' part of the ble coding region, the *A. nidulans* trpC terminator, a lox71 site, a 2500 bp 3' downstream flanking region of the ReKu80 ORF, and the backbone of pUC19 (Invitrogen, Breda, The Netherlands). The *E. coli* DNA was removed by digestion with restriction enzyme NotI, prior to transformation of the *R. emersonii* strains.

Two replacement vectors for ReKu80, pEBA1001 and pEBA1002, were constructed according to routine cloning procedures (see FIGS. 11 and 12). The insert fragments of both vectors together can be applied in the so-called "bipartite gene-targeting" method (Nielsen et al., 2006, 43: 54-64). This method is using two non-functional DNA fragments of a selection marker which are overlapping (see also WO2008113847 for further details of the bipartite method) together with gene-targeting sequences. Upon correct homologous recombination the selection marker becomes functional by integration at a homologous target locus. The deletion vectors pEBA1001 and pEBA1002 were designed as described in WO 2008113847, to be able to provide the two overlapping DNA molecules for bipartite gene-targeting.

The pEBA1001 vector comprises a 2500 bp 5' flanking region of the ReKu80 ORF for targeting in the ReKu80 locus, a lox66 site, and the non-functional 5' part of the ble coding region driven by the *A. nidulans* gpdA promoter (PgpdA-ble sequence missing the last 104 bases of the coding sequence at the 3' end of ble, SEQ ID NO: 60) (FIG. 11). The pEBA1002 vector comprises the non-functional 3' part of the ble coding region and the *A. nidulans* trpC terminator (ble-TtrpC sequence missing the first 12 bases of the coding sequence at the 5' end of ble, SEQ ID NO: 61), the *A. nidulans* trpC terminator, a lox71 site, and a 2500 bp 3' flanking region of the ReKu80 ORF for targeting in the ReKu80 locus (FIG. 12).

Example 7

Inactivation of the ReKu80 Gene in *Rasamsonia emersonii*

Figure 13:
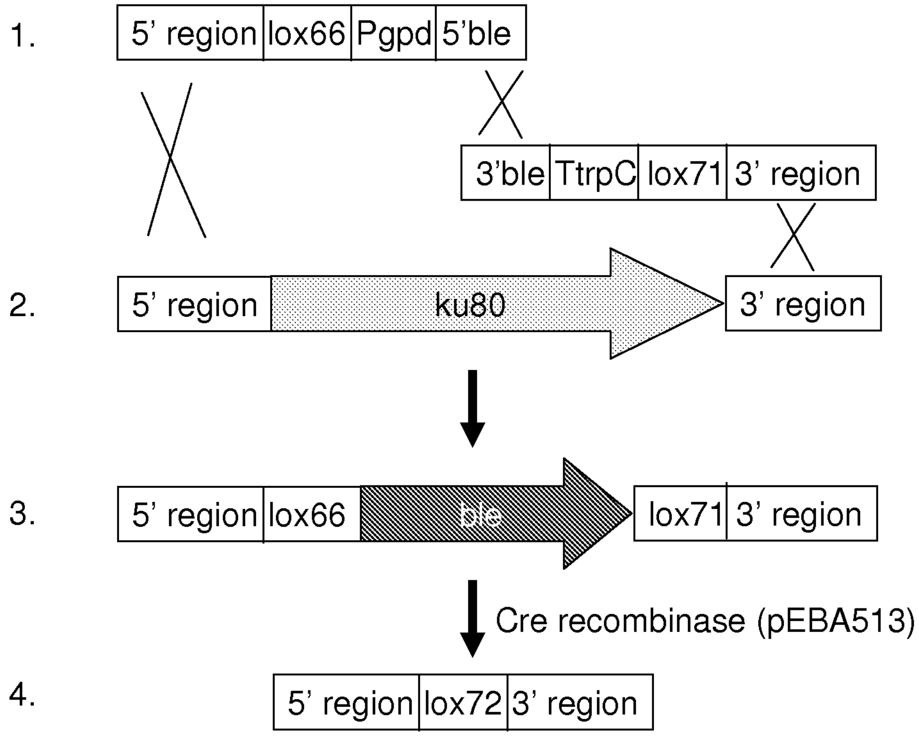
FIG. 13 depicts the strategy used to delete the ReKu80 gene of *R. emersonii*. The vectors for deletion of ReKu80 comprise the overlapping non-functional ble selection marker fragments (split marker) flanked by loxP sites and 5' and 3' homologous regions of the ReKu80 gene for targeting (1). The constructs integrate through triple homologous recombination (X) at the genomic ReKu80 locus and at the overlapping homologous non-functional ble selection marker fragment (2) and replaces the genomic ReKu80 gene copy (3). Subsequently, the selection marker is removed by transient expression of cre recombinase leading to recombination between the lox66 and lox71 sites resulting in the deletion of the ble gene with a remainder double-mutant lox72 site left within the genome (4). Using this overall strategy, the ReKu80 ORF is removed from the genome.

Linear DNA of the deletion constructs pEBA1001 and pEBA1002 were isolated and used to transform *Rasamsonia emersonii* strain TEC-142S using method as described earlier in WO2011\054899. These linear DNAs can integrate into the genome at the ReKu80 locus, thus substituting the ReKu80 gene by the ble gene as depicted in FIG. 13. Transformants were selected on phleomycin media and colony purified and tested according to procedures as described in WO2011\054899. Growing colonies were diagnosed by PCR for integration at the ReKu80 locus using a primer in the gpdA promoter of the deletion cassette and a primer directed against the genomic sequence directly upstream of the 5' targeting region. From a pool of approximately 250 transformants, 4 strains showed a removal of the genomic ReKu80 gene.

Subsequently, 3 candidate ReKu80 knock out strains were transformed with pEBA513 to remove the ble selection marker by transient expression of the cre recombinase. pEBA513 transformants were plated in overlay on regeneration medium containing 50 μg/m of hygromycin B. Hygromycin-resistant transformants were grown on PDA containing 50 μg/m of hygromycin B to allow expression of the cre recombinase. Single colonies were plated on non-selective *Rasamsonia* agar medium to obtain purified spore batches. Removal of the ble marker was tested phenotypically by growing the transformants on media with and without 10 μg/m of phleomycin. The majority (>90%) of the transformants after transformation with pEBA513 (with the cre recombinase) were phleomycin sensitive, indicating removal of the pEBA1001 and pEBA1002-based ble marker. Removal of the pEBA513 construct in ble-negative strains was subsequently diagnosed phenotypically by growing the transformants on media with and without 50 μg/ml of hygromycin. Approximately 50% of the transformants lost hygromycin resistance due to spontaneously loss of the pEBA513 plasmid.

Figure 14:
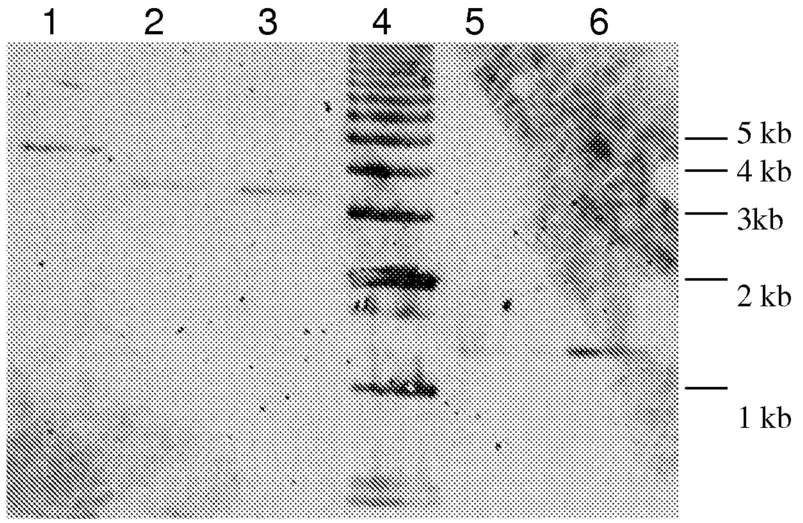
FIG. 14 shows the Southern blot analysis of ReKu80 knock out strains. Genomic DNA was isolated from strains and digested with restriction enzyme HindIII. The Southern blot was hybridized using a probe directed against the 3' region of the ReKu80 gene. Lane 1: wild-type strain; lanes 2 and 3: two phleomycin resistant strains showing fragment size for correct ReKu80 knock out integration; lane 4: labeled molecular weight marker; lanes 5 and 6: two phleomycin sensitive strains with fragment size for correct ReKu80 knock out integration.

Candidate marker-free knock-out strains were tested by Southern analysis for deletion of the ReKu80 gene. Chromosomal DNA was isolated and digested with restriction enzyme HindIII. Southern blots were hybridized with a probe directed against the 3' region of the ReKu80 gene (FIG. 14). The following primers were used to generate the probe:

```
SEQ ID NO: Ku80-For:
                                      (SEQ ID NO: 55)
AGGGTATATGTGGTCTAGTAACGC

SEQ ID NO: Ku80-Rev:
                                      (SEQ ID NO: 56)
TCACAAGTCCATCACGGAACCGGG
```

The expected fragment sizes in wild-type strains, phleomycin resistant ReKu80 knock-out strains and in the phleomycin sensitive strains, were, respectively, 4132 bp, 3197 bp and 1246 bp. The wild-type control strain showed the expected 4132 bp fragment (FIG. 14, lane 1). The 2 candidate phleomycin resistant ReKu80 knock out strains indeed showed the expected 3197 bp fragment (lanes 2 and 3). Removal of the ble gene by cre recombinase resulted in a size reduction of the fragment; a 1246 bp band was detectable on the Southern blot (lanes 5 and 6). In conclusion, we confirmed by Southern blotting that we obtained 2 independent marker-free ReKu80 deletion strains.

Strain deltaReKu80-2 was selected as a representative strain with the ReKu80 gene inactivated.

Example 8

Cloning of RePepA Deletion Vectors

Genomic DNA of *Rasamsonia emersonii* strain CBS393.64 was sequenced and analyzed. The gene with translated protein annotated as protease pepA was identified. Sequences of *Rasamsonia emersonii* pepA (RePepA), comprising the genomic sequence of the ORF and approximately 2500 bp of the 5' and 3' flanking regions, cDNA and protein sequence, are shown in sequence listings 57, 58 and 59 respectively.

Figure 15:
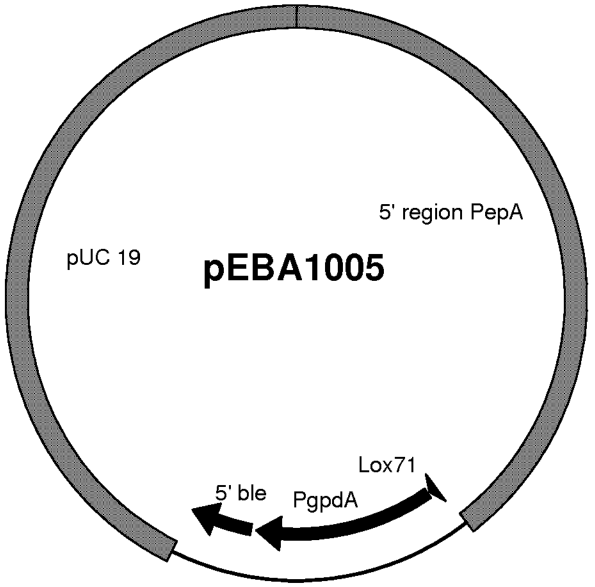
FIG. 15 depicts the pEBA1005 vector that was used in bipartite gene-targeting method in combination with the pEBA1006 vector with the goal to delete the RePepA ORF in *Rasamsonia emersonii*. The vector comprises a 2500 bp 5' flanking region, a lox66 site, the 5' part of the ble coding region driven by the *A. nidulans* gpdA promoter and the backbone of pUC19 (Invitrogen, Breda, The Netherlands).
Figure 16:
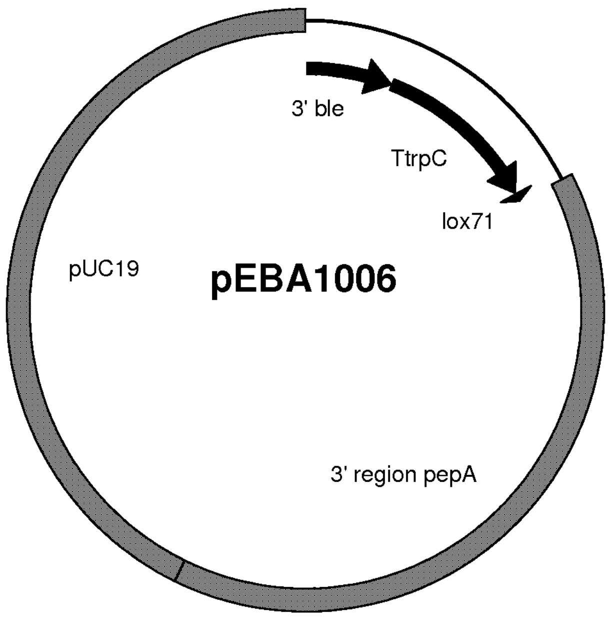
FIG. 16 depicts the pEBA1006 vector that was used in bipartite gene-targeting method in combination with the pEBA1005 vector with the goal to delete the RePepA ORF in *Rasamsonia emersonii*. The vector comprises the 3' part of the ble coding region, the *A. nidulans* trpC terminator, a lox71 site, a 2500 bp 3' flanking region of the ReKu80 ORF, and the backbone of pUC19 (Invitrogen, Breda, The Netherlands).
Figure 17:
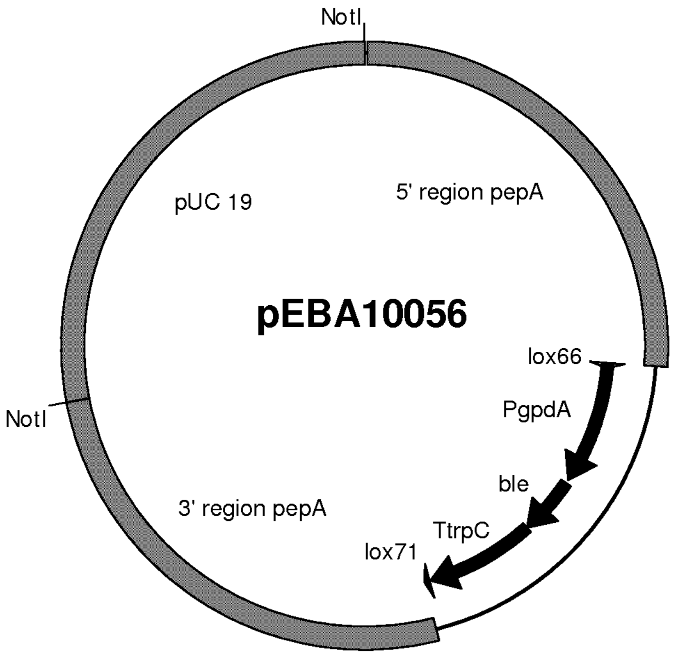
FIG. 17 depicts the pEBA10056 vector that was used to delete the RePepA ORF in *Rasamsonia emersonii*. The vector comprises a 2500 bp 5' flanking region, a lox66 site, the ble expression cassette consisting of the *A. nidulans* gpdA promoter, ble coding region and *A. nidulans* trpC terminator, a lox71 site, a 2500 bp 3' flanking region of the ReKu80 ORF, and the backbone of pUC19 (Invitrogen, Breda, The Netherlands).

Gene replacement vectors for RePepA were designed using the bipartite gene-targeting method and constructed according to routine cloning procedures (see FIGS. 15 and 16). The pEBA1005 construct comprises a 2500 bp 5' flanking region of the RePepA ORF for targeting in the RePepA locus, a lox66 site, and the 5' part of the ble coding region driven by the *A. nidulans* gpdA promoter (PgpdA-ble sequence missing the last 104 bases of the coding sequence at the 3' end of ble, SEQ ID NO: 60). (FIG. 15). The pEBA1006 construct comprises the 3' part of the ble coding region (ble-TtrpC sequence missing the first 12 bases of the coding sequence at the 5' end of ble, SEQ ID NO: 61), the *A. nidulans* trpC terminator, a lox71 site, and a 2500 bp 3' flanking region of the RePepA ORF for targeting in the RePepA locus (FIG. 16). In addition, pEBA10056 was constructed carrying a complete RePepA deletion cassette (FIG. 17). The pEBA10056 construct comprises a 2500 bp 5' flanking region of the RePepA ORF for targeting in the RePepA locus, a lox66 site, the ble expression cassette containing the *A. nidulans* gpdA promoter, ble coding region and the *A. nidulans* trpC terminator, a lox71 site, and a 2500 bp 3' flanking region of the RePepA ORF for targeting in the RePepA locus.

In addition to pEBA1005 and pEBA1006 containing 1500 bp RePepA flanks, constructs were generated consisting of 500, 1000 and 1500 bp RePepA flanks to test the optimal flank length. pEBA1005 and pEBA1006 are representative for those constructs that only differ in flank length.

Example 9

Improved Targeting for Homologous Recombination Events at the RePepA Locus

The targeting efficiency in the ReKu80 knock out strain vs a wild-type strain was assessed by transformation of TEC- 142S and the deltaReKu80-2 strain with deletion vectors designed for the inactivation of the RePepA gene encoding the major extracellular acid aspartyl protease from the genome. The RePepA deletion vectors were amplified by PCR and the PCR product was used to transform protoplasts of TEC-142S and the deltaReKu80-2 strain. Transformant selection was performed as described in Example 7.

Figure 18:
FIG. 18 shows a picture of PDA plates supplemented with 1% Casein sodium salt with TEC-142S and the delta ReKu80-2 strains transformed with RePepA deletion constructs containing 2.5 kb flanks.

The targeting frequency was assessed by activity-based plate assays indicative of the inactivation of RePepA. The plate assays were performed by propagating transformants on PDA plates supplemented with 1% Casein sodium salt. In total 20 transformants of each transformation were analysed for halo formation. Most transformants of CBS393.64 still showed halo formation after transformation with 2.5 kb RePepA deletion constructs, whereas no halo formation was observed in transformants of deltaReKu80-2 (FIG. 18). In Table 3, the targeting frequency, as judged by halo formation on casein plates is shown.

TABLE 3

Targeting frequencies of RePepA deletion vectors with different flanking lengths in the deltaReKu80-2 strain as compared with strain CBS393.64. Deletion vectors using the bipartite gene-targeting method are indicated with "(bipartite)"

| | Targeting (%) | |
|---|---|---|
| Flanking length | TEC-142S | deltaReKu80-2 |
| 2.5 kb | <5 | 90 |
| 2.5 kb (bipartite) | 10 | 100 |
| 1.5 kb (bipartite) | 5 | 100 |
| 1 kb (bipartite) | <5 | 85 |
| 0.5 kb (bipartite) | <5 | n.d.* |

*not determined because of low amount of transformants

The targeting efficiency was significantly improved in de deltaReKu80-2 strain compared to the CBS393.64 strain. In the wild-type strain highest targeting efficiencies (10%) were observed when using 2.5 flanks using the bipartite gene-targeting method. Deletion of RePepA using a plasmid carrying the complete deletion cassette was successful in 90% of the transformants of the deltaReKu80-2 strain. When using the bipartite gene-targeting method, in the deltaReKu80-2 strain 1.5 kb flanks are already sufficient to obtain 100% targeting and 1 kb flanks to obtain correct transformants with high efficiency.

These findings indicate that strains with improved efficiency for homologous recombination after inactivation of at least one of the genes involved in non homologous end joining in *Rasamsonia emersonii* results in a significant increase of the targeting efficiency of vectors for integration through double homologous recombination. In this example this has been illustrated for disruption of ReKU80.

Example 10

Figure 19:
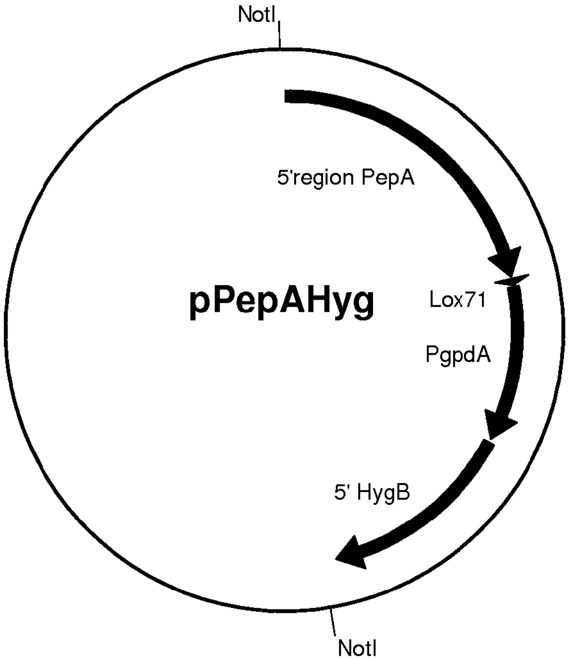
FIG. 19 sets out a schematic diagram of plasmid pPepAHyg, which comprises part of a replacement cassette to inactivate the RePepA gene in *R. emersonii*. The replacement cassette comprises a 1500 nuleotice RePepA 5' flanking region, part of a hygB marker cassette, a mutant loxP site and *E. coli* DNA. More details for pPepAHyg can be found in the Examples section (vide infra).
Figure 20:
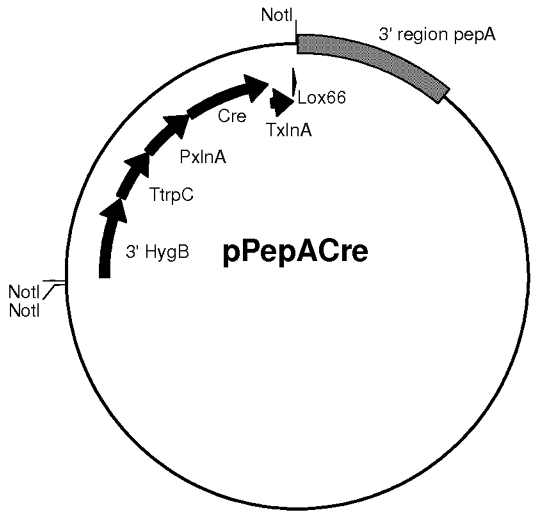
FIG. 20 sets out a schematic diagram of plasmid pPepACre, which comprises part of a replacement cassette to inactivate the RePepA gene in *R. emersonii*. The replacement cassette comprises a RePepA 3' flanking region, part of a hygB marker cassette, a mutant loxP site, a cre recombinase expression cassette and *E. coli* DNA. More details for pPepACre can be found in the Examples section (vide infra).

Construction of *Rasamsonia* Deletion Vector for Simultaneous Gene Deletion Using Multiple Overlapping DNA Fragments without a Functional Marker with loxP Sites and Marker Removal after a Single Transformation Step Gene replacement vectors for RePepA were designed using the bipartite-targeting method as described in Example 3, with one exception: RePepA flanking regions of approximately 1500 base-pairs were used for homologous recombination at the RePepA ORF. The first vector pPepAHyg (General layout as in FIG. 19) comprises a first non-functional hygB marker fragment (PgpdA-HygB sequence missing the last 27 bases of the coding sequence at the 3' end of hygB, SEQ ID NO: 4) and at one side of the hygB cassette a Lox71 sequence site and the 5'-upstream gene flanking region of the RePepA ORF (5' region pepA). The second pPepACre vector (General layout as in FIG. 20) comprises a non-functional hygB fragment (HygB-TtrpC) sequence missing the first 44 bases of the coding sequence at the 5' end of hygB, SEQ ID NO: 5) and at one side of the hygB cassette, a cre recombinase cassette, a Lox66 sequence site and the 3'-downstream gene flanking region of the RePepA ORF (3' region RePepA). The cre recombinase cassette contains the *A. nidulans* xylanase A promoter, a cre recombinase and xylanase A terminator, to allow xylose-inducible expression of the cre recombinase (SEQ ID NO: 6). Upon homologous recombination, the first and second non-functional fragments become functional producing a functional hygB cassette. Both RePepA upstream and downstream gene flanking regions target for homologous recombination of the bipartite fragments at the predestined RePepA genomic locus.

In the following example we will show that the cre-lox system as used herein is a very efficient system for gene disruption and marker removal after a single transformation. In addition, when using strains deficient in NHEJ, the bipartite gene-targeting approach combined with the cre-lox system results in a highly efficient system for making marker-free strains with defined modifications.

Example 11

Efficient Gene Deletion Using Multiple Overlapping DNA Fragments without a Functional Marker (Bipartite Gene-Targeting Approach) and a Small Overlapping Sequence Use of a mutant which is deficient in a gene encoding a component involved in NHEJ, such as inactivation of at least one of the Ku genes results in a significant increase of the targeting efficiency of integration vectors through (double) homologous recombination (see Example 9).

In addition, increase of the targeting efficiency for homologous recombination can be obtained as described in Example 9. This bipartite gene-targeting method comprises providing two sets of DNA molecules of which the first set comprises DNA molecules each comprising a first non-functional fragment of the replacement sequence of interest flanked at its 5'-side by a DNA sequence substantially homologous to a sequence of the chromosomal DNA flanking the target sequence and the second set comprises DNA molecules each comprising a second non-functional fragment of the DNA replacement sequence of interest overlapping with the first non-functional fragment and flanked at its 3'-side by a DNA sequence substantially homologous to a sequence of the chromosomal DNA flanking the target sequence, wherein the first and second non-functional fragments become functional upon recombination.

Gene replacement vectors pPepAHyg and pPepACre (layouts as described in Example 10) both comprise approximately a 1.5 kb flanking region for homologous recombination at the RePepA ORF. In addition, they both contain a (non functional) hygB selection marker and a loxP site (lox71 or lox66). The pPepACre construct also contains the bacteriophage P1 Cre gene under control of the *A. nidulans* xylanase A promoter to allow inducible Cre expression upon xylose induction.

Figure 21:
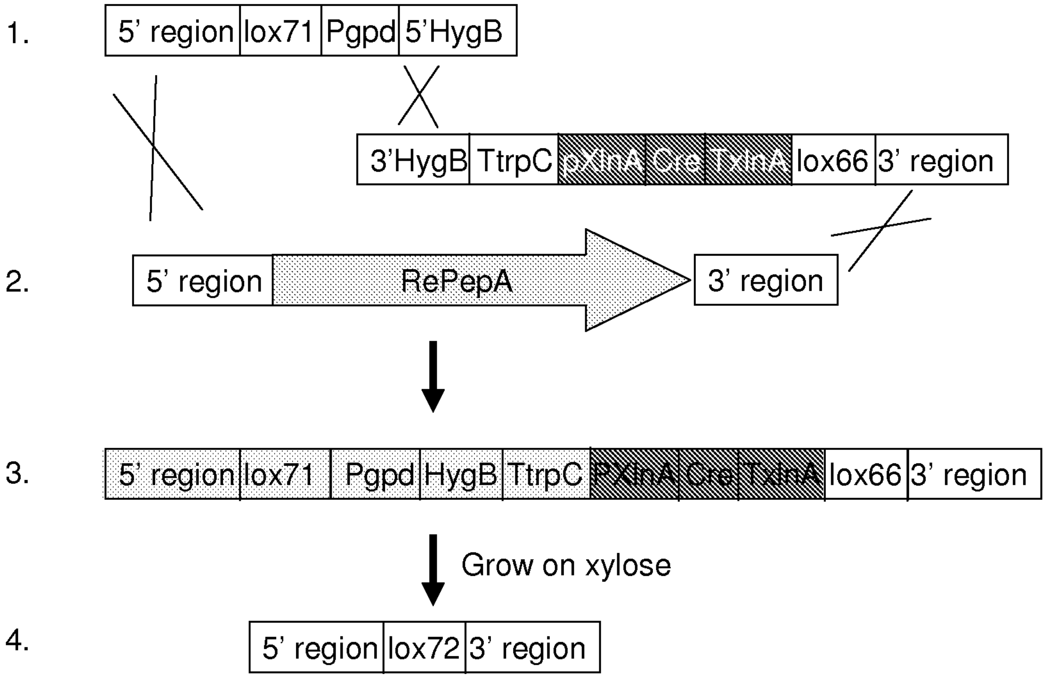
FIG. 21 sets out a schematic representation for fragment use in transformation and recombination in *R. emersonii*. The vectors for deletion of RePepA comprise the overlapping non-functional hygB selection marker fragments (split marker) flanked by loxP sites and 5' and 3' homologous regions of the RePepA gene for targeting (1). The constructs integrate through triple homologous recombination (X) at the genomic RePepA locus and at the overlapping homologous non-functional hygB selection marker fragment (2) and replaces the genomic RePepA gene copy (3). Subsequently, the selection marker is removed by growing transformants on xylose to induce cre recombinase expression leading to recombination between the lox66 and lox71 sites resulting in the deletion of the hygB and Cre expression cassettes with a remainder double-mutant lox72 site left within the genome (4).

The two linear bipartite gene-targeting fragments for RePepA disruption were generated by PCR in sufficient quantities using the pPepAHyg and pPepACre plasmids as template. The overlap of the two nucleotide fragments at the non-functional hygB gene was around 1 kb in this case. These linear DNAs can integrate into the genome at the RePepA locus, thus substituting the RePepA gene by the hygB gene as depicted in FIG. 21.

For each fragment, 2 μg of DNA was used to transform *R. emersonii* strain deltaReKu80-2. Transformants were selected based on hygromycin B resistance, colony purified according to standard procedures as described in Example 5 and subsequently analyzed after purification.

For inducing the cre-recombinase under control of the xylanase promoter, minimal medium agar plates containing 1% xylose and 1% glucose (xylanase induction medium) and 0.2% yeast extract were used. Transformants were transferred from PDA plates to xylanase induction medium with yeast extract. Subsequently, the plates were incubated for 5 days at 42° C. Resulting colonies after growth on xylose were plated on non-selective Rasamsonia agar medium to obtain purified spore batches. When Cre recombinase is induced by xylose, deletion of the DNA cassette in between the two specific loxP sites can occur by excision.

Figure 22:
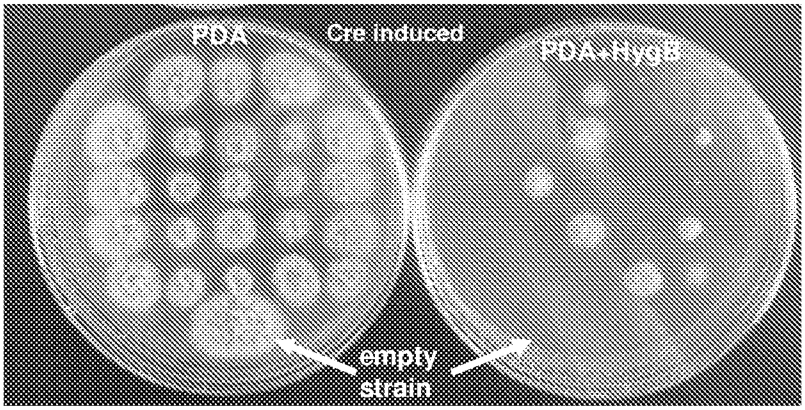
FIG. 22 sets out Cre induced loss of loxP flanked hygB selection marker in *Rasamsonia emersonii*. Transformants carrying the loxP flanked hygB selection marker and cre recombinase expression cassette integrated into the RePepA locus were plated on xylose as carbon source to induce cre recombinase. After cre induction colonies were transferred to PDA without selection (left) and PDA with hygromycinB selection (right). An empty strain was included as a control for selection.

Removal of the hygB marker was tested phenotypically by growing the transformants on media with and without 50 g/ml of hygromycin B. Approximately, 65% of the cre-induced transformants were not able to grow on hygromycin B (FIG. 22). Loss of hygromycin B resistance likely is coupled to loss of the hygB marker cassette through cre recombinase activity. Indeed marker removal was confirmed by PCR analysis of the RePepA locus.

This Example shows that in a strain deficient in NHEJ, use of bipartite gene-targeting and combination with an inducible recombination system according the invention allows for a very efficient strain construction/disruption in building marker-free strains without the need of a second transformation or counter-selection procedures in strain construction.

The invention claimed is:

1. A method for carrying out recombination at a target locus in a *Rasamsonia* cell, which method comprises:

(a) providing a first nucleic acid comprising, in order:

(i) a region capable of homologous recombination with a 5' region of the target locus, (ii) a first site-specific recombination site, (iii) a first promoter, and (iv) a sequence encoding a first non-functional portion of a marker gene;

(b) providing a second nucleic acid comprising, in order:

(v) a sequence encoding a second non-functional portion of the marker gene of (a) and capable of homologous recombination with the first non-functional portion, (vi) a first terminator sequence, (vii) a second promoter, (viii) a sequence encoding a site-specific recombinase, (ix) a second terminator sequence, (x) a second site-specific recombination site, and (xi) a region capable of homologous recombination with a 3' region of the target locus, (c) recombining the sequence encoding a first non-functional portion of a marker gene with the sequence encoding a second non-functional portion of the marker gene to give rise to a single nucleic acid comprising, in order, the region capable of homologous recombination with the 5' region of the target locus, the first site-specific recombination site, the first promoter, a sequence encoding the functional marker gene, the first terminator sequence, the second promoter, the sequence encoding the site-specific recombinase, the second terminator sequence, the second site-specific recombination site, and the region capable of homologous recombination with the 3' region of the target locus; and (d) recombining the single nucleic acid of (c) with the homologous 5' region and 3' region of the target locus in the *Rasamsonia* cell, thereby to carry out recombination at the target locus in the *Rasamsonia* cell.

2. A method according to claim 1, which further comprises expressing the site-specific recombinase so that the sequence located between the site-specific recombination sites is out-recombined.

3. A method according to claim 2, wherein expression of the site-specific recombinase is controlled by an inducible promoter.

4. A method according to claim 1, wherein recombination of the first and second nucleic acids with each other and with the homologous 5' region and 3' region flanking the target locus is carried out in vivo.

5. A method according to claim 2, wherein out-recombination of a nucleic acid sequence between the site-specific recombination sites is carried out in vivo.

6. A method according to claim 1, wherein the in vivo recombination is carried out in a *Rasamsonia emersonii* cell.

7. A method according to claim 1, wherein the host cell is a variant of a parent host cell, the parent host cell having a preference for non-homologous recombination, wherein the ratio of non-homologous recombination/homologous recombination is decreased in the variant as compared to said ratio in said parent organism measured under the same conditions.

8. A method according to claim 1, wherein: the site-specific recombination sites are lox sites and the site-specific recombinase is Cre; the site-specific recombination sites are FRT sites and the site-specific recombinase is Flp; the recombination sites are Vlox sites and the site-specific recombinase is VCre; or the recombination sites are Slox and the site-specific recombinase is SCre.

9. A method according to claim 2, wherein the site-specific recombination sites are such that out-recombination following site-specific recombinase expression gives rise to a single mutant site-specific recombination site at the target locus which is not recognized by the site-specific recombinase.

10. A method according to claim 1, wherein the target locus comprises a coding sequence which is disrupted and/or partially or fully deleted.

11. The method according to claim 1, wherein the first nucleic acid further comprises one or more expression cassettes and each expression cassette comprising, in order, a promoter, a coding sequence encoding a polypeptide of interest, and a terminator sequence; wherein the one or more expression cassettes are positioned between (i) the region capable of homologous recombination with the 5' region of the target locus and (ii) the first site-specific recombination site.

12. The method according to claim 1, wherein the second nucleic acid further comprises one or more expression cassettes and each expression cassette comprising, in order, a promoter, a coding sequence encoding a polypeptide of interest, and a terminator sequence; wherein the one or more expression cassettes are positioned between (x) the second site-specific recombination site and (xi) the region capable of homologous recombination with a 3' region of the target locus.

* * * * *

SEQUENCE LISTING

```
<160> NUMBER OF SEQ ID NOS: 61

<210> SEQ ID NO 1
<211> LENGTH: 34
<212> TYPE: DNA
<213> ORGANISM: Artificial Sequence
<220> FEATURE:
<223> OTHER INFORMATION: mutant loxP site, lox66

<400> SEQUENCE: 1

ataacttcgt atagcataca ttatacgaac ggta                              34


<210> SEQ ID NO 2
<211> LENGTH: 34
<212> TYPE: DNA
<213> ORGANISM: Artificial Sequence
<220> FEATURE:
<223> OTHER INFORMATION: mutant loxP site, lox71

<400> SEQUENCE: 2

taccgttcgt atagcataca ttatacgaag ttat                              34


<210> SEQ ID NO 3
<211> LENGTH: 34
<212> TYPE: DNA
<213> ORGANISM: Artificial Sequence
<220> FEATURE:
<223> OTHER INFORMATION: double-mutant loxP site, lox72 site

<400> SEQUENCE: 3

taccgttcgt ataatgtatg ctatacgaac ggta                              34


<210> SEQ ID NO 4
<211> LENGTH: 1790
<212> TYPE: DNA
<213> ORGANISM: Artificial Sequence
<220> FEATURE:
<223> OTHER INFORMATION: non-functional hygB marker fragment (PgpdA-HygB
      sequence missing the last 27 bases of the coding sequence at the
      3 end of hygB)

<400> SEQUENCE: 4

cagacagctc tggcggctct gaggtgcagt ggatgattat taatccggga ccggccgccc     60

ctccgccccg aagtggaaag gctggtgtgc ccctcgttga ccaagaatct attgcatcat    120
```

```
cggagaatat ggagcttcat cgaatcaccg gcagtaagcg aaggagaatg tgaagccagg    180

ggtgtatagc cgtcggcgaa atagcatgcc attaacctag gtacagaagt ccaattgctt    240

ccgatctggt aaaagattca cgagatagta ccttctccga agtaggtaga gcgagtaccc    300

ggcgcgtaag ctccctaatt ggcccatccg gcatctgtag ggcgtccaaa tatcgtgcct    360

ctcctgcttt gcccggtgta tgaaaccgga aaggccgctc aggagctggc cagcggcgca    420

gaccgggaac acaagctggc agtcgaccca tccggtgctc tgcactcgac ctgctgaggt    480

ccctcagtcc ctggtaggca gctttgcccc gtctgtccgc ccggtgtgtc ggcggggttg    540

acaaggtcgt tgcgtcagtc caacatttgt tgccatattt tcctgctctc cccaccagct    600

gctcttttct tttctctttc ttttcccatc ttcagtatat tcatcttccc atccaagaac    660

ctttatttcc cctaagtaag tactttgcta catccatact ccatccttcc catcccttat    720

tcctttgaac ctttcagttc gagctttccc acttcatcgc agcttgacta acagctaccc    780

cgcttgagca gacatcacca tgcctgaact caccgcgacg tctgtcgaga agtttctgat    840

cgaaaagttc gacagcgtct ccgacctgat gcagctctcg gagggcgaag aatctcgtgc    900

tttcagcttc gatgtaggag ggcgtggata tgtcctgcgg gtaaatagct gcgccgatgg    960

tttctacaaa gatcgttatg tttatcggca ctttgcatcg gccgcgctcc cgattccgga   1020

agtgcttgac attggggaat tcagcgagag cctgacctat tgcatctccc gccgtgcaca   1080

gggtgtcacg ttgcaagacc tgcctgaaac cgaactgccc gctgttctgc agccggtcgc   1140

ggaggccatg gatgcgatcg ctgcggccga tcttagccag acgagcgggt tcggcccatt   1200

cggaccgcaa ggaatcggtc aatacactac atggcgtgat ttcatatgcg cgattgctga   1260

tccccatgtg tatcactggc aaactgtgat ggacgacacc gtcagtgcgt ccgtcgcgca   1320

ggctctcgat gagctgatgc tttgggccga ggactgcccc gaagtccggc acctcgtgca   1380

cgcggatttc ggctccaaca atgtcctgac ggacaatggc cgcataacag cggtcattga   1440

ctggagcgag gcgatgttcg gggattccca atacgaggtc gccaacatct tcttctggag   1500

gccgtggttg gcttgtatgg agcagcagac gcgctacttc gagcggaggc atccggagct   1560

tgcaggatcg ccgcggctcc gggcgtatat gctccgcatt ggtcttgacc aactctatca   1620

gagcttggtt gacggcaatt tcgatgatgc agcttgggcg cagggtcgat gcgacgcaat   1680

cgtccgatcc ggagccggga ctgtcgggcg tacacaaatc gcccgcagaa gcgcggccgt   1740

ctggaccgat ggctgtgtag aagtactcgc cgatagtgga aaccgacgcc              1790
```

<210> SEQ ID NO 5
<211> LENGTH: 1682
<212> TYPE: DNA
<213> ORGANISM: Artificial Sequence
<220> FEATURE:
<223> OTHER INFORMATION: non-functional hygB fragment (HygB-TtrpC sequence missing the first 44 bases of the coding sequence at the 5' end of hygB)

<400> SEQUENCE: 5

```
aaagttcgac agcgtctccg acctgatgca gctctcggag ggcgaagaat ctcgtgcttt     60

cagcttcgat gtaggagggc gtggatatgt cctgcgggta aatagctgcg ccgatggttt    120

ctacaaagat cgttatgttt atcggcactt tgcatcggcc gcgctcccga ttccggaagt    180

gcttgacatt ggggaattca gcgagagcct gacctattgc atctcccgcc gtgcacaggg    240

tgtcacgttg caagacctgc ctgaaaccga actgcccgct gttctgcagc cggtcgcgga    300
```

-continued

```
ggccatggat gcgatcgctg cggccgatct tagccagacg agcgggttcg gcccattcgg    360

accgcaagga atcggtcaat acactacatg gcgtgatttc atatgcgcga ttgctgatcc    420

ccatgtgtat cactggcaaa ctgtgatgga cgacaccgtc agtgcgtccg tcgcgcaggc    480

tctcgatgag ctgatgcttt gggccgagga ctgccccgaa gtccggcacc tcgtgcacgc    540

ggatttcggc tccaacaatg tcctgacgga caatggccgc ataacagcgg tcattgactg    600

gagcgaggcg atgttcgggg attcccaata cgaggtcgcc aacatcttct tctggaggcc    660

gtggttggct tgtatggagc agcagacgcg ctacttcgag cggaggcatc cggagcttgc    720

aggatcgccg cggctccggg cgtatatgct ccgcattggt cttgaccaac tctatcagag    780

cttggttgac ggcaatttcg atgatgcagc ttgggcgcag ggtcgatgcg acgcaatcgt    840

ccgatccgga gccgggactg tcgggcgtac acaaatcgcc cgcagaagcg cggccgtctg    900

gaccgatggc tgtgtagaag tactcgccga tagtggaaac cgacgcccca gcactcgtcc    960

gagggcaaag gaatagagta gatgccgacc gcgggatcca cttaacgtta ctgaaatcat   1020

caaacagctt gacgaatctg gatataagat cgttggtgtc gatgtcagct ccggagttga   1080

gacaaatggt gttcaggatc tcgataagat acgttcattt gtccaagcag caaagagtgc   1140

cttctagtga tttaatagct ccatgtcaac aagaataaaa cgcgttttcg ggtttacctc   1200

ttccagatac agctcatctg caatgcatta atgcattgac tgcaacctag taacgccttt   1260

caggctccgg cgaagagaag aatagcttag cagagctatt ttcattttcg ggagacgaga   1320

tcaagcagat caacggtcgt caagagacct acgagactga ggaatccgct cttggctcca   1380

cgcgactata tatttgtctc taattgtact ttgacatgct cctcttcttt actctgatag   1440

cttgactatg aaaattccgt caccagccct gggttcgcaa agataattgc atgtttcttc   1500

cttgaactct caagcctaca ggacacacat tcatcgtagg tataaacctc gaaatcattc   1560

ctactaagat ggtatacaat agtaaccatg catggttgcc tagtgaatgc tccgtaacac   1620

ccaatacgcc ggtcctggaa gtgcgttgat cattattccc cgaaaatgta gtacccagta   1680

ag                                                                  1682
```

```
<210> SEQ ID NO 6
<211> LENGTH: 2009
<212> TYPE: DNA
<213> ORGANISM: Artificial Sequence
<220> FEATURE:
<223> OTHER INFORMATION: cre recombinase cassette containing the
      A. nidulans xylanase A promoter, a cre recombinase and xylanase
      A terminator, to allow xylose-inducible expression of the cre
      recombinase

<400> SEQUENCE: 6
```

```
tcctggaagt gcgttgatca ttattccccg aaaatgtagt acccagtaag tggtctagcg     60

gtggctatgg taggacatct atgcctaagc tggagttctc attgaacgtg taccggccga    120

ttgccctaaa ctctgattga gagccggaaa cctcatctac ctgatgctca ggggccatcc    180

aatagcttcc gatagcatta cagacagatg gactcgtctt ggcccacggg tctagaacag    240

tcgccggaac tgcctctatt tgaaacggag ctgaaccatg atacttaagc gtgccaagcg    300

gcgccgtttc ccactggaac aaggagcaat agaattctgc agagattctt cattcaggct    360

attcagcaat tcggtttgtg gagcggatcg gggtccactg ggtttagtct ggggtttttc    420

tttgcccgca tgggctctag cacatgcaca gcttgcagtt gctgctacgc tatctgggaa    480

aacgaatggc tattcaggag tttataacca aaagagccgg aaacaggctg attgccctct    540
```

-continued

```
cacggggaga cgttgtactt ctgatccaga ggctattaac cggacactac ctataaagga    600

ggtagcattc ctttctgtcc ggctcccaga ttccaacaac ccaactgaca ggatcagcac    660

aatgcaggaa ttccaccatg tccaatttac tgaccgtaca ccaaaatttg cctgcattac    720

cggtcgatgc aacgagtgat gaggttcgca agaacctgat ggacatgttc agggatcgcc    780

aggcgttttc tgagcatacc tggaaaatgc ttctgtccgt ttgccggtcg tgggcggcat    840

ggtgcaagtt gaataaccgg aaatggtttc ccgcagaacc tgaagatgtt cgcgattatc    900

ttctatatct tcaggcgcgc ggtctggcag taaaaactat ccagcaacat ttgggccagc    960

taaacatgct tcatcgtcgg tccgggctgc cacgaccaag tgacagcaat gctgtttcac   1020

tggttatgcg gcggatccga aaagaaaacg ttgatgccgg tgaacgtgca aaacaggctc   1080

tagcgttcga acgcactgat ttcgaccagg ttcgttcact catggaaaat agcgatcgct   1140

gccaggatat acgtaatctg gcatttctgg ggattgctta taacaccctg ttacgtatag   1200

ccgaaattgc caggatcagg gttaaagata tctcacgtac tgacggtggg agaatgttaa   1260

tccatattgg cagaacgaaa acgctggtta gcaccgcagg tgtagagaag gcacttagcc   1320

tgggggtaac taaactggtc gagcgatgga tttccgtctc tggtgtagct gatgatccga   1380

ataactacct gttttgccgg gtcagaaaaa atggtgttgc cgcgccatct gccaccagcc   1440

agctatcaac tcgcgccctg gaagggattt ttgaagcaac tcatcgattg atttacggcg   1500

ctaaggatga ctctggtcag agatacctgg cctggtctgg acacagtgcc cgtgtcggag   1560

ccgcgcgaga tatggcccgc gctggagttt caataccgga gatcatgcaa gctggtggct   1620

ggaccaatgt aaatattgtc atgaactata tccgtaacct ggatagtgaa acaggggcaa   1680

tggtgcgcct gctggaagat ggcgattaga gttctgtagc gaagtcagga cctttgtccg   1740

cgcttccttg atcctgcacg ggctgccgt catctctggt ttctgatatg gtattcagct   1800

atactgtcac tcgaagtcct ataactctct tactagcaat atgcttagcc aagaactata   1860

tcaggagagt tttactaaac aggatctctc aataacatgg agtagcctgg caattataaa   1920

tctagtatta aatctagtac taactcgata gatatagggc ttttctggcg aatgcctgta   1980

tggtagctgg aactcgcact gctgcagga                                     2009


<210> SEQ ID NO 7
<211> LENGTH: 19
<212> TYPE: DNA
<213> ORGANISM: Artificial Sequence
<220> FEATURE:
<223> OTHER INFORMATION: Ble-For primer

<400> SEQUENCE: 7

agttgaccag tgccgttcc                                                  19


<210> SEQ ID NO 8
<211> LENGTH: 19
<212> TYPE: DNA
<213> ORGANISM: Artificial Sequence
<220> FEATURE:
<223> OTHER INFORMATION: Ble-Rev primer

<400> SEQUENCE: 8

cacgaagtgc acgcagttg                                                  19


<210> SEQ ID NO 9
<211> LENGTH: 21
<212> TYPE: DNA
<213> ORGANISM: Artificial Sequence
```

-continued

<220> FEATURE:
<223> OTHER INFORMATION: EBA205-For primer

<400> SEQUENCE: 9
cttctgctga gcagctctgc c 21

<210> SEQ ID NO 10
<211> LENGTH: 22
<212> TYPE: DNA
<213> ORGANISM: Artificial Sequence
<220> FEATURE:
<223> OTHER INFORMATION: EBA205-Rev primer

<400> SEQUENCE: 10
gttcagaccg caaggaaggt tg 22

<210> SEQ ID NO 11
<211> LENGTH: 21
<212> TYPE: DNA
<213> ORGANISM: Artificial Sequence
<220> FEATURE:
<223> OTHER INFORMATION: EBA4-For primer

<400> SEQUENCE: 11
cgagaacctg gcctactctc c 21

<210> SEQ ID NO 12
<211> LENGTH: 22
<212> TYPE: DNA
<213> ORGANISM: Artificial Sequence
<220> FEATURE:
<223> OTHER INFORMATION: EBA4-Rev primer

<400> SEQUENCE: 12
cagagttgta gtcggtgtca cg 22

<210> SEQ ID NO 13
<211> LENGTH: 22
<212> TYPE: DNA
<213> ORGANISM: Artificial Sequence
<220> FEATURE:
<223> OTHER INFORMATION: EBA8-For primer

<400> SEQUENCE: 13
gaagggtatc aagaagcgtg cc 22

<210> SEQ ID NO 14
<211> LENGTH: 22
<212> TYPE: DNA
<213> ORGANISM: Artificial Sequence
<220> FEATURE:
<223> OTHER INFORMATION: EBA8-Rev primer

<400> SEQUENCE: 14
gccgaagttg tgagggtcaa tg 22

<210> SEQ ID NO 15
<211> LENGTH: 20
<212> TYPE: DNA
<213> ORGANISM: Artificial Sequence
<220> FEATURE:
<223> OTHER INFORMATION: Pdx-For primer

<400> SEQUENCE: 15
ttgagctgtt gctccggtag 20

<210> SEQ ID NO 16
<211> LENGTH: 21
<212> TYPE: DNA
<213> ORGANISM: Artificial Sequence
<220> FEATURE:
<223> OTHER INFORMATION: Pdx-Rev primer

<400> SEQUENCE: 16
ctccgtagtc atcgtcaatg g 21

<210> SEQ ID NO 17
<211> LENGTH: 18
<212> TYPE: DNA
<213> ORGANISM: Artificial Sequence
<220> FEATURE:
<223> OTHER INFORMATION: Hyg-For primer

<400> SEQUENCE: 17
gcgtcggttt ccactatc 18

<210> SEQ ID NO 18
<211> LENGTH: 18
<212> TYPE: DNA
<213> ORGANISM: Artificial Sequence
<220> FEATURE:
<223> OTHER INFORMATION: Hyg-Rev primer

<400> SEQUENCE: 18
gaggtcgcca acatcttc 18

<210> SEQ ID NO 19
<211> LENGTH: 4198
<212> TYPE: DNA
<213> ORGANISM: Rasamsonia emersonii

<400> SEQUENCE: 19
cgagttcgta gagcgtctcg atgtggtcgc tggtaaaagc aatggggacg aggattatgt 60
ccgtctgccc ccgtttgacg tactcttgca ccgtatcgtt cgtctgagct cccagccagg 120
cggatggtcc cacctgggac tgccagcaga gccggtaggg gttggaaaac ccgagacgct 180
gcatgacggc gtgcaccgtc gcagcaacct cggccggata cgggtcgcct ggggtcttgt 240
cagcgcccat cagccatggg atagaaagcg cgcagcaact gacctcgatt gacaacgctc 300
atgggcaagc tgtgggcgga gaacagcagc acgactgaat tcctccgctc ttcggggtac 360
gtcgccagct ggtcctcgat gttcttcgca aacgcctcga ccaggcccgg atgcgtcggc 420
caccggtcga tcacgctcca ctggatcgtg ccctcctcgt cttcgttggc gcgccggccc 480
tcgaggcggt tcctccattt ccacagctca ttgagagagc tccccgtcgt ggaacaggag 540
tattgaggat actgcgtgaa tgcaaccgcg cgaccgcccc ggcctctgcc aaacccgtcc 600
tccagcagtt tcgcgtacat ctcctccgtc agcggtgctg cgtatctgaa cgcgacgtat 660
ggcttatgcg gcgccgtctc gggggaaatc tcatccaaaa tcttgcacat ctccgcgcat 720
tggtattccg accacttgcg aatcggggac ccgcctccga tgtctgcgta ttgtttttgg 780
atcattgggg ttcggcggcg agcgatgaga gggccaaggt atttctgaag acgtccaagc 840
ggtatcaagt cgccatcggc ctagaaatgg aacagaaccg gtcagctgta gactctagca 900
gggagaagag gcagcaccta caaataatcg gctcaagaag tcctcaacat cgtcggtcgt 960
tgacgggccg cccatgttga gaaagaccat ggccgtcggg cctttggagc ccttcgccgg 1020
cgacaccgac gtcgccaggc cagacctctg attccaattg catgctagaa gactccgcgc 1080

-continued

```
cgcgggtctg atgttggcac atggatagct tgagcttatg cgcccgggta ttaagaaggg   1140
attgcgcagc gccatggtgg ctggcacttg cagacgacct cagtcgctgc tatataagag   1200
gaaagagacc aagattggaa tggagatgtg aataaaaaaa tatagataga tatcttggca   1260
agaccccgaa ttgactggaa cggttcggat ggcacagctc cggctgcatt gggaaaaccc   1320
ggggaagccc accaatcaga ccgaaggcgg aagtcatcaa tggccgggcg tcacgtgacc   1380
atcgtgtctc cccgcgtcgg catcgcgtca ccgacacgag caggcagcag tgcatctaca   1440
cttttctaaa gctgattttc tgaagttgaa ctcagctcag gagatgatat agtgtccaaa   1500
atggctgatc cacacgactc gcgagaggac gaggccgtcg aggaagaaga ggagatcgac   1560
gagacggtat ggctgcacca gagatagcca gtagccgctg ctgacgatcg atcagggata   1620
taaatcagtg aacgatgccg ttctcttcgc gatcgaagtc agcgaatcca tgctggcgcc   1680
ccggcccagc gctgatctga agaaagccgg gccagagtcg cccgcgagag ccgccatcaa   1740
atgtgcatac cacctgatgc agcagcgcat catctccaac ccgaaggaca tgatgggcgt   1800
gttgtttttt gggactgagg cgtcgaagtt ctatgatgag gacgagaaca gccggggcga   1860
cctctcctac cctcactgct acctgttcac tgacctggac gtccccgccg ctgaggatgt   1920
gaagaaactt cgggcgctgg cggaggacga cgaggagacg aaccagatat tggtgccgtc   1980
gaaggagcgg gtgtcgatgg cgaacgtgct gttctgcgca aaccagatct tcacgtccaa   2040
ggcatccaat ttcctgtcga gacggctctt tgttgtaacg gacaacgata atccgcatgg   2100
cgacgaccgg tccttgcggt ctgctgccac tgttcgagcg aaggatctgt acgaccttgg   2160
agtcatcatc gagctgttcc ccatatccag accagatcac gagttcgaca ggaccaagtt   2220
ttatgatgtg ggttcttcca cttctttcct tcctcgtgct caatctctac ttacactgtg   2280
gaggatatta tttataaaac ctctcccacc gatccggaag ctccttccgc tgatccggcc   2340
agcacgcaaa ccccgtcagt tgggggcgac gggattactt tgctcaagtc tcttttgtct   2400
tctatcagct ccaagtctgt gccccggcga gcgctgttct ccaatatacc actggagatc   2460
ggcccgggtt tcaagatttc cgtgaaggga tatcttattt tcaagcgtca ggaaccggcg   2520
agaagctgct atatctggct aggaggggag aaacccgaga tcgccaaagg cgtaaccacg   2580
cagatagcgg atgataccgc gcggacggtg gagaaatggg agatacgaaa agcatacaag   2640
ttcggcggcg aacaaatctc gtttactccg gaggagcaac aggcattgcg gaatttcggc   2700
gatcctgtga tccagattat cggattcaaa ccgatctcag ccctcccgtt ctgggcttcg   2760
atcaaacatc ccaccttcat ttacccgtcc gaagaggatt atgttgggtc gacacgggta   2820
ttctccgccc tgtatcagaa gctcctcaag gaccagaaga tggcgcttgt ctggttcatc   2880
gcgcgacgga acgcaagtcc ggtgctggct gcgatgctcc caggcgctga gaagctggac   2940
gagaatggag tgcaaaggat cccaccgggg atgtggcttt tgcctctgcc atttgcggac   3000
gatatccgac agaacccgga gacgaacctg gtggtggcgc cggagccgtt gatcgaccag   3060
atgaggacgg tgatccagca gctgcagctg cccaaggcgc agtacgatcc tctcaagtac   3120
cccaacccgt cgctgcagtg gcattatcgg attctgcagg cgctcgcgtt ggacgaagac   3180
ctgccggagc aaccggagga caagacgatt ccgcggtacc ggcagatcga caagcgggcg   3240
ggagagtatg tcatctcgtg gggggaggag ctagaagcgc agtaccggaa gatgttcgag   3300
gagcagccca agacatcgac cctggctaag aggccgggca gagcagaggc agcggaaggt   3360
ccgtcaaaga gggccaaaac cgaggccgac ggcggacagg gcgtgacagc cgaagtccga   3420
```

-continued agccactatg agagaggcga tctgtcgaag ctgacactgc cggtgctgaa ggaattcctt 3480
gctgcgcaga agctgtcgac agcggggaag aaggcagaac tgatcgagcg ggttgaagag 3540
tatttcgaac ggaagggcgg gtagtctagt attaactgtc aactatgtcg actcatggat 3600
gagaagaacg cagtatttga ttgagggcac ttttttttga tgtcacgaca tggatatgga 3660
tatgatatcc tggtctagtc tagtcctaat tagctgttgc tattatcttg tataatagat 3720
accatatcaa acatattaga atgggaatga aagaaaaaaa aggtacatta cagtacatca 3780
gcagaacata catatataca tatacatata tgaacagagc acggacacac tccctcctct 3840
tcggacagaa aagttcagat attacatcca catcttaccg cggaggtaaa ttaaatcaag 3900
acttaattaa acaatatata ccttaggtac ctaggttgat aagctaatag atatcttgac 3960
taaaccaata gcttttattt atttatttat tcacttagtc aatatttact taatagacta 4020
gggatgtagg tataatataa tataagttaa aatttatcta gactaaatac gtattctaga 4080
taatagtcaa tgtatgtact gcatctgagt cttctgagaa tgtttctctc tctttgctag 4140
ttatattatg atctttatta acgacaatac ttctcagttg atcaagaaag aggagttt 4198

<210> SEQ ID NO 20
<211> LENGTH: 1959
<212> TYPE: DNA
<213> ORGANISM: Rasamsonia emersonii

<400> SEQUENCE: 20
atggctgatc cacacgactc gcgagaggac gaggccgtcg aggaagaaga ggagatcgac 60
gagacgggat ataaatcagt gaacgatgcc gttctcttcg cgatcgaagt cagcgaatcc 120
atgctggcgc cccggcccag cgctgatctg aagaaagccg ggccagagtc gcccgcgaga 180
gccgccatca aatgtgcata ccacctgatg cagcagcgca tcatctccaa cccgaaggac 240
atgatgggcg tgttgttttt tgggactgag gcgtcgaagt tctatgatga ggacgagaac 300
agccggggcg acctctccta ccctcactgc tacctgttca ctgacctgga cgtccccgcc 360
gctgaggatg tgaagaaact tcgggcgctg gcggaggacg acgaggagac gaaccagata 420
ttggtgccgt cgaaggagcg ggtgtcgatg gcgaacgtgc tgttctgcgc aaaccagatc 480
ttcacgtcca aggcatccaa tttcctgtcg agacggctct ttgttgtaac ggacaacgat 540
aatccgcatg gcgacgaccg gtccttgcgg tctgctgcca ctgttcgagc gaaggatctg 600
tacgaccttg gagtcatcat cgagctgttc cccatatcca gaccagatca cgagttcgac 660
aggaccaagt tttatgatga tattatttat aaaacctctc ccaccgatcc ggaagctcct 720
tccgctgatc cggccagcac gcaaaccccg tcagttgggg gcgacgggat tactttgctc 780
aagtctcttt tgtcttctat cagctccaag tctgtgcccc ggcgagcgct gttctccaat 840
ataccactgg agatcggccc gggtttcaag atttccgtga agggatatct tattttcaag 900
cgtcaggaac cggcgagaag ctgctatatc tggctaggag gggagaaacc cgagatcgcc 960
aaaggcgtaa ccacgcagat agcggatgat accgcgcgga cggtggagaa atgggagata 1020
cgaaaagcat acaagttcgg cggcgaacaa atctcgttta ctccggagga gcaacaggca 1080
ttgcggaatt tcggcgatcc tgtgatccag attatcggat tcaaaccgat ctcagccctc 1140
ccgttctggg cttcgatcaa acatcccacc ttcatttacc cgtccgaaga ggattatgtt 1200
gggtcgacac gggtattctc cgccctgtat cagaagctcc tcaaggacca gaagatggcg 1260
cttgtctggt tcatcgcgcg acggaacgca agtccggtgc tggctgcgat gctcccaggc 1320
gctgagaagc tggacgagaa tggagtgcaa aggatcccac cggggatgtg gcttttgcct 1380

```
ctgccatttg cggacgatat ccgacagaac ccggagacga acctggtggt ggcgccggag   1440

ccgttgatcg accagatgag gacggtgatc cagcagctgc agctgcccaa ggcgcagtac   1500

gatcctctca agtaccccaa cccgtcgctg cagtggcatt atcggattct gcaggcgctc   1560

gcgttggacg aagacctgcc ggagcaaccg gaggacaaga cgattccgcg gtaccggcag   1620

atcgacaagc gggcgggaga gtatgtcatc tcgtgggggg aggagctaga agcgcagtac   1680

cggaagatgt tcgaggagca gcccaagaca tcgaccctgg ctaagaggcc gggcagagca   1740

gaggcagcgg aaggtccgtc aaagagggcc aaaaccgagg ccgacggcgg acagggcgtg   1800

acagccgaag tccgaagcca ctatgagaga ggcgatctgt cgaagctgac actgccggtg   1860

ctgaaggaat tccttgctgc gcagaagctg tcgacagcgg ggaagaaggc agaactgatc   1920

gagcgggttg aagagtattt cgaacggaag ggcgggtag                          1959
```

```
<210> SEQ ID NO 21
<211> LENGTH: 652
<212> TYPE: PRT
<213> ORGANISM: Rasamsonia emersonii

<400> SEQUENCE: 21

Met Ala Asp Pro His Asp Ser Arg Glu Asp Glu Ala Val Glu Glu Glu
1               5                   10                  15

Glu Glu Ile Asp Glu Thr Gly Tyr Lys Ser Val Asn Asp Ala Val Leu
            20                  25                  30

Phe Ala Ile Glu Val Ser Glu Ser Met Leu Ala Pro Arg Pro Ser Ala
        35                  40                  45

Asp Leu Lys Lys Ala Gly Pro Glu Ser Pro Ala Arg Ala Ala Ile Lys
    50                  55                  60

Cys Ala Tyr His Leu Met Gln Gln Arg Ile Ile Ser Asn Pro Lys Asp
65                  70                  75                  80

Met Met Gly Val Leu Phe Phe Gly Thr Glu Ala Ser Lys Phe Tyr Asp
                85                  90                  95

Glu Asp Glu Asn Ser Arg Gly Asp Leu Ser Tyr Pro His Cys Tyr Leu
            100                 105                 110

Phe Thr Asp Leu Asp Val Pro Ala Ala Glu Asp Val Lys Lys Leu Arg
        115                 120                 125

Ala Leu Ala Glu Asp Asp Glu Glu Thr Asn Gln Ile Leu Val Pro Ser
    130                 135                 140

Lys Glu Arg Val Ser Met Ala Asn Val Leu Phe Cys Ala Asn Gln Ile
145                 150                 155                 160

Phe Thr Ser Lys Ala Ser Asn Phe Leu Ser Arg Arg Leu Phe Val Val
                165                 170                 175

Thr Asp Asn Asp Asn Pro His Gly Asp Asp Arg Ser Leu Arg Ser Ala
            180                 185                 190

Ala Thr Val Arg Ala Lys Asp Leu Tyr Asp Leu Gly Val Ile Ile Glu
        195                 200                 205

Leu Phe Pro Ile Ser Arg Pro Asp His Glu Phe Asp Arg Thr Lys Phe
    210                 215                 220

Tyr Asp Asp Ile Ile Tyr Lys Thr Ser Pro Thr Asp Pro Glu Ala Pro
225                 230                 235                 240

Ser Ala Asp Pro Ala Ser Thr Gln Thr Pro Ser Val Gly Gly Asp Gly
                245                 250                 255

Ile Thr Leu Leu Lys Ser Leu Leu Ser Ser Ile Ser Ser Lys Ser Val
            260                 265                 270
```

```
Pro Arg Arg Ala Leu Phe Ser Asn Ile Pro Leu Glu Ile Gly Pro Gly
        275                 280                 285

Phe Lys Ile Ser Val Lys Gly Tyr Leu Ile Phe Lys Arg Gln Glu Pro
    290                 295                 300

Ala Arg Ser Cys Tyr Ile Trp Leu Gly Gly Glu Lys Pro Glu Ile Ala
305                 310                 315                 320

Lys Gly Val Thr Thr Gln Ile Ala Asp Asp Thr Ala Arg Thr Val Glu
                325                 330                 335

Lys Trp Glu Ile Arg Lys Ala Tyr Lys Phe Gly Gly Glu Gln Ile Ser
            340                 345                 350

Phe Thr Pro Glu Glu Gln Gln Ala Leu Arg Asn Phe Gly Asp Pro Val
        355                 360                 365

Ile Gln Ile Ile Gly Phe Lys Pro Ile Ser Ala Leu Pro Phe Trp Ala
    370                 375                 380

Ser Ile Lys His Pro Thr Phe Ile Tyr Pro Ser Glu Glu Asp Tyr Val
385                 390                 395                 400

Gly Ser Thr Arg Val Phe Ser Ala Leu Tyr Gln Lys Leu Leu Lys Asp
                405                 410                 415

Gln Lys Met Ala Leu Val Trp Phe Ile Ala Arg Arg Asn Ala Ser Pro
            420                 425                 430

Val Leu Ala Ala Met Leu Pro Gly Ala Glu Lys Leu Asp Glu Asn Gly
        435                 440                 445

Val Gln Arg Ile Pro Pro Gly Met Trp Leu Leu Pro Leu Pro Phe Ala
    450                 455                 460

Asp Asp Ile Arg Gln Asn Pro Glu Thr Asn Leu Val Val Ala Pro Glu
465                 470                 475                 480

Pro Leu Ile Asp Gln Met Arg Thr Val Ile Gln Gln Leu Gln Leu Pro
                485                 490                 495

Lys Ala Gln Tyr Asp Pro Leu Lys Tyr Pro Asn Pro Ser Leu Gln Trp
            500                 505                 510

His Tyr Arg Ile Leu Gln Ala Leu Ala Leu Asp Glu Asp Leu Pro Glu
        515                 520                 525

Gln Pro Glu Asp Lys Thr Ile Pro Arg Tyr Arg Gln Ile Asp Lys Arg
    530                 535                 540

Ala Gly Glu Tyr Val Ile Ser Trp Gly Glu Glu Leu Glu Ala Gln Tyr
545                 550                 555                 560

Arg Lys Met Phe Glu Glu Gln Pro Lys Thr Ser Thr Leu Ala Lys Arg
                565                 570                 575

Pro Gly Arg Ala Glu Ala Ala Glu Gly Pro Ser Lys Arg Ala Lys Thr
            580                 585                 590

Glu Ala Asp Gly Gly Gln Gly Val Thr Ala Glu Val Arg Ser His Tyr
        595                 600                 605

Glu Arg Gly Asp Leu Ser Lys Leu Thr Leu Pro Val Leu Lys Glu Phe
    610                 615                 620

Leu Ala Ala Gln Lys Leu Ser Thr Ala Gly Lys Lys Ala Glu Leu Ile
625                 630                 635                 640

Glu Arg Val Glu Glu Tyr Phe Glu Arg Lys Gly Gly
                645                 650
```

<210> SEQ ID NO 22
<211> LENGTH: 7890
<212> TYPE: DNA
<213> ORGANISM: Rasamsonia emersonii -continued

<400> SEQUENCE: 22

```
ggagcctggc tcagcatgct cacggactgc aggatgaaca cgcgtctccg aaggtgcaac      60
cggggagaag ataaccaccg tccttgaggg aagaacatct gtcatcatcg aaacagaagc     120
agtctcagtc tcggtctcgg tctcagtccc gtcatctata gtcgtcacag ttgggatcgg     180
aaacgtggcc gaccagtccc tggtcttgta ccaggtgtta ttctcgtatc gcggcggcgc     240
gatcatgtcg agcgcctcac caatccttcc gaggacatag cccatcctga acccgccctg     300
gaggcgctcg atgaagttgt tggcgggatg aacggcggtg aaagggatgg catggaagat     360
gccgaggatg gccatggcca tggagaacat gaacaggccg aaggggtcca tggtgatgat     420
gattcgatcg atatcagaca gctgaatatg tattagcttt ccaaatttct tctatcatga     480
aattcgacag gaaatagaaa aagaaaggat gctggctttg attaaagaga gtagctgggt     540
cttatcacaa gagattaaaa agtgtcttaa acaaagacaa gacaagacaa gcatccgtct     600
gatgcatgag tttcgagata tatataatac aaaggatgga ttcactgaac agttcgttga     660
cttctgaaga acaaaggctg gtctctgcat gcccgagaat agtaacaaca ataaagagca     720
aatacaacgt tgtgtacagc aagcgaatga cctgccttga atgagtctgg cagatttatt     780
cccccatcta ctaccttcaa gtacctcatc agatggccag cagaaggtgc aagtgggtat     840
atcttctcat tcgaagaact tagtgtttag ttttctgagc agcaatatag ctagttgcaa     900
gttagaaaag agtataaaga accgtttccg caacaccagc taccctcaaa gaaaggaatt     960
gaacaaactg ggaactaccg attactacca agctggaggg cataggcaat gaacgccagg    1020
aattggtaaa gactgaagat aggaaggtat ggtgaatact gcatagtgca atgtagacct    1080
tcagtatcat aaggatcatc cattcattat agacgctaat ataaagtatt tctgaaaaaa    1140
aatgttggag aggagatcaa gtctttttat tcaacggctt tcaaagacta aaagctggaa    1200
aaggcaggct atcatcatga tacctagcat agcataccat gtttgcgttt atcacttcat    1260
attcaggaca acctcctgcc caggaccacg ccataggcaa ctgtcgccag gagaccgccc    1320
aggttgacca gcgtcgagat tccatgcagc ttggcaaact tcttgttgag ctcggtcatc    1380
tccttggagt gaggaggcgg gtcataactc ttcttgccgt cgatcgattc tgccagagat    1440
catatatatc agcccgtacc tatacagtgt actcgtgcgt actcggcagc agccaaaccg    1500
gtaggtagta ggcaggtacc aaccttgctg ccacctctgc ttgataactc ccacaacctt    1560
cggggtcaga tagagcaggt tggtcagtcc cgaaacgaag acgatcgaaa gcggcagcaa    1620
caccgtcaga cgattctcct cgagaagcac ccccgcgagg ctagagggcc cagttcccag    1680
gaccgttctg gctcccgggt aggtcagcgc tgcgacaacg gggagagcgc tctgcagggt    1740
gaagtagatc gggaacaggc tattctggag cgtcgagaac tgctgacggg gaagcgtcct    1800
gaacgcgacg gttccgccaa cgaaggtcta catatataac ggaatgttgt aggagctttt    1860
gatgagttat ctatcctcct gaccaattga ccagaaacaa aactcaggat gtcaaacctg    1920
atagatctcg actcccagaa gggtgccgta gctgattgaa gtgtgatgtc agccgatcta    1980
ttagtagcag ccgtagtact ggtgacgcac cttagtatgt ggaaggggcc caggatagac    2040
atcctgctct gttgtactga tatggaaaca cctcgtgact ggaacagaac tatatgggat    2100
tatacttaga cagataccc actgactggg aattcagagg gaagagtaag ttgtgttatg    2160
ctacgggtag gttagagaag ctgtcaagct tgggtctccc gagctaacgc tagctgcatg    2220
tggggcatgt tcttatctcc acggcccgct caaacctaga tctgcttcca acaaagcaca    2280
aatatctata cacacggcct tttccgtaag gcccacgcac cttcccgacg tcatgtgcac    2340
```

-continued tcgcgtctgc cgcgcctcaa aaaggaaata tcacgcgtct gcctggaggc gctccttagt 2400
catagaaaga aacgcatcta cgccatgcag tgatttattt atctgacatt tccttcctct 2460
tcgttgcagc aggagggaca gctgacatct cttttgcaaa atggctgaca aggaggccac 2520
cgtctacgtg atcgatgtgg gaaagtccat ggggaggcgc cgccatggac ggccggtatc 2580
tgacctggaa tgggcaatgc aatatgtctg ggacaagatt acgacaaccg tatgctgaca 2640
cttgatccgg tctcctggaa attaaattcc tgcgttgaga actgacatat cttctgttag 2700
gttgccacgg ggcggaaaac ggctacaatt ggagtggtcg ggctgaggac agatggtgag 2760
attttaccgt gcccgaatca ggtaaatatg atttactgat gtatctggac agaaacatcg 2820
aacgacttgc aggatgatga cagctattcg cacatctctg tctttcagga aattggacag 2880
tatgtgcctc agctgacact gatgactagt gacttttcct cgcatatact aaataaatca 2940
ctgccagggt cctcatgcct gatctgcgaa aactgcgcga cctgatcaag cctagcaaca 3000
ctgatgaagg agatggtgag ttttgcccgt atcttcggac tcatttgatt tgatattgag 3060
acctatctac ctatagctat ctcctccctt gtcgtcgcga tccagatgat caccacttat 3120
accaaaaagc tgaagtatcg acggaaaatc attctcgtga cgaacgggga aggatccatg 3180
agtaccgatg gtcttgatga gatcgtgaaa aagctcaagt ccgatagcat tgaattggtg 3240
gtcttgtatg tttttcactt ctctttgact tttcttgtgg ctggtatgca aaatggctaa 3300
actggtttcg ttgcaggggt gttgactttg atgatcctga atttggtgtc aaagaggagg 3360
acaagaatcc agcaaaagta ttcaatgttt ttttttagc aggttggaag agttgctgat 3420
tcgatctgcc gcaggctgag aatgaagcgg tcctcagagg tctcgttgat tcctgcgacg 3480
gagtctacgg gacattacaa caggccatat tggagctgga cacaccgcgt gtgaaggttg 3540
ttcgtggaat accctccttt agaggagagc tccgactggg gaaccctgaa gagtattcgt 3600
ctgcccttcg tatcccagtc gaaagatact accgaactta tgttgccaag ccgccgacag 3660
cgagctcctt tgtcctacga tctgacgctg cagctggtca agagggtgca gagaatgcac 3720
tgacaagcgt ccgaaacgca cggacatatc acgtcagtga tgagtccgca ccaggaggca 3780
agagagacgt ggagcgagaa gatctcgcca agggctacga gtatgggaga accgcggtgc 3840
acattagtga gtccgatgag aatatcacca aactccagac gaaccctggt ctggaaatca 3900
tcggcttcat tcagagtgac catgtatgtt tctcgtcaag ggtatctcat ctgaaccgtg 3960
attaacctag gatccagtac gaccgataca tgcacatgtc taccagcaat gtcataattg 4020
cacagaaagc aaacgaaaag gcgatccttg ctctttcatc tttcattcac gccttgttcg 4080
agttggactg ttatgctgtg gccagacttg ttaccaagga caacaagccc ccactcatcg 4140
tattactggc accatctatt gaagcagact ttgaatgtct tctagaagtc cagctccctt 4200
ttgctgaaga tgttcggtcg taccgtttcc ctcccttgga caaggtggtc actgtctctg 4260
gaaagacagt caaagagcac cgacatctcc caagtgacga attgctgaat gcgatgagca 4320
aatacgtcga cagcatggag ctcgtcgaca aggatgaaaa cgggtgagtc atcacaggga 4380
aaccgtcatg ctgctcatct caagtatact gacaactcca cagagaacca gttgacagcc 4440
tggctcccag actggaggat tcgtactctc cactgctgca caggatcgag caagctatcc 4500
ggtggcgtgc catccatcca aacgagcctc ttccgccccc ttctgagaag ttgacgcagc 4560
tgtcacgacc gccagcagat ctgcaagcgc gcgcgaagaa atacctggat cgggtcattg 4620
ccgccgccga tgtgaagaaa ggtctgtcaa cttctacgct cccccagaat gcatctgact 4680

-continued

```
aaaaaatgct gcacagttcc accaaaagca aaaggtcgca agcggaatcg cgaagccgac   4740
aaacccctat cgggtcttga cgttgacgag ctccttcgtc gcgagaagcg cgccaagatc   4800
tcagccaaca acgccatccc cgagttcaaa cagtcgctgg tcaacgccga gaccatcgac   4860
gccgtccgtg acgcagtcag ccagatggaa agcatcatcg agaaccacat ccgaagcagc   4920
tttggagacg ccaactacga ccgcgtgatc gaggagctgg gtgtcctccg cgaggagctg   4980
atcgcctacg aagagccgga tctctacaac gacttcctgc ggaggctgaa ggacaagatc   5040
ctcaatgagg agctgggcgg agacagacga gagctgtggt ggctcgtcag gaggcaacgg   5100
gtcggtctga tagacaagaa ggcgtcggaa cgggttgaag ttactgaaca ggaagccagg   5160
gaggtaagta agcagataca ttattccttt agttccatta aacgagctgc atgatgagct   5220
gacttttgtt cactagttca tgacctcgaa ataaaatagt ccattattgc tatgtatgtc   5280
aaggcgcctg gccgtagtag tcttaacatg ctgatgctgt gaatcaaagc gccagatgaa   5340
caataataga aataatacca cttggtagct gtctccattc tcacagatag acaacgttaa   5400
agaaaagaaa aacgtaaaaa gagggtatat gtggtctagt aacgccgcaa ggaaaaaaaa   5460
actcatacgt tagtttcgaa cgcaaatctc aaaatcgagc acttcgagta aatactctgt   5520
cgtatcgttt cgcctcagga tatcttcccg agccttctct ttccgatatc gattttccgt   5580
tgtaatctag ttattattac tccagttagt aaatgcacga cgggcagtat tgtaaataat   5640
gaaatcagca gcgagagtac gaacatgtcc acatcctcat cggctttccg gagcaactcg   5700
ttctggatct ccagctcatt gttaatggcg atccccagct ccttctgtcg agcgacgatt   5760
ttcatcaact cctccacgct ccggtcctgc tcttccatcg tctgcttctg cagctggagc   5820
acgccctggt tgtcgagttc ccgcgtcttg tccgtttcct tgcccaggac tcgtccagaa   5880
cggggtttgg cgctccccac cagggcgtcc ttgtcctgca tcgaagcgac agcgttgtcg   5940
agcttgctct tcgtcaccat cgcgttgtgc agattctcca atccgtcctt ctctttcttg   6000
gcgctcgcga tgagatcctt cctccgacgg atctctccct cgcctaacct gctgccgccc   6060
catccagacg acttgtcgct caggttcttc agcccttcct caagagcgcc gatcatcgac   6120
cctgctttca ccaagctgct tttggcctgt gccgagctct cgtgttgttt ctgtggagtc   6180
gtggcctgat cacgtctcgt cagatgcagc ctcgtctcgt gtaagtgcgc cttcatctcc   6240
cggtagcaat ccagccacag gactggatcc gtgatcggtc cgccgcctgg cgcgcccggt   6300
tccgtgatgg acttgtgaag cttcgatgcg gcagagctat ccgacagggc ttgggagggg   6360
aggtttagaa aggacctcca gacgcttgtt tgacgccatc gcgggtcctc gctctcgttg   6420
atggcccgca ggtatctttc caggcctttg cgccgctctt cgcgcagagt ctcgttcgag   6480
ttcgtgttgg aaaaccagga cttcccgggc agagcgacgg gtggttgggc gccaacctgg   6540
cggactagtg cgtcatggaa cgatgcaaat tctgaatagc gtttctggac aacgaacgac   6600
cgtagaggca gccggatggt gatgttgtat agcgtatacg gactgggagc gtccgcgatg   6660
gtggctgtcg ggatggaaat ttcgacattc ggggccatga ttatagttca gacgggaaaa   6720
agaacaaaac aaagagcagg cccttgttat cgaccaggaa gcataattcc cgccgcttct   6780
cttgcggtat ctctgtcgtt gcagagttgg ttgcagagta gtggagtcgg ccggcgggtg   6840
gaaactcccg caatgacgca ggcgccccat cttcttctgc caccgccgat ctgtggctta   6900
gcttcttctt gtcaagactc gactccacca tcgcgactcc aggcagcacg aatcgcacga   6960
ttgccgaaaa actacaccgt actaggggaa ggcctaatta atctattacc ctagctaaaa   7020
atggggttgt caaacttatc atatagccgt gcgacccgcc cttggaggtc actagatcca   7080
```

acctgcgcac ggcctggtta cggttgatgg gagctaaaat tagaacgaaa gatatactgg 7140
cggtccgtcc ccgcgtctat ccacaatcca aaactcgtat gcagagttat ctacaggtcg 7200
atccaatcat gagtcctttg tgacatgtcg ttgaatacat ggtctcaatc gagtctgccg 7260
ttcttacatg accatcctca ccaagatcaa tgtcccgtga ttcgactgtc agccaagata 7320
cgtctcacct ggccccatct ctactgtcga caacgtctgc ctatactgta ggtgatcaga 7380
atacgcagtc ccggggagtc tactcgcgat ggggtggttc atacgtcggc tcctcgtcga 7440
cgttgtctct gggtccgtcg gagagcgtca atatagacgg gagacgaaag ttgctcttga 7500
tctatatcca tggcttcatg ggtgaagaag cgagcttcca caagttccct gctcatgtcc 7560
ataaccttgt caccattgct ctggccgagt cgcacgttgt gtattcgaag gtatatcctc 7620
gatacaaatc ccgccgagca atggacattg cacgtgatga tttcagtcga tggtgcgttt 7680
gcagactggc atatctctct ttagagatca tcctagaaag aaacgcatga tactaagtgt 7740
cgaataggct atcaccgcat gagtcggaag atacagatgt gatcctactc ggccacagcc 7800
tgggtgggat cctagccgca gaggttgcgc tgctcccatc agcccctggg agcaaggaga 7860
tcttcgagca tcgtatcctg ggactcatca 7890

<210> SEQ ID NO 23
<211> LENGTH: 2145
<212> TYPE: DNA
<213> ORGANISM: Rasamsonia emersonii

<400> SEQUENCE: 23
atggctgaca aggaggccac cgtctacgtg atcgatgtgg gaaagtccat ggggaggcgc 60
cgccatggac ggccggtatc tgacctggaa tgggcaatgc aatatgtctg ggacaagatt 120
acgacaaccg ttgccacggg gcggaaaacg gctacaattg gagtggtcgg gctgaggaca 180
gatgaaacat cgaacgactt gcaggatgat gacagctatt cgcacatctc tgtctttcag 240
gaaattggac aggtcctcat gcctgatctg cgaaaactgc gcgacctgat caagcctagc 300
aacactgatg aaggagatgc tatctcctcc cttgtcgtcg cgatccagat gatcaccact 360
tataccaaaa agctgaagta tcgacggaaa atcattctcg tgacgaacgg ggaaggatcc 420
atgagtaccg atggtcttga tgagatcgtg aaaaagctca agtccgatag cattgaattg 480
gtggtcttgg gtgttgactt tgatgatcct gaatttggtg tcaaagagga ggacaagaat 540
ccagcaaaag ctgagaatga agcggtcctc agaggtctcg ttgattcctg cgacggagtc 600
tacgggacat tacaacaggc catattggag ctggacacac cgcgtgtgaa ggttgttcgt 660
ggaataccct cctttagagg agagctccga ctggggaacc ctgaagagta ttcgtctgcc 720
cttcgtatcc cagtcgaaag atactaccga acttatgttg ccaagccgcc gacagcgagc 780
tcctttgtcc tacgatctga cgctgcagct ggtcaagagg gtgcagagaa tgcactgaca 840
agcgtccgaa acgcacggac atatcacgtc agtgatgagt ccgcaccagg aggcaagaga 900
gacgtggagc gagaagatct cgccaagggc tacgagtatg ggagaaccgc ggtgcacatt 960
agtgagtccg atgagaatat caccaaactc cagacgaacc ctggtctgga aatcatcggc 1020
ttcattcaga gtgaccatta cgaccgatac atgcacatgt ctaccagcaa tgtcataatt 1080
gcacagaaag caaacgaaaa ggcgatcctt gctctttcat ctttcattca cgccttgttc 1140
gagttggact gttatgctgt ggccagactt gttaccaagg acaacaagcc cccactcatc 1200
gtattactgg caccatctat tgaagcagac tttgaatgtc ttctagaagt ccagctccct 1260

-continued

```
tttgctgaag atgttcggtc gtaccgtttc cctcccttgg acaaggtggt cactgtctct   1320

ggaaagacag tcaaagagca ccgacatctc ccaagtgacg aattgctgaa tgcgatgagc   1380

aaatacgtcg acagcatgga gctcgtcgac aaggatgaaa acggagaacc agttgacagc   1440

ctggctccca gactggagga ttcgtactct ccactgctgc acaggatcga gcaagctatc   1500

cggtggcgtg ccatccatcc aaacgagcct cttccgcccc cttctgagaa gttgacgcag   1560

ctgtcacgac cgccagcaga tctgcaagcg cgcgcgaaga aatacctgga tcgggtcatt   1620

gccgccgccg atgtgaagaa agttccacca aaagcaaaag gtcgcaagcg gaatcgcgaa   1680

gccgacaaac ccctatcggg tcttgacgtt gacgagctcc ttcgtcgcga gaagcgcgcc   1740

aagatctcag ccaacaacgc catccccgag ttcaaacagt cgctggtcaa cgccgagacc   1800

atcgacgccg tccgtgacgc agtcagccag atggaaagca tcatcgagaa ccacatccga   1860

agcagctttg gagacgccaa ctacgaccgc gtgatcgagg agctgggtgt cctccgcgag   1920

gagctgatcg cctacgaaga gccggatctc tacaacgact tcctgcggag gctgaaggac   1980

aagatcctca atgaggagct gggcggagac agacgagagc tgtggtggct cgtcaggagg   2040

caacgggtcg gtctgataga caagaaggcg tcggaacggg ttgaagttac tgaacaggaa   2100

gccagggagt ccattattgc tatctgtctc cattctcaca gatag                   2145
```

```
<210> SEQ ID NO 24
<211> LENGTH: 714
<212> TYPE: PRT
<213> ORGANISM: Rasamsonia emersonii

<400> SEQUENCE: 24

Met Ala Asp Lys Glu Ala Thr Val Tyr Val Ile Asp Val Gly Lys Ser
1               5                   10                  15

Met Gly Arg Arg Arg His Gly Arg Pro Val Ser Asp Leu Glu Trp Ala
            20                  25                  30

Met Gln Tyr Val Trp Asp Lys Ile Thr Thr Thr Val Ala Thr Gly Arg
        35                  40                  45

Lys Thr Ala Thr Ile Gly Val Val Gly Leu Arg Thr Asp Glu Thr Ser
    50                  55                  60

Asn Asp Leu Gln Asp Asp Asp Ser Tyr Ser His Ile Ser Val Phe Gln
65                  70                  75                  80

Glu Ile Gly Gln Val Leu Met Pro Asp Leu Arg Lys Leu Arg Asp Leu
                85                  90                  95

Ile Lys Pro Ser Asn Thr Asp Glu Gly Asp Ala Ile Ser Ser Leu Val
            100                 105                 110

Val Ala Ile Gln Met Ile Thr Thr Tyr Thr Lys Lys Leu Lys Tyr Arg
        115                 120                 125

Arg Lys Ile Ile Leu Val Thr Asn Gly Glu Gly Ser Met Ser Thr Asp
    130                 135                 140

Gly Leu Asp Glu Ile Val Lys Lys Leu Lys Ser Asp Ser Ile Glu Leu
145                 150                 155                 160

Val Val Leu Gly Val Asp Phe Asp Asp Pro Glu Phe Gly Val Lys Glu
                165                 170                 175

Glu Asp Lys Asn Pro Ala Lys Ala Glu Asn Glu Ala Val Leu Arg Gly
            180                 185                 190

Leu Val Asp Ser Cys Asp Gly Val Tyr Gly Thr Leu Gln Gln Ala Ile
        195                 200                 205

Leu Glu Leu Asp Thr Pro Arg Val Lys Val Val Arg Gly Ile Pro Ser
    210                 215                 220
```

```
Phe Arg Gly Glu Leu Arg Leu Gly Asn Pro Glu Glu Tyr Ser Ser Ala
225                 230                 235                 240

Leu Arg Ile Pro Val Glu Arg Tyr Tyr Arg Thr Tyr Val Ala Lys Pro
                245                 250                 255

Pro Thr Ala Ser Ser Phe Val Leu Arg Ser Asp Ala Ala Ala Gly Gln
            260                 265                 270

Glu Gly Ala Glu Asn Ala Leu Thr Ser Val Arg Asn Ala Arg Thr Tyr
        275                 280                 285

His Val Ser Asp Glu Ser Ala Pro Gly Gly Lys Arg Asp Val Glu Arg
    290                 295                 300

Glu Asp Leu Ala Lys Gly Tyr Glu Tyr Gly Arg Thr Ala Val His Ile
305                 310                 315                 320

Ser Glu Ser Asp Glu Asn Ile Thr Lys Leu Gln Thr Asn Pro Gly Leu
                325                 330                 335

Glu Ile Ile Gly Phe Ile Gln Ser Asp His Tyr Asp Arg Tyr Met His
            340                 345                 350

Met Ser Thr Ser Asn Val Ile Ile Ala Gln Lys Ala Asn Glu Lys Ala
        355                 360                 365

Ile Leu Ala Leu Ser Ser Phe Ile His Ala Leu Phe Glu Leu Asp Cys
    370                 375                 380

Tyr Ala Val Ala Arg Leu Val Thr Lys Asp Asn Lys Pro Pro Leu Ile
385                 390                 395                 400

Val Leu Leu Ala Pro Ser Ile Glu Ala Asp Phe Glu Cys Leu Leu Glu
                405                 410                 415

Val Gln Leu Pro Phe Ala Glu Asp Val Arg Ser Tyr Arg Phe Pro Pro
            420                 425                 430

Leu Asp Lys Val Val Thr Val Ser Gly Lys Thr Val Lys Glu His Arg
        435                 440                 445

His Leu Pro Ser Asp Glu Leu Leu Asn Ala Met Ser Lys Tyr Val Asp
    450                 455                 460

Ser Met Glu Leu Val Asp Lys Asp Glu Asn Gly Glu Pro Val Asp Ser
465                 470                 475                 480

Leu Ala Pro Arg Leu Glu Asp Ser Tyr Ser Pro Leu Leu His Arg Ile
                485                 490                 495

Glu Gln Ala Ile Arg Trp Arg Ala Ile His Pro Asn Glu Pro Leu Pro
            500                 505                 510

Pro Pro Ser Glu Lys Leu Thr Gln Leu Ser Arg Pro Pro Ala Asp Leu
        515                 520                 525

Gln Ala Arg Ala Lys Lys Tyr Leu Asp Arg Val Ile Ala Ala Ala Asp
    530                 535                 540

Val Lys Lys Val Pro Pro Lys Ala Lys Gly Arg Lys Arg Asn Arg Glu
545                 550                 555                 560

Ala Asp Lys Pro Leu Ser Gly Leu Asp Val Asp Glu Leu Leu Arg Arg
                565                 570                 575

Glu Lys Arg Ala Lys Ile Ser Ala Asn Asn Ala Ile Pro Glu Phe Lys
            580                 585                 590

Gln Ser Leu Val Asn Ala Glu Thr Ile Asp Ala Val Arg Asp Ala Val
        595                 600                 605

Ser Gln Met Glu Ser Ile Ile Glu Asn His Ile Arg Ser Ser Phe Gly
    610                 615                 620

Asp Ala Asn Tyr Asp Arg Val Ile Glu Glu Leu Gly Val Leu Arg Glu
625                 630                 635                 640
```

-continued

```
Glu Leu Ile Ala Tyr Glu Glu Pro Asp Leu Tyr Asn Asp Phe Leu Arg
                645                 650                 655

Arg Leu Lys Asp Lys Ile Leu Asn Glu Glu Leu Gly Gly Asp Arg Arg
            660                 665                 670

Glu Leu Trp Trp Leu Val Arg Arg Gln Arg Val Gly Leu Ile Asp Lys
        675                 680                 685

Lys Ala Ser Glu Arg Val Glu Val Thr Glu Gln Glu Ala Arg Glu Ser
    690                 695                 700

Ile Ile Ala Ile Cys Leu His Ser His Arg
705                 710


<210> SEQ ID NO 25
<211> LENGTH: 6954
<212> TYPE: DNA
<213> ORGANISM: Rasamsonia emersonii

<400> SEQUENCE: 25

cttaggagga gcgctattaa ctccaatacc gtggttaaat aacacggacc cggacggtaa     60

taatacggat tcgactgcgg aaggtaagtg gactatggat tcgaattctg cacgcgatgt    120

gtcatcgatc aacgtgctga tttatgacga tataggagcc gcgagtcaaa gcgggcttgt    180

cggacaagag caggaggttg gcaccgttat gagtccgcgt ccagaacatg ccactgctgt    240

aaccgttgag aatgaaacag gagagtcgca tacgtccccg ccgcctgaag aaatccccca    300

tgcgcgtggt ccaccagtgg taggtgtgga ggacatgggg ctgcagaacg ggaggggcat    360

cgagatgtct cttgcaacga atgccgcgcc agacagcgat gagtctggaa acaaacccga    420

gcaggtgaca ggggattctg gtgccaagag caataccggt ggagatgctg atggggatgg    480

ggacattgtt ctggacgatg ttacgggcaa gggagttgat caaggacagg ccggcccaga    540

atcagaagaa cggcagcaag agcaacaacg accatcggaa acggataccc ctacagatta    600

attaattgat taattgcaaa actaatctaa tctgacgggt tgtgatgacc atgacacgga    660

atttaatgac ttgaaaagca attacttttc tatacaagtc tccagacatg accaattctg    720

aataatagtc aagtcgtata ttagctaatt caaacatagg ctgtattaga ctgctcaaac    780

actttatatt cagttaatgt aaactaggat atctgatttt ttcctccccg acaagttaac    840

atgcaaagtt cactccatag atcgacacta caaatatacg taattcatat gatagaaccg    900

gttcaaggaa accctcccat cttctttttg atgaatcttg aaaccctcta acagactcca    960

tgtgatagtt tattcttggg tcatggtgta gatacaaaat accaattagg taaacaagac   1020

tgagttaatc acgtgacctc gcgccaccga ccccgcgtct ctgacgcgcc aggcagcctc   1080

atctcatttc ggtaagaagc tacctgcacc gccttcaaac cggacggacg gttgagagga   1140

gagagagcac atcaaagctt tctcctactc agcgttcatt cctcagagag agctggtcaa   1200

gatgtaagtt ttctatcttc gtccctttat gagacaaaaa acaaagaaga aagtctgttg   1260

ctaactccgt taggtgtaag tttttctgga cataacggct ttagggaatt ggaactctgg   1320

tctgatactc ttgcagcgag aatcgacaag ctttccattc ttgggtgggt cttctttttc   1380

tcgattcgac gacgtggttt gttatagatc taacgagtcg atgtagtgta cgttcgttcg   1440

acaataccag gagcgagacc atccagttcc acacgccttt gaccttgatc gttggatata   1500

atgggtcggg aaagactgta cgtgggagaa ttgctctctg tcttgatatg tgcttacaca   1560

tcccagacga tcattgaatg cctcaaatat gccaccactg gcgagctacc gcccaacagc   1620

aagggcggag ccttcatcca cgatcccaag gtgcgcacct ttgacctttg gagccgacgt   1680
```

-continued

```
ttgctaaaat taggatatag ctatgtggag aaaaggaggt tcttgcccaa gtgaagctcg   1740
cgttcaagag tacgtcgggg gctaagatgg tggcgacccg gagtttgcag ctcacagtga   1800
agaagacaac gcgacagcag aaaactctgg agggccagct cttgatggtc aaggatggcg   1860
aaaggactgc gatctcttcc cgtgttgcgg agctggacca gattatgccc cagtaccttg   1920
gtgtttctaa agcgatcctc gactcggtca tattctgcca ccaggacgaa agtctctggc   1980
cgatgagtga gccttctgtt ctaaagaaaa aatttgatga gattttcgaa gccatgaaat   2040
acaccaaggc tatcgagaac atcaaagctc taaggaagaa acaaaaacgaa gagcttgcaa   2100
aatacaaaat tatggagcag cacgcgaaag aggacaagga taaagccgat cgtgctgaaa   2160
agagatcgat caagcttcag gaggagatcg aggccttgcg cgaagagaca cataaactct   2220
cgcaggagat gcggcaagct gctgagttgg ccgacaaagc ttggaaggaa tcagagagct   2280
acgctcaaat tatcggtgcc ctggaaggaa agcgtattga ggctaagagc atccagacga   2340
gtatcgataa cttaaagcgg catctggttg aagtcgacga accagacgaa tggctccagt   2400
cgactttgga gcagttcgag tctaggcaga tccagctcca gaaccaggag gaagaacaga   2460
aggaaaggta tatgaatatc aaggaacaga tcgcgagagc ccggcgacag ctgggtttga   2520
agcaggccga atgcggcaag ttcgaaaatg acaaagcaca gtttgagcga caggtggaaa   2580
gaagggaaaa tatgatcaag gaaatcgcgc gtcgaaataa tatccgcggg tttgacgaca   2640
ctcttgacga aacccagatt gatgaattca tgcagaggat gcggaaactt gtcaaggatc   2700
acaaccaagc cctagagcgc accagaaagg aggggcaggc cgagctgcga gaaacgcaaa   2760
atattctcaa ccagattgca cagcgcaaat ctgcgcttca ggaaagcaag aatgttgcaa   2820
gaaggcaaat ttcagagtat gacaaagagg catcaaagta tcaaaccaga cttgacgaga   2880
tcgacgtcga tgagggaaca atcgctgttc tcgaatccaa aaaagaaagt gtcgaggctc   2940
gcttaagtaa actcaaagag actgcacgca ctgcttcttg ggacaaggaa atccaaaatg   3000
ccaatgccga gctcaagtcc ctcgaggacg agagctcccg gctgaacgca gagctcatag   3060
cgggaacaaa aaaggaccgg agatctagct cgcttggatc atctgaagaa ggagctcaaa   3120
gatcgcgagc gtcaattgga gactatgaag ggagcacatg gggataggct ggccaagctc   3180
ataagcccaa gttggcatcc tgagacttta gagcaagatt tccaaaagac tctagaggaa   3240
gaatctaggt ctctgacgct tgcagagcgt gatcgtgatg gagttggaag gggctggaa    3300
catgtggagt tcaagctcaa gaacgtcagg aaagaactga gacagcggca gaaagagctt   3360
gacgaatgcg ttaaaaggat tcgtgaggcg atcgatgatg agccttccga gtatcctgac   3420
gttgtcaaac aacgccaagc acagctagat atggctaaaa gggacgcaga ccagtatgct   3480
gggatgggtg aatatctcaa taaatgtttg gaagcagcga aacagagaaa ggtttgcaga   3540
acctgtgcaa ggccgttcaa gacagaagca gaattccagg cgttcaaaaa taaattggaa   3600
gcgcttgtca agaaggccac ccaagatgcc gaggatgaaa atctgcagca actcgaagag   3660
gacctggaaa atgcgcgagc agctagtact gattacgata catgggttcg cctgtctcag   3720
actgatatcc cgggccttga gaaggaagaa gagcaatgtg aatctcagag ggaagggctc   3780
ttggctaaga tcgaagaaca cgacaatatt gttagtgagc ggatggacaa gaagagagag   3840
gttgagtctc ttaccaaaac ggtggcgtcg attgttcgat atgacggcga aatcaagtct   3900
cttcgatctc aaatccagga tcttacttcg aaacagcaag attcagattc ttcacggact   3960
ctggaggaca ttcaagacga aattgctgcc gttggagaga agtctcgggc tgtcaagaaa   4020
accatatcga aacttactgc cgagaaggac cagtcgcgaa ctgacataaa caagctggaa   4080
```

-continued

```
ctagaattga gagacgtgca aagtagtctc gataacgcta gccaccagtt ggagaagaag   4140
tctggactcg ttgctcggat cgaagagtac aagaaattga ttgccaagca gcgggaggcc   4200
attgagaaag ccgacgaaga catcgagaag cttgctcccg aaatggcaaa agcccaagct   4260
aggcatgatg atatcagtca acgtgctgaa gctagagaga gggagctgca gcaaactcta   4320
tcgcacctgt ctgaaagcct gcatcagctg aaccttgcaa atgaggagat caagtcctac   4380
aatgaccgag gggggccaga tcaattagcc aagagcagga atgacttgag agcgattgag   4440
gaagagatca actccctcga agcagaacag gccaatatca cgcgggagat aaacaaaatc   4500
tcggctcagt tgaaggatag tgagaatacc aaacggcagt attcggacaa tcttgcctac   4560
cgccaggcat gcagagcgct agagcaagtg caggcggaaa tcgaaaagct ggaggctcaa   4620
aacgcagaga ttgaccgtaa tcgctttaag gaagaatccg agcgctggac ccggaaacac   4680
aatgctctcg cggcacagca agcaagcaag atgggcgaga tgaagtccaa ggatgatcag   4740
ctcatgcagc tcttggcgga ctggaatacc gattataaag atgcggcaca gaagtacaag   4800
gaggctcata taaaagtgga aacgacaaag gcggctgttg aagacctggg tcgatatgga   4860
agcgcgcttg acaaggccat catgaagtac cacagcctaa agatggagga gattaaccgg   4920
atcatcgaag agctgtggca aaagacgtat agaggcaccg atgtagatac catccaaatc   4980
cgctccgaca atgaaaatgc caagggaaac cggtcttata actaccgtgt tgtcatggtc   5040
aagcaaggtg ctgaaatgga catgcgtggc cgttgcagcg ctgggcaaaa ggtgcttgcc   5100
agtatcatta tccgtcttgc tcttgcagaa tgttttggcg ttaactgcgg acttattgcg   5160
cttgatgagc cgactacgaa ccttgaccgg gacaacattc ggtctctcgc tgaatcgctc   5220
cacgacatca ttaaggctcg tcagcagcag gctaatttcc agctgattgt cattactcac   5280
gacgaagaat ttctgcatca tatgcagtgc ggagacttca gtgactatta ttaccgagtg   5340
tcaaggaacg agaagcagaa atcgatcatt gagaggcagt ctatcgctga ggtgtgtctt   5400
ctgttgagaa attatatcat tgtatggact aactgacaag aataggttat gtgatattgc   5460
gtacgatttt acctgccact ctattccgtc ttccgagttt cttaggaggc cagggcggtt   5520
gtccttgata gcttctgaaa gttgttagtc gaaccttggt atttacgtta tcattgtata   5580
gatagagtgc tccactggag ttagggcgtt ccggttatct gcagctggat ataatgggaa   5640
tatagatgag aatgaaccac atcgtacagt acgttactct ggtctttaca tgtagtggca   5700
tacgtaagga aaagcacttg cgtttttttt tttgaattct ttttccaaca aagaagcaga   5760
gcttcttaat gcgtgagact aaactatacg atgtatcaag gtaagggcag ccggggtttc   5820
acaacaaact acacggtaca gtgtacctca tccctacaga tcgtcctctc ctccgtcatc   5880
accatcatca tactcttctc ccacttccct atcgtcgttg tcctcctcct cctcatcatc   5940
gaccaacggc acaaaccgga agtcgacgaa gctcacgttg ctgccgaagc cgccactcgg   6000
cagcggcaca cctcccgaag aagctccatt gttgctgtca ttatttcccc cgagctcgat   6060
catgaattgc agactcagca cgccctgtat gtcgccgcga atgctgactt tgctggcgac   6120
ggccattgcg cgggcggctt tgcggattag agagaagcgg tagttttgtt tgacgcgact   6180
gcccatggat gacggtgggt tgacgaggaa ggtctccgtt actgtaggag cgagcttgga   6240
cttcttcttc gaaggctggg gtctaccgtc cccagttagg actttgtaat gggtgtgaga   6300
tagcgagctt ccactgccct cgccgtcttt ttctatcgag aactcgacgg tggactcgct   6360
gaacgggcca ccagagccag agagtgcaaa gaacggttct cgcttggctg atgcggagat   6420
```

```
cgtgaggatg tttgggttcg tcgcatctag ttcggttatg gcattgtgca gccacgctga   6480

tcgcatgatg atcttcatta ttatcgcatc gcgttgcagc gggatgtcca gctcgccagc   6540

cgccgaaccg aaggaaggat cgtctgggtc gtaggtcgtg agttcgcagg tcgtcgttac   6600

gcccgcttcg gaaaggatga tgctgagagg actcccgaca tgggagtagc gcaatgtgca   6660

tgaccgattg agaagtaagg ccggggttgt gaaagcgtct gaacctgtgg ggttctgttg   6720

ttgcgcactt gttgctgctg cgaacgagtt actactcgct gacgtgttgt tatcgctgat   6780

gccgaaaatc tggagtgtct ccaggagagc ggaaagggag atcaagaaat ggggatataa   6840

tacgccggcg tccgagtcat catcgttgtc gttgttgtta ttattggggc cgggaggtgg   6900

gttgaagcta taagtcgtaa agagggcctt gtctagaaac gccaatccct gcat         6954


<210> SEQ ID NO 26
<211> LENGTH: 3813
<212> TYPE: DNA
<213> ORGANISM: Rasamsonia emersonii

<400> SEQUENCE: 26

atgggtcggg aaagactgta cgtgggagaa ttgctctctg tcttgatatg tgcttacaca     60

tcccagacga tcattgaatg cctcaaatat gccaccactg gcgagctacc gcccaacagc    120

aagggcggag ccttcatcca cgatcccaag ctatgtggag aaaaggaggt tcttgcccaa    180

gtgaagctcg cgttcaagag tacgtcgggg gctaagatgg tggcgacccg gagtttgcag    240

ctcacagtga agaagacaac gcgacagcag aaaactctgg agggccagct cttgatggtc    300

aaggatggcg aaaggactgc gatctcttcc cgtgttgcgg agctggacca gattatgccc    360

cagtaccttg gtgtttctaa agcgatcctc gactcggtca tattctgcca ccaggacgaa    420

agtctctggc cgatgagtga gccttctgtt ctaaagaaaa aatttgatga gattttcgaa    480

gccatgaaat acaccaaggc tatcgagaac atcaaagctc taaggaagaa acaaaacgaa    540

gagcttgcaa aatacaaaat tatggagcag cacgcgaaag aggacaagga taaagccgat    600

cgtgctgaaa agagatcgat caagcttcag gaggagatcg aggccttgcg cgaagagaca    660

cataaactct cgcaggagat gcggcaagct gctgagttgg ccgacaaagc ttggaaggaa    720

tcagagagct acgctcaaat tatcggtgcc ctggaaggaa agcgtattga ggctaagagc    780

atccagacga gtatcgataa cttaaagcgg catctggttg aagtcgacga accagacgaa    840

tggctccagt cgactttgga gcagttcgag tctaggcaga tccagctcca gaaccaggag    900

gaagaacaga aggaaaggta tatgaatatc aaggaacaga tcgcgagagc ccggcgacag    960

ctgggtttga agcaggccga atgcggcaag ttcgaaaatg acaaagcaca gtttgagcga   1020

caggtggaaa gaagggaaaa tatgatcaag gaaatcgcgc gtcgaaataa tatccgcggg   1080

tttgacgaca ctcttgacga aacccagatt gatgaattca tgcagaggat gcggaaactt   1140

gtcaaggatc acaaccaagc cctagagcgc accagaaagg aggggcaggc cgagctgcga   1200

gaaacgcaaa atattctcaa ccagattgca cagcgcaaat ctgcgcttca ggaaagcaag   1260

aatgttgcaa gaaggcaaat ttcagagtat gacaaagagg catcaaagta tcaaaccaga   1320

cttgacgaga tcgacgtcga tgagggaaca atcgctgttc tcgaatccaa aaaagaaagt   1380

gtcgaggctc gcttaagtaa actcaaagag actgcacgca ctgcttcttg ggacaaggaa   1440

atccaaaatg ccaatgccga gctcaagtcc ctcgaggacg agagctcccg gctgaacgca   1500

gagctcatag cgggaacaaa aaaggaccgg agatctagct cgcttggatc atctgaagaa   1560

ggagctcaaa gatcgcgagc gctggccaag ctcataagcc caagttggca tcctgagact   1620
```

```
ttagagcaag atttccaaaa gactctagag gaagaatcta ggtctctgac gcttgcagag   1680
cgtgatcgtg atggagttgg aagggggctg gaacatgtgg agttcaagct caagaacgtc   1740
aggaaagaac tgagacagcg gcagaaagag cttgacgaat gcgttaaaag gattcgtgag   1800
gcgatcgatg atgagccttc cgagtatcct gacgttgtca aacaacgcca agcacagcta   1860
gatatggcta aaagggacgc agaccagtat gctgggatgg gtgaatatct caataaatgt   1920
ttggaagcag cgaaacagag aaaggtttgc agaacctgtg caaggccgtt caagacagaa   1980
gcagaattcc aggcgttcaa aaataaattg gaagcgcttg tcaagaaggc cacccaagat   2040
gccgaggatg aaaatctgca gcaactcgaa gaggacctgg aaaatgcgcg agcagctagt   2100
actgattacg atacatgggt tcgcctgtct cagactgata tcccgggcct tgagaaggaa   2160
gaagagcaat gtgaatctca gagggaaggg ctcttggcta agatcgaaga acacgacaat   2220
attgttagtg agcggatgga caagaagaga gaggttgagt ctcttaccaa aacggtggcg   2280
tcgattgttc gatatgacgg cgaaatcaag tctcttcgat ctcaaatcca ggatcttact   2340
tcgaaacagc aagattcaga ttcttcacgg actctggagg acattcaaga cgaaattgct   2400
gccgttggag agaagtctcg ggctgtcaag aaaaccatat cgaaacttac tgccgagaag   2460
gaccagtcgc gaactgacat aaacaagctg gaactagaat tgagagacgt gcaaagtagt   2520
ctcgataacg ctagccacca gttggagaag aagtctggac tcgttgctcg gatcgaagag   2580
tacaagaaat tgattgccaa gcagcgggag gccattgaga aagccgacga agacatcgag   2640
aagcttgctc ccgaaatggc aaaagcccaa gctaggcatg atgatatcag tcaacgtgct   2700
gaagctagag agagggagct gcagcaaact ctatcgcacc tgtctgaaag cctgcatcag   2760
ctgaaccttg caaatgagga gatcaagtcc tacaatgacc gagggggggcc agatcaatta   2820
gccaagagca ggaatgactt gagagcgatt gaggaagaga tcaactccct cgaagcagaa   2880
caggccaata tcacgcggga gataaacaaa atctcggctc agttgaagga tagtgagaat   2940
accaaacggc agtattcgga caatcttgcc taccgccagg catgcagagc gctagagcaa   3000
gtgcaggcgg aaatcgaaaa gctggaggct caaaacgcag agattgaccg taatcgcttt   3060
aaggaagaat ccgagcgctg gacccggaaa cacaatgctc tcgcggcaca gcaagcaagc   3120
aagatgggcg agatgaagtc caaggatgat cagctcatgc agctcttggc ggactggaat   3180
accgattata aagatgcggc acagaagtac aaggaggctc atataaaagt ggaaacgaca   3240
aaggcggctg ttgaagacct gggtcgatat ggaagcgcgc ttgacaaggc catcatgaag   3300
taccacagcc taaagatgga ggagattaac cggatcatcg aagagctgtg gcaaaagacg   3360
tatagaggca ccgatgtaga taccatccaa atccgctccg acaatgaaaa tgccaaggga   3420
aaccggtctt ataactaccg tgttgtcatg gtcaagcaag gtgctgaaat ggacatgcgt   3480
ggccgttgca gcgctgggca aaaggtgctt gccagtatca ttatccgtct tgctcttgca   3540
gaatgttttg gcgttaactg cggacttatt gcgcttgatg agccgactac gaaccttgac   3600
cgggacaaca ttcggtctct cgctgaatcg ctccacgaca tcattaaggc tcgtcagcag   3660
caggctaatt tccagctgat tgtcattact cacgacgaag aatttctgca tcatatgcag   3720
tgcggagact tcagtgacta ttattaccga gtgtcaagga acgagaagca gaaatcgatc   3780
attgagaggc agtctatcgc tgaggttatg tga                                3813
```

<210> SEQ ID NO 27
<211> LENGTH: 1270
<212> TYPE: PRT

<213> ORGANISM: Rasamsonia emersonii

<400> SEQUENCE: 27

Met Gly Arg Glu Arg Leu Tyr Val Gly Glu Leu Leu Ser Val Leu Ile
1               5                   10                  15

Cys Ala Tyr Thr Ser Gln Thr Ile Ile Glu Cys Leu Lys Tyr Ala Thr
            20                  25                  30

Thr Gly Glu Leu Pro Pro Asn Ser Lys Gly Gly Ala Phe Ile His Asp
        35                  40                  45

Pro Lys Leu Cys Gly Glu Lys Glu Val Leu Ala Gln Val Lys Leu Ala
    50                  55                  60

Phe Lys Ser Thr Ser Gly Ala Lys Met Val Ala Thr Arg Ser Leu Gln
65                  70                  75                  80

Leu Thr Val Lys Lys Thr Thr Arg Gln Gln Lys Thr Leu Glu Gly Gln
                85                  90                  95

Leu Leu Met Val Lys Asp Gly Glu Arg Thr Ala Ile Ser Ser Arg Val
            100                 105                 110

Ala Glu Leu Asp Gln Ile Met Pro Gln Tyr Leu Gly Val Ser Lys Ala
        115                 120                 125

Ile Leu Asp Ser Val Ile Phe Cys His Gln Asp Glu Ser Leu Trp Pro
    130                 135                 140

Met Ser Glu Pro Ser Val Leu Lys Lys Lys Phe Asp Glu Ile Phe Glu
145                 150                 155                 160

Ala Met Lys Tyr Thr Lys Ala Ile Glu Asn Ile Lys Ala Leu Arg Lys
                165                 170                 175

Lys Gln Asn Glu Glu Leu Ala Lys Tyr Lys Ile Met Glu Gln His Ala
            180                 185                 190

Lys Glu Asp Lys Asp Lys Ala Asp Arg Ala Glu Lys Arg Ser Ile Lys
        195                 200                 205

Leu Gln Glu Glu Ile Glu Ala Leu Arg Glu Glu Thr His Lys Leu Ser
    210                 215                 220

Gln Glu Met Arg Gln Ala Ala Glu Leu Ala Asp Lys Ala Trp Lys Glu
225                 230                 235                 240

Ser Glu Ser Tyr Ala Gln Ile Ile Gly Ala Leu Glu Gly Lys Arg Ile
                245                 250                 255

Glu Ala Lys Ser Ile Gln Thr Ser Ile Asp Asn Leu Lys Arg His Leu
            260                 265                 270

Val Glu Val Asp Glu Pro Asp Glu Trp Leu Gln Ser Thr Leu Glu Gln
        275                 280                 285

Phe Glu Ser Arg Gln Ile Gln Leu Gln Asn Gln Glu Glu Glu Gln Lys
    290                 295                 300

Glu Arg Tyr Met Asn Ile Lys Glu Gln Ile Ala Arg Ala Arg Arg Gln
305                 310                 315                 320

Leu Gly Leu Lys Gln Ala Glu Cys Gly Lys Phe Glu Asn Asp Lys Ala
                325                 330                 335

Gln Phe Glu Arg Gln Val Glu Arg Arg Glu Asn Met Ile Lys Glu Ile
            340                 345                 350

Ala Arg Arg Asn Asn Ile Arg Gly Phe Asp Asp Thr Leu Asp Glu Thr
        355                 360                 365

Gln Ile Asp Glu Phe Met Gln Arg Met Arg Lys Leu Val Lys Asp His
    370                 375                 380

Asn Gln Ala Leu Glu Arg Thr Arg Lys Glu Gly Gln Ala Glu Leu Arg
385                 390                 395                 400

```
Glu Thr Gln Asn Ile Leu Asn Gln Ile Ala Gln Arg Lys Ser Ala Leu
                405                 410                 415

Gln Glu Ser Lys Asn Val Ala Arg Arg Gln Ile Ser Glu Tyr Asp Lys
            420                 425                 430

Glu Ala Ser Lys Tyr Gln Thr Arg Leu Asp Glu Ile Asp Val Asp Glu
        435                 440                 445

Gly Thr Ile Ala Val Leu Glu Ser Lys Lys Glu Ser Val Glu Ala Arg
    450                 455                 460

Leu Ser Lys Leu Lys Glu Thr Ala Arg Thr Ala Ser Trp Asp Lys Glu
465                 470                 475                 480

Ile Gln Asn Ala Asn Ala Glu Leu Lys Ser Leu Glu Asp Glu Ser Ser
                485                 490                 495

Arg Leu Asn Ala Glu Leu Ile Ala Gly Thr Lys Lys Asp Arg Arg Ser
            500                 505                 510

Ser Ser Leu Gly Ser Ser Glu Glu Gly Ala Gln Arg Ser Arg Ala Leu
        515                 520                 525

Ala Lys Leu Ile Ser Pro Ser Trp His Pro Glu Thr Leu Glu Gln Asp
    530                 535                 540

Phe Gln Lys Thr Leu Glu Glu Glu Ser Arg Ser Leu Thr Leu Ala Glu
545                 550                 555                 560

Arg Asp Arg Asp Gly Val Gly Arg Gly Leu Glu His Val Glu Phe Lys
                565                 570                 575

Leu Lys Asn Val Arg Lys Glu Leu Arg Gln Arg Gln Lys Glu Leu Asp
            580                 585                 590

Glu Cys Val Lys Arg Ile Arg Glu Ala Ile Asp Asp Glu Pro Ser Glu
        595                 600                 605

Tyr Pro Asp Val Val Lys Gln Arg Gln Ala Gln Leu Asp Met Ala Lys
    610                 615                 620

Arg Asp Ala Asp Gln Tyr Ala Gly Met Gly Glu Tyr Leu Asn Lys Cys
625                 630                 635                 640

Leu Glu Ala Ala Lys Gln Arg Lys Val Cys Arg Thr Cys Ala Arg Pro
                645                 650                 655

Phe Lys Thr Glu Ala Glu Phe Gln Ala Phe Lys Asn Lys Leu Glu Ala
            660                 665                 670

Leu Val Lys Lys Ala Thr Gln Asp Ala Glu Asp Glu Asn Leu Gln Gln
        675                 680                 685

Leu Glu Glu Asp Leu Glu Asn Ala Arg Ala Ala Ser Thr Asp Tyr Asp
    690                 695                 700

Thr Trp Val Arg Leu Ser Gln Thr Asp Ile Pro Gly Leu Glu Lys Glu
705                 710                 715                 720

Glu Glu Gln Cys Glu Ser Gln Arg Glu Gly Leu Leu Ala Lys Ile Glu
                725                 730                 735

Glu His Asp Asn Ile Val Ser Glu Arg Met Asp Lys Lys Arg Glu Val
            740                 745                 750

Glu Ser Leu Thr Lys Thr Val Ala Ser Ile Val Arg Tyr Asp Gly Glu
        755                 760                 765

Ile Lys Ser Leu Arg Ser Gln Ile Gln Asp Leu Thr Ser Lys Gln Gln
    770                 775                 780

Asp Ser Asp Ser Ser Arg Thr Leu Glu Asp Ile Gln Asp Glu Ile Ala
785                 790                 795                 800

Ala Val Gly Glu Lys Ser Arg Ala Val Lys Lys Thr Ile Ser Lys Leu
                805                 810                 815

Thr Ala Glu Lys Asp Gln Ser Arg Thr Asp Ile Asn Lys Leu Glu Leu
```

```
            820                 825                 830

Glu Leu Arg Asp Val Gln Ser Ser Leu Asp Asn Ala Ser His Gln Leu
        835                 840                 845

Glu Lys Lys Ser Gly Leu Val Ala Arg Ile Glu Glu Tyr Lys Lys Leu
    850                 855                 860

Ile Ala Lys Gln Arg Glu Ala Ile Glu Lys Ala Asp Glu Asp Ile Glu
865                 870                 875                 880

Lys Leu Ala Pro Glu Met Ala Lys Ala Gln Ala Arg His Asp Asp Ile
                885                 890                 895

Ser Gln Arg Ala Glu Ala Arg Glu Arg Glu Leu Gln Gln Thr Leu Ser
            900                 905                 910

His Leu Ser Glu Ser Leu His Gln Leu Asn Leu Ala Asn Glu Glu Ile
        915                 920                 925

Lys Ser Tyr Asn Asp Arg Gly Gly Pro Asp Gln Leu Ala Lys Ser Arg
    930                 935                 940

Asn Asp Leu Arg Ala Ile Glu Glu Glu Ile Asn Ser Leu Glu Ala Glu
945                 950                 955                 960

Gln Ala Asn Ile Thr Arg Glu Ile Asn Lys Ile Ser Ala Gln Leu Lys
                965                 970                 975

Asp Ser Glu Asn Thr Lys Arg Gln Tyr Ser Asp Asn Leu Ala Tyr Arg
            980                 985                 990

Gln Ala Cys Arg Ala Leu Glu Gln  Val Gln Ala Glu Ile  Glu Lys Leu
        995                  1000                 1005

Glu Ala  Gln Asn Ala Glu Ile  Asp Arg Asn Arg Phe  Lys Glu Glu
    1010                 1015                 1020

Ser Glu  Arg Trp Thr Arg Lys  His Asn Ala Leu Ala  Ala Gln Gln
    1025                 1030                 1035

Ala Ser  Lys Met Gly Glu Met  Lys Ser Lys Asp Asp  Gln Leu Met
    1040                 1045                 1050

Gln Leu  Leu Ala Asp Trp Asn  Thr Asp Tyr Lys Asp  Ala Ala Gln
    1055                 1060                 1065

Lys Tyr  Lys Glu Ala His Ile  Lys Val Glu Thr Thr  Lys Ala Ala
    1070                 1075                 1080

Val Glu  Asp Leu Gly Arg Tyr  Gly Ser Ala Leu Asp  Lys Ala Ile
    1085                 1090                 1095

Met Lys  Tyr His Ser Leu Lys  Met Glu Glu Ile Asn  Arg Ile Ile
    1100                 1105                 1110

Glu Glu  Leu Trp Gln Lys Thr  Tyr Arg Gly Thr Asp  Val Asp Thr
    1115                 1120                 1125

Ile Gln  Ile Arg Ser Asp Asn  Glu Asn Ala Lys Gly  Asn Arg Ser
    1130                 1135                 1140

Tyr Asn  Tyr Arg Val Val Met  Val Lys Gln Gly Ala  Glu Met Asp
    1145                 1150                 1155

Met Arg  Gly Arg Cys Ser Ala  Gly Gln Lys Val Leu  Ala Ser Ile
    1160                 1165                 1170

Ile Ile  Arg Leu Ala Leu Ala  Glu Cys Phe Gly Val  Asn Cys Gly
    1175                 1180                 1185

Leu Ile  Ala Leu Asp Glu Pro  Thr Thr Asn Leu Asp  Arg Asp Asn
    1190                 1195                 1200

Ile Arg  Ser Leu Ala Glu Ser  Leu His Asp Ile Ile  Lys Ala Arg
    1205                 1210                 1215

Gln Gln  Gln Ala Asn Phe Gln  Leu Ile Val Ile Thr  His Asp Glu
    1220                 1225                 1230
```

```
Glu Phe  Leu His His Met Gln  Cys Gly Asp Phe Ser  Asp Tyr Tyr
    1235                 1240                 1245

Tyr Arg  Val Ser Arg Asn Glu  Lys Gln Lys Ser Ile  Ile Glu Arg
    1250                 1255                 1260

Gln Ser  Ile Ala Glu Val Met
    1265                 1270


<210> SEQ ID NO 28
<211> LENGTH: 4322
<212> TYPE: DNA
<213> ORGANISM: Rasamsonia emersonii

<400> SEQUENCE: 28

atcttactcc tgtcaagcct gttccctttt catctttttt taatcaggcc gccgagacct     60

tctactgaca aactcatcac acataaatcc cacggccctc tggttcgaac cacacaaaaa    120

gcggacaaag ctaagtcttc gctcttcaca aagagaacaa acttcaccat gaagttctgg    180

gatggttggg aggcatggga gaagatggtt tttgtatggc tatgactgct cgcaatatcc    240

aatgccattt caatttgcta accactgaga aatgagacag atccttggct gcgccatagt    300

aatcaaccac accaccacat tacaaccgtg ctgctaacaa tgttaggtta ttgtcatcgt    360

cattgccttt ggtgttctga gctatagcag gtggagactc aggaagtatg ctagagcaca    420

gtcataccag gtggccgagc gtgcgagggg cgtggatttg aacgaaatgt tgatagatga    480

cgtccctttt ggtgcaaggg cactcgagag tggagtacgg gttgagggta tctggactcc    540

aaaccacaac acgccgtcgc caaacgtcag cccatatcta tcctgtactc cagtgggaag    600

cagaccacca agtccacctc tacgtctgcc acgtccagag cagcggcctt tggcctaccc    660

ttctctgcct caagtgaaca gctactcacc gaaacggagc tcagatgtct cacttatcaa    720

caacaataca atgcttccat agagctcttg catggggagc gagttcgcgg gaaagagatc    780

ggcctagaca gaatagttgg acggtcaact gaagacattg ccatcttacc agaaacactg    840

ttatgtttca agggaaaata cgcatggtgg attgtactgg gcattgaact gggggcgttg    900

atgagtcgag aagataaaga cttggcgtga tccagaagtc actacggagt acatgagatt    960

gatagcattg atggaacgtc aataatcatg acagttggaa ctttagctct tccaagaatc   1020

tgaaaactaa aaatcagtgt aaagcctttt aaacgacgta aaaagcattg tttttctgga   1080

ttaagtagat ttgtcataac tttctgtgta cagccgttag gtaaacagtg gttgcggaaa   1140

taatgttctt gtttccggtt tgttatcttc acgtgatgtc gcgacgtggc gacgcctcgg   1200

acgcgtccat gtcctctccc gatgaccaca attagtgacc ccaacaatca ggggcattac   1260

caagtcctag agactagagc tgaataatca tttcttcatc aatcgtctca tgcagtgatc   1320

tgtggagaat tacctggctt tgaattcctg cttttgctat tccatttgag aaccatcacg   1380

agaatcgtct ggccctgatt gcgtcgagtc tcggataacc cctcaccact cgcatattcg   1440

tccagcacac ccacctcttt gcaccattcc ccgttattga cagcggccgg accaagcgat   1500

atggctgccg acgaagaaac gcagaatgaa tatgatgaca atgggcttcc tggccctggg   1560

gcgcctactc ctatcacggc cctcgaggta aacaaaccga ctgatcagga gagattgggg   1620

aattctgggg tagtctcaaa gtgaattagt attaggaggc taacatgtcc tttgcagggt   1680

gttgctggct taacggcgag agacatcaag ctcataatcg atgcaggttt tcataccgtg   1740

gaagcggtag catacacgta cgtctctata tcaatttcct atactttttg tcgtgttcta   1800

tagatgtctt gaagggtaat tttgaatttt gtactgacag agttacctct acatagaccg   1860
```

aaacgggtac tggagcagat taagggtatc tcagaacaga aagccgcgaa gattttggct 1920
gagggtgagt aactcgcaga ggcaaaaagt ttgcatgcat ttccttggag acaacattga 1980
agctcattta attttttcc cttgaattag catctaagct agttccaatg ggcttcacga 2040
cggccacgga gatgcacgca cgccggagcg agctcatatg tatcaccact ggttcgaaac 2100
aactggacac cctactggca ggaggcattg agacagggtc gatcacagaa atattcggag 2160
aattcaggac tggaaagagt cagatttgtc atacacttgc tgtaacgtgc caattaccgt 2220
tcgacatggg cggaggagaa ggaaagtgtc tgtatatcga taccgagggc acgttccgac 2280
cagttaggtt gctggccgtt gctcagcggt acggattggt tggagaagag gtcctggata 2340
acgttgccta cgctcgagca tacaattcgg accatcaact gcagttgctg aatcaagcat 2400
ctcaaatgat gaccgagaca cgcttctcac ttctcattgt cgactcagcc acatctctct 2460
atcgaacgga cttcaatggt cgcggtgaat tgtcctctcg tcaaactcat ctcgccaaat 2520
tcctccgtac cttacagcgg ttggcagatg agttcggtat tgctgtggtt atcaccaacc 2580
aagtggtctc tcaagtcgat ggaggcccca gttctatgtt caaccctgac ccgaagaaac 2640
caataggagg gaacatcatt gcacatgcga gcacaaccag gctgagcctg aagaagggtc 2700
gcggggaaac taggatttgt aagatctatg acagtccctg tctccccgaa agcgactgta 2760
tgttcgcgat cagagaggat gggattggtg accccagccc taaggatctg gagggcgagt 2820
gagacacctt tgtacctgcg ctcgtctgac atgatttcga tcacgagcaa tgcttacgaa 2880
ctgtcttttg ttgctgtgta ttctgtgtct ttccatctcg catagcagcc ggtgctggga 2940
ttgaagaagt cattgcatta gtcagttttt gttttttttt tttaattttt gctgttgata 3000
tgtgttcgct tctattcatg acgaaaaaat atatcactga ttgtacttaa gattaatgag 3060
aaatacgagg aatgctagag ataagatgtt tgtagtgaat gaatagattt aaatctgcaa 3120
ggcaaactcc gcctgtttga gcttggcgtt gcttcggtac cctgcgcgta ctccgtaagc 3180
gcgcgctaac agtttttcgg agctcccagc tgcccgccct ttgtataaca agacttcgcg 3240
caccgcaaga ccaaccaccg tgagcatggg cttctaaatg tgacacccct ctgagccgtg 3300
gattcctcca gcctcctcaa tgaccatggc caaaatttac aaggaaacta aagtcgacgt 3360
ccggcccatc gcgccgaatg ccgtcgtcga catccagatt ccgacgcagg agaacgccca 3420
gcgtcgggcc cgattctcga tttcttcagt gacggcgcaa gatatcccca gtatcaagga 3480
cgaggacgat ttcgcgagac gatttctagc aacacaaggc tcactttatt tccgacgacg 3540
gaaagtctat cctcgaacgt ttctgtggag agtcgtcgat gacaacaagg tcctggagat 3600
tcaatctgcg gacttggtga ggggtggcat tgagcaccat gaagtgaatc tcatgctccg 3660
gtttgatttc caggaggcga ttctgccttc aggagtcgca ctggcagata cggaggaaca 3720
cgaggtgctg aatgtcttcg tgctcacggc ttccaggcgt cttcatactc tagctctgcg 3780
accggagttc tttcgacggg cttccgcgat cgatgaaaat atcctagact ggtgcaaagc 3840
gtgtacaccg tcgccactga ccttctcgca tcctcatcgc cttcacgcga gcagtaccac 3900
ggagctattc atctcgttgg acagtggggc gctgcttcgg ttgactagga gagctggcga 3960
cgatggtaca gtttcttctg ttactataca caaaagtgtg ggtgacgttt gctgacttct 4020
gctgggttga aaggttcaca ctggtcccaa ataactttcg atgaaaaggg ctggggtgct 4080
tcgcttcgtg gtcttatgaa atggggcaca caaccgacaa tccgctataa cgggcgcagc 4140
ctcgatcaga atacaccgaa tgccattgct acgacatctg atcagaccta tgtcttcgcg 4200

-continued gtttgtttga atcacactct aaaggtttgg aatctcgcaa cgaacaaact ggttggttcg 4260
aaggatctcc tcgaccgtca ggtacagcag caggactcag cagcgtactt tttgaacccg 4320
tc 4322

<210> SEQ ID NO 29
<211> LENGTH: 1035
<212> TYPE: DNA
<213> ORGANISM: Rasamsonia emersonii

<400> SEQUENCE: 29
atggctgccg acgaagaaac gcagaatgaa tatgatgaca atgggcttcc tggccctggg 60
gcgcctactc ctatcacggc cctcgagggt gttgctggct taacggcgag agacatcaag 120
ctcataatcg atgcaggttt tcataccgtg gaagcggtag catacacacc gaaacgggta 180
ctggagcaga ttaagggtat ctcagaacag aaagccgcga agattttggc tgaggttcca 240
atgggcttca cgacggccac ggagatgcac gcacgccgga gcgagctcat atgtatcacc 300
actggttcga aacaactgga caccctactg gcaggaggca ttgagacagg gtcgatcaca 360
gaaatattcg gagaattcag gactggaaag agtcagattt gtcatacact tgctgtaacg 420
tgccaattac cgttcgacat gggcggagga gaaggaaagt gtctgtatat cgataccgag 480
ggcacgttcc gaccagttag gttgctggcc gttgctcagc ggtacggatt ggttggagaa 540
gaggtcctgg ataacgttgc ctacgctcga gcatacaatt cggaccatca actgcagttg 600
ctgaatcaag catctcaaat gatgaccgag acacgcttct cacttctcat tgtcgactca 660
gccacatctc tctatcgaac ggacttcaat ggtcgcggtg aattgtcctc tcgtcaaact 720
catctcgcca aattcctccg taccttacag cggttggcag atgagttcgg tattgctgtg 780
gttatcacca accaagtggt ctctcaagtc gatggaggcc ccagttctat gttcaaccct 840
gacccgaaga aaccaatagg agggaacatc attgcacatg cgagcacaac caggctgagc 900
ctgaagaagg gtcgcgggga aactaggatt tgtaagatct atgacagtcc ctgtctcccc 960
gaaagcgact gtatgttcgc gatcagagag gatgggattg gtgaccccag ccctaaggat 1020
ctggagggcg agtga 1035

<210> SEQ ID NO 30
<211> LENGTH: 344
<212> TYPE: PRT
<213> ORGANISM: Rasamsonia emersonii

<400> SEQUENCE: 30

Met Ala Ala Asp Glu Glu Thr Gln Asn Glu Tyr Asp Asp Asn Gly Leu
1 5 10 15

Pro Gly Pro Gly Ala Pro Thr Pro Ile Thr Ala Leu Glu Gly Val Ala
20 25 30

Gly Leu Thr Ala Arg Asp Ile Lys Leu Ile Ile Asp Ala Gly Phe His
35 40 45

Thr Val Glu Ala Val Ala Tyr Thr Pro Lys Arg Val Leu Glu Gln Ile
50 55 60

Lys Gly Ile Ser Glu Gln Lys Ala Ala Lys Ile Leu Ala Glu Val Pro
65 70 75 80

Met Gly Phe Thr Thr Ala Thr Glu Met His Ala Arg Arg Ser Glu Leu
85 90 95

Ile Cys Ile Thr Thr Gly Ser Lys Gln Leu Asp Thr Leu Leu Ala Gly
100 105 110

```
Gly Ile Glu Thr Gly Ser Ile Thr Glu Ile Phe Gly Glu Phe Arg Thr
        115                 120                 125

Gly Lys Ser Gln Ile Cys His Thr Leu Ala Val Thr Cys Gln Leu Pro
    130                 135                 140

Phe Asp Met Gly Gly Gly Glu Gly Lys Cys Leu Tyr Ile Asp Thr Glu
145                 150                 155                 160

Gly Thr Phe Arg Pro Val Arg Leu Leu Ala Val Ala Gln Arg Tyr Gly
                165                 170                 175

Leu Val Gly Glu Glu Val Leu Asp Asn Val Ala Tyr Ala Arg Ala Tyr
            180                 185                 190

Asn Ser Asp His Gln Leu Gln Leu Leu Asn Gln Ala Ser Gln Met Met
        195                 200                 205

Thr Glu Thr Arg Phe Ser Leu Leu Ile Val Asp Ser Ala Thr Ser Leu
    210                 215                 220

Tyr Arg Thr Asp Phe Asn Gly Arg Gly Glu Leu Ser Ser Arg Gln Thr
225                 230                 235                 240

His Leu Ala Lys Phe Leu Arg Thr Leu Gln Arg Leu Ala Asp Glu Phe
                245                 250                 255

Gly Ile Ala Val Val Ile Thr Asn Gln Val Val Ser Gln Val Asp Gly
            260                 265                 270

Gly Pro Ser Ser Met Phe Asn Pro Asp Pro Lys Lys Pro Ile Gly Gly
        275                 280                 285

Asn Ile Ile Ala His Ala Ser Thr Thr Arg Leu Ser Leu Lys Lys Gly
    290                 295                 300

Arg Gly Glu Thr Arg Ile Cys Lys Ile Tyr Asp Ser Pro Cys Leu Pro
305                 310                 315                 320

Glu Ser Asp Cys Met Phe Ala Ile Arg Glu Asp Gly Ile Gly Asp Pro
                325                 330                 335

Ser Pro Lys Asp Leu Glu Gly Glu
            340


<210> SEQ ID NO 31
<211> LENGTH: 5101
<212> TYPE: DNA
<213> ORGANISM: Rasamsonia emersonii

<400> SEQUENCE: 31

tctgatatcg gttccccgct gacatgttat tcgacctgta gtgcaaggcg ctctcgaatg      60

gctcgaagcc aaccaagata aatctctcga agaaattaag gcggccgaat cacgttcaga     120

agagacacag gagggacctc cgctcaaaga gggtgaacag cctcgaagtc tcgtttgcaa     180

cgagtgcgga aagaaattca ggagccaagc acaggctgaa ttccatgcat ccaagacaga     240

gcatgtcgat ttttcggaat caacggaaga gattgctccc ctaacggagg aggagaaaaa     300

ggcgaaactg gcagaattac gggagaaact cgcggcgaaa cgagcaatgc aatcggagca     360

aaacaagctg aaccagaaga gaaacgaggt aaatacacca agctgtcact aacgacacgc     420

ttttccactt ttacttacca ttcgctagga aatccggcgg aagagcacca aggaggctca     480

agacatcaga gaagaactac agaagaagga gctgatgagg gaggcagcca agaaacggaa     540

agagaagcaa gaagaactcg aagcgaagca gaaaatcagg gccaagatag ctgcagacaa     600

agaagagcgg agactgaaag ccgaaagaga gaaggctgag cgggcaggcc aggctccccc     660

accgcaacca gcagcacccg ctccaacgac gtctggaccg gtgacatcca aacctgcatc     720

cgcctacaca gaaactcgcc tgcggttcca gacgtccaaa ggaaacatta tgaagacctt     780
```

-continued

```
ccccgtggat acaacccttt tcgaggttgc cgccgccctc aacaaggacg aaggattgga    840
agttcagagt ttcacacaaa atttcccgaa aaagatcttc gacgccgaat atttcggtga    900
aacattgaag gagcttggtc tggtgcctag cgccagtctt attgtgaaat aatctaattg    960
ctctaactga tgacggcatg actatctgcg tgttttgatt catcgggaag agcgtagtat   1020
cgaatctaac gtggacgacg acatgataat caatttctac acctgaatta ttcgcgcttt   1080
tcgatttgaa attactacat aagcaatgtc tcgctagatc actccaaaag aaagcagtat   1140
tagagactgt atagtcaatt tggggaaggg atggaagagc caaaatagtc gtcatgagaa   1200
gcgtttctta tcttaagcta tttatcttaa gctatttaga gctctcttga ataaacatcg   1260
caaaagagat cttttagaat gcatgtgttg tcgtatacat gtactccgta gagcaagtgt   1320
ttccaattcg atcacgtgaa caggcgcccc gtcgtgttga tgacataagc agcatccgtc   1380
gcgtcgacac gtcggtgcct gtggagggcc gtgatagcgg gcaatcgcgt tgttaagagt   1440
tagatcagcc agcatcctct tgttgttgat gtccgccatt gtgctcttgg tccttacaaa   1500
atgcctgcgt aagtctgaat ttcatctgtt ctgatgagtt agtttttact aacttgtacc   1560
ttaacagtgt cggtgaccag caccgtgtag gaccgggtac tgtgatatca accatggctg   1620
gtaccgtctc tgcgaatcct ttcgaggaac caccccgtcg aattagcgaa tatactgctc   1680
aggaaattgc cactcttcaa tctcgccttg ataagcagct gggaccagag tacatctcct   1740
caagagccgg cccctctggg cagaaggtgc actacctagc ggcagagaaa tgtataaacc   1800
ttgcgaacga ggtctttgga ttcaatggct ggtccagttc gatccaaagt atacagatcg   1860
actttgtgag tgcaacaggt tggacgattg ttgagcaatg ggctgattgt cgggtactag   1920
gttgatgaga gtccaagcac gggtaagata agtctggggt tatccgtgat tgtgagagtc   1980
acattgaagg atggcacata tcatgaggta cgggagcgat atgtcacgtt atcatcggct   2040
ctgtggagga gactgactgt ggtggcttct aggatatcgg ctatggccat attgagaatt   2100
gcaaaggcaa agcggcagct tttgagaaag caaagaagga gggaacaaca gatgctctta   2160
aacgagctct gaggacattt ggcaatgttc tgggcaactg catctacgac aaagagtatc   2220
ttgccagagt cactagagtc aaagtggctc ctgtaagttc cattcccttc atgtctcttg   2280
atcagtctac taattaggag tagaccaagt gggatgtgga taaccttcat cgtcaccctg   2340
attacgcccc ggtcaaaaag gagcctgtcg aagacaagaa ggtctctgaa gataatgatc   2400
ttcctccccg tccaactgaa gcttccacga acaacgcgaa tccttcttct cccgcattcg   2460
acggagacgg cgaatttggc agtaagctct tcctgatttg tggaattggc ctgatgctca   2520
aatattggca ggtgatcttt tcgacgaggc agacttcgcg gtgtgcaacc ctgatgaggt   2580
ggttttagac ccagaacctc cacaacagca gcagcagcag cagcaacagc agtcgcatcc   2640
acaagctcag gtgccccagc aagggcctca agggaacaac tcacgacccg ctcgacctcc   2700
tcctgagatg gttactccct caaaaccaga aaggtcttgg aatgccggcc ctactcctgc   2760
tgcacgacag ccagcacaga cgccgcagaa caagacagct tcaggagctc aacataatat   2820
gtctatgaac cgtcctcagg gcatgatgca aaggcagccg acccctggtc cgcgaccaca   2880
gcaaccagag cgcaactcag cggctgcccc tcaggcttat tcaagatcta gccaagaaat   2940
gtcatcaaat gctcaaggcg gttcaggaat caaatcagag gcgtctgcta gctccgcgga   3000
ctctaagcct cagcaagcca ataataataa tcagggacaa tcttcgggaa gcgattcgga   3060
gaacagggtc cagccggatc cagcagctgg ctttttctct gcaaaagcag ttgacatact   3120
acgagaaaac cctcaggcac ctccatcaat ggcaccgaag tttaacccgc atgccgagag   3180
```

```
tccttcaatc cgcaaaacag caggtatcga ccatagcaag agccttccta tttctaaacc   3240

gatgcttgca ggagtttctc cttcccaaaa tagtacacgg gattttataa atccttctgc   3300

agatatgcat cgcagaatag gcgctcctgg cggtagtgga atcgccagcc cagtgggcag   3360

gccgcagagc acatcctctt atcgcccatt aacccgaccg aacattgacc caagaaatgc   3420

tggaagcaat actgggttta atcgagaaaa ccctgcacag cagaatgcaa gcctgaagag   3480

accgccgctc aacgacgtga caaattcttc cctctcatcg ggcacgtctg ggcccggtga   3540

tcccaaaaga cccaaagtca acgccgaaga acagactgcg ccacagcaac aaaagtgttg   3600

acatgtttgc caatcagtaa agttctcctg tgttattcat ctgtcgtgaa cattagcgct   3660

ttgttatttg acatgactcg gtgagtatat ggcgtttagg aggccaagga atagtatatg   3720

acgcactcgt ctgtgcaatt gtcctgaact ggttattttg ctgtggggat tcggtacctg   3780

ttaacatata ttatttacgt tgcatatcca tcaactctat cataacttac ttcatttttt   3840

tattcttggt gtttgggaag aggaatgaac ggcaatggtt tctttcgtgt ggcttgctgg   3900

tgttaaaatg gatggatgtt atactctgtg tattaattag ttgatcaagg atggaaaagg   3960

atcgatctat caatcagctg gcgttggtat tgatatagtc aatattgaaa tttctgatat   4020

tgatattctg acatggtcag agcttctcac cattacattg cgcgcgttct aaaaaagtat   4080

cagagtggaa cgaaaaaaaa atgaatacac cgtagctggc tagttatgac tgacacttgc   4140

attaacttca ctaatcctac atacgtacat acatgacaca tgaaaaactg ttgttggatt   4200

ttttttcgg aatgagtttt tgttttcgaa aacagcaaac aaacaactaa agaaaagaaa   4260

agaaagaagg gctttttga gggatgatag taatgataca ggtcaaacgg aagaaagaag   4320

aagcaaagaa aggaggaaaa aaaaactacc accacacaac ttttcgcttt catctcaggt   4380

aagtagttat gacaccgcta atcgatcgaa actggatatc atcaatcaat cgaaaatggg   4440

gaaaatgaat attcgttatc atcatcctcg tgagaatcat aaccggacgt atcactcttt   4500

agggcttttt ttttctaacc cccgcaccgc gattcgtcat cttcgcttgg agcaagtacg   4560

tcatctgagc ttagcggaga ggtttcttct tgtcgtcgtc gggtaggatc gcatatctag   4620

atgcgtagag actgcgggtt tgcggaagag gagggctctg tggactttgt gctgcggctg   4680

ctacaggagg ctgctgctgg tattggctcg gttgcattgg ttgattggaa gaagaagaag   4740

acactcctgc tgcagacgca gcggaccagg gatgtgggaa tcctcgttgc tgaaagctag   4800

gagcagcctg attctgacgt gcaaacggct ggttggtgtg ttgctctgct tgttggtgac   4860

taaaccgtgg ggaaggagaa gccgcaggac ttgaagaagc cgtaggcgca tgtctcgagg   4920

cgtaaaggct gcgcgtagga ggggcagggc taggctgttg ctcagtctgc actggagcct   4980

ggtattgcgc tggttgcgac ggttgaccga accctcctgg gagagacgca ctcgctgtcg   5040

gcgcgtgcct ggaagcacac aaactgtggg aagcgtggtg cgcaggagat tggttctctc   5100

c                                                                   5101
```

```
<210> SEQ ID NO 32
<211> LENGTH: 1821
<212> TYPE: DNA
<213> ORGANISM: Rasamsonia emersonii

<400> SEQUENCE: 32

atgcctgctg tcggtgacca gcaccgtgta ggaccgggta ctgtgatatc aaccatggct     60

ggtaccgtct ctgcgaatcc tttcgaggaa ccaccccgtc gaattagcga atatactgct    120
```

-continued

```
caggaaattg ccactcttca atctcgcctt gataagcagc tgggaccaga gtacatctcc    180

tcaagagccg gcccctctgg gcagaaggtg cactacctag cggcagagaa atgtataaac    240

cttgcgaacg aggtctttgg attcaatggc tggtccagtt cgatccaaag tatacagatc    300

gactttgttg atgagagtcc aagcacgggt aagataagtc tggggttatc cgtgattgtg    360

agagtcacat tgaaggatgg cacatatcat gaggatatcg gctatggcca tattgagaat    420

tgcaaaggca aagcggcagc ttttgagaaa gcaaagaagg agggaacaac agatgctctt    480

aaacgagctc tgaggacatt tggcaatgtt ctgggcaact gcatctacga caaagagtat    540

cttgccagag tcactagagt caaagtggct cctaccaagt gggatgtgga taaccttcat    600

cgtcaccctg attacgcccc ggtcaaaaag gagcctgtcg aagacaagaa ggtctctgaa    660

gataatgatc ttcctccccg tccaactgaa gcttccacga acaacgcgaa tccttcttct    720

cccgcattcg acggagacgg cgaatttggc agtgatcttt tcgacgaggc agacttcgcg    780

gtgtgcaacc ctgatgaggt ggttttagac ccagaacctc cacaacagca gcagcagcag    840

cagcaacagc agtcgcatcc acaagctcag gtgccccagc aagggcctca agggaacaac    900

tcacgacccg ctcgacctcc tcctgagatg gttactccct caaaaccaga aaggtcttgg    960

aatgccggcc ctactcctgc tgcacgacag ccagcacaga cgccgcagaa caagacagct   1020

tcaggagctc aacataatat gtctatgaac cgtcctcagg gcatgatgca aaggcagccg   1080

acccctggtc cgcgaccaca gcaaccagag cgcaactcag cggctgcccc tcaggcttat   1140

tcaagatcta gccaagaaat gtcatcaaat gctcaaggcg gttcaggaat caaatcagag   1200

gcgtctgcta gctccgcgga ctctaagcct cagcaagcca ataataataa tcagggacaa   1260

tcttcgggaa gcgattcgga gaacagggtc cagccggatc cagcagctgg ctttttctct   1320

gcaaaagcag ttgacatact acgagaaaac cctcaggcac ctccatcaat ggcaccgaag   1380

tttaacccgc atgccgagag tccttcaatc cgcaaaacag caggtatcga ccatagcaag   1440

agccttccta tttctaaacc gatgcttgca ggagtttctc cttcccaaaa tagtacacgg   1500

gattttataa atccttctgc agatatgcat cgcagaatag gcgctcctgg cggtagtgga   1560

atcgccagcc cagtgggcag gccgcagagc acatcctctt atcgcccatt aacccgaccg   1620

aacattgacc caagaaatgc tggaagcaat actgggttta atcgagaaaa ccctgcacag   1680

cagaatgcaa gcctgaagag accgccgctc aacgacgtga caaattcttc cctctcatcg   1740

ggcacgtctg ggcccggtga tcccaaaaga cccaaagtca acgccgaaga acagactgcg   1800

ccacagcaac aaaagtgttg a                                             1821
```

<210> SEQ ID NO 33
<211> LENGTH: 606
<212> TYPE: PRT
<213> ORGANISM: Rasamsonia emersonii

<400> SEQUENCE: 33

```
Met Pro Ala Val Gly Asp Gln His Arg Val Gly Pro Gly Thr Val Ile
1               5                   10                  15

Ser Thr Met Ala Gly Thr Val Ser Ala Asn Pro Phe Glu Glu Pro Pro
            20                  25                  30

Arg Arg Ile Ser Glu Tyr Thr Ala Gln Glu Ile Ala Thr Leu Gln Ser
        35                  40                  45

Arg Leu Asp Lys Gln Leu Gly Pro Glu Tyr Ile Ser Ser Arg Ala Gly
    50                  55                  60

Pro Ser Gly Gln Lys Val His Tyr Leu Ala Ala Glu Lys Cys Ile Asn
```

-continued

```
65                  70                  75                  80

Leu Ala Asn Glu Val Phe Gly Phe Asn Gly Trp Ser Ser Ser Ile Gln
                85                  90                  95

Ser Ile Gln Ile Asp Phe Val Asp Glu Ser Pro Ser Thr Gly Lys Ile
            100                 105                 110

Ser Leu Gly Leu Ser Val Ile Val Arg Val Thr Leu Lys Asp Gly Thr
        115                 120                 125

Tyr His Glu Asp Ile Gly Tyr Gly His Ile Glu Asn Cys Lys Gly Lys
    130                 135                 140

Ala Ala Ala Phe Glu Lys Ala Lys Lys Glu Gly Thr Thr Asp Ala Leu
145                 150                 155                 160

Lys Arg Ala Leu Arg Thr Phe Gly Asn Val Leu Gly Asn Cys Ile Tyr
                165                 170                 175

Asp Lys Glu Tyr Leu Ala Arg Val Thr Arg Val Lys Val Ala Pro Thr
            180                 185                 190

Lys Trp Asp Val Asp Asn Leu His Arg His Pro Asp Tyr Ala Pro Val
        195                 200                 205

Lys Lys Glu Pro Val Glu Asp Lys Lys Val Ser Glu Asp Asn Asp Leu
    210                 215                 220

Pro Pro Arg Pro Thr Glu Ala Ser Thr Asn Asn Ala Asn Pro Ser Ser
225                 230                 235                 240

Pro Ala Phe Asp Gly Asp Gly Glu Phe Gly Ser Asp Leu Phe Asp Glu
                245                 250                 255

Ala Asp Phe Ala Val Cys Asn Pro Asp Glu Val Val Leu Asp Pro Glu
            260                 265                 270

Pro Pro Gln Gln Gln Gln Gln Gln Gln Gln Gln Gln Ser His Pro Gln
        275                 280                 285

Ala Gln Val Pro Gln Gln Gly Pro Gln Gly Asn Asn Ser Arg Pro Ala
    290                 295                 300

Arg Pro Pro Pro Glu Met Val Thr Pro Ser Lys Pro Glu Arg Ser Trp
305                 310                 315                 320

Asn Ala Gly Pro Thr Pro Ala Ala Arg Gln Pro Ala Gln Thr Pro Gln
                325                 330                 335

Asn Lys Thr Ala Ser Gly Ala Gln His Asn Met Ser Met Asn Arg Pro
            340                 345                 350

Gln Gly Met Met Gln Arg Gln Pro Thr Pro Gly Pro Arg Pro Gln Gln
        355                 360                 365

Pro Glu Arg Asn Ser Ala Ala Ala Pro Gln Ala Tyr Ser Arg Ser Ser
    370                 375                 380

Gln Glu Met Ser Ser Asn Ala Gln Gly Gly Ser Gly Ile Lys Ser Glu
385                 390                 395                 400

Ala Ser Ala Ser Ser Ala Asp Ser Lys Pro Gln Gln Ala Asn Asn Asn
                405                 410                 415

Asn Gln Gly Gln Ser Ser Gly Ser Asp Ser Glu Asn Arg Val Gln Pro
            420                 425                 430

Asp Pro Ala Ala Gly Phe Phe Ser Ala Lys Ala Val Asp Ile Leu Arg
        435                 440                 445

Glu Asn Pro Gln Ala Pro Pro Ser Met Ala Pro Lys Phe Asn Pro His
    450                 455                 460

Ala Glu Ser Pro Ser Ile Arg Lys Thr Ala Gly Ile Asp His Ser Lys
465                 470                 475                 480

Ser Leu Pro Ile Ser Lys Pro Met Leu Ala Gly Val Ser Pro Ser Gln
                485                 490                 495
```

-continued

```
Asn Ser Thr Arg Asp Phe Ile Asn Pro Ser Ala Asp Met His Arg Arg
            500                 505                 510

Ile Gly Ala Pro Gly Gly Ser Gly Ile Ala Ser Pro Val Gly Arg Pro
        515                 520                 525

Gln Ser Thr Ser Ser Tyr Arg Pro Leu Thr Arg Pro Asn Ile Asp Pro
    530                 535                 540

Arg Asn Ala Gly Ser Asn Thr Gly Phe Asn Arg Glu Asn Pro Ala Gln
545                 550                 555                 560

Gln Asn Ala Ser Leu Lys Arg Pro Pro Leu Asn Asp Val Thr Asn Ser
                565                 570                 575

Ser Leu Ser Ser Gly Thr Ser Gly Pro Gly Asp Pro Lys Arg Pro Lys
            580                 585                 590

Val Asn Ala Glu Glu Gln Thr Ala Pro Gln Gln Gln Lys Cys
        595                 600                 605


<210> SEQ ID NO 34
<211> LENGTH: 6043
<212> TYPE: DNA
<213> ORGANISM: Rasamsonia emersonii

<400> SEQUENCE: 34

acctcacgtg ctacatttat ccccagaaga acggacatca cccctgtgag caatattctc      60

aatctgctaa gcccaacaag atctgcgggc ttgaaggaga ggaactgcca acgacaattg     120

cgatacccat tttctatctg aattccatga agcgaaggaa attttacgaa tgcgacgctc     180

gactcactag gctaattctt ggatccagag ttccagacga gtgagttgtt cgaagttccg     240

attttcgcca tcaaattttc cgcaatagcc ggtccgaggt agtcagagtt ccgattcacg     300

gcagaaaccg ctccttcgga acagcactgg ccatagcagg tatcacggcc cgccggatta     360

tctccctcaa ttaggtagct tttcatgtgc cgaggtatta ttattttta cgccactgta     420

ctctttttc tctattactg ttcttcttgt ggattcctgt cattatcata tacccacttg     480

agctgggtct aaagatccgc ttaatacttt catgagccat tcgtatgtcg cccactttgt     540

attagataat cgaatgagta agcaatcgcc gccatctttg tgcagtttac ctgggataat     600

aatggaacaa catacctgaa cggcatttac tataaatgct ctaatgctac aaattcccag     660

gccgcgatag aatacttgga aaccctctgt gcgataagct tgctgagcga tctccaatga     720

ccccattatt cgttccgtag gcattgtcgg ccgaagaagt gatcgtgtct caggagatat     780

gtctctcgaa ggctccagaa acgattgggc ttgcagcctt gtctttatga cgtcgagtgg     840

gaaaacagag gcccatgtca ctatcccagc aattccgccg cagatgagaa ccttcaatgc     900

agcctgatga gcagtttcgt ccgcagaagt catacttcgc ttacatagct cataggacca     960

gaaactgtag caactgacgt caatatcctg cttgggccga tggcgggtat ctctggagtc    1020

aaggggatga ttcgtactaa aatccgtaac ccacggaatc tctgatactt gttattgctc    1080

ccccgaaata gagtcccttc catcctgctt ttcggatgat atcactggca actgtccacg    1140

atgagatttg cggatttcta ctcagctgcg cccggcattt aatgagctct gttggtgacg    1200

aaaccaccca actggcaatg ccgcccgcgg cgccagctag ccagattttg tttaacgaga    1260

cgccgtctgg tttggttgga tcagtcacgg aagaatccag tgctttcagg cttcggttgt    1320

aggcaacgta aagcagggca tttagagcac catagccaag aataggggca gcagcgccta    1380

attcaacgtc aatagaggat gaataatgtc cacacagtta cacgcacctc gcaccaagga    1440

ggtggcggtc tcaaattgac ctcgagataa ccgcggggtt ggttctggag agctcccagt    1500
```

-continued

```
atggtatgcc tgcaggcgga ctttgactag gtcgagtgga ttgccaatga ttataccaat   1560
ggctccgctt atgtagcctg cccaaaagtc ggaggacatt ggttttaaaa atcacaaatg   1620
taagttttca ttactcagtt ggtaaatgcc atgattgttc tgacaatcat cggcacagcg   1680
gagccccgcg atgacggcgg attgatatca cgtgagttcg cgacactttg gcgaaacagg   1740
ggaaatccga acgcgcttac gaacgacgcg tacttgattg ccagcaaacg gagcagtcat   1800
tattccgact tgaaccagct cggtgaccat accaacggtg ggactgtgag aagagttgat   1860
ccgacctagg ggcttcattt tttactttct cttccaatgt atggaggtct ttgaatgttc   1920
attatccaga aaccaatgct aaccttttgt taggcatcgt ccacggccca ccacggtaga   1980
aggtggtcaa acattagtat cagcacagaa gccagttcga ctctacggcc catcacaaca   2040
gtcgatcgat cgcctctcga agccattcaa atgtccaggc caggcaacag cttctgtagc   2100
atccgataga ccggccagaa agaggcgcaa agtggattat agcggtgctg acggaagcgc   2160
tgaggatgga agcaaaccat ggaccaacga ggagcgtctt gctcttgcaa accgcgacgc   2220
taacaaattc ccggtctata aagtgaaaga caaagaagta gcacttaaac aacgattctc   2280
tgtaccttta atcgataaga catccagcaa ttatgatccc tccagacctg caccgactct   2340
tggaatgagg cgaggcgcct catttgtcgt gaaacctttg cacgatccga gtggagagtt   2400
cgcaattgtc ttgtatgacc ctacagttga tgacaaaccg gagccaaaga aggaggagga   2460
cggggagaaa accgaagaaa agccaaagct ggatgcaccc attgtgcata agagtttggc   2520
cgatattctt ggtctaaaga aacgcgtcga gtctcgtcct aaggtccctg tggtcattga   2580
cccaagactt gccaaggtct tgcggccaca tcaagtagag ggagtaaagg tgaggcacta   2640
ctcaatcatc tggcatgttt ggtttttaat ataataattg tttttcttcc acagtttctt   2700
tatcgttgca caactggcat gattgatgag aatgcgaatg gctgcatcat ggcagacgaa   2760
atgggcttgg gcaagacggt aatctccagc cctcaattct gtcggattga tgctgatggc   2820
gacagctcca atgtatcact ctgatgtgga cactccttaa gcaatcgcct gaagcgggaa   2880
agccaactat ccagaagtgt gtcattgctt gcccatcaag cttagttaaa aactgggcca   2940
atgaactagg tatgtgatat gtaggccttc ttctacgttg ctactgacag ttatagtgaa   3000
atggcttgga aatgacgcca ttacaccgtt tgcagttgac ggtaaagcct caaaggctga   3060
gctttcctcg cagcttaaac agtgggcaat tgcctcgggt cgctcaatcg tccggccggt   3120
cctcatagtg tcatacgaga cattaaggct atacgttgaa gacctaaagg acacacagat   3180
aggtttgcta ctatgtgacg aaggacacag actcaaaaat aaagagagct tgacctggac   3240
agcgttgaac agcctcaacg tcagccgccg ggtcatcctt tctgggacac ctatacagaa   3300
cgatttgtct gaatatttcg ccctttttgca ttttgcaaac ccaaacttgc tcgggactca   3360
ggctgaattc agaaaaagat ttgaaattcc gattttgaaa ggaagggatg ctgcagggac   3420
ggatgaggat cgaaggaaag gtgatgagcg cttggcagag ctctccagca tcgtcaacaa   3480
attcattata cggcgcacca acgacattct ttcaaagtac ttgccgatca agtacgaaca   3540
tgttgtgttc tgcaatctta gcaagtttca ggttgaccta tataaccatt tcttacagag   3600
cccagacatc aaaagtctgc tcaaaggcaa gggaagccag ccattgaaag cgattggaat   3660
tttgaagaaa ctctgcaatc atccggacct gctggatctg tcaacggaat tgcctggatg   3720
tgaacaattt ttccctgatg actatgttcc accggaagcc agaggccgcg acagagacgt   3780
caaatcctgg tattccggga aaatgatggt tcttgagcgc atgctggcgc gaatacgcca   3840
```

-continued

```
ggacactaat gataagatcg ttctgatcag taactataca caaacacttg accttttcga   3900

gagactttgc cgctctcgag ggtatgggtg tttgcgactg gacggcacca tgaatgtcaa   3960

taagcgacaa aaactggtgg acaaattcaa tgaccccgat ggtgaagaat ttatattttt   4020

gttaagcagc aaggcaggcg gctgtggttt gaacctgatt ggagcgaatc gtttggtttt   4080

atttgatcca gactggaatc ctgctgccga ccagcaagca ctggctcggg tctggcgtga   4140

cggccaaaag aaggactgtt ttgtttatcg gttcattgca accggatcga tcgaagaaaa   4200

gatcttccag aggcagtccc acaagcagtc actctcttcc tgcgttgtcg attctgcgga   4260

agacgttgaa cgtcactttt ctctcgactc ccttcgagaa cttttccagt tcaagccaaa   4320

cacgcggagc gacacacatg acacgttcaa atgcaagagg tgcaggccag atgggaccca   4380

gtttatcaag gctccagcca tgttatatgg cgatacgagt acatggaatc attttgtcaa   4440

cgacggtgag aacggaccat tgaacaaaat acaggacttg ctcttaagac aagaaacctc   4500

cgagaaggat gtttccgctg tttttcaata tatcagtcat tgatacgttg gtggccgctg   4560

ttggcttggt cgatgcaatc gacgatctgt attgaaaccg acatgcatac ttggacagga   4620

tagctttcaa cgtaaatgga tatgtttctt taatttagga atataatgat tgcatagaga   4680

ttattaaatg tttgtttctt tgttgtgaag tactccagcc atcggttctc agttgatgta   4740

ggctccgcgg ataccgtacg atacacggct tgtgacaata catcactacc actgaagccg   4800

catctgcatt gacgctccgc gctgttgaca acacatgcat gctccccgca tacctggcat   4860

caggaagctg aaatgattgt tccgcatgtg cctgcatcca ctacagtttg agacgcagtg   4920

tctgacaatt catgttaccg cccagagcag cttcccggca gtgcagttta taatcccagc   4980

agcatcagcc caccttgctc ccacgcattc cattcgcaac cacgatgagt gttgcctaac   5040

acgaatacgg agtctgtgac ttgtagaaag tcaaccgcca tttcacaatg gaccaatcag   5100

ttcagcgtct gctgaacgac aagctctacg acaagagaaa acagggtgcc ttagagtacg   5160

ttgcagcttc tgtagacaag tgtcccgaaa gctgcagtgc tgaccacaat aatgttctta   5220

ggcttgaaaa gatcgtccgc gatgccatat tcagaggaga gcacgataaa atccagaaga   5280

tcgtcgatca gctctgccac gactatgcct acgctgttca ccaaccacac gcgcgaaatg   5340

gaggtctgat cggtctggcc gccgcctcga tagcattggg atctgtgagt tgagacaata   5400

ttataggatg gtttgtggat ttcagggctg atcaagcgca ggagggggtc gctccttacc   5460

tccaagagat cgttcctcct gttctcgctt gcttctctga tcaggatgcg cgtgttaggt   5520

attatgcatg cgagagcatg tacaacattg cgaaggtggc taagggagag atactggttt   5580

tcttcaatga tatatttgat gcattatgca aggtctgtgt gctcggtgta gcgtccacgg   5640

atgtatatct ctcctactga cacacaccag ctagcatccg actcggagct ctccgtaaag   5700

aacggagctg agctacttga ccgacttgtg aaagacattg tcgctgaatc ggcagcttcc   5760

tatgtctccg tcttacagta tccggagaag aacgtgcaag acctagatgc tactcgagaa   5820

gcagaagaaa tctcaaatga tctgccaaca gcattctcac tggccaagtt cataccgctg   5880

ttgcaggagc gaatacatgt cctgaatcct tttacccgaa cattcctcgt atcatggttg   5940

actttgttag acacaattcc ggacctggag ctcgtgtgtt acttaccagc ttttctcggc   6000

ggattgataa agttcctagg agatccaaac aaggatgttc atg                     6043
```

<210> SEQ ID NO 35
<211> LENGTH: 2568
<212> TYPE: DNA
<213> ORGANISM: Rasamsonia emersonii

<400> SEQUENCE: 35
atgcctgccc aaaagtcgga ggacattggt tttaaaaatc acaaatcgga gccccgcgat 60
gacggcggat tgatatcacg tgagttcgcg acactttggc gaaacagggg aaatccgaac 120
gcgcttacga acgacgcgca tcgtccacgg cccaccacgg tagaaggtgg tcaaacatta 180
gtatcagcac agaagccagt tcgactctac ggcccatcac aacagtcgat cgatcgcctc 240
tcgaagccat tcaaatgtcc aggccaggca acagcttctg tagcatccga tagaccggcc 300
agaaagaggc gcaaagtgga ttatagcggt gctgacggaa gcgctgagga tggaagcaaa 360
ccatggacca acgaggagcg tcttgctctt gcaaaccgcg acgctaacaa attcccggtc 420
tataaagtga aagacaaaga agtagcactt aaacaacgat tctctgtacc tttaatcgat 480
aagacatcca gcaattatga tccctccaga cctgcaccga ctcttggaat gaggcgaggc 540
gcctcatttg tcgtgaaacc tttgcacgat ccgagtggag agttcgcaat tgtcttgtat 600
gaccctacag ttgatgacaa accggagcca aagaaggagg aggacgggga gaaaaccgaa 660
gaaaagccaa agctggatgc acccattgtg cataagagtt tggccgatat tcttggtcta 720
aagaaacgcg tcgagtctcg tcctaaggtc cctgtggtca ttgacccaag acttgccaag 780
gtcttgcggc cacatcaagt agagggagta aagtttcttt atcgttgcac aactggcatg 840
attgatgaga atgcgaatgg ctgcatcatg gcagacgaaa tgggcttggg caagacgctc 900
caatgtatca ctctgatgtg gacactcctt aagcaatcgc ctgaagcggg aaagccaact 960
atccagaagt gtgtcattgc ttgcccatca agcttagtta aaaactgggc caatgaacta 1020
gtgaaatggc ttggaaatga cgccattaca ccgtttgcag ttgacggtaa agcctcaaag 1080
gctgagcttt cctcgcagct taaacagtgg gcaattgcct cgggtcgctc aatcgtccgg 1140
ccggtcctca tagtgtcata cgagacatta aggctatacg ttgaagacct aaaggacaca 1200
cagataggtt tgctactatg tgacgaagga cacagactca aaaataaaga gagcttgacc 1260
tggacagcgt tgaacagcct caacgtcagc cgccgggtca tcctttctgg gacacctata 1320
cagaacgatt tgtctgaata tttcgccctt ttgcattttg caaacccaaa cttgctcggg 1380
actcaggctg aattcagaaa aagatttgaa attccgattt tgaaaggaag ggatgctgca 1440
gggacggatg aggatcgaag gaaaggtgat gagcgcttgg cagagctctc cagcatcgtc 1500
aacaaattca ttatacggcg caccaacgac attctttcaa agtacttgcc gatcaagtac 1560
gaacatgttg tgttctgcaa tcttagcaag tttcaggttg acctatataa ccatttctta 1620
cagagcccag acatcaaaag tctgctcaaa ggcaagggaa gccagccatt gaaagcgatt 1680
ggaattttga agaaactctg caatcatccg gacctgctgg atctgtcaac ggaattgcct 1740
ggatgtgaac aatttttccc tgatgactat gttccaccgg aagccagagg ccgcgacaga 1800
gacgtcaaat cctggtattc cgggaaaatg atggttcttg agcgcatgct ggcgcgaata 1860
cgccaggaca ctaatgataa gatcgttctg atcagtaact atacacaaac acttgacctt 1920
ttcgagagac tttgccgctc tcgagggtat gggtgtttgc gactggacgg caccatgaat 1980
gtcaataagc gacaaaaact ggtggacaaa ttcaatgacc ccgatggtga agaatttata 2040
tttttgttaa gcagcaaggc aggcggctgt ggtttgaacc tgattggagc gaatcgtttg 2100
gttttatttg atccagactg gaatcctgct gccgaccagc aagcactggc tcgggtctgg 2160
cgtgacggcc aaaagaagga ctgttttgtt tatcggttca ttgcaaccgg atcgatcgaa 2220
gaaaagatct tccagaggca gtcccacaag cagtcactct cttcctgcgt tgtcgattct 2280

-continued

```
gcggaagacg ttgaacgtca cttttctctc gactcccttc gagaactttt ccagttcaag   2340

ccaaacacgc ggagcgacac acatgacacg ttcaaatgca agaggtgcag gccagatggg   2400

acccagttta tcaaggctcc agccatgtta tatggcgata cgagtacatg gaatcatttt   2460

gtcaacgacg gtgagaacgg accattgaac aaaatacagg acttgctctt aagacaagaa   2520

acctccgaga aggatgtttc cgctgttttt caatatatca gtcattga               2568


<210> SEQ ID NO 36
<211> LENGTH: 855
<212> TYPE: PRT
<213> ORGANISM: Rasamsonia emersonii

<400> SEQUENCE: 36

Met Pro Ala Gln Lys Ser Glu Asp Ile Gly Phe Lys Asn His Lys Ser
1               5                   10                  15

Glu Pro Arg Asp Asp Gly Gly Leu Ile Ser Arg Glu Phe Ala Thr Leu
            20                  25                  30

Trp Arg Asn Arg Gly Asn Pro Asn Ala Leu Thr Asn Asp Ala His Arg
        35                  40                  45

Pro Arg Pro Thr Thr Val Glu Gly Gly Gln Thr Leu Val Ser Ala Gln
    50                  55                  60

Lys Pro Val Arg Leu Tyr Gly Pro Ser Gln Gln Ser Ile Asp Arg Leu
65                  70                  75                  80

Ser Lys Pro Phe Lys Cys Pro Gly Gln Ala Thr Ala Ser Val Ala Ser
                85                  90                  95

Asp Arg Pro Ala Arg Lys Arg Arg Lys Val Asp Tyr Ser Gly Ala Asp
            100                 105                 110

Gly Ser Ala Glu Asp Gly Ser Lys Pro Trp Thr Asn Glu Glu Arg Leu
        115                 120                 125

Ala Leu Ala Asn Arg Asp Ala Asn Lys Phe Pro Val Tyr Lys Val Lys
    130                 135                 140

Asp Lys Glu Val Ala Leu Lys Gln Arg Phe Ser Val Pro Leu Ile Asp
145                 150                 155                 160

Lys Thr Ser Ser Asn Tyr Asp Pro Ser Arg Pro Ala Pro Thr Leu Gly
                165                 170                 175

Met Arg Arg Gly Ala Ser Phe Val Val Lys Pro Leu His Asp Pro Ser
            180                 185                 190

Gly Glu Phe Ala Ile Val Leu Tyr Asp Pro Thr Val Asp Asp Lys Pro
        195                 200                 205

Glu Pro Lys Lys Glu Glu Asp Gly Glu Lys Thr Glu Glu Lys Pro Lys
    210                 215                 220

Leu Asp Ala Pro Ile Val His Lys Ser Leu Ala Asp Ile Leu Gly Leu
225                 230                 235                 240

Lys Lys Arg Val Glu Ser Arg Pro Lys Val Pro Val Val Ile Asp Pro
                245                 250                 255

Arg Leu Ala Lys Val Leu Arg Pro His Gln Val Glu Gly Val Lys Phe
            260                 265                 270

Leu Tyr Arg Cys Thr Thr Gly Met Ile Asp Glu Asn Ala Asn Gly Cys
        275                 280                 285

Ile Met Ala Asp Glu Met Gly Leu Gly Lys Thr Leu Gln Cys Ile Thr
    290                 295                 300

Leu Met Trp Thr Leu Leu Lys Gln Ser Pro Glu Ala Gly Lys Pro Thr
305                 310                 315                 320

Ile Gln Lys Cys Val Ile Ala Cys Pro Ser Ser Leu Val Lys Asn Trp
```

-continued

```
                325                 330                 335

Ala Asn Glu Leu Val Lys Trp Leu Gly Asn Asp Ala Ile Thr Pro Phe
            340                 345                 350

Ala Val Asp Gly Lys Ala Ser Lys Ala Glu Leu Ser Ser Gln Leu Lys
        355                 360                 365

Gln Trp Ala Ile Ala Ser Gly Arg Ser Ile Val Arg Pro Val Leu Ile
    370                 375                 380

Val Ser Tyr Glu Thr Leu Arg Leu Tyr Val Glu Asp Leu Lys Asp Thr
385                 390                 395                 400

Gln Ile Gly Leu Leu Leu Cys Asp Glu Gly His Arg Leu Lys Asn Lys
                405                 410                 415

Glu Ser Leu Thr Trp Thr Ala Leu Asn Ser Leu Asn Val Ser Arg Arg
            420                 425                 430

Val Ile Leu Ser Gly Thr Pro Ile Gln Asn Asp Leu Ser Glu Tyr Phe
        435                 440                 445

Ala Leu Leu His Phe Ala Asn Pro Asn Leu Leu Gly Thr Gln Ala Glu
    450                 455                 460

Phe Arg Lys Arg Phe Glu Ile Pro Ile Leu Lys Gly Arg Asp Ala Ala
465                 470                 475                 480

Gly Thr Asp Glu Asp Arg Arg Lys Gly Asp Glu Arg Leu Ala Glu Leu
                485                 490                 495

Ser Ser Ile Val Asn Lys Phe Ile Ile Arg Arg Thr Asn Asp Ile Leu
            500                 505                 510

Ser Lys Tyr Leu Pro Ile Lys Tyr Glu His Val Val Phe Cys Asn Leu
        515                 520                 525

Ser Lys Phe Gln Val Asp Leu Tyr Asn His Phe Leu Gln Ser Pro Asp
    530                 535                 540

Ile Lys Ser Leu Leu Lys Gly Lys Gly Ser Gln Pro Leu Lys Ala Ile
545                 550                 555                 560

Gly Ile Leu Lys Lys Leu Cys Asn His Pro Asp Leu Leu Asp Leu Ser
                565                 570                 575

Thr Glu Leu Pro Gly Cys Glu Gln Phe Phe Pro Asp Asp Tyr Val Pro
            580                 585                 590

Pro Glu Ala Arg Gly Arg Asp Arg Asp Val Lys Ser Trp Tyr Ser Gly
        595                 600                 605

Lys Met Met Val Leu Glu Arg Met Leu Ala Arg Ile Arg Gln Asp Thr
    610                 615                 620

Asn Asp Lys Ile Val Leu Ile Ser Asn Tyr Thr Gln Thr Leu Asp Leu
625                 630                 635                 640

Phe Glu Arg Leu Cys Arg Ser Arg Gly Tyr Gly Cys Leu Arg Leu Asp
                645                 650                 655

Gly Thr Met Asn Val Asn Lys Arg Gln Lys Leu Val Asp Lys Phe Asn
            660                 665                 670

Asp Pro Asp Gly Glu Glu Phe Ile Phe Leu Leu Ser Ser Lys Ala Gly
        675                 680                 685

Gly Cys Gly Leu Asn Leu Ile Gly Ala Asn Arg Leu Val Leu Phe Asp
    690                 695                 700

Pro Asp Trp Asn Pro Ala Ala Asp Gln Gln Ala Leu Ala Arg Val Trp
705                 710                 715                 720

Arg Asp Gly Gln Lys Lys Asp Cys Phe Val Tyr Arg Phe Ile Ala Thr
                725                 730                 735

Gly Ser Ile Glu Glu Lys Ile Phe Gln Arg Gln Ser His Lys Gln Ser
            740                 745                 750
```

-continued

```
Leu Ser Ser Cys Val Val Asp Ser Ala Glu Asp Val Glu Arg His Phe
        755                 760                 765

Ser Leu Asp Ser Leu Arg Glu Leu Phe Gln Phe Lys Pro Asn Thr Arg
    770                 775                 780

Ser Asp Thr His Asp Thr Phe Lys Cys Lys Arg Cys Arg Pro Asp Gly
785                 790                 795                 800

Thr Gln Phe Ile Lys Ala Pro Ala Met Leu Tyr Gly Asp Thr Ser Thr
                805                 810                 815

Trp Asn His Phe Val Asn Asp Gly Glu Asn Gly Pro Leu Asn Lys Ile
            820                 825                 830

Gln Asp Leu Leu Leu Arg Gln Glu Thr Ser Glu Lys Asp Val Ser Ala
        835                 840                 845

Val Phe Gln Tyr Ile Ser His
    850                 855
```

<210> SEQ ID NO 37
<211> LENGTH: 6139
<212> TYPE: DNA
<213> ORGANISM: Rasamsonia emersonii

<400> SEQUENCE: 37

```
acagcaagat gcacaatccg ttcaatgcaa cgctggtctg cggcctgctc atcacggtcc     60
ttgcatgcat ctatgtcggc tcgaccactg ctttcaacgc cttcgttggc tcctatgtcc    120
aactctcgac cctctcttac tttgcggcca tcttccctca cgtcctgaac cgtcgttcgc    180
tcatcacacc gggatacttc tggatgaagg gtccaatcgg ctacatcgtt aacattctga    240
gttgcatcta catcttagct ttcattgtca ttttctgctt ccctgcttcc cttcctacca    300
atgcgcaatc catgaactac gcgagtttga tcactggcgg tttcaccatt ttcatcgccg    360
cctggtggtt cgtccggcag cgccactacc aaggaccgca agtcatccca ctgaccgatc    420
ggaaaatcgc tgaagacgca aagtgaatct cgttgtaaat ccaacattgg ttttggcgac    480
cactgtgact ggaaatgaca atcgttatgt caatatttta ccacctttgt gtatccccca    540
cattgtaaat tcgcggacaa ttttgcttac taataatttc tgcacgtgtg attggttgaa    600
ttcgcggata atgttgctta ctaagacatt tccggctgca tgattggtta aaaccgctta    660
aaaatcacgt gcctgaaact tttacgtaag catctgtctg cttacagttg gctacggccc    720
tgggactccc tataggccta tgggcttcat attggcaccc ttagaggcct cacgctggca    780
cccctagagg ctttatatag gcttgcatta aaggtatgcg gagggccgaa ggtccggagc    840
atttaggtat aagcacttaa gtatactagg cttcatatta gcttatatgg gcttcataat    900
ggctctctta tgggcttcct cagaggtttt ataaaggctt acatatatta taggctggcg    960
gagggccgaa ggtcccgagc attataggca ttagtaagcc tagatagtct tccccttcaa   1020
gcctagacga gcggagcgag tcgttaaagg cttgtgaggt ctataaagag actggagttc   1080
cccatgtttt cgtcatgttc aaatatgttt catttcttgg atatatatgc acatgtagta   1140
tatctgttgt caacatgggg taacagcctc gatacatgat cctaattgta atgggatttt   1200
aatgcgccac aatctcagct gactgatctg gaaacacact ctgtttacat tctttcgtag   1260
atacaacact cattcttgct gttcaattca attgtatgta caatgcaata aaaatcacag   1320
aaacaccaga tgttcgttcg aagtcggtaa taatcaagcg tgatcacgtg ggttcgcgtt   1380
tccctcgcgt cgcggatggc cttggcaaag agcacgtgtc agcttatctc aacaggatgg   1440
aacagtcgaa gtgtctccgg tccataacga ggcattattg aaaatcatcg gctggccgcc   1500
```

-continued

```
atggttttca agccttttcg tcctccgctg ataagaaagc cccctcctcc agcggaatct   1560
tcaacaccga taactggaga tagtggaaac cctcacccgt cgaaacgacc gcggttgagt   1620
gaggacgacg atcagtccgc aaaagatgag aagacatcca cttctgtggt cgagagcaag   1680
agcactaagg ataagccgaa gccacagctt gcgtaccgca agccgttgat ccaggtgaag   1740
aacttgactg gaaaggcggc tccgtccgta gacgatgcca gcaactctgc gaacacggaa   1800
aataataatg gctctactca ggaagtggag gcttattata atgttctctg gttagttgcc   1860
ttttctattc gatgccttta ctcagacatt aaccattccc cttctaccgt atcttaggcg   1920
aaaattcacg actaagaaac acaaaacctg ggatggcgat ggcattctct ccatccgtgg   1980
aggatacggc tatcttcagg atgtatcagg ccgagacatg gggcgcataa tgatcaactc   2040
gactctggaa cctggagcaa ctttgacgat tgggggaaaa gatgtcgagg tgcaatccgc   2100
catgtcgaaa gaagagtact tgtctggtcg atcttttctg ggaggggcaa agaaaaccct   2160
gacgtctcct ctcgcgtctc gtgagaagac acaagcctct gttgtcccta ctcaagcatc   2220
aaagctgccg aaagtctccg cgacgctaac tgaaggcgca aagaagccat tgagtcggac   2280
aagctctcgg aatgacagtg aaaaagatgc cttcgtgaaa aatctcaatg ttgccgctcc   2340
aagaagcgca gcattgggca acgctttcaa gaacccggtg aaagagagca cagtttcttc   2400
cgcaaaaccg gcagcacagc ctattccccg tcatgatcca aatgcgccgg gcgccttggt   2460
catgaaacgg ccggatgtcg ttccaaaggg aaagacgatt gttgatgtcg tcgtggaccc   2520
catccttacc aaacacctcc gcgaacacca acgggagggt gtcaaatttc tttacgagtg   2580
tgtcatgggg ttaagggatt acaatggtga aggagcaatc ctagcggacg agatgggtct   2640
ggggaagacc ctgcaaacaa tcacactctt gtggacattg ctcaaacaaa atccgatcta   2700
cgaagagccc ccagtcgtca agaaggcgtt gattgtttgc ccagtaaccc tcatcaacaa   2760
ctggagaaaa gaattccgca aatggctggg aaatgaacgg ataggcgtgt tcgtcttcga   2820
tgacaagagg aaacgactga cggactttac tatgggcaaa gcctataatg ttatgatcgt   2880
cgggtacgaa aagctgcgaa ccgtccagga agggctcatc aaaggtgccg ggtcgatat    2940
cgtcattgca gatgaaggcc acagactaaa gacactacag aacaagagcg gccaggccat   3000
tcaagcgctc aacaccacga agaggatcat cctctctggc actccgattc agaatgatct   3060
gagtgaattc ttcgcggcgg tcgacctggt caatcctggg attctgggta catacaagaa   3120
cttcatgaaa gaattcgagg ggcctattat gaggagtagg cagcccgagg caacaaaaag   3180
agagattgag aaaggagagg cgaggagtga ggagctcaga aatctcacgt ccatgttcat   3240
gctacgcagg acggcggata tcctgtccaa atacctgccg ccaaaaacgg agtatgtgct   3300
cctgtgcgaa cctacggcga tacaagcaag catctaccgt cacgtcctcg cgtcgcccat   3360
ctttcaaagc gctcttggta acaccgaggg tgcattccat ctcattacta ttctcaagaa   3420
attatgtaac agcccatcgt tgctcactgc gaagacggaa gacgaaacac cgaatgctac   3480
ggtttccgcg ctgctgtcta cgctgccacc gaatcttctg cgtcatttct ccccttcctc   3540
gagcgggaaa ttgagggtac tcgaccaact cctccataat ctgcgcacaa ccacgtcgga   3600
aaagatcgtg ctggtctcca actatacctc gacattgaac cttctcgcca cgctgctcac   3660
gtcgctttcg ctcccgttcc tgcgtctgga cggcaccacg ccgtcctcga aacggcagtc   3720
gctcgttgac gacttcaatc gcagtcccgc gagtacctgc tttgcgtttc tactctccgc   3780
aaaggccgga ggcacaggcc tgaatctgat tggggccagc cgcctcgtcc ttttcgacgt   3840
```

-continued

```
cgattggaat ccggcgacgg acatgcaggc catggcgcgg atccatcgag acggacaaac   3900
acgccactgc tggatatatc gcatcatgct gaaaggcggg ctggaggaga agatctggca   3960
gagacaagtg accaaaatcg ggctggcgga cagcgtcatg gaacagaaag gcggcatggc   4020
acagttctcg cgggaggagc tcaaggacct atttcgactg tatgagggcg aaggatgcca   4080
gacacatgat cttctgtgct gtaactgcgg cgggcggggg acaccatcca ccgacggagg   4140
tgatcgtcca gtctccacag attccgacga taaatccagc agcagctgtt cttcagcaga   4200
agacgaggag gagactgatg atgaagacga tgaagaagac atcgatctac cagacctccc   4260
aactctcatc aaagtatcac aactagacat cgacgcgcaa gaggcccaaa tccgacgagg   4320
ctcccatcct ctccagcgac gtcagagcaa caagaccaag gacaagaaca agaaaaaaga   4380
cacaaagaac ccgcgtggga ggaagaagaa gaacagcgac caagccagga tgcagcaatt   4440
cctctccgaa tactcgcaca tcgacccttc cgcctttggt gcagacgacc atggggagga   4500
gggcacggat ctagccagcc agatccgcga tccggtgctc ctttctctct tgagggagga   4560
ggatcatggc gtggggttca tctttgagaa gacggcgttt cctgctgctg atgctgatgc   4620
tcctgctgag aagaaataag aaatctctac ccgccttcct acttacgcaa ggtagtagga   4680
acagactaga tcctcaccat ccttttttttt tgcatttatg tgtatacact ataatcatga   4740
taataaccac tgcatatatc catatgatac tatcgatctc gtacggttat agcatagcca   4800
tgatcagggt cagggtcagg gtcagggaca gggacagggt tcgtcaggaa gtaattgcat   4860
ggatggattc atttaacatt tctctacggc tactcgatag acagatagat aggtatacag   4920
caatgaatac aatgagcatt aacgaacgac tgactaactg actgactgac tgactagtca   4980
atcagttgaa ctgattaatt cctgaaacac tccagtacta tctatttatt ctttaccacc   5040
ttctttctta cccttacata tacatatatt taatatttag acataaatac gaacgaactg   5100
caccagctag ctagctagct aactacacaa gctagacaag tcgtgaccat ggatgacgat   5160
gacggataga tagatagata cgatgagaga gggatggatg gaaatgaact ggaaaatgga   5220
aaaatggaaa atgcaactca actcaacaat gcaatcttct tctacctacc tcctccatct   5280
atcaacacgt aaattggtat aaaattggta taaagcttga agtatgaagg gtgaagggga   5340
gacttgagcg gccaaaacta catacatacg tacgtcaaat gtcgtagaca gggcatgaga   5400
catgacataa agacatgaca tgagacataa catgaggaca tgaagacatg aaggcatgaa   5460
ggcatgaggg gatagttggg ggggggggga aatagttcca aaaaatgaac aaaaaaaggc   5520
aaatagagaa gtctccacaa tcatcgaaaa tgtagactag atatattgca aaacaccacc   5580
aatgcagtgg attacattcc aacatgatag gcaagttaat accgcagctt tcctaccagt   5640
gaaaacgtat aagctgcctc ggcctcgctc ttcatctgga tcatatatac tcggaacgag   5700
ccgccggtga caccgccctc cttgctgact gcaccgcctt cattctcttc ccagaccgag   5760
actgcaatgc ccgttctggc cacgcgctca aatgagctct cgcccagagt agcatcgagc   5820
aagacctctc cccgcgtctt tccccggatc agaatccgtt tttcctgtgg tatagcgaca   5880
cgacgtggtg atgcagcggc cggagtagcg gcggcctctg ccactggtgc atcaccctcc   5940
cctgtttcac ctgctgcggc attggcattg gcatcagcag gagcagcaac gctccccgct   6000
gtgccagggc gagaggatct tggcgtcgca ggcatgatgg tcaatcgagc tgctcccaga   6060
tcacgccatt tcgacacact ttcacggaca taaagccgga tcttcgcatt ggacaagcca   6120
atcccgtccg caccccttga                                               6139
```

-continued

<210> SEQ ID NO 38
<211> LENGTH: 3072
<212> TYPE: DNA
<213> ORGANISM: Rasamsonia emersonii

<400> SEQUENCE: 38
atggttttca agccttttcg tcctccgctg ataagaaagc cccctcctcc agcggaatct 60
tcaacaccga taactggaga tagtggaaac cctcacccgt cgaaacgacc gcggttgagt 120
gaggacgacg atcagtccgc aaaagatgag aagacatcca cttctgtggt cgagagcaag 180
agcactaagg ataagccgaa gccacagctt gcgtaccgca agccgttgat ccaggtgaag 240
aacttgactg gaaaggcggc tccgtccgta gacgatgcca gcaactctgc gaacacggaa 300
aataataatg gctctactca ggaagtggag gcttattata atgttctctg gcgaaaattc 360
acgactaaga aacacaaaac ctgggatggc gatggcattc tctccatccg tggaggatac 420
ggctatcttc aggatgtatc aggccgagac atggggcgca taatgatcaa ctcgactctg 480
gaacctggag caactttgac gattggggga aaagatgtcg aggtgcaatc cgccatgtcg 540
aaagaagagt acttgtctgg tcgatctttt ctgggagggg caaagaaaac cctgacgtct 600
cctctcgcgt ctcgtgagaa gacacaagcc tctgttgtcc ctactcaagc atcaaagctg 660
ccgaaagtct ccgcgacgct aactgaaggc gcaaagaagc cattgagtcg gacaagctct 720
cggaatgaca gtgaaaaaga tgccttcgtg aaaaatctca atgttgccgc tccaagaagc 780
gcagcattgg gcaacgcttt caagaacccg gtgaaagaga gcacagtttc ttccgcaaaa 840
ccggcagcac agcctattcc ccgtcatgat ccaaatgcgc cgggcgcctt ggtcatgaaa 900
cggccggatg tcgttccaaa gggaaagacg attgttgatg tcgtcgtgga ccccatcctt 960
accaaacacc tccgcgaaca ccaacgggag ggtgtcaaat ttctttacga gtgtgtcatg 1020
gggttaaggg attacaatgg tgaaggagca atcctagcgg acgagatggg tctggggaag 1080
accctgcaaa caatcacact cttgtggaca ttgctcaaac aaaatccgat ctacgaagag 1140
cccccagtcg tcaagaaggc gttgattgtt tgcccagtaa ccctcatcaa caactggaga 1200
aaagaattcc gcaaatggct gggaaatgaa cggataggcg tgttcgtctt cgatgacaag 1260
aggaaacgac tgacggactt tactatgggc aaagcctata atgttatgat cgtcgggtac 1320
gaaaagctgc gaaccgtcca ggaagggctc atcaaaggtg ccggggtcga tatcgtcatt 1380
gcagatgaag gccacagact aaagacacta cagaacaaga gcggccaggc cattcaagcg 1440
ctcaacacca cgaagaggat catcctctct ggcactccga ttcagaatga tctgagtgaa 1500
ttcttcgcgg cggtcgacct ggtcaatcct gggattctgg gtacatacaa gaacttcatg 1560
aaagaattcg aggggcctat tatgaggagt aggcagcccg aggcaacaaa aagagagatt 1620
gagaaaggag aggcgaggag tgaggagctc agaaatctca cgtccatgtt catgctacgc 1680
aggacggcgg atatcctgtc caaatacctg ccgccaaaaa cggagtatgt gctcctgtgc 1740
gaacctacgg cgatacaagc aagcatctac cgtcacgtcc tcgcgtcgcc catctttcaa 1800
agcgctcttg gtaacaccga gggtgcattc catctcatta ctattctcaa gaaattatgt 1860
aacagcccat cgttgctcac tgcgaagacg gaagacgaaa caccgaatgc tacggtttcc 1920
gcgctgctgt ctacgctgcc accgaatctt ctgcgtcatt tctccccttc ctcgagcggg 1980
aaattgaggg tactcgacca actcctccat aatctgcgca caaccacgtc ggaaaagatc 2040
gtgctggtct ccaactatac ctcgacattg aaccttctcg ccacgctgct cacgtcgctt 2100
tcgctcccgt tcctgcgtct ggacggcacc acgccgtcct cgaaacggca gtcgctcgtt 2160

-continued

```
gacgacttca atcgcagtcc cgcgagtacc tgctttgcgt ttctactctc cgcaaaggcc   2220

ggaggcacag gcctgaatct gattggggcc agccgcctcg tccttttcga cgtcgattgg   2280

aatccggcga cggacatgca ggccatggcg cggatccatc gagacggaca aacacgccac   2340

tgctggatat atcgcatcat gctgaaaggc gggctggagg agaagatctg gcagagacaa   2400

gtgaccaaaa tcgggctggc ggacagcgtc atggaacaga aaggcggcat ggcacagttc   2460

tcgcgggagg agctcaagga cctatttcga ctgtatgagg gcgaaggatg ccagacacat   2520

gatcttctgt gctgtaactg cggcgggcgg gggacaccat ccaccgacgg aggtgatcgt   2580

ccagtctcca cagattccga cgataaatcc agcagcagct gttcttcagc agaagacgag   2640

gaggagactg atgatgaaga cgatgaagaa gacatcgatc taccagacct cccaactctc   2700

atcaaagtat cacaactaga catcgacgcg caagaggccc aaatccgacg aggctcccat   2760

cctctccagc gacgtcagag caacaagacc aaggacaaga acaagaaaaa agacacaaag   2820

aacccgcgtg ggaggaagaa gaagaacagc gaccaagcca ggatgcagca attcctctcc   2880

gaatactcgc acatcgaccc ttccgccttt ggtgcagacg accatgggga ggagggcacg   2940

gatctagcca gccagatccg cgatccggtg ctcctttctc tcttgaggga ggaggatcat   3000

ggcgtggggt tcatctttga gaagacggcg tttcctgctg ctgatgctga tgctcctgct   3060

gagaagaaat aa                                                       3072
```

<210> SEQ ID NO 39
<211> LENGTH: 1023
<212> TYPE: PRT
<213> ORGANISM: Rasamsonia emersonii

<400> SEQUENCE: 39

```
Met Val Phe Lys Pro Phe Arg Pro Pro Leu Ile Arg Lys Pro Pro Pro
1               5                   10                  15

Pro Ala Glu Ser Ser Thr Pro Ile Thr Gly Asp Ser Gly Asn Pro His
            20                  25                  30

Pro Ser Lys Arg Pro Arg Leu Ser Glu Asp Asp Asp Gln Ser Ala Lys
        35                  40                  45

Asp Glu Lys Thr Ser Thr Ser Val Val Glu Ser Lys Ser Thr Lys Asp
    50                  55                  60

Lys Pro Lys Pro Gln Leu Ala Tyr Arg Lys Pro Leu Ile Gln Val Lys
65                  70                  75                  80

Asn Leu Thr Gly Lys Ala Ala Pro Ser Val Asp Asp Ala Ser Asn Ser
                85                  90                  95

Ala Asn Thr Glu Asn Asn Asn Gly Ser Thr Gln Glu Val Glu Ala Tyr
            100                 105                 110

Tyr Asn Val Leu Trp Arg Lys Phe Thr Thr Lys Lys His Lys Thr Trp
        115                 120                 125

Asp Gly Asp Gly Ile Leu Ser Ile Arg Gly Gly Tyr Gly Tyr Leu Gln
    130                 135                 140

Asp Val Ser Gly Arg Asp Met Gly Arg Ile Met Ile Asn Ser Thr Leu
145                 150                 155                 160

Glu Pro Gly Ala Thr Leu Thr Ile Gly Gly Lys Asp Val Glu Val Gln
                165                 170                 175

Ser Ala Met Ser Lys Glu Glu Tyr Leu Ser Gly Arg Ser Phe Leu Gly
            180                 185                 190

Gly Ala Lys Lys Thr Leu Thr Ser Pro Leu Ala Ser Arg Glu Lys Thr
        195                 200                 205
```

```
Gln Ala Ser Val Val Pro Thr Gln Ala Ser Lys Leu Pro Lys Val Ser
    210                 215                 220

Ala Thr Leu Thr Glu Gly Ala Lys Lys Pro Leu Ser Arg Thr Ser Ser
225                 230                 235                 240

Arg Asn Asp Ser Glu Lys Asp Ala Phe Val Lys Asn Leu Asn Val Ala
                245                 250                 255

Ala Pro Arg Ser Ala Ala Leu Gly Asn Ala Phe Lys Asn Pro Val Lys
            260                 265                 270

Glu Ser Thr Val Ser Ser Ala Lys Pro Ala Ala Gln Pro Ile Pro Arg
        275                 280                 285

His Asp Pro Asn Ala Pro Gly Ala Leu Val Met Lys Arg Pro Asp Val
    290                 295                 300

Val Pro Lys Gly Lys Thr Ile Val Asp Val Val Val Asp Pro Ile Leu
305                 310                 315                 320

Thr Lys His Leu Arg Glu His Gln Arg Glu Gly Val Lys Phe Leu Tyr
                325                 330                 335

Glu Cys Val Met Gly Leu Arg Asp Tyr Asn Gly Glu Gly Ala Ile Leu
            340                 345                 350

Ala Asp Glu Met Gly Leu Gly Lys Thr Leu Gln Thr Ile Thr Leu Leu
        355                 360                 365

Trp Thr Leu Leu Lys Gln Asn Pro Ile Tyr Glu Glu Pro Pro Val Val
    370                 375                 380

Lys Lys Ala Leu Ile Val Cys Pro Val Thr Leu Ile Asn Asn Trp Arg
385                 390                 395                 400

Lys Glu Phe Arg Lys Trp Leu Gly Asn Glu Arg Ile Gly Val Phe Val
                405                 410                 415

Phe Asp Asp Lys Arg Lys Arg Leu Thr Asp Phe Thr Met Gly Lys Ala
            420                 425                 430

Tyr Asn Val Met Ile Val Gly Tyr Glu Lys Leu Arg Thr Val Gln Glu
        435                 440                 445

Gly Leu Ile Lys Gly Ala Gly Val Asp Ile Val Ile Ala Asp Glu Gly
    450                 455                 460

His Arg Leu Lys Thr Leu Gln Asn Lys Ser Gly Gln Ala Ile Gln Ala
465                 470                 475                 480

Leu Asn Thr Thr Lys Arg Ile Ile Leu Ser Gly Thr Pro Ile Gln Asn
                485                 490                 495

Asp Leu Ser Glu Phe Phe Ala Ala Val Asp Leu Val Asn Pro Gly Ile
            500                 505                 510

Leu Gly Thr Tyr Lys Asn Phe Met Lys Glu Phe Glu Gly Pro Ile Met
        515                 520                 525

Arg Ser Arg Gln Pro Glu Ala Thr Lys Arg Glu Ile Glu Lys Gly Glu
    530                 535                 540

Ala Arg Ser Glu Glu Leu Arg Asn Leu Thr Ser Met Phe Met Leu Arg
545                 550                 555                 560

Arg Thr Ala Asp Ile Leu Ser Lys Tyr Leu Pro Pro Lys Thr Glu Tyr
                565                 570                 575

Val Leu Leu Cys Glu Pro Thr Ala Ile Gln Ala Ser Ile Tyr Arg His
            580                 585                 590

Val Leu Ala Ser Pro Ile Phe Gln Ser Ala Leu Gly Asn Thr Glu Gly
        595                 600                 605

Ala Phe His Leu Ile Thr Ile Leu Lys Lys Leu Cys Asn Ser Pro Ser
    610                 615                 620

Leu Leu Thr Ala Lys Thr Glu Asp Glu Thr Pro Asn Ala Thr Val Ser
```

-continued

```
625                 630                 635                 640

Ala Leu Leu Ser Thr Leu Pro Pro Asn Leu Leu Arg His Phe Ser Pro
                645                 650                 655

Ser Ser Ser Gly Lys Leu Arg Val Leu Asp Gln Leu Leu His Asn Leu
            660                 665                 670

Arg Thr Thr Thr Ser Glu Lys Ile Val Leu Val Ser Asn Tyr Thr Ser
        675                 680                 685

Thr Leu Asn Leu Leu Ala Thr Leu Leu Thr Ser Leu Ser Leu Pro Phe
    690                 695                 700

Leu Arg Leu Asp Gly Thr Thr Pro Ser Ser Lys Arg Gln Ser Leu Val
705                 710                 715                 720

Asp Asp Phe Asn Arg Ser Pro Ala Ser Thr Cys Phe Ala Phe Leu Leu
                725                 730                 735

Ser Ala Lys Ala Gly Gly Thr Gly Leu Asn Leu Ile Gly Ala Ser Arg
            740                 745                 750

Leu Val Leu Phe Asp Val Asp Trp Asn Pro Ala Thr Asp Met Gln Ala
        755                 760                 765

Met Ala Arg Ile His Arg Asp Gly Gln Thr Arg His Cys Trp Ile Tyr
    770                 775                 780

Arg Ile Met Leu Lys Gly Gly Leu Glu Glu Lys Ile Trp Gln Arg Gln
785                 790                 795                 800

Val Thr Lys Ile Gly Leu Ala Asp Ser Val Met Glu Gln Lys Gly Gly
                805                 810                 815

Met Ala Gln Phe Ser Arg Glu Glu Leu Lys Asp Leu Phe Arg Leu Tyr
            820                 825                 830

Glu Gly Glu Gly Cys Gln Thr His Asp Leu Leu Cys Cys Asn Cys Gly
        835                 840                 845

Gly Arg Gly Thr Pro Ser Thr Asp Gly Gly Asp Arg Pro Val Ser Thr
    850                 855                 860

Asp Ser Asp Asp Lys Ser Ser Ser Ser Cys Ser Ser Ala Glu Asp Glu
865                 870                 875                 880

Glu Glu Thr Asp Asp Glu Asp Asp Glu Glu Asp Ile Asp Leu Pro Asp
                885                 890                 895

Leu Pro Thr Leu Ile Lys Val Ser Gln Leu Asp Ile Asp Ala Gln Glu
            900                 905                 910

Ala Gln Ile Arg Arg Gly Ser His Pro Leu Gln Arg Arg Gln Ser Asn
        915                 920                 925

Lys Thr Lys Asp Lys Asn Lys Lys Lys Asp Thr Lys Asn Pro Arg Gly
    930                 935                 940

Arg Lys Lys Lys Asn Ser Asp Gln Ala Arg Met Gln Gln Phe Leu Ser
945                 950                 955                 960

Glu Tyr Ser His Ile Asp Pro Ser Ala Phe Gly Ala Asp Asp His Gly
                965                 970                 975

Glu Glu Gly Thr Asp Leu Ala Ser Gln Ile Arg Asp Pro Val Leu Leu
            980                 985                 990

Ser Leu Leu Arg Glu Glu Asp His  Gly Val Gly Phe Ile  Phe Glu Lys
        995                 1000                1005

Thr Ala  Phe Pro Ala Ala Asp  Ala Asp Ala Pro Ala  Glu Lys Lys
    1010                1015                1020
```

<210> SEQ ID NO 40
<211> LENGTH: 4591
<212> TYPE: DNA
<213> ORGANISM: Rasamsonia emersonii

<400> SEQUENCE: 40 acccctagctc tgatgaacgt ctctgatgtg tttcggcatc aagcgcaatt gcccgaatcc 60
taatgtgcaa ggagccggcc gtggtggagt cgctgctcgt ggaggtttca acggacctta 120
tcgcggtggc tatggcggat accccagagc tgcgacttgc tacaagtgcg gtggtcccaa 180
ccacttcgct cgggactgcc aagctcaggc catgaaatgc tatgcctgtg gcaagctggt 240
gagtcaggtt tcttgatgaa atcacatgga tataccatct aatgcgctcc cagggccata 300
tctcgcgcga ttgcactgct cccaacggtg ggcccctgag ctctgcaggc aaggtctgct 360
ataagtgctc gcaggctggc cacatctccc gagactgccc caacaacgaa tccaacaaca 420
cacagtcggc tgctgagact actacctccg cccctctgc cccggccgcc actgcctctg 480
ccagtgcccc tgtcgttgag agcactgctg aggttgctgc ccctgttgct caggctgctc 540
cggctgccgc agtcgcttag agtgggtttt tgaaacgaaa cccatcctac taccattctt 600
ctttttgtat taggttcgcc gactcggtct atctttcaat ccttttttt ttcctctcga 660
cctttcttct gttacatata ttatgccctt gtttcaggtt ttcggcaacg gcacttgtta 720
tgtatacgac gaacaaaaag tttcacgaag tcccaggatt cttccatgac ttggatcctc 780
tgcatggctc aagcctcatg attggcgtct tatttttcta tcgaatgtgt ctcaggaatt 840
tgaggaaaga aaaaagggtg caaccggagg agacgaggca agactgaggg ttaattgagc 900
agtggagagt tgtcggtgga tcgaaacaag cgagttgctg tgtggacctg acttcaaggt 960
gtatggatga agtggttgat gtccaagaag tatatcacaa aaatatcaaa aaaatgcgag 1020
gcatgaggta cctacctcta tcagtctaca aaatctctat catatatact cgttagactg 1080
agtattaaaa caaatattga caaaaaaaag cacttattgc atcatctatg gtcttgcaag 1140
gcagcgtttc aactttgcgc gttcgagata actggtgttg agaatacctc acgttccatc 1200
aaggatctat ctcaggcact gcattttatg ctcagctgta aaagcttcta ttttgtcata 1260
tcgtatccag ttcattcccg ccgatcaaac agattgcttc gtagagattc agcttgctgg 1320
tcagccaccc tttccagaca gaccccgtga catccatttc cccaacactt ccccctcgat 1380
cttctgatgg tccgcctttc gtctcgctca ctgtccctac gagctgaaac aagcaacgtg 1440
gccatctctc tctctctgtt taatctctct gcattgcgtc cctgactacg aagttccaag 1500
atgcctggct ccactgcaag cgatgaattc gacgatgatg tacgatgtct ctcccttgga 1560
ccataggctt cagaatcagg atctaacaag ccatcgtccg ttattcttga tagggtttta 1620
ttgtggacat tgacactatt caagctcatg gtatgatctt tcaaacccgt aaatgacatc 1680
tcctttgtct cttctttctt tccatgtctg ttatgactac cggacattac tgagggagac 1740
ataggcattg gcgtagcgga tatcacgaaa ctcaaggcca atggattcta tacagttgcc 1800
gtatctactt ctcacctgca gtctgttgtc cttctttgcc ttttgtgctg atctatggcc 1860
ccgactccac agtctgtcca cggagccacc cgcagaacgc tgttgaagat caaaggattc 1920
agcgaagtca aggtcgagaa gatcaaggaa gctattcaga aatgtttggt atggagatgg 1980
agatatccag cctattctcc ctcacagaag cgggtcttgg tcactgacat acatcgtaca 2040
gccatctgca agtggtttca ttaccgcaat ggaactgaac catcagcgta aaagggtgtt 2100
caagatttcc actggcagca agcaatttga cgctattcta ggggggtcag ttggctctat 2160
cctcgtctga tttacgcttc taatcagttg ccatccagtg gcttccaaag catgagtatc 2220
agcgaggtgt acggcgagtt tcgctgtggc aaaacccagc tgtcccatac catgtccgtc 2280

-continued

```
atcgcgcagc ttcccaaaga aatggggggc ggagagggca aagtcgcata cattgacaca   2340
gaaggaacat tcagaccgga acgtatcgcc cagatagcgg aacgttttgg tgttgaccct   2400
gagtctgctc aagagaacat tgcttacgct cgcgcactca acagcgaaca tcagctagaa   2460
ttgctcaaca cgctttcgaa ggaattcgct ggtggtgatt acaggctcct tatcatcgac   2520
agcatcatga attgcttccg cgtggattat tgcggccgtg gagaactcgc cgaacgccag   2580
cagaagttga accaatttct gataaaactg gcgcatatgg ccgaaggtag tttttccaat   2640
cttttttta tctctgcaaa tcgcagataa gctagcataa actgacagtc catcttccag   2700
aattcaacgt ctgtgtgctg atggtatggc ccctggacac ccgttatctg agttatctat   2760
catctatctt accttttcc ccaaaagacc aatcaagtgc aaagcgatcc tggagccagc   2820
gctctctttg caggcgccga tggtcgtaag cccgtgggcg gtcatgtcct cgctcatgcc   2880
tcgacgactc gggtccttct tcgcaagggt agaggtgaag agcgcgttgc taagattcag   2940
gactctccag gtctgccttc tgctttttct tgagtaatgg gaatttgtaa ggatattcct   3000
cactgacgca tttcgcttca cagactgccc cgagcgcgag gcaacgtacg tcatcactaa   3060
cggtggcatt aatgatcccg ataaggtcta ggtaggagag tccgtaggac attaagaaaa   3120
aaatacctgg gggagaagaa ccgatgtgag agacattttc tattgaacga atcttcgacg   3180
ggatttcagt tttcatgatc actaaaacat gcagaaggga tcgtctagtg aagttgatgt   3240
gtctgtatat tttagacgct gagaattacg gaatgcagtt agtttgaccg gttgaggagt   3300
agctccctag ataaactatc ccgagaccag caggtcgcca gatacccttt ccgttctagg   3360
gttggaggca cgccgccttt gaataccccc ctcgcgctgt agtagggtga ggcaggctgc   3420
ggccaggtga ggcagtgctg agggccaaga tcgagaacat tatatgagtg aatggcatga   3480
tcacccatgt ccaattaaac acggctaaag ttgccgcacg ttatggaact taatctgaca   3540
ggtttattat tggcctgttc tatagtgtac gactactaaa tcgtattaag agtcatactt   3600
gtcaatcgtt aataaaacca gcatgaacta ttattatatc agaaagcaag caatgtcact   3660
actatatata taactactgc cgcagatatc gatcagcata gacaggaagg ccatagatta   3720
ataatctact cattaactca tataggaaat ggtctgttag tccttgcttc gaaccgaata   3780
ttaactagac ttgctgctct cctcctaatg ccttttccat cctataggta accagtttcg   3840
atattaaatc tattttttaa atctaaattt ttcaacttta tttgaaattc caggataggc   3900
tttttatat atctctataa ctggccagta tagtctatat tatggcattt gatttatcct   3960
ttctaggggc tgctatatct attcttcccc ctgctagata ctaaagagtt ggcaggggct   4020
tctcaggaag ttctacataa tataagctgg cagtaatttt aagattttta atgtcttacc   4080
agtcttctgt gataccataa agcttctaaa agttatatta ctatctatgc tgctataacg   4140
cgaactgcta atagtaggca taagtgccaa aacttattat atctaaaaca ccattagaaa   4200
gaaatgttat atacttcctc acaatattag cattatagag cagagtatgg aagcatacca   4260
taataaagct aatatctacc ttattttggg aaaatacctg cttattgcca catgtttggc   4320
tattagtccc tataaggaat atattaatct tgagtactat ctaactagca atcttaagta   4380
atatatcaat caatagtaac cacataagta ttatagaggc agacctgaag cattaggcct   4440
attaaacatt taaaagtatt acatatatct atttaaaggg tgttaggtat tctaatatca   4500
ggcttaatta ggagctggta gctataagct taaatgccta gctcagcaac tttaacacat   4560
ccagatttaa ctgttatgag ccaacaggaa t                                  4591
```

-continued

<210> SEQ ID NO 41
<211> LENGTH: 840
<212> TYPE: DNA
<213> ORGANISM: Rasamsonia emersonii

<400> SEQUENCE: 41
atgcctggct ccactgcaag cgatgaattc gacgatgatt ctgtccacgg agccacccgc 60
agaacgctgt tgaagatcaa aggattcagc gaagtcaagg tcgagaagat caaggaagct 120
attcagaaat gtttgttgcc atccagtggc ttccaaagca tgagtatcag cgaggtgtac 180
ggcgagtttc gctgtggcaa aacccagctg tcccatacca tgtccgtcat cgcgcagctt 240
cccaaagaaa tgggggggcgg agagggcaaa gtcgcataca ttgacacaga aggaacattc 300
agaccggaac gtatcgccca gatagcggaa cgttttggtg ttgaccctga gtctgctcaa 360
gagaacattg cttacgctcg cgcactcaac agcgaacatc agctagaatt gctcaacacg 420
ctttcgaagg aattcgctgg tggtgattac aggctcctta tcatcgacag catcatgaat 480
tgcttccgcg tggattattg cggccgtgga gaactcgccg aacgccagca gaagttgaac 540
caatttctga taaaactggc gcatatggcc gaagtccatc ttccagaatt caacgtctgt 600
gtgctgatga ccaatcaagt gcaaagcgat cctggagcca gcgctctctt tgcaggcgcc 660
gatggtcgta agcccgtggg cggtcatgtc ctcgctcatg cctcgacgac tcgggtcctt 720
cttcgcaagg gtagaggtga agagcgcgtt gctaagattc aggactctcc agactgcccc 780
gagcgcgagg caacgtacgt catcactaac ggtggcatta atgatcccga taaggtctag 840

<210> SEQ ID NO 42
<211> LENGTH: 279
<212> TYPE: PRT
<213> ORGANISM: Rasamsonia emersonii

<400> SEQUENCE: 42

Met Pro Gly Ser Thr Ala Ser Asp Glu Phe Asp Asp Asp Ser Val His
1               5                   10                  15

Gly Ala Thr Arg Arg Thr Leu Leu Lys Ile Lys Gly Phe Ser Glu Val
            20                  25                  30

Lys Val Glu Lys Ile Lys Glu Ala Ile Gln Lys Cys Leu Leu Pro Ser
        35                  40                  45

Ser Gly Phe Gln Ser Met Ser Ile Ser Glu Val Tyr Gly Glu Phe Arg
    50                  55                  60

Cys Gly Lys Thr Gln Leu Ser His Thr Met Ser Val Ile Ala Gln Leu
65                  70                  75                  80

Pro Lys Glu Met Gly Gly Gly Glu Gly Lys Val Ala Tyr Ile Asp Thr
                85                  90                  95

Glu Gly Thr Phe Arg Pro Glu Arg Ile Ala Gln Ile Ala Glu Arg Phe
            100                 105                 110

Gly Val Asp Pro Glu Ser Ala Gln Glu Asn Ile Ala Tyr Ala Arg Ala
        115                 120                 125

Leu Asn Ser Glu His Gln Leu Glu Leu Leu Asn Thr Leu Ser Lys Glu
    130                 135                 140

Phe Ala Gly Gly Asp Tyr Arg Leu Leu Ile Ile Asp Ser Ile Met Asn
145                 150                 155                 160

Cys Phe Arg Val Asp Tyr Cys Gly Arg Gly Glu Leu Ala Glu Arg Gln
                165                 170                 175

Gln Lys Leu Asn Gln Phe Leu Ile Lys Leu Ala His Met Ala Glu Val
            180                 185                 190

-continued

```
His Leu Pro Glu Phe Asn Val Cys Val Leu Met Thr Asn Gln Val Gln
        195                 200                 205

Ser Asp Pro Gly Ala Ser Ala Leu Phe Ala Gly Ala Asp Gly Arg Lys
    210                 215                 220

Pro Val Gly Gly His Val Leu Ala His Ala Ser Thr Thr Arg Val Leu
225                 230                 235                 240

Leu Arg Lys Gly Arg Gly Glu Glu Arg Val Ala Lys Ile Gln Asp Ser
                245                 250                 255

Pro Asp Cys Pro Glu Arg Glu Ala Thr Tyr Val Ile Thr Asn Gly Gly
            260                 265                 270

Ile Asn Asp Pro Asp Lys Val
        275
```

<210> SEQ ID NO 43
<211> LENGTH: 4626
<212> TYPE: DNA
<213> ORGANISM: Rasamsonia emersonii

<400> SEQUENCE: 43

```
atcttttcct tttttttct actctcgtcc ccttgcagat gacatctctc atgcatgtgc     60

atgcacggta cttccctaat ctgataaaac tccgaaaggc aaaaaaaaaa gactcaagct    120

cggagacaat agtctaagtc taacgaaatg atccaccaga tgataagcac ctccaaggga    180

tggtgtggtg tggtgtggag aggacggagt aatagtaata gtcgtcctca tgacccgaac    240

gccctcgtgc tgcctgtcac cacttccagt ctgtcgggtg ggatgacttc ataggaataa    300

ttactgatca tatgcaaatg aagtatggag tattctgggt gggacaaatc ggcatttgtg    360

aatgacttat ctagtgcctt ttttttttgg ttcttcggca attttggaaa tgtattctat    420

cgagtcagtt cagcgattgc tctgctgtct ttccgtccag agtgtgattt cgttttgagt    480

ttgatatcat tcgtccatat ccattgcttt actgttcagg tgaggaaact cccgtccgta    540

gaaggttgac tcgtttggga tattattatt ccttgcgttt ttgagcttca aaactagtag    600

aataataaac gaaagagaaa aaaaaaagtg cagcttcgcg aaataggaaa cgtactgtgc    660

gattttctgg agaatgcttt tctcgtcaga cgaaatgctt aacagttatg ctatagaatt    720

ttcaaaatac tggttagtgc atcgggctct tgtgtcgagg atatgggatt gttattggta    780

gttattcttc ctttgacaat aactgggcag tgtaatggta tatttggtgg ttaatcatca    840

tatatctatt ctaatagctc tgagcctgtg tttagatcct aagagtcact ggtgcagctt    900

tttttatatc aaccacgcat aggtgtgata gtgtcattct gttttatata ttaactctac    960

tgtattaagg ggcatcggaa cgaaaaaaaa atcaaattat tatgatagta ttctaagttt   1020

gtccggagtt cttcatgtct ctttgctgtc gatacagtca gatacccttc agtttctaca   1080

ggtttcagta aatcaaaata aatatagctt attatgatga gttgacgctg caaagcatac   1140

cttattgcga gtctgtgtgt ggctttctga tattagtgac taatggtctg gatctatgta   1200

atgggttcag tgtaaccgta aactggaaat atatatattt caacaaatac atgctcaacg   1260

tattgcaatc tctgatcatc ttagttctag taaatcacaa cagaaattct ttcgatgctt   1320

ctcaattatg aattaataaa ttcattgaaa cctacatgaa aaaagtaggt tgaacatgga   1380

tgttgaaact agataattgt ttccagtgtt ctggtaccgc ggaaaggaag cggaagcaac   1440

tctgactgcg aacgtacgcg tgcacagtag aaagaacatc actcaacgcc tctcacttgc   1500

atggatctcc tatcaatcct gcccagattg tcgacaaaac aatacaccca tatcctcccg   1560

tccctcgaga ggaagcacat cagcactgtc gacttgatca ccctcgacac gcttgagatc   1620
```

-continued

```
gcgaaacgcg cgcacgttcc ccccgccgat gtccgtcgcc tgtgcgccga tgtcctcgag   1680
gcattacacc gcgacctggg attcgagcgc gaacagccca agaccaaggt gcaggatgag   1740
gaagaaacaa gcccaagcac cctggatgag ccccgtctca tccctgggcc gtcaaccaag   1800
ctagatcttt cgcattggag cacgatcagc actcttgacc ccgcgctgga cgcgctcttg   1860
gatggtggaa taccaacggg atatctcacg gaagtgactg gagagaggtt cgttgcactt   1920
cgtttctgac actttcttta cacgagcagg tctgaccgcg gttgcagcgg gagtggtaag   1980
acgcaattcc tgctcaatct tctcctcaca gcccagcttc cccgacctcg aggcctcggc   2040
aagagagcga tctacatatc gacggaggca ccgttgtcaa cgacgaggct gtcccagctg   2100
ttggagaccc atccgtatct atctactcta cctcccgata ctgcgccgtc tctcgccaat   2160
atcctttcta tcaacgctat cgacttggaa acccaggacc acatcctcaa ttaccagctc   2220
ccggttgcca tatcgcgtta cgatgtcggc cttgtggtta ttgattcgat cgctgcgaat   2280
taccgtgccg aacacgaatc gcacaatgtg tccgggatat ccacgcgctc gggagaactg   2340
gcaagactgg gtcagatgtt gcgaaatctc gctgtcaagg aagacattgc tgtcgtagtc   2400
gcaaaccagg tctctgaccg gttcgattcc ttcgacgacc aaccgcgatt gaggtccagc   2460
caaaccttga cgcctgcgat gcgagagcgt gagtctggtg ccagatcccc cctgccgaga   2520
aatcgagtcg aaggttggaa cgcggagaca acccccttcct catcaccagg cccgtcttcg   2580
ccgtacgtcg aggatgaatc tttcgatggc gcgtacatcg ttggccatcc ggtgagaaac   2640
gagactctca gtctagccca tcaacagcgc tttttcaccg gttggggtga cgcaccggag   2700
ctcgagtttt cagagtctca aaagacgccg gctttgggct ttgtctggtc aaaccagata   2760
gcttgtcgca tatcactgaa gaaggaggac gaaattcaac ctctaccggt tcctgtcgac   2820
acggttcctg cggcgacccc ctcttcacag acacggccac cggaagcaac tccagtccca   2880
gacgattcga agacagcttc tcaagagaca gattccaccg acgtaaagcc aacagcaagc   2940
caaggggacg agaggggtct gtccgcgaga gtacccacgt caacaccatc cctagttgca   3000
gacaagatta ccaagagacg gctcaaactg gtatttgcgc cgtggacagc cggaagggcg   3060
gacaatgcca gcgatgaggt agaattcgag atatggaagg gcggaattag aagtataaag   3120
caataaaatg aacttgttat cttgaacgga gtgtttcaca acagaggcac acttctatgc   3180
tgctagtccg cagcatgttc ttgcggatat gctttctata atatgatgta ctagaccctt   3240
gaatatgagc aggcattcga aagtatagga atgcgacaac tatgcccctg catttcctca   3300
ggaatcaagc agtgcttgct acagctacag gatccatcgt gcataggcga cgtaagctca   3360
gtccaagctc ctgagcgctg tagctctcat taccgaacaa tatcgaactg cctcttatta   3420
tcattacaaa tccagtgtca gatcaatgtc atactccagc ttcatttcag ctcaatctca   3480
gattgttatt ttattagaga gattctaagg ccagagcttg cctggcggcg gtgtgcggaa   3540
gcttaggaag caccttcccc gcactttaga cagtaaatag taaacacacc ctcttgatga   3600
tttcattctg ttgtcttcga ttatccttca tttctgtcac cattaatctt gcctttcctc   3660
cttccatact ctgactactc tcatgcaagc tactacactg actcctgttt actcttgtcg   3720
acattctcat ccactttact acccaaacag gtctagattc ttctcgtcta tgatctctat   3780
tctcattgca ctcatccttt catccatact atggatggct cctccactct cgatgcatct   3840
gtcgcaacat aacatccacg gtggatggaa gtgaagccga aagggaacaa caagctcgaa   3900
tacatatgcg atcatggctg gcacaaacat ccaagaaaca aaaaaatcta tctggcagaa   3960
```

```
cactaacaga ttaacaaagt gtaatatagc aatgagaaga gatcactcct gatgccttga   4020
acgcagagtc cacgatatct acagtgaagc gctcaatcgt ggccgctcga tccggcgaga   4080
gtaccacaaa aagcactcaa gtgtcatcga ctcgcagttg atcgctcgct tcaagaagaa   4140
ggcgggggga tcttggccgg gggaacacca agtccgttcc tgttgcggta gaacaggaca   4200
cctttgcttt caccctcggc accctccgtg ggctcaaccc actggcatac acggcagctg   4260
gtccagagcg ccttgaagaa acccagaggg ccggtgtgcg cttcgctgcg gtagtgcttg   4320
cccatcacct tcttgatggc ctcgctcgcc tcatcagcat ggtagaatgg gatggtgctc   4380
acataatggt gcagaacatg ggtttcgatg atgccgtgga aaaggtgacg gccaacccag   4440
ccaaagtcgc ggtcgatggt ggcagctgca ccacgagtga agttccagac ctcgggttca   4500
tagtgaggga gagtcgggtc ggtgtgctgc aggtaggtga tggcgactgc aaacctatca   4560
gaagaaaccc ttaaaaaaat ctgctgatgg agtaagactt accaagccag tggttcaccc   4620
agagat                                                              4626
```

<210> SEQ ID NO 44
<211> LENGTH: 1584
<212> TYPE: DNA
<213> ORGANISM: Rasamsonia emersonii

<400> SEQUENCE: 44

```
atggatctcc tatcaatcct gcccagattg tcgacaaaac aatacaccca tatcctcccg     60
tccctcgaga ggaagcacat cagcactgtc gacttgatca ccctcgacac gcttgagatc    120
gcgaaacgcg cgcacgttcc ccccgccgat gtccgtcgcc tgtgcgccga tgtcctcgag    180
gcattacacc gcgacctggg attcgagcgc gaacagccca agaccaaggt gcaggatgag    240
gaagaaacaa gcccaagcac cctggatgag ccccgtctca tccctgggcc gtcaaccaag    300
ctagatcttt cgcattggag cacgatcagc actcttgacc ccgcgctgga cgcgctcttg    360
gatggtggaa taccaacggg atatctcacg gaagtgactg gagagaggtc tgaccgcggt    420
tgcagcggga gtggtaagac gcaattcctg ctcaatcttc tcctcacagc ccagcttccc    480
cgacctcgag gcctcggcaa gagagcgatc tacatatcga cggaggcacc gttgtcaacg    540
acgaggctgt cccagctgtt ggagacccat ccgtatctat ctactctacc tcccgatact    600
gcgccgtctc tcgccaatat cctttctatc aacgctatcg acttggaaac ccaggaccac    660
atcctcaatt accagctccc ggttgccata tcgcgttacg atgtcggcct tgtggttatt    720
gattcgatcg ctgcgaatta ccgtgccgaa cacgaatcgc acaatgtgtc cgggatatcc    780
acgcgctcgg gagaactggc aagactgggt cagatgttgc gaaatctcgc tgtcaaggaa    840
gacattgctg tcgtagtcgc aaaccaggtc tctgaccggt tcgattcctt cgacgaccaa    900
ccgcgattga ggtccagcca aaccttgacg cctgcgatgc gagagcgtga gtctggtgcc    960
agatcccccc tgccgagaaa tcgagtcgaa ggttggaacg cggagacaac cccttcctca   1020
tcaccaggcc cgtcttcgcc gtacgtcgag gatgaatctt tcgatggcgc gtacatcgtt   1080
ggccatccgg tgagaaacga gactctcagt ctagcccatc aacagcgctt tttcaccggt   1140
tggggtgacg caccggagct cgagttttca gagtctcaaa agacgccggc tttgggcttt   1200
gtctggtcaa accagatagc ttgtcgcata tcactgaaga aggaggacga aattcaacct   1260
ctaccggttc ctgtcgacac ggttcctgcg gcgaccccct cttcacagac acggccaccg   1320
gaagcaactc cagtcccaga cgattcgaag acagcttctc aagagacaga ttccaccgac   1380
gtaaagccaa cagcaagcca aggggacgag aggggtctgt ccgcgagagt acccacgtca   1440
```

acaccatccc tagttgcaga caagattacc aagagacggc tcaaactggt atttgcgccg 1500
tggacagccg gaagggcgga caatgccagc gatgaggtag aattcgagat atggaagggc 1560
ggaattagaa gtataaagca ataa 1584

<210> SEQ ID NO 45
<211> LENGTH: 527
<212> TYPE: PRT
<213> ORGANISM: Rasamsonia emersonii

<400> SEQUENCE: 45

Met Asp Leu Leu Ser Ile Leu Pro Arg Leu Ser Thr Lys Gln Tyr Thr
1 5 10 15

His Ile Leu Pro Ser Leu Glu Arg Lys His Ile Ser Thr Val Asp Leu
20 25 30

Ile Thr Leu Asp Thr Leu Glu Ile Ala Lys Arg Ala His Val Pro Pro
35 40 45

Ala Asp Val Arg Arg Leu Cys Ala Asp Val Leu Glu Ala Leu His Arg
50 55 60

Asp Leu Gly Phe Glu Arg Glu Gln Pro Lys Thr Lys Val Gln Asp Glu
65 70 75 80

Glu Glu Thr Ser Pro Ser Thr Leu Asp Glu Pro Arg Leu Ile Pro Gly
85 90 95

Pro Ser Thr Lys Leu Asp Leu Ser His Trp Ser Thr Ile Ser Thr Leu
100 105 110

Asp Pro Ala Leu Asp Ala Leu Leu Asp Gly Gly Ile Pro Thr Gly Tyr
115 120 125

Leu Thr Glu Val Thr Gly Glu Arg Ser Asp Arg Gly Cys Ser Gly Ser
130 135 140

Gly Lys Thr Gln Phe Leu Leu Asn Leu Leu Leu Thr Ala Gln Leu Pro
145 150 155 160

Arg Pro Arg Gly Leu Gly Lys Arg Ala Ile Tyr Ile Ser Thr Glu Ala
165 170 175

Pro Leu Ser Thr Thr Arg Leu Ser Gln Leu Leu Glu Thr His Pro Tyr
180 185 190

Leu Ser Thr Leu Pro Pro Asp Thr Ala Pro Ser Leu Ala Asn Ile Leu
195 200 205

Ser Ile Asn Ala Ile Asp Leu Glu Thr Gln Asp His Ile Leu Asn Tyr
210 215 220

Gln Leu Pro Val Ala Ile Ser Arg Tyr Asp Val Gly Leu Val Val Ile
225 230 235 240

Asp Ser Ile Ala Ala Asn Tyr Arg Ala Glu His Glu Ser His Asn Val
245 250 255

Ser Gly Ile Ser Thr Arg Ser Gly Glu Leu Ala Arg Leu Gly Gln Met
260 265 270

Leu Arg Asn Leu Ala Val Lys Glu Asp Ile Ala Val Val Val Ala Asn
275 280 285

Gln Val Ser Asp Arg Phe Asp Ser Phe Asp Asp Gln Pro Arg Leu Arg
290 295 300

Ser Ser Gln Thr Leu Thr Pro Ala Met Arg Glu Arg Glu Ser Gly Ala
305 310 315 320

Arg Ser Pro Leu Pro Arg Asn Arg Val Glu Gly Trp Asn Ala Glu Thr
325 330 335

Thr Pro Ser Ser Ser Pro Gly Pro Ser Ser Pro Tyr Val Glu Asp Glu 340 345 350

Ser Phe Asp Gly Ala Tyr Ile Val Gly His Pro Val Arg Asn Glu Thr
355 360 365

Leu Ser Leu Ala His Gln Gln Arg Phe Phe Thr Gly Trp Gly Asp Ala
370 375 380

Pro Glu Leu Glu Phe Ser Glu Ser Gln Lys Thr Pro Ala Leu Gly Phe
385 390 395 400

Val Trp Ser Asn Gln Ile Ala Cys Arg Ile Ser Leu Lys Lys Glu Asp
405 410 415

Glu Ile Gln Pro Leu Pro Val Pro Val Asp Thr Val Pro Ala Ala Thr
420 425 430

Pro Ser Ser Gln Thr Arg Pro Pro Glu Ala Thr Pro Val Pro Asp Asp
435 440 445

Ser Lys Thr Ala Ser Gln Glu Thr Asp Ser Thr Asp Val Lys Pro Thr
450 455 460

Ala Ser Gln Gly Asp Glu Arg Gly Leu Ser Ala Arg Val Pro Thr Ser
465 470 475 480

Thr Pro Ser Leu Val Ala Asp Lys Ile Thr Lys Arg Arg Leu Lys Leu
485 490 495

Val Phe Ala Pro Trp Thr Ala Gly Arg Ala Asp Asn Ala Ser Asp Glu
500 505 510

Val Glu Phe Glu Ile Trp Lys Gly Gly Ile Arg Ser Ile Lys Gln
515 520 525

<210> SEQ ID NO 46
<211> LENGTH: 8136
<212> TYPE: DNA
<213> ORGANISM: Rasamsonia emersonii

<400> SEQUENCE: 46
ccccattgga agttagacca ccagcttccc cacaccgacg tgtggttatt gatgagcacg 60
tcctctgcat acttcgactt ggccgctctc tttggcgctc ccttaatggc tcctgtttcg 120
tcgtattcga catatcgctc attctcgata acagcagcgt catgtgacgg agccgccttc 180
aaatgttctt cgccaccata tttctcaagg agctgtttcc gttgagcctc acgtttggct 240
tcattttccg ccttctcctt ctttctcaag atttcgccag aagttggatt ggcttgcaga 300
tgataagatt tgtctccccg ttcctgcgcc tcccatgcga ggcgttgcgc tttttcgaat 360
tctgcagcat caccagatgc ccgtacgaag ttctcctcgg ctacaagtgc tgctgcttga 420
tctgcttgcg cgcccatatc aaccattttt cttgtcttcg gatcatactt ggctgaatca 480
aggtcaaggt taaggagata tttcgccgta tcttcgcgaa ttcgcagatt ccgggtggct 540
gtactctgct ttcttcccat gtccgattcc tcggcgtatc gggcctcttc ctgttcatcg 600
tcactctcgt cctcgccatc ctgagatttg ttctttttct cagcttcctg cttcgccttg 660
cgcttcaagt tctccagctc ttcgtattcc tcaacgacct tccgatattc tgcggggtca 720
tatccgttcc aacggtcccg cttcgcatcc caaccaagct cgaccttctg aatcacttcg 780
tctggttgta tatccttccc tgtccatcga gctccgagtt tccgcggccg actcaagcat 840
tccttcgttt tgtgtgtcat tgcgccgcag ttctcgcaag cgccctttcg gtatttcgta 900
gcagccggac ctagccgttt gcctctttca taccatttcg actgatccga tgtcgacttc 960
tgtagacgct gatgctctag gtagtcattt gctgaggagt catcgtcgac gtagaagggc 1020
ttcttcgaaa tgaacgaagg aatgtattcg ttgcgctcct tcgacgccac atcggtaggc 1080

-continued

```
cttcgcgaca tcgtggcaat atttgaggag ccgatctcaa aactctcaga gatagctcac   1140
ttgacactca caactaggag tgtctctagt ccaggcgaat agaaaagatg cggtttggag   1200
agcagaggtc gatggagagg cggtggtttg gaatcgccga cgtccgagat aggtagtttt   1260
atatcacgtg accaggagtc tgtcgtgtgg cgcggcaact cggcggggcg cgcctaacta   1320
atgcacgtca tgttcgcctt gttgatagcg gtatgcgacg cgaatatcga gtagattaaa   1380
ggcaaaacga tgccagaaac gctttttcta cacagtctca agtcgttata taacatttgc   1440
gtgcattagc cgttacgcaa tgtttttcag atttttatct ttaccatcct gagagccggg   1500
atggatatct ttcgagttcg tttgaattgt atcgatcatt atcaggcaac tccaacggaa   1560
ttcgaccctc ccgtgccata tggcgtcggt atatcgcaaa gaaatgaaag gccaaaggta   1620
cctgtcattc gcgcctttgg ggcgactgaa acaggccaga aggtctgtgc ccatatccat   1680
ggtgcctttc cttacctcta tattgagtac aagggaagcc tagaaccaga tgaaggtcgg   1740
tacgatttct ctagtatgca aatcagtttt gcttaaagct atattgtttt agtgaacacc   1800
gccattcgta atctacatct ctcaatcgac catgctttgg ctgttagcta ccgtcggaac   1860
gcatacgagg ggaagacggc ttacgtcgcc cacatatccc tggtcaaagg gataccettc   1920
tatggttatc atgtgggata tcagttttat ttcaaaatat acctgttgaa cccactgaat   1980
ataaccaggc tcgctgatct cctacgtcaa ggggctgtgt tgaaacgtcc tatgcagccg   2040
tatgaaagtc accttcaata cataccgcag tggatgtgtg atttcaacct gtatggctgt   2100
gcgtacatgg agtgtgcgaa ggtcaagttc cgctcgccgg ttccaagcta tctcgaactt   2160
tccaatctgg atcatcgttg gcatgatcgc tcaataccta gcgaactcat ttcgaacgaa   2220
tccgaattac cgaagcagag tcattgctcc ttggaagtgg atgtctgtgt ccaggatatc   2280
attaaccggc acgctataaa agagaggccg ttacatcatg actttgttga gcgaatacat   2340
cctctatccc ccgaagagaa actcgttcac agtatggccg gtttgtggca ggatgagacg   2400
cgaaggcgta aaaagagact tggaattaag gatcctggaa gcagcccttt cggcccggag   2460
gagctagtct cgatgtctgc tagccccaga gaccagaaca caggtggctg gatccacgaa   2520
gacgagttct gggagaaatt gcgtgaaatt gttgaggagg aaaagcggaa gagtgatggc   2580
acaagcgtct ctttcgaaac atacgtgaag aaggatcctc tcgaacatac ggtcaagact   2640
gcacttgaga gtgtcgagga tttgtttcca cagaagctgg agcctctgaa tcatgagagc   2700
aatcacctgc aggatggagc tatggatact ggtatcgagg ttgatgaaaa tacagcgctc   2760
tcatttgaat cggatgatcg atatgactat tcagatgacg aggtctctgt ccagccagat   2820
ttcggatttg tgcaagatga tcctgctctc gaggagcttg gtgttaattc agactcaaat   2880
aatgacggac ccaaacaatg cgatggaaac ggtctaccca aacctgacgg tttagctcgt   2940
cgcagaagta ccacagcccg tatcagagaa acagatggga tgcataatgc agaatttgat   3000
cccggcgcca tttcacgacc gcagaaacga tcagatggcg aagaaataaa cgtaggacat   3060
gtggcaaaac gatcgaaaca acttaatggc gaatatattc acaatcgaga aacttattca   3120
actgccacta cggacacagg aatttccccg tttgacactc ccgcagcttt gggggatgtt   3180
gctgctcaaa ctaatcatca aagtagtgca gacggcatgg tcaagccact tccccaacca   3240
aagccgtctt cctcgcagag gatgctcccg ggtagagcct cgagtcaaaa tcagcggctt   3300
tcgtttccgg ttgtcaagga ccctaatgat cctttaacac tgttgcgctt tagtcaaagt   3360
cagaaaagca tttcttcgaa accgacttct caactctccc aggagacgga gaaggtttcc   3420
gcacaaggac atcgtgaaga ctctcaagct aggtcgtctt cgcagttgca ttcaacaaat   3480
```

-continued agcgatcaaa ccctgcaaga tttcaataca gatgaccttc tgacggcctc taaaattcat 3540
gatgcgtttc acatccctag gaatcgcaaa atcctgtgtt actgccaccc ttgtccccgg 3600
cctagtgaaa taatgtcaac gatcaatgac gaaggacgcc cgacagtcgt ttatcagaag 3660
gcctactata gtgacgagag tgatgttcct gagcggcagc gggagtatgc gggacgtgaa 3720
tttcgtctgg ggagtgatac cttacaatac ctacctgagt ttgatagaac aggcaggtcg 3780
ccttcactgc ttggagaaca gattcctcca tccgctacca acctcgaaaa tcagagaaaa 3840
caggatcaga aattgcgcga gctgtcttca tgtcgtatat gggaatttgc tcaggtgcca 3900
ccacgtcgct cagaagtcgt agaatggttc gaaagggaaa tagcgcatcc aaaacaggac 3960
tcatcaaatg gctcccgccg tctgcctgaa acgaagccaa acgtattatg gcagattgag 4020
ggcgcgacac agaaggatcc acacgggttc aaatactccc agaagcaggg gtccacgagt 4080
gtggaacacc agactcaata catgagcgta atgagccttg aagtgcatgt caatactaga 4140
gactctttgg ctccaaatcc ggaagaggat gagatagcct gtgttttttg gtgtctccag 4200
tccgacgacg aagatctcga tgttaacagt gccctggacg gcgttcatgt tggaatcctt 4260
gcccagtcgg gatctgatgc cctgggaaaa gtagcgcggt ctataactgt cgattttgaa 4320
cgggagccaa cggaattgga tttgatcact cgcctggttg atatcgtgcg atactatgac 4380
ccggatattc ttacgggcta tgaggtgcat aatagctctt ggggatattt gattgagcgg 4440
gcgcggtaca agtacgactt ggatttatgc gacgagctct ctcgagtcaa agcacaatcc 4500
catggtagat ttggtaaaga aaacgaccgc tggggtttca accacacctc tagcattcgg 4560
gtgactgggc gacatatgat caacatctgg cgtgcaatga gaagcgagct caatctcttg 4620
caatatacga tggagaatgt tgtctttcat ctgctacaca ggcgaatccc acactacccg 4680
ttcaaagagc taacggcgtg gtacaagagc agcaagccgc gggacgtgat gaaagtcatt 4740
gaatattttg tctccagaac cctgatggat ctggaaattc tcgaagcgaa cgagctaatc 4800
cccagaacta gcgaacaagc tcgtctgctg ggcatcgact tttactctgt tttctctcgt 4860
ggctcgcagt tcaaggtgga gtccctgatg tttcgaatcg ccaagcccga aaatttcata 4920
ttgatctctc caagcaagaa gcaagtcggt caacagaacg ctcttgaatg tcttcctctg 4980
gtgatggaac ctcaaagtga tttttacacc agtccgcttg tggtcttaga ttttcaatct 5040
ctgtatccga gtgtcatgat agcatacaat tattgctatt caaccttcct cggccgactt 5100
gtcagctggc gtgggcggaa caaaatgggg ttcactgact acgagaggcc acctcgtctg 5160
ctggagctcc ttggggacaa tattaatatt gctcctaacg gaatgatgta taccaagcct 5220
gagatacgga agtcacttct cgcccgaatg ctaagcgaaa tcttggagac tcgtgtcatg 5280
gtcaaaagtg gtatgaaagt cgacaaggat gacaggattt tgcagcgctt gctcaataac 5340
cggcaattgg cgctcaagct gattgccaac gtcacatatg gctacacgtc tgcctcgttc 5400
tcgggacgaa tgccatgctc tgaaattgcg gatagtattg tccagacagg acgagagacc 5460
ctagaaaagg cgattgcctt aatacactct gtcgaacgct ggggcgctga ggtggtgtat 5520
ggcgatacgg acagtctctt cgtctatctc aaaggacgtt cacgggacga agcattcact 5580
attggggagg agattgccca ggccgtcact aagatgaatc ctcgtccggt taaactcaaa 5640
tttgagaagg tttatcatcc atgcgttctc ctggcgaaga agcgatatgt tggcttcaag 5700
tacgaacgta gagaacagac agaacccgag ttcgatgcga aggggatcga gactgttcgt 5760
cgagatggca caccggctga gcagaagatt gaagagaagg ccctcaagat tcttttcagg 5820

-continued

```
acggcagatt tgagtcaggt caagaggtac ttccagagtc aatgttcgaa aatcatgcag   5880
ggcaaggtgt ccatccagga tttctgtttt gcgagagaag tgaggctggg aacgtacagc   5940
gagaagggct tgcttcctcc tggagctttg atcagtgcca agaggatgct catggaccct   6000
cgtttggagc cccaatacgg cgagcgcgtg ccatacgtgg tggtcactgg tgctcccggg   6060
tcgagactgg ttgatcgctg tgtcgccccc gaagtacttc ttgacaaccc gcatcttgag   6120
ctcgatgccg agtattatat aaccaagaac atcattccgc cattggaacg tatattcaac   6180
ctggttgggg cgaacgtccg ccagtggtac gacgaaatgc cgaagttcca acgaattcga   6240
cgcatcgagg gcgtggctac tgctgctggg gaggccggat cctccaaaaa gacccttgag   6300
tcgtacatga aatcgtccgc ttgtatcctc tgcaaggata aactcgacga tgctgaactc   6360
cccatttgca gctcttgtgc caatcaacct cacatttccc ttttcaccct aacgtctcgc   6420
ctcaagcagg ccgagaggag agtcaacgat cttctcaaga tctgtcggtc atgcatgggc   6480
gttccatttg gcgatgatgt caagtgcgac agtaaggact gtccagtatt ctactcgagg   6540
acaagggata tggccaattg gaagcattcg aatgccgtcc tcgaacccgt catcaggatg   6600
ctggaagaac ggagcgagag cgtcttggaa tggtagcaaa cgacagaaga cacggaggga   6660
aattataata tgatcaggag ataggtttct tttagataac cgctggcatg tgtatttggc   6720
tgttgcatgt tggaagggac ggtaggcagt gataccccgg cgtctatttc ggagttgttt   6780
ggttacctga gttagtcgtg ctttctctct gggacgagct tggtctgcta atctgatatg   6840
gttgttcctt cctcattggt atgtccgtat gataaagtat acagtaaata aaatttatca   6900
cgtggctcta gcctcgtgta ctgtctccgg agcactcttg tccggaccaa tgtgagacat   6960
gtccgtactt cttaatcatc tcgtggttct ccatagacct gcagtctggc accaggacaa   7020
tgggccggga acagaccatc ccacggggtg gctagactcg gaacagggcc gccggcgcta   7080
agtcctccgg tacgccgtcc tccgtgttga gcacaattaa ttgcagaatc cctgcactcc   7140
acccccttaca accggcctta ttccttctga tcccaatctc atgatggcgt gcgtatcaag   7200
attgactaaa caactgggta agttcctttt ttctggacag gctttgacag aatcgttggc   7260
taaagacatc caactccgca gcctgagtcc agttccgatg ggtctcgagt cggtcacaca   7320
cgagccttat tcggcaaagg atcgccgatg gaaacttcca tcccccgcag gaggaaaaaa   7380
ctggggaagc ctcggggttt cccccgcact cttcagctac catcccgaga accgaccaat   7440
cccggtctca taacaggccg gagtacagta ctccgctgtc atcctagatt agcttgggcc   7500
taatcttaaa acaaagaaaa gctccaattc gggaaggacg gggagctgtg tagcccgggt   7560
aattggctcg tgcggatgaa gtataaaatg gaggccgttg gcacttgcag ggatcctgca   7620
tattccgtct ttacatgggt gttgaaaagt gcccgcgaca gacagttgca tggcagtttg   7680
actgtgacgg ttagttgagg gagacctgac catcggcttt gggaatccat gatggcgtcc   7740
gtatcggacc tggagggcca ggcctccaag gctggcggct ttcagcttgt atacaggaat   7800
ccatatctct ttggagtcgc gttggtaagc atctgggcaa tttatggacg atctaacggc   7860
tgtacctcgc taacttgatt ctgcacagtt ttcgaccttg ggtggtctgt tgtttggcta   7920
tgaccagggt gtcgtgtccg gtatcctgac gatggaatcg tttggagctc gattccctcg   7980
gatctactct gacagcagct tcaagggatg gtttgtctcg acgcttctac taagtacgtc   8040
cggccgatat ccaatgatta tacgttctgt tttccatatc tacccatctt catccgacta   8100
acagagctag atagctgcgt ggttcggatc tcttgt                             8136
```

<210> SEQ ID NO 47
<211> LENGTH: 5079
<212> TYPE: DNA
<213> ORGANISM: Rasamsonia emersonii

<400> SEQUENCE: 47
atggatatct ttcgagttcg tttgaattgt atcgatcatt atcaggcaac tccaacggaa 60
ttcgaccctc ccgtgccata tggcgtcggt atatcgcaaa gaaatgaaag gccaaaggta 120
cctgtcattc gcgcctttgg ggcgactgaa acaggccaga aggtctgtgc ccatatccat 180
ggtgcctttc cttacctcta tattgagtac aagggaagcc tagaaccaga tgaagtgaac 240
accgccattc gtaatctaca tctctcaatc gaccatgctt tggctgttag ctaccgtcgg 300
aacgcatacg aggggaagac ggcttacgtc gcccacatat ccctggtcaa agggataccc 360
ttctatggtt atcatgtggg atatcagttt tatttcaaaa tatacctgtt gaacccactg 420
aatataacca ggctcgctga tctcctacgt caaggggctg tgttgaaacg tcctatgcag 480
ccgtatgaaa gtcaccttca atacataccg cagtggatgt gtgatttcaa cctgtatggc 540
tgtgcgtaca tggagtgtgc gaaggtcaag ttccgctcgc cggttccaag ctatctcgaa 600
ctttccaatc tggatcatcg ttggcatgat cgctcaatac ctagcgaact catttcgaac 660
gaatccgaat taccgaagca gagtcattgc tccttggaag tggatgtctg tgtccaggat 720
atcattaacc ggcacgctat aaaagagagg ccgttacatc atgactttgt tgagcgaata 780
catcctctat cccccgaaga gaaactcgtt cacagtatgg ccggtttgtg gcaggatgag 840
acgcgaaggc gtaaaaagag acttggaatt aaggatcctg gaagcagccc tttcggcccg 900
gaggagctag tctcgatgtc tgctagcccc agagaccaga acacaggtgg ctggatccac 960
gaagacgagt tctgggagaa attgcgtgaa attgttgagg aggaaaagcg gaagagtgat 1020
ggcacaagcg tctctttcga aacatacgtg aagaaggatc ctctcgaaca tacggtcaag 1080
actgcacttg agagtgtcga ggatttgttt ccacagaagc tggagcctct gaatcatgag 1140
agcaatcacc tgcaggatgg agctatggat actggtatcg aggttgatga aaatacagcg 1200
ctctcatttg aatcggatga tcgatatgac tattcagatg acgaggtctc tgtccagcca 1260
gatttcggat ttgtgcaaga tgatcctgct ctcgaggagc ttggtgttaa ttcagactca 1320
aataatgacg gacccaaaca atgcgatgga aacggtctac ccaaacctga cggtttagct 1380
cgtcgcagaa gtaccacagc ccgtatcaga gaaacagatg ggatgcataa tgcagaattt 1440
gatcccggcg ccatttcacg accgcagaaa cgatcagatg gcgaagaaat aaacgtagga 1500
catgtggcaa aacgatcgaa acaacttaat ggcgaatata ttcacaatcg agaaacttat 1560
tcaactgcca ctacggacac aggaatttcc ccgtttgaca ctcccgcagc tttgggggat 1620
gttgctgctc aaactaatca tcaaagtagt gcagacggca tggtcaagcc acttccccaa 1680
ccaaagccgt cttcctcgca gaggatgctc ccgggtagag cctcgagtca aaatcagcgg 1740
ctttcgtttc cggttgtcaa ggaccctaat gatcctttaa cactgttgcg ctttagtcaa 1800
agtcagaaaa gcatttcttc gaaaccgact tctcaactct cccaggagac ggagaaggtt 1860
tccgcacaag gacatcgtga agactctcaa gctaggtcgt cttcgcagtt gcattcaaca 1920
aatagcgatc aaaccctgca agatttcaat acagatgacc ttctgacggc ctctaaaatt 1980
catgatgcgt ttcacatccc taggaatcgc aaaatcctgt gttactgcca cccttgtccc 2040
cggcctagtg aaataatgtc aacgatcaat gacgaaggac gcccgacagt cgtttatcag 2100
aaggcctact atagtgacga gagtgatgtt cctgagcggc agcgggagta tgcgggacgt 2160

-continued

```
gaatttcgtc tggggagtga taccttacaa tacctacctg agtttgatag aacaggcagg   2220

tcgccttcac tgcttggaga acagattcct ccatccgcta ccaacctcga aaatcagaga   2280

aaacaggatc agaaattgcg cgagctgtct tcatgtcgta tatgggaatt tgctcaggtg   2340

ccaccacgtc gctcagaagt cgtagaatgg ttcgaaaggg aaatagcgca tccaaaacag   2400

gactcatcaa atggctcccg ccgtctgcct gaaacgaagc caaacgtatt atggcagatt   2460

gagggcgcga cacagaagga tccacacggg ttcaaatact cccagaagca ggggtccacg   2520

agtgtggaac accagactca atacatgagc gtaatgagcc ttgaagtgca tgtcaatact   2580

agagactctt tggctccaaa tccggaagag gatgagatag cctgtgtttt ttggtgtctc   2640

cagtccgacg acgaagatct cgatgttaac agtgccctgg acggcgttca tgttggaatc   2700

cttgcccagt cgggatctga tgccctggga aaagtagcgc ggtctataac tgtcgatttt   2760

gaacgggagc caacggaatt ggatttgatc actcgcctgg ttgatatcgt gcgatactat   2820

gacccggata ttcttacggg ctatgaggtg cataatagct cttggggata tttgattgag   2880

cgggcgcggt acaagtacga cttggattta tgcgacgagc tctctcgagt caaagcacaa   2940

tcccatggta gatttggtaa agaaaacgac cgctggggtt tcaaccacac ctctagcatt   3000

cgggtgactg ggcgacatat gatcaacatc tggcgtgcaa tgagaagcga gctcaatctc   3060

ttgcaatata cgatggagaa tgttgtcttt catctgctac acaggcgaat cccacactac   3120

ccgttcaaag agctaacggc gtggtacaag agcagcaagc cgcgggacgt gatgaaagtc   3180

attgaatatt ttgtctccag aaccctgatg gatctggaaa ttctcgaagc gaacgagcta   3240

atccccagaa ctagcgaaca agctcgtctg ctgggcatcg acttttactc tgttttctct   3300

cgtggctcgc agttcaaggt ggagtccctg atgtttcgaa tcgccaagcc cgaaaatttc   3360

atattgatct ctccaagcaa gaagcaagtc ggtcaacaga acgctcttga atgtcttcct   3420

ctggtgatgg aacctcaaag tgatttttac accagtccgc ttgtggtctt agattttcaa   3480

tctctgtatc cgagtgtcat gatagcatac aattattgct attcaacctt cctcggccga   3540

cttgtcagct ggcgtgggcg gaacaaaatg gggttcactg actacgagag gccacctcgt   3600

ctgctggagc tccttgggga caatattaat attgctccta acggaatgat gtataccaag   3660

cctgagatac ggaagtcact tctcgcccga atgctaagcg aaatcttgga gactcgtgtc   3720

atggtcaaaa gtggtatgaa agtcgacaag gatgacagga ttttgcagcg cttgctcaat   3780

aaccggcaat tggcgctcaa gctgattgcc aacgtcacat atggctacac gtctgcctcg   3840

ttctcgggac gaatgccatg ctctgaaatt gcggatagta ttgtccagac aggacgagag   3900

accctagaaa aggcgattgc cttaatacac tctgtcgaac gctggggcgc tgaggtggtg   3960

tatggcgata cggacagtct cttcgtctat ctcaaaggac gttcacggga cgaagcattc   4020

actattgggg aggagattgc ccaggccgtc actaagatga atcctcgtcc ggttaaactc   4080

aaatttgaga aggtttatca tccatgcgtt ctcctggcga agaagcgata tgttggcttc   4140

aagtacgaac gtagagaaca gacagaaccc gagttcgatg cgaaggggat cgagactgtt   4200

cgtcgagatg gcacaccggc tgagcagaag attgaagaga aggccctcaa gattcttttc   4260

aggacggcag atttgagtca ggtcaagagg tacttccaga gtcaatgttc gaaaatcatg   4320

cagggcaagg tgtccatcca ggatttctgt tttgcgagag aagtgaggct gggaacgtac   4380

agcgagaagg gcttgcttcc tcctggagct ttgatcagtg ccaagaggat gctcatggac   4440

cctcgtttgg agccccaata cggcgagcgc gtgccatacg tggtggtcac tggtgctccc   4500

gggtcgagac tggttgatcg ctgtgtcgcc cccgaagtac ttcttgacaa cccgcatctt   4560
```

```
gagctcgatg ccgagtatta tataaccaag aacatcattc cgccattgga acgtatattc   4620

aacctggttg gggcgaacgt ccgccagtgg tacgacgaaa tgccgaagtt ccaacgaatt   4680

cgacgcatcg agggcgtggc tactgctgct ggggaggccg gatcctccaa aaagaccctt   4740

gagtcgtaca tgaaatcgtc cgcttgtatc ctctgcaagg ataaactcga cgatgctgaa   4800

ctccccattt gcagctcttg tgccaatcaa cctcacattt ccccttttcac cctaacgtct   4860

cgcctcaagc aggccgagag gagagtcaac gatcttctca agatctgtcg gtcatgcatg   4920

ggcgttccat ttggcgatga tgtcaagtgc gacagtaagg actgtccagt attctactcg   4980

aggacaaggg atatggccaa ttggaagcat tcgaatgccg tcctcgaacc cgtcatcagg   5040

atgctggaag aacggagcga gagcgtcttg gaatggtag                          5079
```

<210> SEQ ID NO 48
<211> LENGTH: 1692
<212> TYPE: PRT
<213> ORGANISM: Rasamsonia emersonii

<400> SEQUENCE: 48

```
Met Asp Ile Phe Arg Val Arg Leu Asn Cys Ile Asp His Tyr Gln Ala
1               5                   10                  15

Thr Pro Thr Glu Phe Asp Pro Pro Val Pro Tyr Gly Val Gly Ile Ser
            20                  25                  30

Gln Arg Asn Glu Arg Pro Lys Val Pro Val Ile Arg Ala Phe Gly Ala
        35                  40                  45

Thr Glu Thr Gly Gln Lys Val Cys Ala His Ile His Gly Ala Phe Pro
    50                  55                  60

Tyr Leu Tyr Ile Glu Tyr Lys Gly Ser Leu Glu Pro Asp Glu Val Asn
65                  70                  75                  80

Thr Ala Ile Arg Asn Leu His Leu Ser Ile Asp His Ala Leu Ala Val
                85                  90                  95

Ser Tyr Arg Arg Asn Ala Tyr Glu Gly Lys Thr Ala Tyr Val Ala His
            100                 105                 110

Ile Ser Leu Val Lys Gly Ile Pro Phe Tyr Gly Tyr His Val Gly Tyr
        115                 120                 125

Gln Phe Tyr Phe Lys Ile Tyr Leu Leu Asn Pro Leu Asn Ile Thr Arg
    130                 135                 140

Leu Ala Asp Leu Leu Arg Gln Gly Ala Val Leu Lys Arg Pro Met Gln
145                 150                 155                 160

Pro Tyr Glu Ser His Leu Gln Tyr Ile Pro Gln Trp Met Cys Asp Phe
                165                 170                 175

Asn Leu Tyr Gly Cys Ala Tyr Met Glu Cys Ala Lys Val Lys Phe Arg
            180                 185                 190

Ser Pro Val Pro Ser Tyr Leu Glu Leu Ser Asn Leu Asp His Arg Trp
        195                 200                 205

His Asp Arg Ser Ile Pro Ser Glu Leu Ile Ser Asn Glu Ser Glu Leu
    210                 215                 220

Pro Lys Gln Ser His Cys Ser Leu Glu Val Asp Val Cys Val Gln Asp
225                 230                 235                 240

Ile Ile Asn Arg His Ala Ile Lys Glu Arg Pro Leu His His Asp Phe
                245                 250                 255

Val Glu Arg Ile His Pro Leu Ser Pro Glu Glu Lys Leu Val His Ser
            260                 265                 270

Met Ala Gly Leu Trp Gln Asp Glu Thr Arg Arg Arg Lys Lys Arg Leu
```

-continued

```
        275                 280                 285

Gly Ile Lys Asp Pro Gly Ser Ser Pro Phe Gly Pro Glu Glu Leu Val
    290                 295                 300

Ser Met Ser Ala Ser Pro Arg Asp Gln Asn Thr Gly Gly Trp Ile His
305                 310                 315                 320

Glu Asp Glu Phe Trp Glu Lys Leu Arg Glu Ile Val Glu Glu Glu Lys
                325                 330                 335

Arg Lys Ser Asp Gly Thr Ser Val Ser Phe Glu Thr Tyr Val Lys Lys
            340                 345                 350

Asp Pro Leu Glu His Thr Val Lys Thr Ala Leu Glu Ser Val Glu Asp
        355                 360                 365

Leu Phe Pro Gln Lys Leu Glu Pro Leu Asn His Glu Ser Asn His Leu
    370                 375                 380

Gln Asp Gly Ala Met Asp Thr Gly Ile Glu Val Asp Glu Asn Thr Ala
385                 390                 395                 400

Leu Ser Phe Glu Ser Asp Asp Arg Tyr Asp Tyr Ser Asp Asp Glu Val
                405                 410                 415

Ser Val Gln Pro Asp Phe Gly Phe Val Gln Asp Asp Pro Ala Leu Glu
            420                 425                 430

Glu Leu Gly Val Asn Ser Asp Ser Asn Asn Asp Gly Pro Lys Gln Cys
        435                 440                 445

Asp Gly Asn Gly Leu Pro Lys Pro Asp Gly Leu Ala Arg Arg Arg Ser
    450                 455                 460

Thr Thr Ala Arg Ile Arg Glu Thr Asp Gly Met His Asn Ala Glu Phe
465                 470                 475                 480

Asp Pro Gly Ala Ile Ser Arg Pro Gln Lys Arg Ser Asp Gly Glu Glu
                485                 490                 495

Ile Asn Val Gly His Val Ala Lys Arg Ser Lys Gln Leu Asn Gly Glu
            500                 505                 510

Tyr Ile His Asn Arg Glu Thr Tyr Ser Thr Ala Thr Thr Asp Thr Gly
        515                 520                 525

Ile Ser Pro Phe Asp Thr Pro Ala Ala Leu Gly Asp Val Ala Ala Gln
    530                 535                 540

Thr Asn His Gln Ser Ser Ala Asp Gly Met Val Lys Pro Leu Pro Gln
545                 550                 555                 560

Pro Lys Pro Ser Ser Ser Gln Arg Met Leu Pro Gly Arg Ala Ser Ser
                565                 570                 575

Gln Asn Gln Arg Leu Ser Phe Pro Val Val Lys Asp Pro Asn Asp Pro
            580                 585                 590

Leu Thr Leu Leu Arg Phe Ser Gln Ser Gln Lys Ser Ile Ser Ser Lys
        595                 600                 605

Pro Thr Ser Gln Leu Ser Gln Glu Thr Glu Lys Val Ser Ala Gln Gly
    610                 615                 620

His Arg Glu Asp Ser Gln Ala Arg Ser Ser Ser Gln Leu His Ser Thr
625                 630                 635                 640

Asn Ser Asp Gln Thr Leu Gln Asp Phe Asn Thr Asp Asp Leu Leu Thr
                645                 650                 655

Ala Ser Lys Ile His Asp Ala Phe His Ile Pro Arg Asn Arg Lys Ile
            660                 665                 670

Leu Cys Tyr Cys His Pro Cys Pro Arg Pro Ser Glu Ile Met Ser Thr
        675                 680                 685

Ile Asn Asp Glu Gly Arg Pro Thr Val Val Tyr Gln Lys Ala Tyr Tyr
    690                 695                 700
```

```
Ser Asp Glu Ser Asp Val Pro Glu Arg Gln Arg Glu Tyr Ala Gly Arg
705                 710                 715                 720

Glu Phe Arg Leu Gly Ser Asp Thr Leu Gln Tyr Leu Pro Glu Phe Asp
                725                 730                 735

Arg Thr Gly Arg Ser Pro Ser Leu Leu Gly Glu Gln Ile Pro Pro Ser
            740                 745                 750

Ala Thr Asn Leu Glu Asn Gln Arg Lys Gln Asp Gln Lys Leu Arg Glu
        755                 760                 765

Leu Ser Ser Cys Arg Ile Trp Glu Phe Ala Gln Val Pro Pro Arg Arg
    770                 775                 780

Ser Glu Val Val Glu Trp Phe Glu Arg Glu Ile Ala His Pro Lys Gln
785                 790                 795                 800

Asp Ser Ser Asn Gly Ser Arg Arg Leu Pro Glu Thr Lys Pro Asn Val
                805                 810                 815

Leu Trp Gln Ile Glu Gly Ala Thr Gln Lys Asp Pro His Gly Phe Lys
            820                 825                 830

Tyr Ser Gln Lys Gln Gly Ser Thr Ser Val Glu His Gln Thr Gln Tyr
        835                 840                 845

Met Ser Val Met Ser Leu Glu Val His Val Asn Thr Arg Asp Ser Leu
    850                 855                 860

Ala Pro Asn Pro Glu Glu Asp Glu Ile Ala Cys Val Phe Trp Cys Leu
865                 870                 875                 880

Gln Ser Asp Asp Glu Asp Leu Asp Val Asn Ser Ala Leu Asp Gly Val
                885                 890                 895

His Val Gly Ile Leu Ala Gln Ser Gly Ser Asp Ala Leu Gly Lys Val
            900                 905                 910

Ala Arg Ser Ile Thr Val Asp Phe Glu Arg Glu Pro Thr Glu Leu Asp
        915                 920                 925

Leu Ile Thr Arg Leu Val Asp Ile Val Arg Tyr Tyr Asp Pro Asp Ile
    930                 935                 940

Leu Thr Gly Tyr Glu Val His Asn Ser Ser Trp Gly Tyr Leu Ile Glu
945                 950                 955                 960

Arg Ala Arg Tyr Lys Tyr Asp Leu Asp Leu Cys Asp Glu Leu Ser Arg
                965                 970                 975

Val Lys Ala Gln Ser His Gly Arg Phe Gly Lys Glu Asn Asp Arg Trp
            980                 985                 990

Gly Phe Asn His Thr Ser Ser Ile  Arg Val Thr Gly Arg  His Met Ile
        995                 1000                1005

Asn Ile  Trp Arg Ala Met Arg  Ser Glu Leu Asn Leu  Leu Gln Tyr
    1010                1015                1020

Thr Met  Glu Asn Val Val Phe  His Leu Leu His Arg  Arg Ile Pro
    1025                1030                1035

His Tyr  Pro Phe Lys Glu Leu  Thr Ala Trp Tyr Lys  Ser Ser Lys
    1040                1045                1050

Pro Arg  Asp Val Met Lys Val  Ile Glu Tyr Phe Val  Ser Arg Thr
    1055                1060                1065

Leu Met  Asp Leu Glu Ile Leu  Glu Ala Asn Glu Leu  Ile Pro Arg
    1070                1075                1080

Thr Ser  Glu Gln Ala Arg Leu  Leu Gly Ile Asp Phe  Tyr Ser Val
    1085                1090                1095

Phe Ser  Arg Gly Ser Gln Phe  Lys Val Glu Ser Leu  Met Phe Arg
    1100                1105                1110
```

-continued

```
Ile Ala  Lys Pro Glu Asn Phe  Ile Leu Ile Ser Pro  Ser Lys Lys
    1115                 1120                 1125

Gln Val  Gly Gln Gln Asn Ala  Leu Glu Cys Leu Pro  Leu Val Met
    1130                 1135                 1140

Glu Pro  Gln Ser Asp Phe Tyr  Thr Ser Pro Leu Val  Val Leu Asp
    1145                 1150                 1155

Phe Gln  Ser Leu Tyr Pro Ser  Val Met Ile Ala Tyr  Asn Tyr Cys
    1160                 1165                 1170

Tyr Ser  Thr Phe Leu Gly Arg  Leu Val Ser Trp Arg  Gly Arg Asn
    1175                 1180                 1185

Lys Met  Gly Phe Thr Asp Tyr  Glu Arg Pro Pro Arg  Leu Leu Glu
    1190                 1195                 1200

Leu Leu  Gly Asp Asn Ile Asn  Ile Ala Pro Asn Gly  Met Met Tyr
    1205                 1210                 1215

Thr Lys  Pro Glu Ile Arg Lys  Ser Leu Leu Ala Arg  Met Leu Ser
    1220                 1225                 1230

Glu Ile  Leu Glu Thr Arg Val  Met Val Lys Ser Gly  Met Lys Val
    1235                 1240                 1245

Asp Lys  Asp Asp Arg Ile Leu  Gln Arg Leu Leu Asn  Asn Arg Gln
    1250                 1255                 1260

Leu Ala  Leu Lys Leu Ile Ala  Asn Val Thr Tyr Gly  Tyr Thr Ser
    1265                 1270                 1275

Ala Ser  Phe Ser Gly Arg Met  Pro Cys Ser Glu Ile  Ala Asp Ser
    1280                 1285                 1290

Ile Val  Gln Thr Gly Arg Glu  Thr Leu Glu Lys Ala  Ile Ala Leu
    1295                 1300                 1305

Ile His  Ser Val Glu Arg Trp  Gly Ala Glu Val Val  Tyr Gly Asp
    1310                 1315                 1320

Thr Asp  Ser Leu Phe Val Tyr  Leu Lys Gly Arg Ser  Arg Asp Glu
    1325                 1330                 1335

Ala Phe  Thr Ile Gly Glu Glu  Ile Ala Gln Ala Val  Thr Lys Met
    1340                 1345                 1350

Asn Pro  Arg Pro Val Lys Leu  Lys Phe Glu Lys Val  Tyr His Pro
    1355                 1360                 1365

Cys Val  Leu Leu Ala Lys Lys  Arg Tyr Val Gly Phe  Lys Tyr Glu
    1370                 1375                 1380

Arg Arg  Glu Gln Thr Glu Pro  Glu Phe Asp Ala Lys  Gly Ile Glu
    1385                 1390                 1395

Thr Val  Arg Arg Asp Gly Thr  Pro Ala Glu Gln Lys  Ile Glu Glu
    1400                 1405                 1410

Lys Ala  Leu Lys Ile Leu Phe  Arg Thr Ala Asp Leu  Ser Gln Val
    1415                 1420                 1425

Lys Arg  Tyr Phe Gln Ser Gln  Cys Ser Lys Ile Met  Gln Gly Lys
    1430                 1435                 1440

Val Ser  Ile Gln Asp Phe Cys  Phe Ala Arg Glu Val  Arg Leu Gly
    1445                 1450                 1455

Thr Tyr  Ser Glu Lys Gly Leu  Leu Pro Pro Gly Ala  Leu Ile Ser
    1460                 1465                 1470

Ala Lys  Arg Met Leu Met Asp  Pro Arg Leu Glu Pro  Gln Tyr Gly
    1475                 1480                 1485

Glu Arg  Val Pro Tyr Val Val  Val Thr Gly Ala Pro  Gly Ser Arg
    1490                 1495                 1500

Leu Val  Asp Arg Cys Val Ala  Pro Glu Val Leu Leu  Asp Asn Pro
```

```
    1505                1510                1515

His Leu  Glu Leu Asp Ala Glu  Tyr Tyr Ile Thr Lys  Asn Ile Ile
    1520                1525                1530

Pro Pro  Leu Glu Arg Ile Phe  Asn Leu Val Gly Ala  Asn Val Arg
    1535                1540                1545

Gln Trp  Tyr Asp Glu Met Pro  Lys Phe Gln Arg Ile  Arg Arg Ile
    1550                1555                1560

Glu Gly  Val Ala Thr Ala Ala  Gly Glu Ala Gly Ser  Ser Lys Lys
    1565                1570                1575

Thr Leu  Glu Ser Tyr Met Lys  Ser Ser Ala Cys Ile  Leu Cys Lys
    1580                1585                1590

Asp Lys  Leu Asp Asp Ala Glu  Leu Pro Ile Cys Ser  Ser Cys Ala
    1595                1600                1605

Asn Gln  Pro His Ile Ser Leu  Phe Thr Leu Thr Ser  Arg Leu Lys
    1610                1615                1620

Gln Ala  Glu Arg Arg Val Asn  Asp Leu Leu Lys Ile  Cys Arg Ser
    1625                1630                1635

Cys Met  Gly Val Pro Phe Gly  Asp Asp Val Lys Cys  Asp Ser Lys
    1640                1645                1650

Asp Cys  Pro Val Phe Tyr Ser  Arg Thr Arg Asp Met  Ala Asn Trp
    1655                1660                1665

Lys His  Ser Asn Ala Val Leu  Glu Pro Val Ile Arg  Met Leu Glu
    1670                1675                1680

Glu Arg  Ser Glu Ser Val Leu  Glu Trp
    1685                1690
```

<210> SEQ ID NO 49
<211> LENGTH: 7127
<212> TYPE: DNA
<213> ORGANISM: Rasamsonia emersonii

<400> SEQUENCE: 49

```
ccgaacccgc cagcgtctct tcgaagccgt caagcccgtc tcgcaccttt cctcgattag     60

gatcgacgtt caagtcgaat ctcaccgctt cattgcgagc catcaagtca gctgcacaga    120

cggtgtcgaa ctttgcgacg ccatcggttc aaccggatga ttttctcacg cgttctctgt    180

tctcgatcac ccccgaatta accgatgacc ggcgccccct tccgatgagc gaaccccctt    240

caccggctct tcgacgctat ctcaatccga tcaccttgtc gcctgccgag atgcatgttt    300

atcatgaatc tccgcagggt tcggaccagt tcgctcacag ctgcccggtg tcgatccaga    360

tgcaaacgta caaccgatct gggtcttcaa ccggccgcag acggagccgt ttcagcacgg    420

gcaacgccag tggatacgaa caacagctgt gctcgttcga tccagagatc ccaatgaccc    480

gtcaacgcga gccgcgcgag aacagtgatt tcctgcgcgt ggtcgtccta gagatgaata    540

tgcggcgcag cggcaaatta cgcgatgaca tcccgagccg ggccaaggtc tggctgcctc    600

cacgcaagcc agcacggttg gtctcgagcg cctacggtga tgaggaggag actgccattc    660

cccaacgatg ggttggggtt tcaatcgagt gcgcttgaac gacctggccg agctctttac    720

cgatctactt tccgatcttc ttcatgattg tacatatgca tcacttcaac gtgtctttta    780

atttgttttt taccccttttt cggcgtcttt tcagaatttg gttcggatct acaatgacat    840

ggcatgagat agcgaggcgt ttgaggagga aatgggcacg gcaatagcat catgggcatt    900

tctttgcatg cttcggagca agggcaggtc gttagttcat tagccatgta ttattctctt    960

ggttttcccg agtgctcgac gatagtgaaa tgaattttgt atccagcgca tttcatgact   1020
```

```
atttctcccg tcctcacgtc attagatatt taccatttct ccagggttat tatcagacat   1080
ttgtgagaaa aggttcaagc atcacagtag gcattaaggc cgtgtgtaca ctccagccat   1140
tgtccattcc attctatcat attccgacgc gtcagtcaac tttacggact catttactga   1200
ccaacgcatt atggagagcg ccacgtgtct gaggaggact ctgcataagt tgccttttca   1260
attacgacga atatgatatg acagtactcc ggagtacgcc agttgattaa tactggcctg   1320
tagatcaata gcgcgcacgg tactctttct gttctggagg tccatgcgca tttgcatgac   1380
catctcctct tccatctttg tttttctttc ctttgaaaaa gaatcctcac ctgtttcctc   1440
tccttcccgc gaatcccgca atgccatacc tgctaatcta gctagctgta ccgtatagac   1500
atgtactgta cagtaggaag tagaaaagat gaggggtaag tgattggaac caggccggca   1560
tagtatggta tagcaacata gcattgatga tatatgcgtc aatggtaagc gataaaagcg   1620
cgctgtgcgg ggtttattag tattattctt ttattcgtgc actccagtcg agtcgagttg   1680
agagtgaggc aacaagagaa ttagtgcctc aggcactaaa ttcaaatgtc gtacagacta   1740
ccgatgacgt cgagtcacat gttctgcgtc tcctctggcg ctgcagcctg gacagaccgc   1800
gtccggaccg tgtattaggt agaaaattaa tataaaattt ggcaattaaa aaaaagaaca   1860
ggaaggttat cgcttccgtt cttttgatgg tgtgatatcc cctggatcac aatattacaa   1920
tgaactggat ctgacagccg atcgctggtc gaaaatggat ccgcatgatg atgaggagca   1980
gctttccgat gctggccccg tggagactga aaaggacctt gatgagaagt aagccagcgg   2040
tgtagaaaga aaaaagtatt gtcttactgg ctgacttgtt atgtgtgaag gtatccaaat   2100
cgacctcata accactcccc tacattgccc ttccacgagc tcttcttgtc cctgttcaac   2160
ccgttaaacg agaataagaa gaagcctacc ggtcctgctg ctgttgcggc tgcaaggagg   2220
aaagtcggcc caaatggcac gagtgcagcg aatctcaccc cccaggaacg tcggcgcgat   2280
atcatccagc ggttcatctc gcgatggaga aaagaagtcg gagacgatat ctacccggcc   2340
ttccgcctca tcgtcccgga caaggaccgc gatcgggcca tgtacgggct gaaagagaaa   2400
gttattggca agctactcgt caaaatcatg aagatcgaca agcactcgga ggatggattt   2460
agtctgctga actggaaact gcccggccag agcgcagcca gccggatggc gggcgacttt   2520
gccggacgat gctacgaagt catctccaaa cggccgatga ggactgaggt cggcgatatg   2580
ctcatcgagg aagtcaacga gaagctggac cagctctctg cggcctccaa ggaagagcag   2640
cagctcccca ttctggcgga gttctaccgg cggatgaacc cggaggagct gatgtggctc   2700
atcaggatca tcctccgaca gatgaagatc ggtgtttcgg agcggacgtt tttcgatgtg   2760
tggcatccgg acgcggagag gctgttcagc atctccagca gccttcgtcg cgtgtgctgg   2820
gagctccacg atccgaatat ccggttggag gccgatgaac ggggcgtttc gcttatgcag   2880
tgctttcagc ctcaactggc ccagttccag atgcattctt tcgaacggat ggtggagcga   2940
atgaggccca cggaggatga tcccgttttc tggatcgaag agaagctcga tggcgagcgc   3000
atgcagcttc acatggtatc agatgactcg atagaaggtg ggaagaggtt tgggttctgg   3060
tcacggaaag ccaaggatta tacgtatctt tacggcaatg ggctgaacga ccccaacggt   3120
gctctcacgc gccatctgaa agacgcgttt gctgagggtg tggacaacat cattctggat   3180
ggcgagatga tcacctggga ccccgagcaa gatgctccgg tcccctttgg gaccctcaaa   3240
accgccgcac tgtcagaaca acgtgacccg ttttctaaag gcccgcggcc actgtttcga   3300
gtcttcgata ttttgtatct taatgatcgg gacctgacca ggtatacact ccgtgaccgg   3360
```

-continued

```
cgaaatgcgt tggagaagag catcaaaccg gttcatcgaa gatttgagat acacccatac   3420
caagaggcca ccaaagcttc cgacatcgag ccgatcctta ggaaggttgt tgcagaagca   3480
tcagaaggac tggtcctgaa gaatccaagg tcgccttacc gtctgaatga acggcacgat   3540
gactggatga aggtcaagcc ggaatacatg tctgagtttg gcgaatcgct ggacgtcatc   3600
gtgattgggg gttattatgg ttctggacgt cgcggtggca atctctccag cttcctatgc   3660
ggactccggg tcgaccaggc tcaggtccag aaaggagcaa atccgatgaa atgctattcc   3720
ttctgcaagg ttggaggcgg cttcaccgcg gccgattatg caaatatccg tcaccacacg   3780
gacgggaaat ggaagccgtg ggaccccaat aaacctccca ctgagtacat tgaattggca   3840
gggggagacg cccagtatga gcggcctgat atgtggatca agccggatga ctcggtagtc   3900
ctctgtgtca aggccgcttc tgtctccgtc agcgaccagt ttcggcttgg tttgacgcta   3960
cgattccctc gattcaagag gctgcgcatg gacaaggact ggaaaaacagc attgtcagtg   4020
caagagtttc tggatctcaa atcgaacgtg gagcaggagc agaaagaaaa gcagtttact   4080
gtcgacaatt cccgcaagaa acggataaag agaaccacca agaagcctct caccgtcgct   4140
ggttacgacg ctgatgcaca agttcaatat cagggccctt cgggacacat tttcgacggg   4200
ttgaatttct gtatgcacga ttccattcac ctttcagtcc aggctaggac gtttgctgat   4260
cattgaatgt cgtagttatc atgacggaat ccagtgcacc ggtaaagaaa tccaagctcg   4320
agttggagca actggtcaaa tcgaacgggg gaaagattta ccagacgaac acggctgctc   4380
cggacaccgt gtgtatcgct gaccgaagta cgttacacct gacgataaat cagttgggag   4440
ggatggtaga gctaaatctt gcctcaatga acaggaacgg tcaaggtagc atccttgcag   4500
aaaagcgcca aagagaacat catccggccg ctgtggcttt tcgactgcat caagcagaat   4560
gaggctgatg cagggttgcc aaactttctc cttccattgg aaccacggta tgtgacgaaa   4620
gtacaccctt gagaacctgc tgactgacac tgagacttct gcagacacat gttctttacc   4680
aaggaggatc agcgagatga gatcgaaggg aacgtggaca agttccatga tagttacgcg   4740
agggacacca ctgtggagga gctcaaggtg gtgagtgctg tctctctccc cctccctctc   4800
tgtttcttac taacaacaaa caatcggaca agctcctcga taacatgaag gtacccggca   4860
agatgaacca cgcccaagtc tcccagatca cagaacgact gtttgcgcgg gctcaacaag   4920
aagggcaaga ccgcggacaa gggatatctc caggctggct cttcaagggt ctcacgatct   4980
acttccacca cgacccgtcg tcggccacca attcgcaccg cctccgtcta gcatccaatc   5040
tggctcgatt tggcggggcc agcattgcca gcacgtacga cacgtcgaac aagaacaaag   5100
acaaaggcgt aacccacgtc atcatcgatc ccttatcgac agaggctccc gagcaacaac   5160
tctcctccct caggaaaact ttatcgtctc acgctgcttc gggcatgcga atcccccatc   5220
tggtcactgt ggaatggatc gaagagtgct ggaaggagcg gacgttgttg gatgaagaga   5280
gtatgtcctc tccctgttac cttcaaaacc gaagatgaca gtcagggttt gtgaaatatt   5340
gaaaagtgag agaagaaact gacgtgttac gtttactttc tgtctaggat tccaaccgcc   5400
gcggtgagat gagacgagat aacgacctat gatacaatga tggagttcct atgttgtgct   5460
taattaattg catttacatg tatgtactgt atgtattgta cattaccttg gatagataga   5520
tagctagcta ggtagtttag gaaacatcca aagctatgct agctatgttc tacgctgtac   5580
ttgtgtactt gtatgtactg tacaatacta ctaccatggt gagatgagta atgaccagga   5640
agaaaaaaat agaaagcgaa gagataataa gtatgtactg tatacacatg gagagaaact   5700
gcatctgcag acttccaagt tcttattgac attttttcca ccttatctcg gtaggaatga   5760
```

gcgtcaatat aatacagaca tatatatata tatattcatg ctatttacgg tacgcttcac 5820
gactccatca atcggacgca gcagatgctg atacagatgc tgatgacgca ggagacgaga 5880
cctgctcgcc caagcgggtt agaatgccga tgtactcatg cgcgatcccc caagacgaca 5940
tcagccccga cagcgtgcgg atgccttcct tcaggatcct cgccggccct gatggtccgc 6000
agatgtcgcc taccccggtc acgttgcccc gcatcgtgtg gccctcgcgc acgaaaagct 6060
gcacgagctc gtcgtcgcag ggccggtcga gatggatgaa tgttggaccg ggggctggct 6120
cggatacgtc aggctgaggt cgcagctcat ccgagtcttc aacattgttg ctgttgttgc 6180
tgttgctgct attgttgttc tggccggagg ctgctgctgt tgctttgtgg tggcatgatc 6240
catatgccca gagggtgagg gtggctagga agacggccac aggctcatgg aaggcattcg 6300
tggaatagcg acggacgtac cacaagacgg aaccggcgtg gatcagtgcc agccgggctt 6360
tatactggtc atgcttgacc cagcgccaga tgtggtgcca ctcgatggct tgctcgtgct 6420
cactccaatg tagggtccct cttgctaaag aagtcgccag tgctcggatc tcccggaacg 6480
ggaccaggag gacaatccgc gcagcgtgta gatgaaggac ggtagggtgc tccaatccgg 6540
ccgctttggc aatcgtgccg ttggctgtcc aatggaggat gtccaagcag tcacaggcgc 6600
tgtttcgcca tttcgagtac acgggtatcc caggaagcca aacagaccca gacgggatcg 6660
cggagtctcg ggattgcttc ttagccgtag gattccaaca agacagcggt cgccggaagt 6720
aatcgctcac ttcccacatt ctctggtaga gagcatggac aagcaggaca tgactgaatt 6780
ccccgatccc agggactagt ctcttttcga tgtatagaat ctgcgttgcg gagtagagcg 6840
attcattttc ttgagtttta ttagcagtgt gcagtcctgt actcggaagt gattgcttac 6900
cacctgaaga ccgttcgtgc agttgccgcc agctttcctc agactttgcc tgccacggat 6960
cctcatgcga cggtaatggg gcttgtgcat cgtcgagcga taagtgcggt cgggtatcaa 7020
aagcatacgc caatgtgcaa tcaaggagct gcaggaatcc atcagcacgc ttctgtatct 7080
gtcgatgata ttatccaagg ctgacgtacc catatacaat agcctgt 7127

<210> SEQ ID NO 50
<211> LENGTH: 3246
<212> TYPE: DNA
<213> ORGANISM: Rasamsonia emersonii

<400> SEQUENCE: 50
atgtactgta cagtaggaag tagaaaagat gagggcaaca tagcattgat gatatatgcg 60
tcaatggaag gttatcgctt ccgttctttt gatggtgtga tatcccctgg atcacaatat 120
tacaatgaac tggatctgac agccgatcgc tggtcgaaaa tggatccgca tgatgatgag 180
gagcagcttt ccgatgctgg ccccgtggag actgaaaagg accttgatga gaagtatcca 240
aatcgacctc ataaccactc ccctacattg cccttccacg agctcttctt gtccctgttc 300
aacccgttaa acgagaataa gaagaagcct accggtcctg ctgctgttgc ggctgcaagg 360
aggaaagtcg gcccaaatgg cacgagtgca gcgaatctca ccccccagga acgtcggcgc 420
gatatcatcc agcggttcat ctcgcgatgg agaaaagaag tcggagacga tatctacccg 480
gccttccgcc tcatcgtccc ggacaaggac cgcgatcggg ccatgtacgg gctgaaagag 540
aaagttattg gcaagctact cgtcaaaatc atgaagatcg acaagcactc ggaggatgga 600
tttagtctgc tgaactggaa actgcccggc cagagcgcag ccagccggat ggcgggcgac 660
tttgccggac gatgctacga agtcatctcc aaacggccga tgaggactga ggtcggcgat 720

-continued

```
atgctcatcg aggaagtcaa cgagaagctg gaccagctct ctgcggcctc caaggaagag    780
cagcagctcc ccattctggc ggagttctac cggcggatga acccggagga gctgatgtgg    840
ctcatcagga tcatcctccg acagatgaag atcggtgttt cggagcggac gtttttcgat    900
gtgtggcatc cggacgcgga gaggctgttc agcatctcca gcagccttcg tcgcgtgtgc    960
tgggagctcc acgatccgaa tatccggttg gaggccgatg aacggggcgt ttcgcttatg   1020
cagtgctttc agcctcaact ggcccagttc cagatgcatt ctttcgaacg gatggtggag   1080
cgaatgaggc ccacggagga tgatcccgtt ttctggatcg aagagaagct cgatggcgag   1140
cgcatgcagc ttcacatggt atcagatgac tcgatagaag gtgggaagag gtttgggttc   1200
tggtcacgga aagccaagga ttatacgtat ctttacggca atgggctgaa cgaccccaac   1260
ggtgctctca cgcgccatct gaaagacgcg tttgctgagg gtgtggacaa catcattctg   1320
gatggcgaga tgatcacctg ggaccccgag caagatgctc cggtcccctt tgggaccctc   1380
aaaaccgccg cactgtcaga acaacgtgac ccgttttcta aaggcccgcg gccactgttt   1440
cgagtcttcg atattttgta tcttaatgat cgggacctga ccaggtatac actccgtgac   1500
cggcgaaatg cgttggagaa gagcatcaaa ccggttcatc gaagatttga gatacaccca   1560
taccaagagg ccaccaaagc ttccgacatc gagccgatcc ttaggaaggt tgttgcagaa   1620
gcatcagaag gactggtcct gaagaatcca aggtcgcctt accgtctgaa tgaacggcac   1680
gatgactgga tgaaggtcaa gccggaatac atgtctgagt ttggcgaatc gctggacgtc   1740
atcgtgattg gggttatta tggttctgga cgtcgcggtg gcaatctctc cagcttccta   1800
tgcggactcc gggtcgacca ggctcaggtc cagaaaggag caaatccgat gaaatgctat   1860
tccttctgca aggttggagg cggcttcacc gcggccgatt atgcaaatat ccgtcaccac   1920
acggacggga aatggaagcc gtgggacccc aataaacctc ccactgagta cattgaattg   1980
gcagggggag acgcccagta tgagcggcct gatatgtgga tcaagccgga tgactcggta   2040
gtcctctgtg tcaaggccgc ttctgtctcc gtcagcgacc agtttcggct tggtttgacg   2100
ctacgattcc ctcgattcaa gaggctgcgc atggacaagg actggaaaac agcattgtca   2160
gtgcaagagt ttctggatct caaatcgaac gtggagcagg agcagaaaga aaagcagttt   2220
actgtcgaca attcccgcaa gaaacggata aagagaacca ccaagaagcc tctcaccgtc   2280
gctggttacg acgctgatgc acaagttcaa tatcagggcc cttcgggaca cattttcgac   2340
gggttgaatt tctttatcat gacggaatcc agtgcaccgg taaagaaatc caagctcgag   2400
ttggagcaac tggtcaaatc gaacgggga aagatttacc agacgaacac ggctgctccg   2460
gacaccgtgt gtatcgctga ccgaagaacg gtcaaggtag catccttgca gaaaagcgcc   2520
aaagagaaca tcatccggcc gctgtggctt ttcgactgca tcaagcagaa tgaggctgat   2580
gcagggttgc caaactttct ccttccattg gaaccacgac acatgttctt taccaaggag   2640
gatcagcgag atgagatcga agggaacgtg gacaagttcc atgatagtta cgcgagggac   2700
accactgtgg aggagctcaa ggtgctcctc gataacatga aggtacccgg caagatgaac   2760
cacgcccaag tctcccagat cacagaacga ctgtttgcgc gggctcaaca agaagggcaa   2820
gaccgcggac aagggatatc tccaggctgg ctcttcaagg gtctcacgat ctacttccac   2880
cacgacccgt cgtcggccac caattcgcac cgcctccgtc tagcatccaa tctggctcga   2940
tttggcgggg ccagcattgc cagcacgtac gacacgtcga acaagaacaa agacaaaggc   3000
gtaacccacg tcatcatcga tcccttatcg acagaggctc ccgagcaaca actctcctcc   3060
ctcaggaaaa ctttatcgtc tcacgctgct tcgggcatgc gaatccccca tctggtcact   3120
```

```
gtggaatgga tcgaagagtg ctggaaggag cggacgttgt tggatgaaga gactatgcta   3180

gctatgttct acgctgtact tgtgtacttg tatgtactgt acaatactac taccatggtg   3240

agatga                                                              3246


<210> SEQ ID NO 51
<211> LENGTH: 1081
<212> TYPE: PRT
<213> ORGANISM: Rasamsonia emersonii

<400> SEQUENCE: 51

Met Tyr Cys Thr Val Gly Ser Arg Lys Asp Glu Gly Asn Ile Ala Leu
1               5                   10                  15

Met Ile Tyr Ala Ser Met Glu Gly Tyr Arg Phe Arg Ser Phe Asp Gly
            20                  25                  30

Val Ile Ser Pro Gly Ser Gln Tyr Tyr Asn Glu Leu Asp Leu Thr Ala
        35                  40                  45

Asp Arg Trp Ser Lys Met Asp Pro His Asp Asp Glu Glu Gln Leu Ser
    50                  55                  60

Asp Ala Gly Pro Val Glu Thr Glu Lys Asp Leu Asp Glu Lys Tyr Pro
65                  70                  75                  80

Asn Arg Pro His Asn His Ser Pro Thr Leu Pro Phe His Glu Leu Phe
                85                  90                  95

Leu Ser Leu Phe Asn Pro Leu Asn Glu Asn Lys Lys Lys Pro Thr Gly
            100                 105                 110

Pro Ala Ala Val Ala Ala Ala Arg Arg Lys Val Gly Pro Asn Gly Thr
        115                 120                 125

Ser Ala Ala Asn Leu Thr Pro Gln Glu Arg Arg Arg Asp Ile Ile Gln
    130                 135                 140

Arg Phe Ile Ser Arg Trp Arg Lys Glu Val Gly Asp Asp Ile Tyr Pro
145                 150                 155                 160

Ala Phe Arg Leu Ile Val Pro Asp Lys Asp Arg Asp Arg Ala Met Tyr
                165                 170                 175

Gly Leu Lys Glu Lys Val Ile Gly Lys Leu Leu Val Lys Ile Met Lys
            180                 185                 190

Ile Asp Lys His Ser Glu Asp Gly Phe Ser Leu Leu Asn Trp Lys Leu
        195                 200                 205

Pro Gly Gln Ser Ala Ala Ser Arg Met Ala Gly Asp Phe Ala Gly Arg
    210                 215                 220

Cys Tyr Glu Val Ile Ser Lys Arg Pro Met Arg Thr Glu Val Gly Asp
225                 230                 235                 240

Met Leu Ile Glu Glu Val Asn Glu Lys Leu Asp Gln Leu Ser Ala Ala
                245                 250                 255

Ser Lys Glu Glu Gln Gln Leu Pro Ile Leu Ala Glu Phe Tyr Arg Arg
            260                 265                 270

Met Asn Pro Glu Glu Leu Met Trp Leu Ile Arg Ile Ile Leu Arg Gln
        275                 280                 285

Met Lys Ile Gly Val Ser Glu Arg Thr Phe Phe Asp Val Trp His Pro
    290                 295                 300

Asp Ala Glu Arg Leu Phe Ser Ile Ser Ser Ser Leu Arg Arg Val Cys
305                 310                 315                 320

Trp Glu Leu His Asp Pro Asn Ile Arg Leu Glu Ala Asp Glu Arg Gly
                325                 330                 335

Val Ser Leu Met Gln Cys Phe Gln Pro Gln Leu Ala Gln Phe Gln Met
```

-continued

```
            340                 345                 350

His Ser Phe Glu Arg Met Val Glu Arg Met Arg Pro Thr Glu Asp Asp
        355                 360                 365

Pro Val Phe Trp Ile Glu Glu Lys Leu Asp Gly Glu Arg Met Gln Leu
    370                 375                 380

His Met Val Ser Asp Asp Ser Ile Glu Gly Gly Lys Arg Phe Gly Phe
385                 390                 395                 400

Trp Ser Arg Lys Ala Lys Asp Tyr Thr Tyr Leu Tyr Gly Asn Gly Leu
                405                 410                 415

Asn Asp Pro Asn Gly Ala Leu Thr Arg His Leu Lys Asp Ala Phe Ala
            420                 425                 430

Glu Gly Val Asp Asn Ile Ile Leu Asp Gly Glu Met Ile Thr Trp Asp
        435                 440                 445

Pro Glu Gln Asp Ala Pro Val Pro Phe Gly Thr Leu Lys Thr Ala Ala
    450                 455                 460

Leu Ser Glu Gln Arg Asp Pro Phe Ser Lys Gly Pro Arg Pro Leu Phe
465                 470                 475                 480

Arg Val Phe Asp Ile Leu Tyr Leu Asn Asp Arg Asp Leu Thr Arg Tyr
                485                 490                 495

Thr Leu Arg Asp Arg Arg Asn Ala Leu Glu Lys Ser Ile Lys Pro Val
            500                 505                 510

His Arg Arg Phe Glu Ile His Pro Tyr Gln Glu Ala Thr Lys Ala Ser
        515                 520                 525

Asp Ile Glu Pro Ile Leu Arg Lys Val Val Ala Glu Ala Ser Glu Gly
    530                 535                 540

Leu Val Leu Lys Asn Pro Arg Ser Pro Tyr Arg Leu Asn Glu Arg His
545                 550                 555                 560

Asp Asp Trp Met Lys Val Lys Pro Glu Tyr Met Ser Glu Phe Gly Glu
                565                 570                 575

Ser Leu Asp Val Ile Val Ile Gly Gly Tyr Tyr Gly Ser Gly Arg Arg
            580                 585                 590

Gly Gly Asn Leu Ser Ser Phe Leu Cys Gly Leu Arg Val Asp Gln Ala
        595                 600                 605

Gln Val Gln Lys Gly Ala Asn Pro Met Lys Cys Tyr Ser Phe Cys Lys
    610                 615                 620

Val Gly Gly Gly Phe Thr Ala Ala Asp Tyr Ala Asn Ile Arg His His
625                 630                 635                 640

Thr Asp Gly Lys Trp Lys Pro Trp Asp Pro Asn Lys Pro Pro Thr Glu
                645                 650                 655

Tyr Ile Glu Leu Ala Gly Gly Asp Ala Gln Tyr Glu Arg Pro Asp Met
            660                 665                 670

Trp Ile Lys Pro Asp Asp Ser Val Val Leu Cys Val Lys Ala Ala Ser
        675                 680                 685

Val Ser Val Ser Asp Gln Phe Arg Leu Gly Leu Thr Leu Arg Phe Pro
    690                 695                 700

Arg Phe Lys Arg Leu Arg Met Asp Lys Asp Trp Lys Thr Ala Leu Ser
705                 710                 715                 720

Val Gln Glu Phe Leu Asp Leu Lys Ser Asn Val Glu Gln Glu Gln Lys
                725                 730                 735

Glu Lys Gln Phe Thr Val Asp Asn Ser Arg Lys Lys Arg Ile Lys Arg
            740                 745                 750

Thr Thr Lys Lys Pro Leu Thr Val Ala Gly Tyr Asp Ala Asp Ala Gln
        755                 760                 765
```

```
Val Gln Tyr Gln Gly Pro Ser Gly His Ile Phe Asp Gly Leu Asn Phe
    770                 775                 780

Phe Ile Met Thr Glu Ser Ser Ala Pro Val Lys Lys Ser Lys Leu Glu
785                 790                 795                 800

Leu Glu Gln Leu Val Lys Ser Asn Gly Gly Lys Ile Tyr Gln Thr Asn
                805                 810                 815

Thr Ala Ala Pro Asp Thr Val Cys Ile Ala Asp Arg Arg Thr Val Lys
            820                 825                 830

Val Ala Ser Leu Gln Lys Ser Ala Lys Glu Asn Ile Ile Arg Pro Leu
        835                 840                 845

Trp Leu Phe Asp Cys Ile Lys Gln Asn Glu Ala Asp Ala Gly Leu Pro
    850                 855                 860

Asn Phe Leu Leu Pro Leu Glu Pro Arg His Met Phe Phe Thr Lys Glu
865                 870                 875                 880

Asp Gln Arg Asp Glu Ile Glu Gly Asn Val Asp Lys Phe His Asp Ser
                885                 890                 895

Tyr Ala Arg Asp Thr Thr Val Glu Glu Leu Lys Val Leu Leu Asp Asn
            900                 905                 910

Met Lys Val Pro Gly Lys Met Asn His Ala Gln Val Ser Gln Ile Thr
        915                 920                 925

Glu Arg Leu Phe Ala Arg Ala Gln Gln Glu Gly Gln Asp Arg Gly Gln
    930                 935                 940

Gly Ile Ser Pro Gly Trp Leu Phe Lys Gly Leu Thr Ile Tyr Phe His
945                 950                 955                 960

His Asp Pro Ser Ser Ala Thr Asn Ser His Arg Leu Arg Leu Ala Ser
                965                 970                 975

Asn Leu Ala Arg Phe Gly Gly Ala Ser Ile Ala Ser Thr Tyr Asp Thr
            980                 985                 990

Ser Asn Lys Asn Lys Asp Lys Gly  Val Thr His Val Ile  Ile Asp Pro
        995                 1000                1005

Leu Ser  Thr Glu Ala Pro Glu  Gln Gln Leu Ser Ser  Leu Arg Lys
    1010                1015                1020

Thr Leu  Ser Ser His Ala Ala  Ser Gly Met Arg Ile  Pro His Leu
    1025                1030                1035

Val Thr  Val Glu Trp Ile Glu  Glu Cys Trp Lys Glu  Arg Thr Leu
    1040                1045                1050

Leu Asp  Glu Glu Thr Met Leu  Ala Met Phe Tyr Ala  Val Leu Val
    1055                1060                1065

Tyr Leu  Tyr Val Leu Tyr Asn  Thr Thr Thr Met Val  Arg
    1070                1075                1080
```

<210> SEQ ID NO 52
<211> LENGTH: 5720
<212> TYPE: DNA
<213> ORGANISM: Rasamsonia emersonii

<400> SEQUENCE: 52

```
gcctcgtcag gtcaagctga gctccctcgg gcgggctgct gctactgctg cgatggactg     60

atggcgatga cgcagaaagt gcgttatcgg tcgtgctcag tcgtcgcaac agcgagccgt    120

catcctcggc cgggacgcga gagggggatg catcagggtc gacgatgtcg acggatgccc    180

cgtggccttc ggcatctcca ctagggagca tgccgaagac cgattcatca cgacaaaggt    240

catttccatg ctggaagagg ttggaaggaa ctgcggggtt ggcgtctacg ggagtacttt    300
```

-continued

```
gggagacggc agtattaggc tctgatggca taaaatgtgg tgacgcggga gtgagggaaa    360
gcgggagcga ctgatccagg ctagactggg tcagtcgaaa gcaatgataa cgagcaatgc    420
gcggggagga gcgacgtgag agaccggctg tgacgtgcga cgatgggaga acaagagagg    480
agggacggag gaaggaggaa cgcgaagatg caacgaaaac gacacgggcg agtcccgatg    540
ctgactaagc cgtttcttgc agcacgttcg ccttcgaaga tatgcaatag gacagacgat    600
tcagatgcag tcaggagagc tttaacgttc aattttctag tattttctct gataagaatg    660
ccctcatctg aatttcattg tgagtctgct tttccagata gaatcacgat caacaatacc    720
gtactcgaag ggtgtcaat tcctcgagac accgtaacgg gataaattag ttaagcgtat     780
cgacactcaa catatgtggc aattcatttc ctgtagtctc ttgtttgctc tcttttcccc    840
ttcatttcct tcctttttc ttccttacat ttacttttga ttctcttctt cttttttgtt     900
tttattttcc tgatcagtgt cccatattgc agtattattg gcaaattacg gtactgaaaa    960
ttaattgcac gtaattttc atgtctgcgg gaacgcgtca cgtggcgagg acgcgccaga    1020
aacacgactg accaggaaga gacgaaatca acaaaagaac aagaggggaa agaaaaggga   1080
aggggatctt aggccgacga gcaacacaaa gggtcgttag gtcgatgcgt gtaataaggc   1140
ctgtgctgtt ttcccccggt gggttttgat cctgggcggc ttctaggcaa catcccgcag   1200
cctcaccctt ttacaaactg acgggggtgg tactttcttt gagggcaatc ttcctttctt   1260
tcctctacta gatagaaagg ataggttttt atcactgagg atgccctcac tcaccggtaa   1320
ggctaactac gccctcgcag tctgtcctcc cgactaaccc gtatagccgc ggatacgatc   1380
cgcatcctcg tctcaaccga caaccatgtc ggctacaatg agcgagatcc tatccggggt   1440
gacgacagtt ggaaaagctt ccacgagatt atgtgtctgg cgaaggagcg cgatgtcgac   1500
atggtcctcc tcgctggcga tctcttccac gagaacaagc cgtctcgcaa gtccatgtac   1560
caggtgatgc ggtcactgcg catgaactgc ttgggcgata agccctgcga gttggagatg   1620
ctcagtgacg ccagtgagaa cttccagggc gctttcaacc acgtcaacta cgaggacctc   1680
gacatcaatg tcgccatccc cgtcttttcc attcatggta accatgacga tccatccggg   1740
gaaggtcatc tggctgccct ggacatactc caagtgtccg gactgatcaa ctacttcggt   1800
cggacgccag agtcggacaa tattcaggtc aaacctgtcc ttctacagaa aggccgcacc   1860
aaattggcgc tctacggcat cagcaacgtt cgtgatgaac ggctgtttcg tacatttcgc   1920
gatgggaaag tcaagttctt ccggccctcg atccagaagg aggactggtt caacctgatc   1980
tgtgtccatc agaaccacca cgcccacacg gagacgggct acctccccga atccttcctg   2040
ccagactttc tcgacctggt catctggggc cacgaacacg agtgtctgat aaaccccaga   2100
cgcaaccctg aaatgaattt ccacgtcatg cagcctggct cctctgtggc cacgtcactg   2160
gtccagggag aagcagcacc caagcatgta gcgattctca gcatcaaggg ccgggagttc   2220
cactgtgaac ctatccgctt gaaaacagtg cgtccatttg tcgtgcgaga aatcgtcctc   2280
tctgaggaga aaggggccca gaaactggcc cgaaaggaga ataatcggac agaagtcacc   2340
cggttcttaa tgtctatagt ggaggagctg attgaacaag ccaaagcaga gtggctggag   2400
gcacaccaag acgacgatgt cgatgagcag gatattcctc tccccttgt acgtcttaga    2460
gtggaggttt ctacaccaga aggtggcagc ttcgactgcg agaaccctca gcggttctcc   2520
aatcggttcg tgggcaaagt cgcgaacgtc aacgacgtgg ttcaattcta ccgtaaaaag   2580
aagtcaacaa cgacttcccg caaggcagat aatctcgatg aggcggtggt gtcgcatctt   2640
tccgagctcg atacggtgaa ggtcgagaag ctagtacggg agattctcac tgcacagtct   2700
```

-continued

```
ctcaccatcc ttcctcagaa ctcgttcagc gatgcagtct cccagttcgt ggacaaggat   2760
gacaagcacg ccatggaaat gttcgtgaac gagtcgctag agaaccaggt caagtatctg   2820
atgtccctgg aacgggaggc cgacatggac gatgaggagg agagtcatca atctttgcgg   2880
aacgccatgg aaaaataccg cagtcagatg gaggagatgt ttgcgaaggg cgccatgaga   2940
cgtacgcgag ggaagaagcg cttcaaaccg aagcccgatg gctgggatac cgatctcgac   3000
ggcgtatggg aagaccagcc gggcgcattg atcctctctg acaatgagga tgccgacccg   3060
aacgaagagg aggccgcaga ggatggtacg gagagacaga ccacgtccac tcgaggcaga   3120
ggtcgaggtc gtggaggccg ggctgcaacc accaccactt ccacgcgcaa gacgactgct   3180
agcaagactc cagcagccag ctcacgaggc cggagacgcc aggctgtttc tgaagacgaa   3240
gacgaagacg agggcgatga tgtggtggtg ctggatgacg atcaggagga gccggaagaa   3300
atggtctcgg atgacgattc tcaggcactc tttgtcaaac aaacacctcc acccaaaacg   3360
ggtcgaacgc gccagacaac actcacttcg accacaacag gcacccagcg gcgatctgga   3420
cgaactgcac cttcgccagc gccctcctct gccactgcag cagcttcgac ggcccgaagt   3480
gggacgcgag gtgccgctgc tagcaaacgg acccagcaga cgacactcaa ctttgcgccg   3540
tcgcagacca gttccgtggg cactggacag gttacaggta ctgttacggg tacgaacacg   3600
agaccgtcac ggacaacacg aggcgttagc gtggtgagtg aggaagatat cgaggatgac   3660
gacgatgatg cgtttgagcc ggcaccagcg acgactcgga ggcggcgata aaaacagtcg   3720
ctcttgaaga gtaataattg ccgtaatgca gcgccatgag catgaaaata cgtgcagtct   3780
ttttttgtt gttattgtat ggattactgt ctaaaatctc aaggattcaa aaagcgtgta   3840
gtaaggagta aggtatctaa tctacaaatg ggaactggaa aaattaaatt agatgaatgc   3900
agggatatat gcccccaaat tgaggactac aaatttagta tctatttgcc taatcatcgg   3960
gatgataggt atatacttct cctgggtttc aattttgtag aatcaatttt ttttacgatg   4020
aaatcatgac cttctagcag ttatatgtag aagcaagtaa tactaatact gaagacagtc   4080
actgggctcc gctgttaacc atgcatgcat tagtaggggc ctttcttggt cgacattcct   4140
cattcgttgc taatccatcc aacaggtctg aagagctcca ggcggggttc tatgctaaaa   4200
ggcaaaagga ggggcaatag caactttgtt ctatagggga aaaaaaatct ccatatgacc   4260
gatacgataa atatcttggg agtgtcataa ttcggcgtgt acagactcgg aactggaggg   4320
gaatacgggc aaaatccata acaaatgtcg atgacagacc gcaactcgtt tacagaatta   4380
gatcgatgga gctgtgatcc ttgatctggt tggctcgtcc cctgagcctg ggtccgggga   4440
atgacctgat cagcggctgg cgcgctgcgg ggtacgaagg ccgaaccccc tccgtcttcc   4500
gtctccccgg acacgccgtc tgttgcggag atttccgggg tgcgcaatcc caaataataa   4560
tatctgtccc gtgcctggcc gcagtgcgtg ccagcgttgg tgatagatat ttagggttgg   4620
tctggcttcg gtcagatggc agttcccttc atgagattag cagtgaatcc tgtatgcata   4680
ttgcgtcatc tgtcgccttc ccgtagatcg accatctttg cttgtcagat atcgatacac   4740
tagcaggctc gaaactccag gattggaatt gttccagcaa cggtcactac tgatgctgat   4800
ccccgccgcg gtcgtagatt gtggagcaaa ctccgtgcgt ttaacccatg tctcttacgt   4860
gtcatctgaa acgcgtttga gagcaatcag cttccagcag gcaaaaaatgc aggcctagaa   4920
ttggaatgtt ttcttagcac gtcgagtgcg ctcaacagct attggatgac agggcgatca   4980
ggaagcgcct cggacgaacg gcgaggagag aaggacgaga ggaagcttct cctgcatgat   5040
```

agaagtcaaa tcagcaatgc agcaccaagg gaatcgattc aggtagaact cactgttatt 5100
gattgcaaat actcctgctg gaaggtattc agccctctca ttcagtcgta tccctgccat 5160
gtcgagggtc tcgggactgg tagaacggca tcggaggtgc tccgatgcta tcctacatcc 5220
atcccgccaa ggcttcctgc gtcacacaag agatcctcag gcggatgcaa ccaggcatgc 5280
ttgaagaact cacgcagaga aacagaatgc acgattcagc agcacgagtg ggatggaacg 5340
acgtgtgaac gaacctccgg aaatccccgc ataacgcagg cagcccactc ccgaaatccc 5400
cggagtggac ccgctgcatg aaccttctgc ggggggcgac gacagcgatg gacaaactgc 5460
atcaactcag cgagtccaga ctgaatctga ttccgcggcg cgcaggccgt actgtacggt 5520
aagctcgctg ccccgtccgt gggaggcagc tccttcgcag ctggcttccc ttggtgcggg 5580
cgggcctatc acgtcgtcgg atttgcggcc ttcttacctc acgtcccctc tgcgagtcac 5640
tattacggcc aaccatgagg aaaggcacgg gtggcggcag aaaccccgca tcggcgatac 5700
agtctgcccg gggaactcga 5720

<210> SEQ ID NO 53
<211> LENGTH: 2376
<212> TYPE: DNA
<213> ORGANISM: Rasamsonia emersonii

<400> SEQUENCE: 53
atggtcctcc tcgctggcga tctcttccac gagaacaagc cgtctcgcaa gtccatgtac 60
caggtgatgc ggtcactgcg catgaactgc ttgggcgata agccctgcga gttggagatg 120
ctcagtgacg ccagtgagaa cttccagggc gctttcaacc acgtcaacta cgaggacctc 180
gacatcaatg tcgccatccc cgtcttttcc attcatggta accatgacga tccatccggg 240
gaaggtcatc tggctgccct ggacatactc caagtgtccg gactgatcaa ctacttcggt 300
cggacgccag agtcggacaa tattcaggtc aaacctgtcc ttctacagaa aggccgcacc 360
aaattggcgc tctacggcat cagcaacgtt cgtgatgaac ggctgtttcg tacatttcgc 420
gatgggaaag tcaagttctt ccggccctcg atccagaagg aggactggtt caacctgatc 480
tgtgtccatc agaaccacca cgcccacacg gagacgggct acctccccga atccttcctg 540
ccagactttc tcgacctggt catctggggc cacgaacacg agtgtctgat aaaccccaga 600
cgcaaccctg aaatgaattt ccacgtcatg cagcctggct cctctgtggc cacgtcactg 660
gtccagggag aagcagcacc caagcatgta gcgattctca gcatcaaggg ccgggagttc 720
cactgtgaac ctatccgctt gaaaacagtg cgtccatttg tcgtgcgaga aatcgtcctc 780
tctgaggaga aaggggccca gaaactggcc cgaaaggaga ataatcggac agaagtcacc 840
cggttcttaa tgtctatagt ggaggagctg attgaacaag ccaaagcaga gtggctggag 900
gcacaccaag acgacgatgt cgatgagcag gatattcctc tccccttgt acgtcttaga 960 gtggaggttt ctacaccaga aggtggcagc ttcgactgcg agaaccctca gcggttctcc 1020
aatcggttcg tgggcaaagt cgcgaacgtc aacgacgtgg ttcaattcta ccgtaaaaag 1080
aagtcaacaa cgacttcccg caaggcagat aatctcgatg aggcggtggt gtcgcatctt 1140
tccgagctcg atacggtgaa ggtcgagaag ctagtacggg agattctcac tgcacagtct 1200
ctcaccatcc ttcctcagaa ctcgttcagc gatgcagtct cccagttcgt ggacaaggat 1260
gacaagcacg ccatggaaat gttcgtgaac gagtcgctag agaaccaggt caagtatctg 1320
atgtccctgg aacgggaggc cgacatggac gatgaggagg agagtcatca atctttgcgg 1380
aacgccatgg aaaaataccg cagtcagatg gaggagatgt ttgcgaaggg cgccatgaga 1440

```
cgtacgcgag ggaagaagcg cttcaaaccg aagcccgatg gctgggatac cgatctcgac   1500

ggcgtatggg aagaccagcc gggcgcattg atcctctctg acaatgagga tgccgacccg   1560

aacgaagagg aggccgcaga ggatggtacg gagagacaga ccacgtccac tcgaggcaga   1620

ggtcgaggtc gtggaggccg ggctgcaacc accaccactt ccacgcgcaa gacgactgct   1680

agcaagactc cagcagccag ctcacgaggc cggagacgcc aggctgtttc tgaagacgaa   1740

gacgaagacg agggcgatga tgtggtggtg ctggatgacg atcaggagga gccggaagaa   1800

atggtctcgg atgacgattc tcaggcactc tttgtcaaac aaacacctcc acccaaaacg   1860

ggtcgaacgc gccagacaac actcacttcg accacaacag gcacccagcg gcgatctgga   1920

cgaactgcac cttcgccagc gccctcctct gccactgcag cagcttcgac ggcccgaagt   1980

gggacgcgag gtgccgctgc tagcaaacgg acccagcaga cgacactcaa ctttgcgccg   2040

tcgcagacca gttccgtggg cactggacag gttacaggta ctgttacggg attcaaaaag   2100

cgtgtagtaa ggagtaaggt atctaatcta caaatgggaa ctggaaaaat taaattagat   2160

gaatgcaggg atatatgccc ccaaattgag gactacaaat ttagtatcta tttgcctaat   2220

catcgggatg atagtcactg ggctccgctg ttaaccatgc atgcattagt aggggccttt   2280

cttggtcgac attcctcatt cgttgctaat ccatccaaca ggtctgaaga gctccaggcg   2340

gggttctatg ctaaaaggca aaaggagggg caatag                              2376
```

<210> SEQ ID NO 54
<211> LENGTH: 791
<212> TYPE: PRT
<213> ORGANISM: Rasamsonia emersonii

<400> SEQUENCE: 54

```
Met Val Leu Leu Ala Gly Asp Leu Phe His Glu Asn Lys Pro Ser Arg
1               5                   10                  15

Lys Ser Met Tyr Gln Val Met Arg Ser Leu Arg Met Asn Cys Leu Gly
            20                  25                  30

Asp Lys Pro Cys Glu Leu Glu Met Leu Ser Asp Ala Ser Glu Asn Phe
        35                  40                  45

Gln Gly Ala Phe Asn His Val Asn Tyr Glu Asp Leu Asp Ile Asn Val
    50                  55                  60

Ala Ile Pro Val Phe Ser Ile His Gly Asn His Asp Asp Pro Ser Gly
65                  70                  75                  80

Glu Gly His Leu Ala Ala Leu Asp Ile Leu Gln Val Ser Gly Leu Ile
                85                  90                  95

Asn Tyr Phe Gly Arg Thr Pro Glu Ser Asp Asn Ile Gln Val Lys Pro
            100                 105                 110

Val Leu Leu Gln Lys Gly Arg Thr Lys Leu Ala Leu Tyr Gly Ile Ser
        115                 120                 125

Asn Val Arg Asp Glu Arg Leu Phe Arg Thr Phe Arg Asp Gly Lys Val
    130                 135                 140

Lys Phe Phe Arg Pro Ser Ile Gln Lys Glu Asp Trp Phe Asn Leu Ile
145                 150                 155                 160

Cys Val His Gln Asn His His Ala His Thr Glu Thr Gly Tyr Leu Pro
                165                 170                 175

Glu Ser Phe Leu Pro Asp Phe Leu Asp Leu Val Ile Trp Gly His Glu
            180                 185                 190

His Glu Cys Leu Ile Asn Pro Arg Arg Asn Pro Glu Met Asn Phe His
        195                 200                 205
```

-continued

```
Val Met Gln Pro Gly Ser Ser Val Ala Thr Ser Leu Val Gln Gly Glu
    210                 215                 220

Ala Ala Pro Lys His Val Ala Ile Leu Ser Ile Lys Gly Arg Glu Phe
225                 230                 235                 240

His Cys Glu Pro Ile Arg Leu Lys Thr Val Arg Pro Phe Val Val Arg
                245                 250                 255

Glu Ile Val Leu Ser Glu Glu Lys Gly Ala Gln Lys Leu Ala Arg Lys
            260                 265                 270

Glu Asn Asn Arg Thr Glu Val Thr Arg Phe Leu Met Ser Ile Val Glu
        275                 280                 285

Glu Leu Ile Glu Gln Ala Lys Ala Glu Trp Leu Glu Ala His Gln Asp
    290                 295                 300

Asp Asp Val Asp Glu Gln Asp Ile Pro Leu Pro Leu Val Arg Leu Arg
305                 310                 315                 320

Val Glu Val Ser Thr Pro Glu Gly Gly Ser Phe Asp Cys Glu Asn Pro
                325                 330                 335

Gln Arg Phe Ser Asn Arg Phe Val Gly Lys Val Ala Asn Val Asn Asp
            340                 345                 350

Val Val Gln Phe Tyr Arg Lys Lys Lys Ser Thr Thr Thr Ser Arg Lys
        355                 360                 365

Ala Asp Asn Leu Asp Glu Ala Val Val Ser His Leu Ser Glu Leu Asp
    370                 375                 380

Thr Val Lys Val Glu Lys Leu Val Arg Glu Ile Leu Thr Ala Gln Ser
385                 390                 395                 400

Leu Thr Ile Leu Pro Gln Asn Ser Phe Ser Asp Ala Val Ser Gln Phe
                405                 410                 415

Val Asp Lys Asp Asp Lys His Ala Met Glu Met Phe Val Asn Glu Ser
            420                 425                 430

Leu Glu Asn Gln Val Lys Tyr Leu Met Ser Leu Glu Arg Glu Ala Asp
        435                 440                 445

Met Asp Asp Glu Glu Glu Ser His Gln Ser Leu Arg Asn Ala Met Glu
    450                 455                 460

Lys Tyr Arg Ser Gln Met Glu Glu Met Phe Ala Lys Gly Ala Met Arg
465                 470                 475                 480

Arg Thr Arg Gly Lys Lys Arg Phe Lys Pro Lys Pro Asp Gly Trp Asp
                485                 490                 495

Thr Asp Leu Asp Gly Val Trp Glu Asp Gln Pro Gly Ala Leu Ile Leu
            500                 505                 510

Ser Asp Asn Glu Asp Ala Asp Pro Asn Glu Glu Glu Ala Ala Glu Asp
        515                 520                 525

Gly Thr Glu Arg Gln Thr Thr Ser Thr Arg Gly Arg Gly Arg Gly Arg
    530                 535                 540

Gly Gly Arg Ala Ala Thr Thr Thr Thr Ser Thr Arg Lys Thr Thr Ala
545                 550                 555                 560

Ser Lys Thr Pro Ala Ala Ser Ser Arg Gly Arg Arg Arg Gln Ala Val
                565                 570                 575

Ser Glu Asp Glu Asp Glu Asp Glu Gly Asp Asp Val Val Val Leu Asp
            580                 585                 590

Asp Asp Gln Glu Glu Pro Glu Glu Met Val Ser Asp Asp Asp Ser Gln
        595                 600                 605

Ala Leu Phe Val Lys Gln Thr Pro Pro Pro Lys Thr Gly Arg Thr Arg
    610                 615                 620
```

-continued

Gln Thr Thr Leu Thr Ser Thr Thr Thr Gly Thr Gln Arg Arg Ser Gly
625 630 635 640

Arg Thr Ala Pro Ser Pro Ala Pro Ser Ser Ala Thr Ala Ala Ala Ser
645 650 655

Thr Ala Arg Ser Gly Thr Arg Gly Ala Ala Ala Ser Lys Arg Thr Gln
660 665 670

Gln Thr Thr Leu Asn Phe Ala Pro Ser Gln Thr Ser Ser Val Gly Thr
675 680 685

Gly Gln Val Thr Gly Thr Val Thr Gly Phe Lys Lys Arg Val Val Arg
690 695 700

Ser Lys Val Ser Asn Leu Gln Met Gly Thr Gly Lys Ile Lys Leu Asp
705 710 715 720

Glu Cys Arg Asp Ile Cys Pro Gln Ile Glu Asp Tyr Lys Phe Ser Ile
725 730 735

Tyr Leu Pro Asn His Arg Asp Asp Ser His Trp Ala Pro Leu Leu Thr
740 745 750

Met His Ala Leu Val Gly Ala Phe Leu Gly Arg His Ser Ser Phe Val
755 760 765

Ala Asn Pro Ser Asn Arg Ser Glu Glu Leu Gln Ala Gly Phe Tyr Ala
770 775 780

Lys Arg Gln Lys Glu Gly Gln
785 790

<210> SEQ ID NO 55
<211> LENGTH: 24
<212> TYPE: DNA
<213> ORGANISM: Artificial Sequence
<220> FEATURE:
<223> OTHER INFORMATION: Ku80-For primer

<400> SEQUENCE: 55
agggtatatg tggtctagta acgc 24

<210> SEQ ID NO 56
<211> LENGTH: 24
<212> TYPE: DNA
<213> ORGANISM: Artificial Sequence
<220> FEATURE:
<223> OTHER INFORMATION: Ku80-Rev primer

<400> SEQUENCE: 56
tcacaagtcc atcacggaac cggg 24

<210> SEQ ID NO 57
<211> LENGTH: 6429
<212> TYPE: DNA
<213> ORGANISM: Rasamsonia emersonii

<400> SEQUENCE: 57
agacaggtat tctgctgata gcatggattt atattatcaa taagcagagg cctaaagaca 60
ttcaaccaga agaaacgtcc ttcatgcaac agcaagctag aacatataca tatgagaaca 120
agcatagtgc caatcaagca gacctatact gtactctatt acaacaaact actatcacgg 180
tagtcgtaca ctggtcaatg aaataatgtg agtaaaaatg atcatgattc tatgacagaa 240
cagctagtac gcttgattta ttggggtata aattttactt tatttaggtg gttaagagcc 300
agcagactag atatatagct cagatataat ataattaata gtcacagaaa aaaataaata 360
aaaataaaaa tagcaagatc catgatatgg tatacacaaa aaaataataa tcataaatca 420

-continued

```
cacaattcca tcctctccaa aaccacctag ccagctccta ccaaacgata catactcagt    480
ccaagcaaat cccccgttcc gtcctcccgt ccgtccgatc agtcccgaat accgaccaaa    540
aaaaaaaaga gacaaaatcc aaatcacggg ttcattcaca tccccacagg atacccatgg    600
atcagtcgtc ctacttactg tggtacagat tagaacagaa aattaggttt ttacacaact    660
cagggtggtt gcattgcatt gcattgtgct gtggagttag ttaacttagt tgtactccat    720
ccagttcata cgcagtacat tattgggcat ttgaccccat cagacaagat atctaaggat    780
aagagtagaa attaggtaat aatagtcaaa agagaagaag agataccaag ggaactagat    840
actaacaacc aatcaggata tgccacagtg tggaacagaa tggaagcaga caggatcaac    900
ataactggaa ataacctttt ctttctttct tcgtacagca tcttggcagg aagtaacttg    960
atattgttaa ttaatgtcca tgtccatgtc catgtctttg ttatgtcttg tcttgtcttt   1020
cttgtgtgct acaagtacag tgtaacagat tcatatccgc tgaaacagac ataacattcg   1080
acacatggaa tacggagata aagaaataaa ttatactata tacggaatga tatcaataaa   1140
tatccgtgtt gtactcctta ttaagaaaga gtggcgcttg gcgcgtctac gtgcatggac   1200
tggtactaca tatttgatta cttcgatttt taataacaac aacctagtag acgtatgtat   1260
gtcatgtgaa actttcgatt gcgtgctttc ttgtctactt gtcgacttgt tacaatcttg   1320
tcgaatatta ataataataa tccatcgcac tgacatcttg gcaagtactc cgtacatcag   1380
gttacataca tactgattct ctaaagctag ataacgaata ggattctcgc acagacagta   1440
tgtgtctctt gtctgtcaga tgataagcag atgaacaaag aaagtataac tgcttactac   1500
ctacatgccg acatttagtc gattcctttc ggagaattta ttatggatta ttaatagcat   1560
accccgggat tggcagaagg ggtaaaaggt ccgactagac aaggatatcc atacagtaca   1620
taccgttgat acagatcgaa tcacatgcat actgctgatg gtgtgatgaa tccttgaatt   1680
agacaatcat ccagacctgt ctggacagag atcctggcac tgaacaatcc actcattgct   1740
atctatcggt actctgtacc tgtttcagct gaagcttgcc aatcgcagac tgccatctgc   1800
aactgatcag cgccaggatg caggtcatga taccccagcg ttgttcccga ggtgtcattg   1860
cttaaacgcg ttaaccagtg tgctaaacgt gctaaacgtg ctaaatgcta aactgctgat   1920
gctatgcagc tgcatcgccg aatctggaga atgcagatca cctgccgacg gcgggctccg   1980
ggcacgtgca cgggggaccc cgtaggacag aaacgtccat cgagagtacg gagtacggag   2040
tattacaaga ccctgtccat cagaccctgt ccatcgtcat tgccaagatc tctcattgtt   2100
tgctgtttca tgctcggatc accagtggac agcaatgccc cgtgaacagc aagccgcatg   2160
ctggtccgtg tcttgtccgt gtgccgatgt agtattgcta acgagaccca gaatggcatc   2220
aatgacgttg cggatgacag aatgaggggg atcatcagta cgtctgctat caggatgatt   2280
atcctacgga gtatttactc agctgaagac aggaacaaga tcgtctgatg gatgaggccc   2340
acggccagcc agcacagact ccgtactctt cagtcttctg gatttgaccg ttcgacggcg   2400
cctccgacgt agcatctcgc tagcctgatc cttggctgcg cctatcgtcg gctcatgccc   2460
ctgttgatga cggggaagtg gagcggcgcc gcgataaggt tgccttgcta atttagcgcc   2520
tgcacgctcc agccaaaaag accaatattg aggtcgatcg tctcccctgg ctccgtgctg   2580
ctggcctgcg atcgccggcg cgatcatacc ctgcaatcac gccgccagcc tatcacagac   2640
catgcggtcc ttgcaccatc tgggagctcg agctctcctg actgccgtcg gggcgtcaat   2700
gcgtccggag cctccgacga gggcctctgc tcctcgtctg tcctactgga gcttgtccgt   2760
cagacgtcgc atcctgagcc gtgtgctgat atcgccatgg ctctgacgtg atcgactgcg   2820
```

-continued

```
agcggccggc gaggctataa gaagccgcaa cttgctgctc gaagtaccgt ctcccatcca   2880
tcgatcagac agtcagcagt cctcactcag tcagtcctca gtcgtccttc accaccatgg   2940
gtctgtccaa agccttcgtg tctgcactct cgctgtgctc cgccgtcgcc gtggccgccc   3000
cgaccgggcc agctcccaac gtgcagttct ccctgaagca ggtcgcggtg ccccggacca   3060
agcctcgtgc gcccccagct gccgactacg cgcgcgctct ggccaagtat ggcgctccaa   3120
ttccgtcgtc tgtgcggacg gccgcgtccg gcacgcagag cggctctgcg gccaacacgc   3180
ccgtcgccgg cgacagcttg tatctcacgc ccgttaccat cggccagagc acgctgaacc   3240
tggactttga cacgggctct gcggatctgt aagtgtccca actctcgcaa gaacaagaac   3300
ggagcagctg actcgtccag ctgggtcttc tccaacgaga cgccctccag cgagcgcggc   3360
aaccacgcca tctacaagcc cagctcgacg gccaagaagc tgaacggcta cacctggagc   3420
atctcgtacg gcgacggcag ctcggccggc ggcgacgtct accaggacag cgtctcggtg   3480
ggcggcgtca acgcctccaa ccaggcggtc gaggccgcca ccaaggtcag ctccgagttc   3540
acgcaggagc cgggcgacgg cttgctgggc ctggccttca gcagcatcaa caccgtcaag   3600
cccaagccgc agacgacctt cttcgacacg gtcaagtcct cgctcgccaa gccgctgttc   3660
gccgtcaccc tcaagcacaa cgagcccggc agctacgact ttggctacat cgacagctcc   3720
aagtacaagg gcagcatcca gtacacccag gtcgacaact cgcagggctt ctggcagttc   3780
acggccgacg gctactcgat tggcggcagc agcggcagcg gtggctccat ttctggcatt   3840
gctggtaaga actcccccta catcagagtt atctagatgc tgatttcgca gacaccggca   3900
ccaccctcct cctgctcgac gaccagatcg tcaacgagta ctaccagcag gtccagggcg   3960
cgcagaacga ccagaacgcc ggcggctaca ccttcccgtg cgacgcgcag ctgcccgagc   4020
tgagcttcac catcggccag tacaccgcca ccgtgccggc cgagtacctc aacttccagc   4080
ccgtgtcgca gggcagccag acctgcttcg gcggtctgca gtccaaccag ggcattggct   4140
tctccatctt cggcgacgtc ttcctcaaga gccagtacgt cgtctttgac tcggacggtc   4200
ctcagctggg ctttgctgct caggcgtaga ccagtcgtcc tccagcccag gttggttggt   4260
aggagatgat tttcgatcg atcgattatc atggtgattg ataggatatg tgcatgagca   4320
gttgcctgta catacataca taatgattta ttgaatcaat tagttatgat caatctcgaa   4380
tatattttca gtgaaatacg tacatggtca tagcataacg atatactccg ttttcttcag   4440
gtagctagta aatatacaca aattcatcgt tctcccggtc cgtcaggtcc aggaaggctt   4500
tgtctccgat cgtcccgtcg ggatcactct cgctggtatc gtgatagcgc tccctcatcg   4560
agtaatcaac caccttggcc ggctttccat tccgcacgcg ccgccgctcc tgcatccggt   4620
tcagcacgac caaattcgcc cactgcgcca gcacgacggc caccagcgcc acgaagatgg   4680
ccagacaagc ccgcacgccc ggccgatacg ccggcgcgtc cttcttgctg aagagcagcg   4740
ggccgacgat gttgcccgcc gagctggccg cgttgtacag gctcatcagc gccgatttct   4800
tcgttgtgcc gcccgtgttg cccacgatcc acgtcacgat cagtgggttg ccgccgaaga   4860
gaaacgcgag caggtagtag cctaccagga gggagggttc gactgagttt tgcttcgtgc   4920
tgttattact gcgtggcacg gcgtacagaa ttgccaggcc cgcgactacc ggcagcatga   4980
agccggccag cacgacgccc ttcatccgcg cccgctgcgc cagatagctc cccgccagga   5040
tgaccagcag ctgcagcgcg ccaaacggca tgttgagcag actcgtcgtg tacgcgtcgt   5100
accccaggcc gttgaggatc agcgggccga acgtgttgct cacgctggcg ccgacgttca   5160
```

gcagcatcgc catgccgatc cagaggtagg ttttgggctc gagcgctgcc tcgacgacgt 5220
gccggatctt gaactcgcgg ctccctgtgc ccgtctggtt cgcgcgcagc cgctcgatgg 5280
cctgcgcttt ttccgtctcc gtcaggaacc gcgctgaggg gatgtcgttg tctagtttcc 5340
agtagatgaa cggcactgag atgatggtca ggaggccgac ggtgaggaag atactgcgcc 5400
agtcgtcagc agtcagtcag tcagcgttcg gggtagaagg ggagtacatc tgccatggcc 5460
tcagaacagg cgactcgata tggcccaacc cgtacgacag ggccgccgcg atgacagtcg 5520
ccgcgccgtt ggtactgtac caggccgcaa tgcgcagcgg ctgctcggcg cggcggtacc 5580
actggctggt gatgacgctg aacagcggca gacaggcggc ctcgaacagg ccgaggaaga 5640
agcgcgcggc catcagggag gcgaaactgc gacaggcggc catggcggcc tgggcgacgc 5700
cccagcccag acacagcgcg ggcatcaggc ggcgatgcgg cacgcgcacg atcagccacg 5760
acgagaacgg ctgccagacg agctgggcga tgggcgcgat cgaccccagc agcgagtact 5820
ggttgcccgt caggtgcgtg tcggcctgca agccgaaggt ggccccgtac ccgagcaccg 5880
acttgtccag gatctgcagg aagtacaccc acacgaggat ggccaggatg acgcggtctg 5940
tcttgcgccg gatgcgcttg ctgtcggcgt ccgtgagtgg gattctctgc tggccgatca 6000
ggcggagcgc cgtgtcgccg tggacggcgg gttgctcttc ttcatgggtg acggtcggtt 6060
tggatgccat ggtagcgatt actagatgta atcaagttgt aatgggagac aaacgaccaa 6120
gttctctctc gacgttttat accggcttat atgtctgttc agcagcattg caagtcaagt 6180
aatgacatcg gaattcctcc ggttccccgc attgcgcggc gatcatcggc tggcactagc 6240
agtatagcta gctcagagtc cgtattactg gattctattg cattgcgctg attgcagacg 6300
ttgactgaca gcaggagctt tgactctatt acccccacgc ttcggcaatt ccccgcgtgc 6360
tcgggcctct atgcaccccc acgtggggga acattccaga gtatgcaggc agtagtatgc 6420
agcatggat 6429

<210> SEQ ID NO 58
<211> LENGTH: 1194
<212> TYPE: DNA
<213> ORGANISM: Rasamsonia emersonii

<400> SEQUENCE: 58
atgggtctgt ccaaagcctt cgtgtctgca ctctcgctgt gctccgccgt cgccgtggcc 60
gccccgaccg ggccagctcc caacgtgcag ttctccctga agcaggtcgc ggtgccccgg 120
accaagcctc gtgcgccccc agctgccgac tacgcgcgcg ctctggccaa gtatggcgct 180
ccaattccgt cgtctgtgcg gacggccgcg tccggcacgc agagcggctc tgcggccaac 240
acgcccgtcg ccggcgacag cttgtatctc acgcccgtta ccatcggcca gagcacgctg 300
aacctggact ttgacacggg ctctgcggat ctctgggtct tctccaacga gacgccctcc 360
agcgagcgcg gcaaccacgc catctacaag cccagctcga cggccaagaa gctgaacggc 420
tacacctgga gcatctcgta cggcgacggc agctcggccg gcggcgacgt ctaccaggac 480
agcgtctcgg tgggcggcgt caacgcctcc aaccaggcgg tcgaggccgc caccaaggtc 540
agctccgagt tcacgcagga gccgggcgac ggcttgctgg gcctggcctt cagcagcatc 600
aacaccgtca agcccaagcc gcagacgacc ttcttcgaca cggtcaagtc ctcgctcgcc 660
aagccgctgt tcgccgtcac cctcaagcac aacgagcccg gcagctacga ctttggctac 720
atcgacagct ccaagtacaa gggcagcatc cagtacaccc aggtcgacaa ctcgcagggc 780
ttctggcagt tcacggccga cggctactcg attggcggca gcagcggcag cggtggctcc 840

```
atttctggca ttgctgacac cggcaccacc ctcctcctgc tcgacgacca gatcgtcaac    900

gagtactacc agcaggtcca gggcgcgcag aacgaccaga acgccggcgg ctacaccttc    960

ccgtgcgacg cgcagctgcc cgagctgagc ttcaccatcg gccagtacac cgccaccgtg   1020

ccggccgagt acctcaactt ccagcccgtg tcgcagggca gccagacctg cttcggcggt   1080

ctgcagtcca accagggcat tggcttctcc atcttcggcg acgtcttcct caagagccag   1140

tacgtcgtct ttgactcgga cggtcctcag ctgggctttg ctgctcaggc gtag         1194


<210> SEQ ID NO 59
<211> LENGTH: 397
<212> TYPE: PRT
<213> ORGANISM: Rasamsonia emersonii

<400> SEQUENCE: 59

Met Gly Leu Ser Lys Ala Phe Val Ser Ala Leu Ser Leu Cys Ser Ala
1               5                   10                  15

Val Ala Val Ala Ala Pro Thr Gly Pro Ala Pro Asn Val Gln Phe Ser
            20                  25                  30

Leu Lys Gln Val Ala Val Pro Arg Thr Lys Pro Arg Ala Pro Pro Ala
        35                  40                  45

Ala Asp Tyr Ala Arg Ala Leu Ala Lys Tyr Gly Ala Pro Ile Pro Ser
    50                  55                  60

Ser Val Arg Thr Ala Ala Ser Gly Thr Gln Ser Gly Ser Ala Ala Asn
65                  70                  75                  80

Thr Pro Val Ala Gly Asp Ser Leu Tyr Leu Thr Pro Val Thr Ile Gly
                85                  90                  95

Gln Ser Thr Leu Asn Leu Asp Phe Asp Thr Gly Ser Ala Asp Leu Trp
            100                 105                 110

Val Phe Ser Asn Glu Thr Pro Ser Ser Glu Arg Gly Asn His Ala Ile
        115                 120                 125

Tyr Lys Pro Ser Ser Thr Ala Lys Lys Leu Asn Gly Tyr Thr Trp Ser
    130                 135                 140

Ile Ser Tyr Gly Asp Gly Ser Ser Ala Gly Gly Asp Val Tyr Gln Asp
145                 150                 155                 160

Ser Val Ser Val Gly Gly Val Asn Ala Ser Asn Gln Ala Val Glu Ala
                165                 170                 175

Ala Thr Lys Val Ser Ser Glu Phe Thr Gln Glu Pro Gly Asp Gly Leu
            180                 185                 190

Leu Gly Leu Ala Phe Ser Ser Ile Asn Thr Val Lys Pro Lys Pro Gln
        195                 200                 205

Thr Thr Phe Phe Asp Thr Val Lys Ser Ser Leu Ala Lys Pro Leu Phe
    210                 215                 220

Ala Val Thr Leu Lys His Asn Glu Pro Gly Ser Tyr Asp Phe Gly Tyr
225                 230                 235                 240

Ile Asp Ser Ser Lys Tyr Lys Gly Ser Ile Gln Tyr Thr Gln Val Asp
                245                 250                 255

Asn Ser Gln Gly Phe Trp Gln Phe Thr Ala Asp Gly Tyr Ser Ile Gly
            260                 265                 270

Gly Ser Ser Gly Ser Gly Gly Ser Ile Ser Gly Ile Ala Asp Thr Gly
        275                 280                 285

Thr Thr Leu Leu Leu Leu Asp Asp Gln Ile Val Asn Glu Tyr Tyr Gln
    290                 295                 300

Gln Val Gln Gly Ala Gln Asn Asp Gln Asn Ala Gly Gly Tyr Thr Phe
```

-continued

```
305                 310                 315                 320

Pro Cys Asp Ala Gln Leu Pro Glu Leu Ser Phe Thr Ile Gly Gln Tyr
                325                 330                 335

Thr Ala Thr Val Pro Ala Glu Tyr Leu Asn Phe Gln Pro Val Ser Gln
            340                 345                 350

Gly Ser Gln Thr Cys Phe Gly Gly Leu Gln Ser Asn Gln Gly Ile Gly
        355                 360                 365

Phe Ser Ile Phe Gly Asp Val Phe Leu Lys Ser Gln Tyr Val Val Phe
    370                 375                 380

Asp Ser Asp Gly Pro Gln Leu Gly Phe Ala Ala Gln Ala
385                 390                 395


<210> SEQ ID NO 60
<211> LENGTH: 1066
<212> TYPE: DNA
<213> ORGANISM: Artificial Sequence
<220> FEATURE:
<223> OTHER INFORMATION: A.nidulans gpdA promoter and 5' part of the
      ble coding region

<400> SEQUENCE: 60

agacagctct ggcggctctg aggtgcagtg gatgattatt aatccgggac cggccgcccc     60

tccgccccga agtggaaagg ctggtgtgcc cctcgttgac caagaatcta ttgcatcatc    120

ggagaatatg gagcttcatc gaatcaccgg cagtaagcga aggagaatgt gaagccaggg    180

gtgtatagcc gtcggcgaaa tagcatgcca ttaacctagg tacagaagtc caattgcttc    240

cgatctggta aaagattcac gagatagtac cttctccgaa gtaggtagag cgagtacccg    300

gcgcgtaagc tccctaattg gcccatccgg catctgtagg gcgtccaaat atcgtgcctc    360

tcctgctttg cccggtgtat gaaaccggaa aggccgctca ggagctggcc agcggcgcag    420

accgggaaca caagctggca gtcgacccat ccggtgctct gcactcgacc tgctgaggtc    480

cctcagtccc tggtaggcag ctttgccccg tctgtccgcc cggtgtgtcg gcggggttga    540

caaggtcgtt gcgtcagtcc aacatttgtt gccatatttt cctgctctcc ccaccagctg    600

ctcttttctt ttctctttct tttcccatct tcagtatatt catcttccca tccaagaacc    660

tttatttccc ctaagtaagt actttgctac atccatactc catccttccc atcccttatt    720

cctttgaacc tttcagttcg agctttccca cttcatcgca gcttgactaa cagctacccc    780

gcttgagcag acatcaccat ggccaagttg accagtgccg ttccggtgct caccgcgcgc    840

gacgtcgccg gagcggtcga gttctggacc gaccggctcg ggttctcccg ggacttcgtg    900

gaggacgact tcgccggtgt ggtccgggac gacgtgaccc tgttcatcag cgcggtccag    960

gaccaggtgg tgccggacaa caccctggcc tgggtgtggg tgcgcggcct ggacgagctg   1020

tacgccgagt ggtcggaggt cgtgtccacg aacttccggg acgcct                  1066


<210> SEQ ID NO 61
<211> LENGTH: 1065
<212> TYPE: DNA
<213> ORGANISM: Artificial Sequence
<220> FEATURE:
<223> OTHER INFORMATION: 3' part of the ble coding region and A.nidulans
      TrpC terminator
<220> FEATURE:
<221> NAME/KEY: misc_feature
<222> LOCATION: (685)..(685)
<223> OTHER INFORMATION: n is a, c, g, or t
<220> FEATURE:
<221> NAME/KEY: misc_feature
<222> LOCATION: (893)..(893)
```

-continued

<223> OTHER INFORMATION: n is a, c, g, or t
<220> FEATURE:
<221> NAME/KEY: misc_feature
<222> LOCATION: (984)..(984)
<223> OTHER INFORMATION: n is a, c, g, or t

<400> SEQUENCE: 61
accagtgccg ttccggtgct caccgcgcgc gacgtcgccg gagcggtcga gttctggacc 60
gaccggctcg ggttctcccg ggacttcgtg gaggacgact tcgccggtgt ggtccgggac 120
gacgtgaccc tgttcatcag cgcggtccag gaccaggtgg tgccggacaa caccctggcc 180
tgggtgtggg tgcgcggcct ggacgagctg tacgccgagt ggtcggaggt cgtgtccacg 240
aacttccggg acgcctccgg gccggccatg accgagatcg gcgagcagcc gtgggggcgg 300
gagttcgccc tgcgcgaccc ggccggcaac tgcgtgcact tcgtggccga ggagcaggac 360
tgaccgacgc cgaccaacac cgccggtccg acggcggccc acgggtccca ggagcttgag 420
atccacttaa cgttactgaa atcatcaaac agcttgacga atctggatat aagatcgttg 480
gtgtcgatgt cagctccgga gttgagacaa atggtgttca ggatctcgat aagatacgtt 540
catttgtcca agcagcaaag agtgccttct agtgatttaa tagctccatg tcaacaagaa 600
taaaacgcgt tttcgggttt acctcttcca gatacagctc atctgcaatg cattaatgca 660
ttgactgcaa cctagtaacg ccttncaggc tccggcgaag agaagaatag cttagcagag 720
ctattttcat tttcgggaga cgagatcaag cagatcaacg gtcgtcaaga gacctacgag 780
actgaggaat ccgctcttgg ctccacgcga ctatatattt gtctctaatt gtactttgac 840
atgctcctct tctttactct gatagcttga ctatgaaaat tccgtcacca gcncctgggt 900
tcgcaaagat aattgcatgt ttcttccttg aactctcaag cctacaggac acacattcat 960
cgtaggtata aacctcgaaa tcanttccta ctaagatggt atacaatagt aaccatgcat 1020
ggttgcctag tgaatgctcc gtaacaccca atacgccggc cggcc 1065